US011952681B2

(12) United States Patent
Luo et al.

(10) Patent No.: US 11,952,681 B2
(45) Date of Patent: Apr. 9, 2024

(54) MASKED ACTIVATABLE CD137 ANTIBODIES

(71) Applicant: Adagene Inc., Grand Cayman (KY)

(72) Inventors: Peter Peizhi Luo, San Mateo, CA (US); Fangyong Du, Jiangsu (CN)

(73) Assignee: Adagene Inc., Grand Cayman (KY)

( * ) Notice: Subject to any disclaimer, the term of this patent is extended or adjusted under 35 U.S.C. 154(b) by 138 days.

(21) Appl. No.: 16/966,848

(22) PCT Filed: Feb. 2, 2019

(86) PCT No.: PCT/CN2019/074581

§ 371 (c)(1),
(2) Date: Jul. 31, 2020

(87) PCT Pub. No.: WO2019/149282

PCT Pub. Date: Aug. 8, 2019

(65) Prior Publication Data

US 2021/0207126 A1 Jul. 8, 2021

(30) Foreign Application Priority Data

Feb. 2, 2018 (WO) ................ PCT/CN2018075065

(51) Int. Cl.
*C07K 16/46* (2006.01)
*A61P 35/00* (2006.01)
(Continued)

(52) U.S. Cl.
CPC .............. *C40B 40/08* (2013.01); *A61P 35/00* (2018.01); *C07K 16/2818* (2013.01); *C07K 16/2878* (2013.01); *C40B 40/10* (2013.01); *A61K 39/001117* (2018.08); *A61K 2039/505* (2013.01); *C07K 2317/55* (2013.01);
(Continued)

(58) Field of Classification Search
None
See application file for complete search history.

(56) References Cited

U.S. PATENT DOCUMENTS 4,399,216 A 8/1983 Axel et al.
4,634,665 A 1/1987 Axel et al.
(Continued)

FOREIGN PATENT DOCUMENTS

AU 2013202755 A1 5/2013
CN 1357009 A 7/2002
(Continued)

OTHER PUBLICATIONS

Kranz et al., Restricted reassociation of heavy and light chains from hapten-specific monoclonal antibodies, Proc. Natl. Acad. Sci. USA, 78(9):5807-5811, Sep. 1981.*
(Continued)

*Primary Examiner* — Claire Kaufman
(74) *Attorney, Agent, or Firm* — Morrison & Foerster LLP

(57) ABSTRACT

Provided herein are libraries containing synthetic polynucleotides that encode activatable binding polypeptides. Further provided herein are activatable binding polypeptides and polypeptide libraries containing such activatable binding polypeptides. Also provided herein are vectors, vector libraries, cells, kits, and methods of making and using activatable polypeptide libraries.

43 Claims, 30 Drawing Sheets

Specification includes a Sequence Listing.

(51) Int. Cl.

| | |
|---|---|
| ***C07K 16/28*** | (2006.01) |
| ***C40B 40/08*** | (2006.01) |
| ***C40B 40/10*** | (2006.01) |
| *A61K 39/00* | (2006.01) |

(52) U.S. Cl.

CPC .... *C07K 2317/622* (2013.01); *C07K 2317/92* (2013.01); *C07K 2319/50* (2013.01); *C07K 2319/74* (2013.01)

(56) References Cited

U.S. PATENT DOCUMENTS

| | | | |
|---|---|---|---|
| 4,816,567 | A | 3/1989 | Cabilly et al. |
| 5,179,017 | A | 1/1993 | Axel et al. |
| 5,648,237 | A | 7/1997 | Carter |
| 5,677,425 | A | 10/1997 | Axel et al. |
| 5,789,199 | A | 8/1998 | Joly et al. |
| 5,840,523 | A | 11/1998 | Simmons et al. |
| 5,959,177 | A | 9/1999 | Hein et al. |
| 5,994,619 | A | 11/1999 | Axel et al. |
| 6,040,498 | A | 3/2000 | Stomp et al. |
| 6,172,197 | B1 | 1/2001 | McCafferty et al. |
| 6,207,156 | B1 | 3/2001 | Kuchroo et al. |
| 6,291,158 | B1 | 9/2001 | Bodmer et al. |
| 6,417,429 | B1 | 7/2002 | Hein et al. |
| 6,420,548 | B1 | 7/2002 | Vezina et al. |
| 6,582,915 | B1 | 6/2003 | Stice et al. |
| 6,593,081 | B1 | 7/2003 | McCafferty et al. |
| 6,696,245 | B2 | 2/2004 | Winter et al. |
| 6,765,087 | B1 | 7/2004 | Casterman et al. |
| 6,838,254 | B1 | 1/2005 | Hamers et al. |
| 6,887,673 | B2 | 5/2005 | Kunkel et al. |
| 6,933,365 | B2 | 8/2005 | Kumagai et al. |
| 6,933,368 | B2 | 8/2005 | Co et al. |
| 7,125,978 | B1 | 10/2006 | Vezina et al. |
| 7,138,500 | B1 | 11/2006 | Goodwin et al. |
| 7,214,493 | B2 | 5/2007 | Kunkel et al. |
| 7,288,638 | B2 | 10/2007 | Jure-Kunkel et al. |
| 7,659,384 | B2 | 2/2010 | Jure-Kunkel et al. |
| 7,879,984 | B2 | 2/2011 | Martin et al. |
| 8,017,114 | B2 | 9/2011 | Korman et al. |
| 8,119,129 | B2 | 2/2012 | Jure-Kunkel et al. |
| 8,137,667 | B2 | 3/2012 | Jure-Kunkel et al. |
| 8,337,850 | B2 | 12/2012 | Ahrens et al. |
| 8,716,452 | B2 | 5/2014 | Jure-Kunkel et al. |
| 8,821,867 | B2 | 9/2014 | Ahrens et al. |
| 9,382,328 | B2 | 7/2016 | Jure-Kunkel et al. |
| 9,468,678 | B2 | 10/2016 | Ahrens et al. |
| 10,066,013 | B2 | 9/2018 | Chen et al. |
| 10,174,122 | B2 | 1/2019 | Kwon et al. |
| 10,279,038 | B2 | 5/2019 | Bobrowicz et al. |
| 10,279,039 | B2 | 5/2019 | Bobrowicz et al. |
| 10,279,040 | B1 | 5/2019 | Bobrowicz et al. |
| 10,350,292 | B1 | 7/2019 | Bobrowicz et al. |
| 10,357,571 | B2 * | 7/2019 | Williams ............... C07K 16/30 |
| 11,078,281 | B2 | 8/2021 | Wang et al. |
| 11,091,557 | B2 | 8/2021 | Altintas et al. |
| 11,242,395 | B2 * | 2/2022 | Luo .................... C07K 16/2878 |
| 11,359,016 | B2 | 6/2022 | Luo et al. |
| 2003/0118588 | A1 | 6/2003 | Diehl et al. |
| 2006/0153808 | A1 | 7/2006 | Cristofanilli et al. |
| 2007/0117809 | A1 | 5/2007 | Fridman |
| 2008/0305113 | A1 | 12/2008 | Kwon et al. |
| 2010/0189651 | A1 | 7/2010 | Stagliano et al. |
| 2011/0059045 | A1 | 3/2011 | Bermejo et al. |
| 2012/0076722 | A1 | 3/2012 | Strome et al. |
| 2016/0145604 | A1 | 5/2016 | Du et al. |
| 2016/0311903 | A1 | 10/2016 | West et al. |
| 2016/0368998 | A1 | 12/2016 | Jure-Kunkel et al. |
| 2017/0022287 | A1 | 1/2017 | Igawa et al. |
| 2018/0194851 | A1 | 7/2018 | Ahrens et al. |
| 2018/0344870 | A1 | 12/2018 | Xiao et al. |
| 2019/0015508 | A1 | 1/2019 | Bobrowicz et al. |
| 2019/0055314 | A1 | 2/2019 | Luo et al. |
| 2019/0169245 | A1 | 6/2019 | Williams et al. |
| 2019/0241662 | A1 | 8/2019 | Luo et al. |
| 2019/0241886 | A1 | 8/2019 | Luo et al. |
| 2020/0017594 | A9 | 1/2020 | Al-Shamkhani et al. |
| 2020/0369776 | A1 | 11/2020 | Luo et al. |
| 2020/0377608 | A1 | 12/2020 | Luo et al. |
| 2021/0206855 | A1 | 7/2021 | Luo et al. |
| 2022/0089757 | A1 | 3/2022 | Luo et al. |
| 2022/0204637 | A1 | 6/2022 | Luo et al. |
| 2023/0133118 | A1 | 5/2023 | Luo et al. |
| 2023/0242663 | A1 | 8/2023 | Luo et al. |

FOREIGN PATENT DOCUMENTS

| | | | |
|---|---|---|---|
| CN | 1749270 | A | 3/2006 |
| CN | 1867585 | A | 11/2006 |
| CN | 1867585 | B | 2/2011 |
| CN | 102482347 | A | 5/2012 |
| CN | 105296433 | A | 2/2016 |
| CN | 106163556 | A | 11/2016 |
| CN | 107840887 | A | 3/2018 |
| EP | 368684 | B1 | 3/1994 |
| EP | 338841 | A1 | 3/1995 |
| EP | 616640 | B1 | 9/2004 |
| EP | 2161336 | A1 | 3/2010 |
| WO | WO-1987004462 | A1 | 7/1987 |
| WO | WO-1989001036 | A1 | 2/1989 |
| WO | WO-1996032495 | A1 | 10/1996 |
| WO | WO-1998042752 | A1 | 10/1998 |
| WO | WO-2000029445 | A1 | 5/2000 |
| WO | WO-2000037504 | A2 | 6/2000 |
| WO | WO-2001014424 | A2 | 3/2001 |
| WO | WO-2002053596 | A2 | 7/2002 |
| WO | WO-2002055106 | A2 | 7/2002 |
| WO | WO-2003002609 | A2 | 1/2003 |
| WO | WO-2003015711 | A2 | 2/2003 |
| WO | WO-2003040170 | A2 | 5/2003 |
| WO | WO-2003048731 | A2 | 6/2003 |
| WO | WO-2003074678 | A2 | 9/2003 |
| WO | WO-2004003019 | A3 | 1/2004 |
| WO | WO-2004010947 | A2 | 2/2004 |
| WO | WO-2004016805 | A2 | 2/2004 |
| WO | WO-2004035607 | A2 | 4/2004 |
| WO | WO-2004056312 | A2 | 7/2004 |
| WO | WO-2004058821 | A2 | 7/2004 |
| WO | WO-2004081026 | A2 | 9/2004 |
| WO | WO-2004101790 | A1 | 11/2004 |
| WO | WO-2005035572 | A2 | 4/2005 |
| WO | WO-2005035584 | A1 | 4/2005 |
| WO | WO-2005044859 | A2 | 5/2005 |
| WO | WO-2005103081 | A2 | 11/2005 |
| WO | WO-2005120568 | A1 | 12/2005 |
| WO | WO-2006029220 | A2 | 3/2006 |
| WO | WO-2006066568 | A2 | 6/2006 |
| WO | WO-2006079372 | A1 | 8/2006 |
| WO | WO-2006088447 | A1 | 8/2006 |
| WO | WO-2006129163 | A1 | 12/2006 |
| WO | WO-2007031875 | A2 | 3/2007 |
| WO | WO-2007059782 | A1 | 5/2007 |
| WO | WO-2009022215 | A1 | 2/2009 |
| WO | WO-2009025846 | A2 | 2/2009 |
| WO | WO-2009079335 | A1 | 6/2009 |
| WO | WO-2010081173 | A2 | 7/2010 |
| WO | WO-2012065086 | A1 | 5/2012 |
| WO | WO-2013192550 | A2 | 12/2013 |
| WO | WO-2015094123 | A1 | 6/2015 |
| WO | WO-2015095410 | A1 | 6/2015 |
| WO | WO-2015125159 | A1 | 8/2015 |
| WO | WO-2015156268 | A1 | 10/2015 |
| WO | WO-2016014974 | A2 | 1/2016 |
| WO | WO-2016115275 | A1 | 7/2016 |
| WO | WO-2016130898 | A2 | 8/2016 |
| WO | WO-2016130986 | A1 | 8/2016 |
| WO | WO-2016134358 | A1 | 8/2016 |
| WO | WO-2016149201 | A2 | 9/2016 |
| WO | WO-2016179285 | A1 | 11/2016 |
| WO | WO-2016179335 | A1 | 11/2016 |
| WO | WO-2016185016 | A1 | 11/2016 |
| WO | WO-2016200645 | A1 | 12/2016 |
| WO | WO-2017011580 | A3 | 1/2017 |

(56) References Cited

FOREIGN PATENT DOCUMENTS

| | | | |
|---|---|---|---|
| WO | WO-2017049452 | A1 | 3/2017 |
| WO | WO-2017077085 | A2 | 5/2017 |
| WO | WO-2017106372 | A1 | 6/2017 |
| WO | WO-2017106656 | A1 | 6/2017 |
| WO | WO-2017112811 | A1 | 6/2017 |
| WO | WO-2017140826 | A1 | 8/2017 |
| WO | WO-2017151940 | A2 | 9/2017 |
| WO | WO-2017194265 | A1 | 11/2017 |
| WO | WO-2017205745 | A1 | 11/2017 |
| WO | WO-2018091740 | A2 | 5/2018 |
| WO | WO-2018127787 | A1 | 7/2018 |
| WO | WO-2018191502 | A2 | 10/2018 |
| WO | WO-2018199595 | A1 | 11/2018 |
| WO | WO-2018202649 | A1 | 11/2018 |
| WO | WO-2018209701 | A1 | 11/2018 |
| WO | WO-2019014328 | A2 | 1/2019 |
| WO | WO-2019036842 | A1 | 2/2019 |
| WO | WO-2019036855 | A1 | 2/2019 |
| WO | WO-2019036856 | A1 | 2/2019 |
| WO | WO-2019037711 | A1 | 2/2019 |
| WO | WO-2019089753 | A2 | 5/2019 |
| WO | WO-2019105468 | A1 | 6/2019 |
| WO | WO-2019148445 | A1 | 8/2019 |
| WO | WO-2019149281 | A1 | 8/2019 |
| WO | WO-2020244574 | A1 | 12/2020 |

OTHER PUBLICATIONS

Desnoyers et al., Tumor-Specific Activation of an EGFR-TargetingProbody Enhances Therapeutic Index, Sci. Transl. Med. 5(207):e144, 10 pages, Oct. 16, 2013.*

Chester et al., Immunotherapy targeting 4-1BB mechanistic rationale, clinical results, and future strategies, Blood, 13(1):49-57, Jan. 4, 2018.*

Zhou et al., Is protein context responsible for peptide-mediated interactions, Mol. Omics, 15:280-295, 2019.*

Chichili et al., Linkers in the structural biology of protein-potein interactions, Prot. Sci. 22:153-167, 2013.*

Andria et al., Diverse VH and VL genes are used to producevantibodies against a defined protein epitope, J. Immunol. 144:2614-2619, 1990.*

Broll, (2001). "CD137 Expression in Tumor Vessel Walls: High Correlation With Malignant Tumors," Amer. J. Clin. Pathol., 115(4):543-549.

Casset et al., (2003). "A peptide mimetic of an anti-CD4 monoclonal antibody by rational design," Biochemical and Biophysical Research Communications, 307:198-205.

Cheuk et al., (2004). "Role of 4-1BB:4-1BB ligand in cancer immunotherapy," Cancer Gene Therapy, 11(3): 215-226.

Chin et al., (2018). "Structure of the 4-1 BB/4-1 BBL complex and distinct binding and functional properties of utomilumab and urelumab," Nat Commun., 9:4679, 13 pages.

Committee for Medicinal Products for Human Use (CHMP). Assessment Report for Yervoy (ipilirnumab). CHMP assessment report EMNCHMP/557664/2011. May 19, 2011(May 19, 2011) pp. 1-71.

Croft, (2009). "The role of TNF superfamily members in T-cell function and diseases," Nat Rev Immunol., 9:271-285.

Drenkard, (2007). "CD137 is expressed on blood vessel walls at sites of Inflammation and enhances monocyte migratory activity," FASEB Journal, 21: 456-463.

Ferrara et al., (2015). "Recombinant renewable polyclonal antibodies," mABs, 7(1):32-41.

Ferrara et al., (2018). "Anti-CTLA-4 immunotherapy does not deplete FOXP3+ regulatory T cells (Tregs) in human cancers—Letter," Clin. Cancer Res, 25(11):3468.

GenBank Accession No. AAH06196.1, "Tumor necrosis factor receptor superfamily, member 9 [*Homo sapiens*]," Jul. 15, 2015, Available at: <https://www.ncbi.nlm.nih.gov/protein/AAH06196.1>, 2 pages.

GenBank Accession No. ABY47575.1, "CD137 [Macaca fascicularis]," Dec. 5, 2008, Available at: < https://www.ncbi.nlm.nih.gov/protein/ABY47575.1>, 2 pages.

Gerspach et al., (2006). "Target-selective activation of a TNF prodrug by urokinase-type plasminogen activator (uPA) mediated proteolytic processing at the cell surface," Cancer Immunol Immunother, 55(12):1590-1600.

Guinn et al., (1999). "4-1BBL Cooperates With B7-1 and B7-2 in Converting a B Cell Lymphoma Cell Line Into a Long-Lasting Antitumor Vaccine," J. Immunol., 162(8):5003-10.

Ha et al., (2019). "Differential control of human Treg and effector T cells in tumor immunity by Fc-engineered anti-CTLA-4 antibody," PNAS, 116(2):609-618.

He et al., (2017). "Remarkably similar CTLA-4 binding properties of therapeutic ipilimumab and tremelimumab antibodies," Oncotarget 8:67129-67139.

Hurwitz et al., (1998). "CTLA-4 blockade synergizes with tumor-derived granulocyte—macrophage colony-stimulating factor for treatment of an experimental mammary carcinoma," Proc Natl Acad Sci USA 95 (17):10067-71.

International Search Report and Written Opinion of the International Searching Authority dated Apr. 28, 2019, issued for PCT/CN2019/074580, filed Feb. 2, 2019, 15 pages.

International Search Report and Written Opinion of the International Searching Authority dated Feb. 27, 2019, issued for PCT/CN2018/118631, filed Nov. 30, 2018, 15 pages.

International Search Report and Written Opinion of the International Searching Authority dated May 25, 2018, issued for PCT/CN2017/098332, filed Aug. 21, 2017, 20 pages.

International Search Report and Written Opinion of the International Searching Authority dated May 8, 2019, issued for PCT/CN2019/074581, filed Feb. 2, 2019, 13 pages.

International Search Report and Written Opinion of the International Searching Authority dated Nov. 14, 2018, issued for PCT/CN2018/101501, filed Aug. 21, 2018, 12 pages.

International Search Report and Written Opinion of the International Searching Authority dated Nov. 6, 2018, issued for PCT/CN2018/075065, filed Feb. 2, 2018, 16 pages.

International Search Report and Written Opinion of the International Searching Authority dated Nov. 7, 2018, issued for PCT/CN2018/075064, filed Feb. 2, 2018, 17 pages.

International Search Report and Written Opinion of the International Searching Authority dated Sep. 4, 2020, issued for PCT/CN2020/094371, filed Jun. 4, 2020, 14 pages.

International Search Report and Written Opinion of the International Searching Authority dated Sep. 7, 2018, issued for PCT/CN2017/0114247, filed Dec. 1, 2017, 14 pages.

Jiang et al., (2004). "Tumor imaging by means of proteolytic activation of cell-penetrating peptides," Proc Natl Acad Sci USA 101(51):17867-72.

Ke et al., (1997). "Optimal Subsite Occupancy and Design of a Selective Inhibitor of Urokinase," J Biol Chem 272(33):20456-62.

Keler et al., (2003). "Activity and Safety of CTLA-4 Blockade Combined with Vaccines in Cynomolgus," The Journal of Immunology, 171:6251-59.

Kwon et al., (1997). "Manipulation of T cell costimulatory and inhibitory signals for immunotherapy of prostate cancer," Proc Natl Acad Sci USA, 94(15):8099-103.

Lee et al., (2016). "Structural basis of checkpoint blockade by monoclonal antibodies in cancer immunotherapy," Nat Commun 7(13354):1-10.

Lei et al., (1987). "Characterization of the Erwinia carotovora pelB gene and its product pectate lyase," J. Bacteriol., 169:4379-83.

Li (2014). "Expression of human CD137 and CD28 proteins and preparation of their specific monoclonal antibodies," Chinese Master's Theses Full-Text Database Medicine And Health Sciences 2:E059-133; pp. 1-73. English Abstract Only.

Li et al., (2013). "Immunotherapy of melanoma with the immune costimulatory monoclonal antibodies targeting CD137," Clin Pharmacol., 5(1):47-53.

Lynch (2008). "The promise of 4-1BB (CD137)-mediated immunomodulation and the immunotherapy of cancer," Immunol Rev., 222(1):277-286.

(56) References Cited

OTHER PUBLICATIONS

MacCallum et al., (1996). "Antibody-antigen interactions: contact analysis and binding site topography," Journal of Molecular Biology, 262:732-745.
Martinet et al., (2000). "Immunomodulatory Gene Therapy With Interleukin 12 and 4-1BB Ligand: Long-Term Remission of Liver Metastases in a Mouse Model," J Natl Cancer Inst., 92(11):931-6.
Martinez-Forero et al., (2013). "T cell costimulation with anti-CD137 monoclonal antibodies is mediated by K63-polyubiquitin-dependent signals from endosomes," J Immunol., 190(12):6694-706.
Melero et al., (1998). "Amplification of Tumor Immunity by Gene Transfer of the Co-Stimulatory 4-1BB Ligand: Synergy With the CD28 Co-Stimulatory Pathway," Eur. J. Immunol., 28(3):1116-21.
Narazaki et al., (2010). "CD137 agonist antibody prevents cancer 1-50 recurrence: contribution of CD 13 7 on both hematopoietic and nonhematopoietic cells," Immunobiology. 10(115):1941-1948.
Olofsson (2008). "CD137 is expressed in human atherosclerosis and promotes development of plaque inflammation in hypercholesterolemic mice," Circulation, 117(10):1292-1301.
Paul, (1993). "Chapter 9: Structure and Function of Immunoglobulins," Fundamental Immunology, 3rd Edition, pp. 292-295.
Peters et al. (2012). "Engineering an improved IgG4 molecule with reduced disulfide bond heterogeneity and increased Fab domain thermal stability," J Biol Chem. 287(29):24525-33.
Ramagopal et al., (2017). "Structural basis for cancer immunotherapy by the first-in-class checkpoint inhibitor ipilimumab," Proc Natl Acad Sci USA 114(21): 4223-4232.
Ribas et al., (2007). "Tremelimumab (CP-675, 206), a Cytotoxic T 1-61 Lymphocyte-Associated Antigen 4 Blocking Monoclonal Antibody in Clinical Development for Patients with Cancer," The Oncologist, 12:873-883.
Schwartz et al., (2001). "Structural basis for co-stimulation by the human CTLA-4/B7-2 complex," Nature 410(6828): 604-608.
Seaman 2007. "Genes that distinguish physiological and pathological angiogenesis," Cancer Cell, 11(6): 539-554.
Shao et al., (2011). "CD137 Ligand, a member of the tumor necrosis factor family, regulates immune responses via reverse signal transduction," J. Leukoc. Biol., 89: 21-29.
Shao, Z. et al. (2015). "Trogocytic CD137 transfer causes an internalization of CD137 ligand on murine APCs leading to reduced T cell costimulation," J. Leukocyte Biol., 97:909-919.
Sharma et al., (2019; epub 2018). "Anti-CTLA-4 Immunotherapy Does Not Deplete FOXP3+ Regulatory T Cells (Tregs) in Human Cancers," Clin. Cancer Res., 25:1233-1238.
Shi et al., (2006). "Augmented antitumor effects of radiation therapy by 4-1BB antibody (BMS-469492) treatment," Anticancer Res., 26(5A):3445-53.
Stamper et al., (2001). "Crystal structure of the B7-1/CTLA-4 complex that inhibits human immune responses," Nature 410(6828): 608-611.
Tian et al. (2015). "In-depth analysis of subclass-specific conformational preferences of IgG antibodies," IUCrJ. 2(Pt 1):9-18.
Tolcher et al., (2017). "Phase Ib Study of Utomilumab (PF-05082566), a 4-1BB/CD137 Agonist, in Combination with Pembrolizumab (MK-3475) in Patients with Advanced Solid Tumor," Clin Cancer Res., 23(18):5349-5357.
Unpublished U.S. Appl. No. 16/966,848, filed Jul. 31, 2020, titled "Activatable Antibodies and Methods of Making and Using Thereof," (Copy not submitted herewith pursuant to the waiver of 37 C.F.R. § 1.98(a)(2)(iii)).
Vajdos et al., (2002). "Comprehensive functional maps of the antigen-binding site of an anti-ErbB2 antibody obtained with shotgun scanning mutagenesis," Journal of Molecular Biology, 320(2):415-28.
Vinay et al., (2006). "Dual immunoregulatory pathways of 4-1BB signaling," J Mol Med, 84(9):726-736.
Wang et al., (2009). "Immune regulation by 4-1BB and 4-1BBL: complexities and challenges," Immunological Reviews, 229(1):192-215.
Wei et al. (2013). "Combinatorial PD-1 blockade and CD137 activation has therapeutic efficacy in murine cancer models and synergizes with cisplatin," PLOS One. 8(12):1-11.
Xiang, (1999). "Expression of Co-Stimulatory 4-1bb Ligand Induces Significant Tumor Regression And Protective Immunity," Cancer Biother. Radiopharm., 14(5):353-61.
Xiao et al., (2007). "Soluble PD-1 facilitates 4-IBBL-triggered antitumor immunity against murine H22 hepatocarcinoma in vivo," Clin Cancer Res., 13(6):1823-30.
Xu et al., (2012). "Preparation and characterization of a chimeric anti-human CTLA-4 monoclonal antibody," Current Immunology, 5(32):359-364. English Abstract Only.
Yang et al., (1997). "Enhanced induction of antitumor T-cell responses by cytotoxic T lymphocyte-associated molecule-4 blockade: the effect is manifested only at the restricted tumor-bearing stages," Cancer Res 57(18):4036-41.
Yi et al., (2009). "Location of extracellular cysteine-rich domains of 4-1BB binding to murine 4-1BB ligand and analysis of its possible structure," Chin. J. Microbiol. Immunol. 4(29):343-344. Abstract Only.
Yonezawa et al., (2015) "Boosting Cancer Immunotherapy with Anti-CD137 Antibody Therapy," Clinical Cancer Research. 14(21):3113-3120.
Chu et al., (2019). "An Update on Anti-CD137 Antibodies in Immunotherapies for Cancer," International Journal of Molecular Sciences, 20(8):1822, 17 pages.
ClinicalTrials.gov, (2017). "T-Cell Infusion, Aldesleukin, and Utomilumab in Treating Patients With Recurrent Ovarian Cancer, NCT03318900," Available online at <https://clinicaltrials.gov/ct2/show/NCT03318900?term=NCT03318900&draw=2&rank=1>, 12 pages.
ClinicalTrials.org, (2019). "Adagene (Suzhou) Limited, NCT03802955: Study of ADG106 With Advanced or Metastatic Solid Tumors and/or Non-Hodgkin Lymphoma," Available online at <https://clinicaltrials.gov/ct2/show/NCT0380295514> obtained on May 21, 2021, 5 pages.
Extended European Search Report received for European Patent Application No. 19747798.7 dated Oct. 19, 2021, 10 pages.
Extended European Search Report received for European Patent Application No. 19748085.8 dated Jun. 1, 2022, 12 pages.
Guillerey et al., (2016). "Abstract B155: Anti-CD137 mAb therapy of multiple myeloma," Cancer Immunol Res., 4(1_Supplement):B155, 2 pages.
Labiano et al., (2016). "Hypoxia-induced soluble CD137 in malignant cells blocks CD137L-costimulation as an immune escape mechanism," Oncoimmunology, 5:e1062967, 10 pages.
Liu et al., (2006). "Inhibition of murine syngeneic graft versus host disease by blockade of CD137/CD137L signaling pathway with anti-CD137L mAb," Chinese Journal of Immunology, 22(7):619-622. Abstract Only.
Quetglas et al., (2012). "Immunotherapeutic Synergy Between AntiCD137 mAb and Intratumoral Administration of a Cytopathic Semliki Forest Virus Encoding IL-12," Molecular Therapy, 20(9):1664-1675.
Segal et al., (2018). "Phase I Study of Single-Agent Utomilumab (PF-05082566), a 4-1BB/CD137 Agonist, in Patients with Advanced Cancer," Clinical Cancer Research, 24:1816-1823.
Senthilkumar et al., (2009). "CD137L- and RANKL-mediated reverse signals inhibit osteoclastogenesis and T lymphocyte proliferation," Immunobiology, 214(2):153-61. Abstract Only.
Won, (2010). "The structure of the trimer of human 4-1BB ligand is unique among members of the tumor necrosis factor superfamily," J Biol Chem., 285(12):9202-10.
Ye et al., (2020). "CD137, an attractive candidate for the immunotherapy of lung cancer," Cancer Science, 111:1461-1467.
Zapata et al., (2015). "CD137 (4-1BB) Signalosome: Complexity Is a Matter of TRAFs," Frontiers in Immunology, 9:2618, 12 pages.
Zhang et al., (2018). "Nanoparticle anchoring targets immune agonists to tumors enabling anti-cancer immunity without systemic toxicity," Nature Communications, 9(6):1-15.
Zhang et al., (2020). "Phase 1, dose-escalation study of ADG106, a fully human anti-CD 137 agonistic antibody, in subjects with

(56) References Cited

OTHER PUBLICATIONS advanced solid tumors or relapsed/refractory non-Hodgkin lymphoma," Journal of Clinical Oncology, 38:A3105, 2 pages. Abstract Only.
Abhinandan et al., (2008). "Analysis and improvements to Kabat and structurally correct numbering of antibody variable domains," Mol Immunol, 45:3832-3839.
Adolf-Bryfogle et al., (2015). "PylgClassify: a database of antibody CDR structural classifications," Nucleic Acids Res, 43:D432-D438.
Al-Lazikani et al., (1997). "Standard conformations for the canonical structures of immunoglobulins," J Mol. Biol., 273:927-948.
Bartkowiak et al., (2015). "4-1 BB agonists: multi-potent potentiators of tumor immunity," Front. Oncol., 5:117, 16 pages.
Bird et al., (1988). "Single-chain antigen-binding proteins," Science, 242(4877):423-426.
Camacho et al., (2004). "Abstract 2505: Phase 1 clinical trial of anti-CTLA4 human monoclonal antibody CP-675,206 in patients (pts) with advanced solid malignancies," J Clin Oncology, 22(14_ suppl), 3 pages.
Chan et al., (2009). "Epitope mapping of a chimeric CD137 mAb: a necessary step for assessing the biologic relevance of non-human primate models," Journal of Molecular Recognition, 22(3):242-249.
Chen et al., (1995). "Enhancement and destruction of antibody function by somatic mutation: unequal occurrence is controlled by V gene combinatorial associations," EMBO J., 14(12):2784-2794.
Chen et al., (1999). "Selection and Analysis of an Optimized Anti-VEGF Antibody: Crystal Structure of an Affinity-matured Fab in Complex with Antigen", J. Mol. Biol., 293:865-881.
Chothia et al., (1987). "Canonical structures for the hypervariable regions of immunoglobulins," J. Mol. Biol., 196:901-917.
Creative-Diagnostics, (2022). "4-1 BB/4-1 Bbl Signaling Pathway," available online at <https://www.creative-diagnostics.com/4-1 bb-4-1 bbl-signaling-pathway.htm>, 5 pages.
Dimberg et al., (2006). "Expression of CD137 and CD137 ligand in colorectal cancer patients," Oncol. Rep., 15(5):1197-1200.
Ehrenmann et al., (2010). "IMGT/3Dstructure-DB and IMGT/DomainGapAlign: a database and a tool for immunoglobulins or antibodies, T cell receptors, MHC, IgSF and MhcSF," Nucleic Acids Res., 38:D301-D307.
Extended European Sear Report and Opinion for European Patent Application No. 18847500.8, dated Apr. 22, 2021, 8 pages.
Extended European Sear Report and Opinion for European Patent Application No. 18883687.8, dated Jul. 30, 2021, 10 pages.
Feldhaus et al., (2003). "Flow-cytometric isolation of human antibodies from a non-immune *Saccharomyces* cerevisiae surface display library," Nat Biotechnol, 21(2):163-170.
Fukunaga et al., (2018). "Improvement of antibody affinity by introduction of basic amino acid residues into the framework region," Biochem. Biophys. Rep., 15:81-85.
Genbank, (2023). Accession No. NM_001561.6: "*Homo sapiens* TNF receptor superfamily member 9 (TNFRSF9), mRNA," Available at: <https://www.ncbi.nlm.nih.gov/nuccore/NM_001561.6/>, 6 pages.
Genbank, (2023). Accession No. NP_001552.2: "tumor necrosis factor receptor superfamily member 9 precursor [*Homo sapiens*]," Available at: <https://www.ncbi.nlm.nih.gov/protein/NP_001552>, 4 pages.
Genbank, (2020). Accession No. NM_001267706.1: "*Homo sapiens* CD274 molecule (CD274), transcript variant 2, mRNA," Available at: <https://www.ncbi.nlm.nih.gov/nuccore/NM_001267706.1/>, 5 pages.
Genbank, (2023). Accession No. NM_001145966.2: "*Homo sapiens* marker of proliferation Ki-67 (MKI67), transcript variant 2, mRNA," Available at: <https://www.ncbi.nlm.nih.gov/nuccore/NM_001145966.2/>, 7 pages.
Gerngross, (2004). "Advances in the Production of Human Therapeutic Proteins in Yeasts and Filamentous Fungi," Nat. Biotech., 22:1409-1414.
Graham et al., (1977). "Characteristics of a Human Cell Line Transformed by DNA From Human Adenovirus Type 5," J. Gen Virol., 36:59-72.
Guillerey et al., (2016). "Abstract 764: Therapeutic potential anti-CD137 mAbs in multiple myeloma," European Journal of Immunology. 46 (Suppl. 1):1005-1006.
Honegger et al., (2001)."Yet another numbering scheme for immunoglobulin variable domains: an automatic modeling and analysis tool," Mol Biol., 309:657-670.
International Search Report and Written Opinion of the International Searching Authority dated Aug. 18, 2021, issued for PCT/CN2021/093511, filed May 13, 2021, 15 pages.
International Search Report and Written Opinion of the International Searching Authority dated Feb. 18, 2021, issued for PCT/CN2020/094278, filed Jun. 4, 2020, 17 pages.
International Search Report and Written Opinion of the International Searching Authority dated Jan. 27, 2021, issued for PCT/CN2020/090073, filed May 13, 2020, 16 pages.
International Search Report and Written Opinion of the International Searching Authority dated Jan. 27, 2021, issued for PCT/CN2020/115795, filed Sep. 17, 2020, 14 pages.
International Search Report and Written Opinion of the International Searching Authority dated Sep. 24, 2021, issued for PCT/US2021/038718, filed Jun. 23, 2021, 12 pages.
Kabat et al., (1977). "Unusual distributions of amino acids in complementarity-determining (hypervariable) segments of heavy and light chains of immunoglobulins and their possible roles in specificity of antibody-combining sites," J. Biol. Chem., 252:6609-6616.
Kamijo et al., (2017). "Abstract 522: Blocking CD137-CD137L interactions inhibits proliferation and survival of cutaneous T-cell lymphoma cells via hampering several signaling pathways," J. Invest. Dermatol., 137(10)Suppl. 2:5282.
Kim et al., (2002). "Induction of 4-1BB (CD137) expression by DNA damaging agents in human T lymphocytes," Immunology, 107:472-479.
Knappik et al., (2000). "Fully Synthetic Human Combinatorial Antibody Libraries (HuCAL) Based on Modular Consensus Frameworks and CDRs Randomized with Trinucleotides," J. Mol. Biol., 296(1):57-86.
Kohler et al., (1975). "Continuous cultures of fused cells secreting antibody of predefined specificity," Nature, 256:495-7.
Kroon et al., (2016). "Concomitant targeting of programmed death-1 (PD-1) and CD 137 improves the efficacy of immunotherapy in a mouse model of human BRAFV600-mutant melanoma," Cancer Immunology, Immunotherapy, 65:753-763.
Lamminmaki et al., (2001). "Crystal structure of a recombinant anti-estradiol Fab fragment in complex with 17B-estradiol," J. Biol. Chem., 276:36687-36694.
Lefranc et al., (2003). "IMGT unique numbering for immunoglobulin and T cell receptor variable domains and Ig superfamily V-like domains," Dev. Comp. Imunnol., 27:55-77.
Lindbom et al., (2005). "PsN-Toolkit—a collection of computer intensive statistical methods for non-linear mixed effect modeling using NONMEM," Comput Methods Programs Biomed., 79(3):241-57. Abstract Only.
Masu et al., (2018). "Anti-CD137 monoclonal antibody enhances trastuzumab-induced, natural killer cell-mediated cytotoxicity against pancreatic cancer cell lines with low human epidermal growth factor-like receptor 2 expression," PLOS ONE, 13(12):e0200664, 18 pages.
Mather et al., (1982). "Culture of Testicular Cells in Hormone-Supplemented Serum-Free Medium," Annals N.Y. Acad. Sci., 383:44-68.
Mather, (1980). "Establishment and Characterization of Two Distinct Mouse Testicular Epithelial Cell Lines," Biol. Reprod., 23:243-251.
Mokyr et al., (1998). "Realization of the therapeutic potential of CTLA-4 blockade in low- dose chemotherapy-treated tumor-bearing mice," Cancer Res, 58:5301-5304.
Nezlin, (1970). "The Structure of Antibodies," Biochemistry of Antibodies, p. 160, 4 pages.

(56) References Cited

OTHER PUBLICATIONS

Segal, (2016). "Results from an Integrated Safety Analysis of Urelumab, an Agonist Anti-CD137 Monoclonal Antibody," Clin. Cane. Res., 23(8):1929-1936.

Sela-Culan et al., (2013). "The structural basis of antibody-antigen recognition," Front. Immunol. 4:302, 13 pages.

Sharma et al., (2020). "Bempegaldesleukin selectively depletes intratumoral Tregs and potentiates T cell-mediated cancer therapy," Nature Communications, 11:661, 11 pages.

Theze et al., (1996). "Interleukin 2 and its receptors: recent advances and new immunological functions," Immunol. Today, 17(10):481-486. Abstract Only.

Tolcher et al., (2019). "A phase 1, first-in-human, dose-escalation study of ADG106, a fully human anti-CD137 agonistic antibody, in subjects with advanced or metastatic solid tumors and/or relapsed/refractory non-Hodgkin lymphoma," Molecular Targets and Cancer Therapeutics, 18:A082, 2 pages. (Abstract Only).

Makko uk et al., (2016). "Rationale for anti-CD137 cancer immunotherapy," Eur J Cancer, 54:112-119.

Sanchez-Paulete et al., (2016). "Deciphering CD137 (4-1BB) signaling in T-cell costimulation for translation into successful cancer immunotherapy," Eur J Immunol., 46(3):513-522.

U.S. Unpublished U.S. Appl. No. 18/153,221, filed Jan. 11, 2023, titled "Activatable Antibodies and Methods of Making and Using Thereof," (Copy not submitted herewith pursuant to the waiver of 37 C.F.R. § 1.98(a)(2)(iii)).

\* cited by examiner

SEQUENCE LISTING

```
<160> NUMBER OF SEQ ID NOS: 133

<210> SEQ ID NO 1
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 3, 4, 5, 6, 7, 8, 9, 10
<223> OTHER INFORMATION: Can be present or absent
<220> FEATURE:
<221> NAME/KEY: VARIANT
<222> LOCATION: 12, 13, 14, 15, 16, 17, 18, 19, 20, 21
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 15, 16, 17, 18, 19, 20, 21
<223> OTHER INFORMATION: Can be present or absent
<220> FEATURE:
<221> NAME/KEY: VARIANT
<222> LOCATION: 23, 24, 25, 26, 27, 28, 29, 30, 31, 32
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 24, 25, 26, 27, 28, 29, 30, 31, 32
<223> OTHER INFORMATION: Can be present or absent

<400> SEQUENCE: 1

Xaa Xaa Xaa Xaa Xaa Xaa Xaa Xaa Xaa Xaa Cys Xaa Xaa Xaa Xaa Xaa
1               5                   10                  15

Xaa Xaa Xaa Xaa Xaa Cys Xaa Xaa Xaa Xaa Xaa Xaa Xaa Xaa Xaa Xaa
            20                  25                  30


<210> SEQ ID NO 2
<211> LENGTH: 96
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 4, 5, 7, 8, 10, 11, 13, 14, 16, 17, 19, 20, 22,
      23, 25, 26, 28, 29, 34, 35, 37, 38, 40, 41, 43, 44, 46, 47,
      49, 50, 52, 53, 55, 56, 58, 59, 61, 62, 67, 70, 73, 76,
      79, 82, 85, 88, 91, 94
<223> OTHER INFORMATION: n = A,T,C or G
<220> FEATURE:
<221> NAME/KEY: misc_feature
<222> LOCATION: (7)..(9), (10)..(12), (13)..(15), (16)..(18), (19)..
      (21), (22)..(24), (25)..(27), (28)..(30)
```

<223> OTHER INFORMATION: Can be present or absent
<220> FEATURE:
<221> NAME/KEY: misc_feature
<222> LOCATION: (43)..(45), (46)..(48), (49)..(51), (52)..(54), (55)..
(57), (58)..(60), (61)..(63)
<223> OTHER INFORMATION: Can be present or absent
<220> FEATURE:
<221> NAME/KEY: misc_feature
<222> LOCATION: (70)..(72), (73)..(75), (76)..(78), (79)..(81), (82)..
(84), (85)..(87), (88)..(90), (91)..(93), (94)..(96)
<223> OTHER INFORMATION: Can be present or absent

<400> SEQUENCE: 2
nnknnknnkn nknnknnknn knnknnknnk tgynnknnkn nknnknnknn knnknnknnk 60
nnktgynhcn hcnhcnhcnh cnhcnhcnhc nhcnhc 96

<210> SEQ ID NO 3
<211> LENGTH: 42
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Ala, Asp, Ile, Asn, Pro, or Tyr
<220> FEATURE:
<221> NAME/KEY: VARIANT
<222> LOCATION: 7
<223> OTHER INFORMATION: Xaa = Ala, Phe, Asn, Ser, or Val
<220> FEATURE:
<221> NAME/KEY: VARIANT
<222> LOCATION: 8
<223> OTHER INFORMATION: Xaa = Ala, His, Leu, Pro, Ser, Val, or Tyr
<220> FEATURE:
<221> NAME/KEY: VARIANT
<222> LOCATION: 9
<223> OTHER INFORMATION: Xaa = Ala, His, Ser, or Tyr
<220> FEATURE:
<221> NAME/KEY: VARIANT
<222> LOCATION: 10
<223> OTHER INFORMATION: Xaa = Ala, Asp, Pro, Ser, Val, or Tyr
<220> FEATURE:
<221> NAME/KEY: VARIANT
<222> LOCATION: 11
<223> OTHER INFORMATION: Xaa = Ala, Asp, Leu, Ser, or Tyr
<220> FEATURE:
<221> NAME/KEY: VARIANT
<222> LOCATION: 13
<223> OTHER INFORMATION: Xaa = Asp, Pro, or Val
<220> FEATURE:
<221> NAME/KEY: VARIANT
<222> LOCATION: 14
<223> OTHER INFORMATION: Xaa = Ala, Asp, His, Pro, Ser, or Thr
<220> FEATURE:
<221> NAME/KEY: VARIANT
<222> LOCATION: 15
<223> OTHER INFORMATION: Xaa = Ala, Asp, Phe, His, Pro, or Tyr
<220> FEATURE:
<221> NAME/KEY: VARIANT
<222> LOCATION: 16
<223> OTHER INFORMATION: Xaa = Leu, Pro, or Tyr
<220> FEATURE:
<221> NAME/KEY: VARIANT
<222> LOCATION: 17
<223> OTHER INFORMATION: Xaa = Phe, Pro, or Tyr
<220> FEATURE:
<221> NAME/KEY: VARIANT
<222> LOCATION: 18
<223> OTHER INFORMATION: Xaa = Ala, Pro, Ser, or Tyr
<220> FEATURE:
<221> NAME/KEY: VARIANT
<222> LOCATION: 20
<223> OTHER INFORMATION: Xaa = Ala, Asp, Asn, Ser, Thr, or Tyr
<220> FEATURE:
<221> NAME/KEY: VARIANT
<222> LOCATION: 21
<223> OTHER INFORMATION: Xaa = Ala, Ser, or Tyr

<400> SEQUENCE: 3

Glu Val Gly Ser Tyr Xaa Xaa Xaa Xaa Xaa Xaa Cys Xaa Xaa Xaa Xaa
1 5 10 15

Xaa Xaa Cys Xaa Xaa Ser Gly Arg Ser Ala Gly Gly Gly Gly Thr Glu
20 25 30

Asn Leu Tyr Phe Gln Gly Ser Gly Gly Ser
35 40

<210> SEQ ID NO 4
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 13, 14, 15, 16, 17, 18, 20, 21
<223> OTHER INFORMATION: Xaa = Asp, Ala, Tyr, Ser, Thr, Asn, Ile, Leu, Phe, Val, His, or Pro

<400> SEQUENCE: 4

Glu Val Gly Ser Tyr Xaa Xaa Xaa Xaa Xaa Xaa Cys Xaa Xaa Xaa Xaa
1 5 10 15

Xaa Xaa Cys Xaa Xaa Ser Gly Arg Ser Ala
20 25

<210> SEQ ID NO 5
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 20, 21
<223> OTHER INFORMATION: Xaa = Asp, Ala, Tyr, Ser, Thr, Asn, Ile, Leu, Phe, Val, His, or Pro
<220> FEATURE:
<221> NAME/KEY: VARIANT
<222> LOCATION: 13, 14, 15, 16, 17, 18
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr

<400> SEQUENCE: 5

Glu Val Gly Ser Tyr Xaa Xaa Xaa Xaa Xaa Xaa Cys Xaa Xaa Xaa Xaa
1 5 10 15

Xaa Xaa Cys Xaa Xaa Ser Gly Arg Ser Ala
20 25

<210> SEQ ID NO 6
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 13, 14, 15, 16, 17, 18, 19, 20, 22, 23
<223> OTHER INFORMATION: Xaa = Asp, Ala, Tyr, Ser, Thr, Asn, Ile, Leu, Phe, Val, His, or Pro

<400> SEQUENCE: 6

Glu Val Gly Ser Tyr Xaa Xaa Xaa Xaa Xaa Xaa Cys Xaa Xaa Xaa Xaa
1 5 10 15

```
Xaa Xaa Xaa Xaa Cys Xaa Xaa Ser Gly Arg Ser Ala
            20                  25


<210> SEQ ID NO 7
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6, 7, 8, 9, 10, 11, 22, 23
<223> OTHER INFORMATION: Xaa = Asp, Ala, Tyr, Ser, Thr, Asn, Ile, Leu,
      Phe, Val, His, or Pro
<220> FEATURE:
<221> NAME/KEY: VARIANT
<222> LOCATION: 13, 14, 15, 16, 17, 18, 19, 20
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr

<400> SEQUENCE: 7

Glu Val Gly Ser Tyr Xaa Xaa Xaa Xaa Xaa Xaa Cys Xaa Xaa Xaa Xaa
1               5                   10                  15

Xaa Xaa Xaa Xaa Cys Xaa Xaa Ser Gly Arg Ser Ala
            20                  25


<210> SEQ ID NO 8
<211> LENGTH: 78
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 19, 22, 25, 28, 31, 37, 40, 43, 46, 49, 52, 58, 61
<223> OTHER INFORMATION: n = A,T,C or G

<400> SEQUENCE: 8

gaggttggat cctacnhcnh cnhcnhcnhc nhctgtnhcn hcnhcnhcnh cnhctgcnhc     60

nhctcaggtc gttccgct                                                   78


<210> SEQ ID NO 9
<211> LENGTH: 78
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 19, 22, 25, 28, 31, 37, 38, 40, 41, 43, 44, 46, 47,
      49, 50, 52, 53, 58, 61
<223> OTHER INFORMATION: n = A,T,C or G

<400> SEQUENCE: 9

gaggttggat cctacnhcnh cnhcnhcnhc nhctgtnnkn nknnknnknn knnktgcnhc     60

nhctcaggtc gttccgct                                                   78


<210> SEQ ID NO 10
<211> LENGTH: 84
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 19, 22, 25, 28, 31, 37, 40, 43, 46, 49, 52, 55, 58,
      64, 67
<223> OTHER INFORMATION: n = A,T,C or G
```

-continued

<400> SEQUENCE: 10
gaggttggat cctacnhcnh cnhcnhcnhc nhctgtnhcn hcnhcnhcnh cnhcnhcnhc 60
tgcnhcnhct caggtcgttc cgct 84

<210> SEQ ID NO 11
<211> LENGTH: 84
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 19, 22, 25, 28, 31, 37, 38, 40, 41, 43, 44, 46, 47,
49, 50, 52, 53, 55, 56, 58, 59, 64, 67
<223> OTHER INFORMATION: n = A,T,C or G

<400> SEQUENCE: 11
gaggttggat cctacnhcnh cnhcnhcnhc nhctgtnnkn nknnknnknn knnknnknnk 60
tgcnhcnhct caggtcgttc cgct 84

<210> SEQ ID NO 12
<211> LENGTH: 20
<212> TYPE: PRT
<213> ORGANISM: Artificial Sequence
<220> FEATURE:
<223> OTHER INFORMATION: Synthetic Construct

<400> SEQUENCE: 12

Ser Gly Arg Ser Ala Gly Gly Gly Gly Ser Pro Leu Gly Leu Ala Gly
1 5 10 15

Ser Gly Gly Ser
20

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Ser Gly Arg Ser Ala
1 5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Pro Leu Gly Leu Ala Gly
1 5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Glu Asn Leu Tyr Phe Gln Gly 1 5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Glu Val Gly Ser Tyr
1 5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Gly Gly Gly Gly Ser
1 5

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

Ser Gly Gly Ser
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Construct

<400> SEQUENCE: 19

Gly Gly Ser Gly
1

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Gly Gly Ser Gly Gly
1 5

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21

Gly Ser Gly Ser Gly
1 5

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

```
Gly Ser Gly Gly Gly
1               5
```

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

```
Gly Gly Gly Ser Gly
1               5
```

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct

<400> SEQUENCE: 24

```
Gly Ser Ser Ser Gly
1               5
```

<210> SEQ ID NO 25
<211> LENGTH: 42
<212> TYPE: PRT
<213> ORGANISM: Artificial Sequence
<220> FEATURE:
<223> OTHER INFORMATION: Synthetic Construct

<400> SEQUENCE: 25

```
Glu Val Gly Ser Tyr Asp Ala Leu His Tyr Ala Cys Pro Pro Asp Tyr
1               5                   10                  15

Tyr Ala Cys Tyr Tyr Ser Gly Arg Ser Ala Gly Gly Gly Gly Thr Glu
            20                  25                  30

Asn Leu Tyr Phe Gln Gly Ser Gly Gly Ser
        35                  40
```

<210> SEQ ID NO 26
<211> LENGTH: 42
<212> TYPE: PRT
<213> ORGANISM: Artificial Sequence
<220> FEATURE:
<223> OTHER INFORMATION: Synthetic Construct

<400> SEQUENCE: 26

```
Glu Val Gly Ser Tyr Asn Ser Tyr His Ala Tyr Cys Pro His Pro Leu
1               5                   10                  15

Tyr Pro Cys Thr Ala Ser Gly Arg Ser Ala Gly Gly Gly Gly Thr Glu
            20                  25                  30

Asn Leu Tyr Phe Gln Gly Ser Gly Gly Ser
        35                  40
```

-continued

<210> SEQ ID NO 27
<211> LENGTH: 42
<212> TYPE: PRT
<213> ORGANISM: Artificial Sequence
<220> FEATURE:
<223> OTHER INFORMATION: Synthetic Construct

<400> SEQUENCE: 27

Glu Val Gly Ser Tyr Ala Ser Ser Ala Val Leu Cys Val Thr Ala Tyr
1 5 10 15

Phe Ser Cys Asn Ser Ser Gly Arg Ser Ala Gly Gly Gly Gly Thr Glu
20 25 30

Asn Leu Tyr Phe Gln Gly Ser Gly Gly Ser
35 40

<210> SEQ ID NO 28
<211> LENGTH: 41
<212> TYPE: PRT
<213> ORGANISM: Artificial Sequence
<220> FEATURE:
<223> OTHER INFORMATION: Synthetic Construct

<400> SEQUENCE: 28

Glu Val Gly Ser Tyr Asn Phe Val Ala Asp Ser Cys Pro Asp His Pro
1 5 10 15

Tyr Pro Cys Ser Ala Ser Gly Arg Ser Ala Gly Gly Gly Gly Ser Pro
20 25 30

Leu Gly Leu Ala Gly Ser Gly Gly Ser
35 40

<210> SEQ ID NO 29
<211> LENGTH: 42
<212> TYPE: PRT
<213> ORGANISM: Artificial Sequence
<220> FEATURE:
<223> OTHER INFORMATION: Synthetic Construct

<400> SEQUENCE: 29

Glu Val Gly Ser Tyr Asn Phe Val Ala Asp Ser Cys Pro Asp His Pro
1 5 10 15

Tyr Pro Cys Ser Ala Ser Gly Arg Ser Ala Gly Gly Gly Gly Thr Glu
20 25 30

Asn Leu Tyr Phe Gln Gly Ser Gly Gly Ser
35 40

<210> SEQ ID NO 30
<211> LENGTH: 41
<212> TYPE: PRT
<213> ORGANISM: Artificial Sequence
<220> FEATURE:
<223> OTHER INFORMATION: Synthetic Construct

<400> SEQUENCE: 30

Glu Val Gly Ser Tyr Ile Val His His Ser Asp Cys Asp Ala Phe Tyr
1 5 10 15

Pro Tyr Cys Asp Ser Ser Gly Arg Ser Ala Gly Gly Gly Gly Ser Pro
20 25 30

Leu Gly Leu Ala Gly Ser Gly Gly Ser
35 40

<210> SEQ ID NO 31
<211> LENGTH: 42
<212> TYPE: PRT

```
<213> ORGANISM: Artificial Sequence
<220> FEATURE:
<223> OTHER INFORMATION: Synthetic Construct

<400> SEQUENCE: 31

Glu Val Gly Ser Tyr Ile Val His His Ser Asp Cys Asp Ala Phe Tyr
1               5                   10                  15

Pro Tyr Cys Asp Ser Ser Gly Arg Ser Ala Gly Gly Gly Gly Thr Glu
            20                  25                  30

Asn Leu Tyr Phe Gln Gly Ser Gly Gly Ser
        35                  40


<210> SEQ ID NO 32
<211> LENGTH: 41
<212> TYPE: PRT
<213> ORGANISM: Artificial Sequence
<220> FEATURE:
<223> OTHER INFORMATION: Synthetic Construct

<400> SEQUENCE: 32

Glu Val Gly Ser Tyr Tyr Ser Ala Tyr Pro Ala Cys Asp Ser His Tyr
1               5                   10                  15

Pro Tyr Cys Asn Ser Ser Gly Arg Ser Ala Gly Gly Gly Gly Ser Pro
            20                  25                  30

Leu Gly Leu Ala Gly Ser Gly Gly Ser
        35                  40


<210> SEQ ID NO 33
<211> LENGTH: 42
<212> TYPE: PRT
<213> ORGANISM: Artificial Sequence
<220> FEATURE:
<223> OTHER INFORMATION: Synthetic Construct

<400> SEQUENCE: 33

Glu Val Gly Ser Tyr Tyr Ser Ala Tyr Pro Ala Cys Asp Ser His Tyr
1               5                   10                  15

Pro Tyr Cys Asn Ser Ser Gly Arg Ser Ala Gly Gly Gly Gly Thr Glu
            20                  25                  30

Asn Leu Tyr Phe Gln Gly Ser Gly Gly Ser
        35                  40


<210> SEQ ID NO 34
<211> LENGTH: 41
<212> TYPE: PRT
<213> ORGANISM: Artificial Sequence
<220> FEATURE:
<223> OTHER INFORMATION: Synthetic Construct

<400> SEQUENCE: 34

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Gly Ser Pro
            20                  25                  30

Leu Gly Leu Ala Gly Ser Gly Gly Ser
        35                  40


<210> SEQ ID NO 35
<211> LENGTH: 42
<212> TYPE: PRT
<213> ORGANISM: Artificial Sequence
<220> FEATURE:
<223> OTHER INFORMATION: Synthetic Construct
```

<400> SEQUENCE: 35

Glu Val Gly Ser Tyr Pro Asn Pro Ser Ser Asp Cys Val Pro Tyr Tyr
1 5 10 15

Tyr Ala Cys Ala Tyr Ser Gly Arg Ser Ala Gly Gly Gly Gly Thr Glu
20 25 30

Asn Leu Tyr Phe Gln Gly Ser Gly Gly Ser
35 40

<210> SEQ ID NO 36
<211> LENGTH: 41
<212> TYPE: PRT
<213> ORGANISM: Artificial Sequence
<220> FEATURE:
<223> OTHER INFORMATION: Synthetic Construct

<400> SEQUENCE: 36

Glu Val Gly Ser Tyr Tyr Ser Ala Tyr Pro Ala Cys Asp Ser His Tyr
1 5 10 15

Pro Tyr Cys Gln Ser Ser Gly Arg Ser Ala Gly Gly Gly Gly Ser Pro
20 25 30

Leu Gly Leu Ala Gly Ser Gly Gly Ser
35 40

<210> SEQ ID NO 37
<211> LENGTH: 41
<212> TYPE: PRT
<213> ORGANISM: Artificial Sequence
<220> FEATURE:
<223> OTHER INFORMATION: Synthetic Construct

<400> SEQUENCE: 37

Glu Val Gly Ser Tyr Tyr Ser Ala Tyr Pro Ala Cys Asp Ser His Tyr
1 5 10 15

Pro Tyr Cys Asn Ser Ala Gly Arg Ser Ala Gly Gly Gly Gly Ser Pro
20 25 30

Leu Gly Leu Ala Gly Ser Gly Gly Ser
35 40

<210> SEQ ID NO 38
<211> LENGTH: 41
<212> TYPE: PRT
<213> ORGANISM: Artificial Sequence
<220> FEATURE:
<223> OTHER INFORMATION: Synthetic Construct

<400> SEQUENCE: 38

Glu Val Gly Ser Tyr Pro Gln Pro Ser Ser Asp Cys Val Pro Tyr Tyr
1 5 10 15

Tyr Ala Cys Ala Tyr Ser Gly Arg Ser Ala Gly Gly Gly Gly Ser Pro
20 25 30

Leu Gly Leu Ala Gly Ser Gly Gly Ser
35 40

<210> SEQ ID NO 39
<211> LENGTH: 41
<212> TYPE: PRT
<213> ORGANISM: Artificial Sequence
<220> FEATURE:
<223> OTHER INFORMATION: Synthetic Construct

<400> SEQUENCE: 39

-continued

Glu Val Gly Ser Tyr Pro Asn Pro Ala Ser Asp Cys Val Pro Tyr Tyr
1 5 10 15

Tyr Ala Cys Ala Tyr Ser Gly Arg Ser Ala Gly Gly Gly Gly Ser Pro
20 25 30

Leu Gly Leu Ala Gly Ser Gly Gly Ser
35 40

<210> SEQ ID NO 40
<211> LENGTH: 41
<212> TYPE: PRT
<213> ORGANISM: Artificial Sequence
<220> FEATURE:
<223> OTHER INFORMATION: Synthetic Construct

<400> SEQUENCE: 40

Glu Val Gly Ser Tyr Pro Thr Asp Leu Asp Ala Cys Ala Asp Ala Pro
1 5 10 15

Asn His Cys His Phe Ser Gly Arg Ser Ala Gly Gly Gly Gly Ser Pro
20 25 30

Leu Gly Leu Ala Gly Ser Gly Gly Ser
35 40

<210> SEQ ID NO 41
<211> LENGTH: 41
<212> TYPE: PRT
<213> ORGANISM: Artificial Sequence
<220> FEATURE:
<223> OTHER INFORMATION: Synthetic Construct

<400> SEQUENCE: 41

Glu Val Gly Ser Tyr Ser Ser Thr His Ala His Cys His His Ser Pro
1 5 10 15

Ala Asn Cys Ile Ser Ser Gly Arg Ser Ala Gly Gly Gly Gly Ser Pro
20 25 30

Leu Gly Leu Ala Gly Ser Gly Gly Ser
35 40

<210> SEQ ID NO 42
<211> LENGTH: 41
<212> TYPE: PRT
<213> ORGANISM: Artificial Sequence
<220> FEATURE:
<223> OTHER INFORMATION: Synthetic Construct

<400> SEQUENCE: 42

Glu Val Gly Ser Tyr Asp Thr Asp Tyr Asp Phe Cys Pro Ile Leu Arg
1 5 10 15

His Arg Cys Asp Ser Ser Gly Arg Ser Ala Gly Gly Gly Gly Ser Pro
20 25 30

Leu Gly Leu Ala Gly Ser Gly Gly Ser
35 40

<210> SEQ ID NO 43
<211> LENGTH: 41
<212> TYPE: PRT
<213> ORGANISM: Artificial Sequence
<220> FEATURE:
<223> OTHER INFORMATION: Synthetic Construct

<400> SEQUENCE: 43

Glu Val Gly Ser Tyr Asn Asp Tyr Asn Tyr His Cys Lys Trp Arg Pro
1 5 10 15

```
Ser Arg Cys His Asn Ser Gly Arg Ser Ala Gly Gly Gly Gly Ser Pro
            20                  25                  30

Leu Gly Leu Ala Gly Ser Gly Gly Ser
        35                  40


<210> SEQ ID NO 44
<211> LENGTH: 41
<212> TYPE: PRT
<213> ORGANISM: Artificial Sequence
<220> FEATURE:
<223> OTHER INFORMATION: Synthetic Construct

<400> SEQUENCE: 44

Glu Val Gly Ser Tyr Tyr His Asp Tyr Asp Asp Cys Arg Val Leu Pro
1               5                   10                  15

Arg Arg Cys Phe Asn Ser Gly Arg Ser Ala Gly Gly Gly Gly Ser Pro
            20                  25                  30

Leu Gly Leu Ala Gly Ser Gly Gly Ser
        35                  40


<210> SEQ ID NO 45
<211> LENGTH: 41
<212> TYPE: PRT
<213> ORGANISM: Artificial Sequence
<220> FEATURE:
<223> OTHER INFORMATION: Synthetic Construct

<400> SEQUENCE: 45

Glu Val Gly Ser Tyr Ser Asn Asn Phe Ala Ser Cys Leu Trp Arg His
1               5                   10                  15

Arg Ser Cys Ala Asp Ser Gly Arg Ser Ala Gly Gly Gly Gly Ser Pro
            20                  25                  30

Leu Gly Leu Ala Gly Ser Gly Gly Ser
        35                  40


<210> SEQ ID NO 46
<211> LENGTH: 41
<212> TYPE: PRT
<213> ORGANISM: Artificial Sequence
<220> FEATURE:
<223> OTHER INFORMATION: Synthetic Construct

<400> SEQUENCE: 46

Glu Val Gly Ser Tyr Thr Asp Asn Tyr Asp Tyr Cys Pro Arg Leu Arg
1               5                   10                  15

Arg Lys Cys Tyr His Ser Gly Arg Ser Ala Gly Gly Gly Gly Ser Pro
            20                  25                  30

Leu Gly Leu Ala Gly Ser Gly Gly Ser
        35                  40


<210> SEQ ID NO 47
<211> LENGTH: 116
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Ser Ser Gly
            20                  25                  30
```

-continued

```
Tyr His Trp Ser Trp Ile Arg Gln Ala Pro Gly Lys Gly Leu Glu Trp
        35                  40                  45

Leu Ala Arg Ile Asp Trp Asp Asp Asp Lys Tyr Tyr Ser Thr Ser Leu
    50                  55                  60

Lys Ser Arg Leu Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Ser Tyr Val Tyr Phe Asp Tyr Trp Gly Gln Gly Thr Leu Val
            100                 105                 110

Thr Val Ser Ser
        115


<210> SEQ ID NO 48
<211> LENGTH: 109
<212> TYPE: PRT
<213> ORGANISM: Artificial Sequence
<220> FEATURE:
<223> OTHER INFORMATION: Synthetic Construct

<400> SEQUENCE: 48

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Arg Gly Arg
            20                  25                  30

Phe Leu Ala Trp Tyr Gln Gln Lys Pro Gly Lys Ala Pro Lys Leu Leu
        35                  40                  45

Ile Tyr Asp Ala Ser Asn Arg Ala Thr Gly Ile Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Ser Ser Trp Pro
                85                  90                  95

Pro Thr Phe Gly Gln Gly Thr Lys Val Glu Ile Lys Arg
            100                 105


<210> SEQ ID NO 49
<211> LENGTH: 123
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Ile Gly Asp Trp Phe Ala Tyr
            100                 105                 110
```

Trp Gly Gln Gly Thr Leu Val Thr Val Ser Ser
115 120

<210> SEQ ID NO 50
<211> LENGTH: 106
<212> TYPE: PRT
<213> ORGANISM: Artificial Sequence
<220> FEATURE:
<223> OTHER INFORMATION: Synthetic Construct

<400> SEQUENCE: 50

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Gly Ser Tyr
20 25 30

Leu Ala Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Tyr Tyr Leu Trp Thr
85 90 95

Phe Gly Gln Gly Thr Lys Val Glu Ile Lys
100 105

<210> SEQ ID NO 51
<211> LENGTH: 21
<212> TYPE: DNA
<213> ORGANISM: Artificial Sequence
<220> FEATURE:
<223> OTHER INFORMATION: Synthetic Construct

<400> SEQUENCE: 51
tcgggtgagg ttggatccta c 21

<210> SEQ ID NO 52
<211> LENGTH: 21
<212> TYPE: DNA
<213> ORGANISM: Artificial Sequence
<220> FEATURE:
<223> OTHER INFORMATION: Synthetic Construct

<400> SEQUENCE: 52
gtacaggttc tcggtaccac c 21

<210> SEQ ID NO 53
<211> LENGTH: 65
<212> TYPE: DNA
<213> ORGANISM: Artificial Sequence
<220> FEATURE:
<223> OTHER INFORMATION: Synthetic Construct

<400> SEQUENCE: 53
tggagacaca gacaggatca ctggagactg ggtcagcagg atatcggatc ctgaaccgcc 60
tgaac 65

<210> SEQ ID NO 54
<211> LENGTH: 66
<212> TYPE: DNA
<213> ORGANISM: Artificial Sequence
<220> FEATURE:

<223> OTHER INFORMATION: Synthetic Construct

<400> SEQUENCE: 54
cttcgctgtt tttcaatatt ttctgttatt gcttcagttt tagcaggatc cgaggttgga 60
tcctac 66

<210> SEQ ID NO 55
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 15, 16
<223> OTHER INFORMATION: Xaa = Asp, Ala, Tyr, Ser, Thr, Asn, Ile, Leu, Phe, Val, His, or Pro
<220> FEATURE:
<221> NAME/KEY: VARIANT
<222> LOCATION: 8, 9, 10, 11, 12, 13
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr

<400> SEQUENCE: 55

Xaa Xaa Xaa Xaa Xaa Xaa Cys Xaa Xaa Xaa Xaa Xaa Xaa Cys Xaa Xaa
1 5 10 15

<210> SEQ ID NO 56
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 17, 18
<223> OTHER INFORMATION: Xaa = Asp, Ala, Tyr, Ser, Thr, Asn, Ile, Leu, Phe, Val, His, or Pro
<220> FEATURE:
<221> NAME/KEY: VARIANT
<222> LOCATION: 8, 9, 10, 11, 12, 13, 14, 15
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr

<400> SEQUENCE: 56

Xaa Xaa Xaa Xaa Xaa Xaa Cys Xaa Xaa Xaa Xaa Xaa Xaa Xaa Xaa Cys
1 5 10 15

Xaa Xaa

<210> SEQ ID NO 57
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 8, 9, 10, 11, 12, 13, 15, 16
<223> OTHER INFORMATION: Xaa = Asp, Ala, Tyr, Ser, Thr, Asn, Ile, Leu, Phe, Val, His, or Pro

<400> SEQUENCE: 57

Xaa Xaa Xaa Xaa Xaa Xaa Cys Xaa Xaa Xaa Xaa Xaa Xaa Cys Xaa Xaa
1 5 10 15

<210> SEQ ID NO 58
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 8, 9, 10, 11, 12, 13, 14, 15, 17, 18
<223> OTHER INFORMATION: Xaa = Asp, Ala, Tyr, Ser, Thr, Asn, Ile, Leu,
      Phe, Val, His, or Pro

<400> SEQUENCE: 58

Xaa Xaa Xaa Xaa Xaa Xaa Cys Xaa Xaa Xaa Xaa Xaa Xaa Xaa Xaa Cys
1               5                   10                  15

Xaa Xaa

<210> SEQ ID NO 59
<211> LENGTH: 12
<212> TYPE: PRT
<213> ORGANISM: Artificial Sequence
<220> FEATURE:
<223> OTHER INFORMATION: Synthetic Construct

<400> SEQUENCE: 59

Tyr Ser Ile Ser Ser Gly Tyr His Trp Ser Trp Ile
1               5                   10

<210> SEQ ID NO 60
<211> LENGTH: 20
<212> TYPE: PRT
<213> ORGANISM: Artificial Sequence
<220> FEATURE:
<223> OTHER INFORMATION: Synthetic Construct

<400> SEQUENCE: 60

Leu Ala Arg Ile Asp Trp Asp Asp Asp Lys Tyr Tyr Ser Thr Ser Leu
1               5                   10                  15

Lys Ser Arg Leu
            20

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Ala Arg Ser Tyr Val Tyr Phe Asp Tyr
1               5

<210> SEQ ID NO 62
<211> LENGTH: 12
<212> TYPE: PRT
<213> ORGANISM: Artificial Sequence
<220> FEATURE:
<223> OTHER INFORMATION: Synthetic Construct

<400> SEQUENCE: 62

Arg Ala Ser Gln Ser Val Arg Gly Arg Phe Leu Ala
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Asp Ala Ser Asn Arg Ala Thr Gly Ile
1 5

<210> SEQ ID NO 64
<211> LENGTH: 11
<212> TYPE: PRT
<213> ORGANISM: Artificial Sequence
<220> FEATURE:
<223> OTHER INFORMATION: Synthetic Construct

<400> SEQUENCE: 64

Tyr Cys Gln Gln Ser Ser Ser Trp Pro Pro Thr
1 5 10

<210> SEQ ID NO 65
<211> LENGTH: 13
<212> TYPE: PRT
<213> ORGANISM: Artificial Sequence
<220> FEATURE:
<223> OTHER INFORMATION: Synthetic Construct

<400> SEQUENCE: 65

Phe Ser Leu Ser Thr Gly Gly Val Gly Val Gly Trp Ile
1 5 10

<210> SEQ ID NO 66
<211> LENGTH: 20
<212> TYPE: PRT
<213> ORGANISM: Artificial Sequence
<220> FEATURE:
<223> OTHER INFORMATION: Synthetic Construct

<400> SEQUENCE: 66

Leu Ala Leu Ile Asp Trp Ala Asp Asp Lys Tyr Tyr Ser Pro Ser Leu
1 5 10 15

Lys Ser Arg Leu
20

<210> SEQ ID NO 67
<211> LENGTH: 15
<212> TYPE: PRT
<213> ORGANISM: Artificial Sequence
<220> FEATURE:
<223> OTHER INFORMATION: Synthetic Construct

<400> SEQUENCE: 67

Ala Arg Gly Gly Ser Asp Thr Val Ile Gly Asp Trp Phe Ala Tyr
1 5 10 15

<210> SEQ ID NO 68
<211> LENGTH: 11
<212> TYPE: PRT
<213> ORGANISM: Artificial Sequence
<220> FEATURE:
<223> OTHER INFORMATION: Synthetic Construct

<400> SEQUENCE: 68

Arg Ala Ser Gln Ser Ile Gly Ser Tyr Leu Ala
1 5 10

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Asp Ala Ser Asn Leu Glu Thr Gly Val
1 5

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct

<400> SEQUENCE: 70

Tyr Cys Gln Gln Gly Tyr Tyr Leu Trp Thr
1 5 10

<210> SEQ ID NO 71
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10, 12, 13, 14, 15, 16, 17, 18, 19, 20, 21, 23, 24, 25, 26, 27, 28, 29, 30, 31, 32
<223> OTHER INFORMATION: Xaa = Asp, Ala, Tyr, Ser, Thr, Asn, Ile, Leu, Phe, Val, His, or Pro
<220> FEATURE:
<221> NAME/KEY: VARIANT
<222> LOCATION: 3, 4, 5, 6, 7, 8, 9, 10
<223> OTHER INFORMATION: Can be present or absent
<220> FEATURE:
<221> NAME/KEY: VARIANT
<222> LOCATION: 15, 16, 17, 18, 19, 20, 21
<223> OTHER INFORMATION: Can be present or absent
<220> FEATURE:
<221> NAME/KEY: VARIANT
<222> LOCATION: 24, 25, 26, 27, 28, 29, 30, 31, 32
<223> OTHER INFORMATION: Can be present or absent

<400> SEQUENCE: 71

Xaa Xaa Xaa Xaa Xaa Xaa Xaa Xaa Xaa Xaa Cys Xaa Xaa Xaa Xaa Xaa
1 5 10 15

Xaa Xaa Xaa Xaa Xaa Cys Xaa Xaa Xaa Xaa Xaa Xaa Xaa Xaa Xaa Xaa
20 25 30

<210> SEQ ID NO 72
<211> LENGTH: 16
<212> TYPE: PRT
<213> ORGANISM: Artificial Sequence
<220> FEATURE:
<223> OTHER INFORMATION: Synthetic Construct

<400> SEQUENCE: 72

Asn Phe Val Ala Asp Ser Cys Pro Asp His Pro Tyr Pro Cys Ser Ala
1 5 10 15

<210> SEQ ID NO 73
<211> LENGTH: 16
<212> TYPE: PRT
<213> ORGANISM: Artificial Sequence
<220> FEATURE:
<223> OTHER INFORMATION: Synthetic Construct

<400> SEQUENCE: 73

Ile Val His His Ser Asp Cys Asp Ala Phe Tyr Pro Tyr Cys Asp Ser
1 5 10 15

-continued

<210> SEQ ID NO 74
<211> LENGTH: 16
<212> TYPE: PRT
<213> ORGANISM: Artificial Sequence
<220> FEATURE:
<223> OTHER INFORMATION: Synthetic Construct

<400> SEQUENCE: 74

Tyr Ser Ala Tyr Pro Ala Cys Asp Ser His Tyr Pro Tyr Cys Asn Ser
1 5 10 15

<210> SEQ ID NO 75
<211> LENGTH: 16
<212> TYPE: PRT
<213> ORGANISM: Artificial Sequence
<220> FEATURE:
<223> OTHER INFORMATION: Synthetic Construct

<400> SEQUENCE: 75

Pro Asn Pro Ser Ser Asp Cys Val Pro Tyr Tyr Tyr Ala Cys Ala Tyr
1 5 10 15

<210> SEQ ID NO 76
<211> LENGTH: 16
<212> TYPE: PRT
<213> ORGANISM: Artificial Sequence
<220> FEATURE:
<223> OTHER INFORMATION: Synthetic Construct

<400> SEQUENCE: 76

Tyr Ser Ala Tyr Pro Ala Cys Asp Ser His Tyr Pro Tyr Cys Gln Ser
1 5 10 15

<210> SEQ ID NO 77
<211> LENGTH: 16
<212> TYPE: PRT
<213> ORGANISM: Artificial Sequence
<220> FEATURE:
<223> OTHER INFORMATION: Synthetic Construct

<400> SEQUENCE: 77

Pro Gln Pro Ser Ser Asp Cys Val Pro Tyr Tyr Tyr Ala Cys Ala Tyr
1 5 10 15

<210> SEQ ID NO 78
<211> LENGTH: 16
<212> TYPE: PRT
<213> ORGANISM: Artificial Sequence
<220> FEATURE:
<223> OTHER INFORMATION: Synthetic Construct

<400> SEQUENCE: 78

Pro Asn Pro Ala Ser Asp Cys Val Pro Tyr Tyr Tyr Ala Cys Ala Tyr
1 5 10 15

<210> SEQ ID NO 79
<211> LENGTH: 16
<212> TYPE: PRT
<213> ORGANISM: Artificial Sequence
<220> FEATURE:
<223> OTHER INFORMATION: Synthetic Construct

<400> SEQUENCE: 79

Pro Thr Asp Leu Asp Ala Cys Ala Asp Ala Pro Asn His Cys His Phe
1 5 10 15

<210> SEQ ID NO 80
<211> LENGTH: 16
<212> TYPE: PRT
<213> ORGANISM: Artificial Sequence
<220> FEATURE:
<223> OTHER INFORMATION: Synthetic Construct

<400> SEQUENCE: 80

Ser Ser Thr His Ala His Cys His His Ser Pro Ala Asn Cys Ile Ser
1 5 10 15

<210> SEQ ID NO 81
<211> LENGTH: 16
<212> TYPE: PRT
<213> ORGANISM: Artificial Sequence
<220> FEATURE:
<223> OTHER INFORMATION: Synthetic Construct

<400> SEQUENCE: 81

Asp Thr Asp Tyr Asp Phe Cys Pro Ile Leu Arg His Arg Cys Asp Ser
1 5 10 15

<210> SEQ ID NO 82
<211> LENGTH: 16
<212> TYPE: PRT
<213> ORGANISM: Artificial Sequence
<220> FEATURE:
<223> OTHER INFORMATION: Synthetic Construct

<400> SEQUENCE: 82

Asn Asp Tyr Asn Tyr His Cys Lys Trp Arg Pro Ser Arg Cys His Asn
1 5 10 15

<210> SEQ ID NO 83
<211> LENGTH: 16
<212> TYPE: PRT
<213> ORGANISM: Artificial Sequence
<220> FEATURE:
<223> OTHER INFORMATION: Synthetic Construct

<400> SEQUENCE: 83

Tyr His Asp Tyr Asp Asp Cys Arg Val Leu Pro Arg Arg Cys Phe Asn
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Synthetic Construct

<400> SEQUENCE: 84

Asn Asn Phe Ala Ser Cys Leu Trp Arg His Arg Ser Cys Ala Asp
1 5 10 15

<210> SEQ ID NO 85
<211> LENGTH: 16
<212> TYPE: PRT
<213> ORGANISM: Artificial Sequence
<220> FEATURE:
<223> OTHER INFORMATION: Synthetic Construct

<400> SEQUENCE: 85

Thr Asp Asn Tyr Asp Tyr Cys Pro Arg Leu Arg Arg Lys Cys Tyr His
1 5 10 15

<210> SEQ ID NO 86

```
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 4, 5, 6, 7, 8, 9, 10, 12, 13, 14, 15, 16, 17,
      18, 19, 20, 21, 23, 24, 25, 26, 27, 28, 29, 30, 31, 32
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 3, 4, 5, 6, 7, 8, 9, 10
<223> OTHER INFORMATION: Can be present or absent
<220> FEATURE:
<221> NAME/KEY: VARIANT
<222> LOCATION: 15, 16, 17, 18, 19, 20, 21
<223> OTHER INFORMATION: Can be present or absent
<220> FEATURE:
<221> NAME/KEY: VARIANT
<222> LOCATION: 24, 25, 26, 27, 28, 29, 30, 31, 32
<223> OTHER INFORMATION: Can be present or absent

<400> SEQUENCE: 86

Xaa Xaa Xaa Xaa Xaa Xaa Xaa Xaa Xaa Xaa Cys Xaa Xaa Xaa Xaa Xaa
1               5                   10                  15

Xaa Xaa Xaa Xaa Xaa Cys Xaa Xaa Xaa Xaa Xaa Xaa Xaa Xaa Xaa Xaa
            20                  25                  30


<210> SEQ ID NO 87
<211> LENGTH: 96
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 4, 5, 7, 8, 10, 11, 13, 14, 16, 17, 19, 20, 22,
      23, 25, 26, 28, 29, 34, 35, 37, 38, 40, 41, 43, 44, 46, 47,
      49, 50, 52, 53, 55, 56, 58, 59, 61, 62, 67, 68, 70, 71,
      73, 74, 76, 77, 79, 80, 82, 83, 85, 86, 88, 89, 91, 92,
      94, 95
<223> OTHER INFORMATION: n = A,T,C or G
<220> FEATURE:
<221> NAME/KEY: misc_feature
<222> LOCATION: (7)..(9), (10)..(12), (13)..(15), (16)..(18), (19)..
      (21), (22)..(24), (25)..(27), (28)..(30)
<223> OTHER INFORMATION: Can be present or absent
<220> FEATURE:
<221> NAME/KEY: misc_feature
<222> LOCATION: (43)..(45), (46)..(48), (49)..(51), (52)..(54), (55)..
      (57), (58)..(60), (61)..(63)
<223> OTHER INFORMATION: Can be present or absent
<220> FEATURE:
<221> NAME/KEY: misc_feature
<222> LOCATION: (70)..(72), (73)..(75), (76)..(78), (79)..(81), (82)..
      (84), (85)..(87), (88)..(90), (91)..(93), (94)..(96)
<223> OTHER INFORMATION: Can be present or absent

<400> SEQUENCE: 87

nnknnknnkn nknnknnknn knnknnknnk tgynnknnkn nknnknnknn knnknnknnk      60

nnktgynnkn nknnknnknn knnknnknnk nnknnk                                96


<210> SEQ ID NO 88
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
```

<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to
      ten

<400> SEQUENCE: 88

Xaa Cys Ala Asp Ala Pro Asn His Cys Xaa Xaa
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to
      ten

<400> SEQUENCE: 89

Xaa Cys His His Ser Pro Ala Asn Cys Xaa Xaa
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to
      ten

<400> SEQUENCE: 90

Xaa Cys Pro Ile Leu Arg His Arg Cys Xaa Xaa
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to
      ten

<400> SEQUENCE: 91

Xaa Cys Lys Trp Arg Pro Ser Arg Cys Xaa Xaa
1 5 10

<210> SEQ ID NO 92
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to ten

<400> SEQUENCE: 92

Xaa Cys Arg Val Leu Pro Arg Arg Cys Xaa Xaa
1 5 10

<210> SEQ ID NO 93
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to ten

<400> SEQUENCE: 93

Xaa Cys Leu Trp Arg His Arg Ser Cys Xaa Xaa
1 5 10

<210> SEQ ID NO 94
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to ten

<400> SEQUENCE: 94

Xaa Cys Pro Arg Leu Arg Arg Lys Cys Xaa Xaa
1 5 10

<210> SEQ ID NO 95
<211> LENGTH: 21
<212> TYPE: PRT
<213> ORGANISM: Artificial Sequence
<220> FEATURE:
<223> OTHER INFORMATION: Synthetic Construct

<400> SEQUENCE: 95

Glu Val Gly Ser Tyr Pro Thr Asp Leu Asp Ala Cys Ala Asp Ala Pro
1 5 10 15

Asn His Cys His Phe
20

<210> SEQ ID NO 96
<211> LENGTH: 21
<212> TYPE: PRT
<213> ORGANISM: Artificial Sequence
<220> FEATURE:
<223> OTHER INFORMATION: Synthetic Construct

<400> SEQUENCE: 96

Glu Val Gly Ser Tyr Ser Ser Thr His Ala His Cys His His Ser Pro
1 5 10 15

Ala Asn Cys Ile Ser
20

<210> SEQ ID NO 97
<211> LENGTH: 21
<212> TYPE: PRT
<213> ORGANISM: Artificial Sequence
<220> FEATURE:
<223> OTHER INFORMATION: Synthetic Construct

<400> SEQUENCE: 97

Glu Val Gly Ser Tyr Asp Thr Asp Tyr Asp Phe Cys Pro Ile Leu Arg
1 5 10 15

His Arg Cys Asp Ser
20

<210> SEQ ID NO 98
<211> LENGTH: 21
<212> TYPE: PRT
<213> ORGANISM: Artificial Sequence
<220> FEATURE:
<223> OTHER INFORMATION: Synthetic Construct

<400> SEQUENCE: 98

Glu Val Gly Ser Tyr Asn Asp Tyr Asn Tyr His Cys Lys Trp Arg Pro
1 5 10 15

Ser Arg Cys His Asn
20

<210> SEQ ID NO 99
<211> LENGTH: 21
<212> TYPE: PRT
<213> ORGANISM: Artificial Sequence
<220> FEATURE:
<223> OTHER INFORMATION: Synthetic Construct

<400> SEQUENCE: 99

Glu Val Gly Ser Tyr Tyr His Asp Tyr Asp Asp Cys Arg Val Leu Pro
1 5 10 15

Arg Arg Cys Phe Asn
20

<210> SEQ ID NO 100
<211> LENGTH: 21
<212> TYPE: PRT
<213> ORGANISM: Artificial Sequence
<220> FEATURE:

-continued

```
<223> OTHER INFORMATION: Synthetic Construct

<400> SEQUENCE: 100

Glu Val Gly Ser Tyr Ser Asn Asn Phe Ala Ser Cys Leu Trp Arg His
1               5                   10                  15

Arg Ser Cys Ala Asp
            20


<210> SEQ ID NO 101
<211> LENGTH: 21
<212> TYPE: PRT
<213> ORGANISM: Artificial Sequence
<220> FEATURE:
<223> OTHER INFORMATION: Synthetic Construct

<400> SEQUENCE: 101

Glu Val Gly Ser Tyr Thr Asp Asn Tyr Asp Tyr Cys Pro Arg Leu Arg
1               5                   10                  15

Arg Lys Cys Tyr His
            20


<210> SEQ ID NO 102
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to
      ten

<400> SEQUENCE: 102

Xaa Cys Pro Asp His Pro Tyr Pro Cys Xaa Xaa
1               5                   10


<210> SEQ ID NO 103
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile,
      Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to
      ten

<400> SEQUENCE: 103

Xaa Cys Asp Ala Phe Tyr Pro Tyr Cys Xaa Xaa
1               5                   10


<210> SEQ ID NO 104
<211> LENGTH: 11
<212> TYPE: PRT
<213> ORGANISM: Artificial Sequence
<220> FEATURE:
<223> OTHER INFORMATION: Synthetic Construct
```

<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to ten

<400> SEQUENCE: 104

Xaa Cys Asp Ser His Tyr Pro Tyr Cys Xaa Xaa
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 10, 11
<223> OTHER INFORMATION: Xaa = Ala, Cys, Asp, Glu, Phe, Gly, His, Ile, Lys, Leu, Met, Asn, Pro, Gln, Arg, Ser, Thr, Val, Trp, or Tyr
<220> FEATURE:
<221> NAME/KEY: VARIANT
<222> LOCATION: 1
<223> OTHER INFORMATION: Present in repeats of at least two and up to ten

<400> SEQUENCE: 105

Xaa Cys Val Pro Tyr Tyr Tyr Ala Cys Xaa Xaa
1               5                   10

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110
<211> LENGTH: 21
<212> TYPE: PRT
<213> ORGANISM: Artificial Sequence
<220> FEATURE:
<223> OTHER INFORMATION: Synthetic Construct

<400> SEQUENCE: 110

Glu Val Gly Ser Tyr Asn Phe Val Ala Asp Ser Cys Pro Asp His Pro
1               5                   10                  15

Tyr Pro Cys Ser Ala
20

<210> SEQ ID NO 111
<211> LENGTH: 21
<212> TYPE: PRT
<213> ORGANISM: Artificial Sequence
<220> FEATURE:
<223> OTHER INFORMATION: Synthetic Construct

<400> SEQUENCE: 111

Glu Val Gly Ser Tyr Ile Val His His Ser Asp Cys Asp Ala Phe Tyr
1 5 10 15

Pro Tyr Cys Asp Ser
20

<210> SEQ ID NO 112
<211> LENGTH: 21
<212> TYPE: PRT
<213> ORGANISM: Artificial Sequence
<220> FEATURE:
<223> OTHER INFORMATION: Synthetic Construct

<400> SEQUENCE: 112

Glu Val Gly Ser Tyr Tyr Ser Ala Tyr Pro Ala Cys Asp Ser His Tyr
1 5 10 15

Pro Tyr Cys Asn Ser
20

<210> SEQ ID NO 113
<211> LENGTH: 21
<212> TYPE: PRT
<213> ORGANISM: Artificial Sequence
<220> FEATURE:
<223> OTHER INFORMATION: Synthetic Construct

<400> SEQUENCE: 113

Glu Val Gly Ser Tyr Pro Asn Pro Ser Ser Asp Cys Val Pro Tyr Tyr
1 5 10 15

Tyr Ala Cys Ala Tyr
20

<210> SEQ ID NO 114
<211> LENGTH: 21
<212> TYPE: PRT
<213> ORGANISM: Artificial Sequence
<220> FEATURE:
<223> OTHER INFORMATION: Synthetic Construct

<400> SEQUENCE: 114

Glu Val Gly Ser Tyr Tyr Ser Ala Tyr Pro Ala Cys Asp Ser His Tyr
1 5 10 15

Pro Tyr Cys Gln Ser
20

<210> SEQ ID NO 115
<211> LENGTH: 21
<212> TYPE: PRT
<213> ORGANISM: Artificial Sequence
<220> FEATURE:
<223> OTHER INFORMATION: Synthetic Construct

<400> SEQUENCE: 115

Glu Val Gly Ser Tyr Tyr Ser Ala Tyr Pro Ala Cys Asp Ser His Tyr

```
1               5                   10                  15

Pro Tyr Cys Asn Ser
            20
```

<210> SEQ ID NO 116
<211> LENGTH: 21
<212> TYPE: PRT
<213> ORGANISM: Artificial Sequence
<220> FEATURE:
<223> OTHER INFORMATION: Synthetic Construct

<400> SEQUENCE: 116

```
Glu Val Gly Ser Tyr Pro Gln Pro Ser Ser Asp Cys Val Pro Tyr Tyr
1               5                   10                  15

Tyr Ala Cys Ala Tyr
            20
```

<210> SEQ ID NO 117
<211> LENGTH: 21
<212> TYPE: PRT
<213> ORGANISM: Artificial Sequence
<220> FEATURE:
<223> OTHER INFORMATION: Synthetic Construct

<400> SEQUENCE: 117

```
Glu Val Gly Ser Tyr Pro Asn Pro Ala Ser Asp Cys Val Pro Tyr Tyr
1               5                   10                  15

Tyr Ala Cys Ala Tyr
            20
```

<210> SEQ ID NO 118
<211> LENGTH: 41
<212> TYPE: PRT
<213> ORGANISM: Artificial Sequence
<220> FEATURE:
<223> OTHER INFORMATION: Synthetic Construct

<400> SEQUENCE: 118

```
Glu Val Gly Ser Tyr Ile Val His His Ser Asp Cys Asp Ala Phe Tyr
1               5                   10                  15

Pro Tyr Cys Asp Ser Ser Gly Arg Ser Ala Gly Gly Gly Gly Thr Pro
            20                  25                  30

Leu Gly Leu Ala Gly Ser Gly Gly Ser
        35                  40
```

<210> SEQ ID NO 119
<211> LENGTH: 36
<212> TYPE: PRT
<213> ORGANISM: Artificial Sequence
<220> FEATURE:
<223> OTHER INFORMATION: Synthetic Construct

<400> SEQUENCE: 119

```
Glu Val Gly His Ser Asp Cys Asp Ala Phe Tyr Pro Tyr Cys Asp Ser
1               5                   10                  15

Ser Gly Arg Ser Ala Gly Gly Gly Gly Thr Pro Leu Gly Leu Ala Gly
            20                  25                  30

Ser Gly Gly Ser
        35
```

<210> SEQ ID NO 120
<211> LENGTH: 32
<212> TYPE: PRT

<213> ORGANISM: Artificial Sequence
<220> FEATURE:
<223> OTHER INFORMATION: Synthetic Construct

<400> SEQUENCE: 120

Glu Asp Cys Asp Ala Phe Tyr Pro Tyr Cys Asp Ser Ser Gly Arg Ser
1               5                   10                  15

Ala Gly Gly Gly Gly Thr Pro Leu Gly Leu Ala Gly Ser Gly Gly Ser
            20                  25                  30

<210> SEQ ID NO 121
<211> LENGTH: 41
<212> TYPE: PRT
<213> ORGANISM: Artificial Sequence
<220> FEATURE:
<223> OTHER INFORMATION: Synthetic Construct

<400> SEQUENCE: 121

Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Gly Gly Gly Gly Thr Pro
            20                  25                  30

Leu Gly Leu Ala Gly Ser Gly Gly Ser
        35                  40

<210> SEQ ID NO 122
<211> LENGTH: 36
<212> TYPE: PRT
<213> ORGANISM: Artificial Sequence
<220> FEATURE:
<223> OTHER INFORMATION: Synthetic Construct

<400> SEQUENCE: 122

Glu Val Gly Ser Ser Asp Cys Val Pro Tyr Tyr Tyr Ala Cys Ala Tyr
1               5                   10                  15

Ser Gly Arg Ser Ala Gly Gly Gly Gly Thr Pro Leu Gly Leu Ala Gly
            20                  25                  30

Ser Gly Gly Ser
        35

<210> SEQ ID NO 123
<211> LENGTH: 32
<212> TYPE: PRT
<213> ORGANISM: Artificial Sequence
<220> FEATURE:
<223> OTHER INFORMATION: Synthetic Construct

<400> SEQUENCE: 123

Glu Asp Cys Val Pro Tyr Tyr Tyr Ala Cys Ala Tyr Ser Gly Arg Ser
1               5                   10                  15

Ala Gly Gly Gly Gly Thr Pro Leu Gly Leu Ala Gly Ser Gly Gly Ser
            20                  25                  30

<210> SEQ ID NO 124
<211> LENGTH: 118
<212> TYPE: PRT
<213> ORGANISM: Artificial Sequence
<220> FEATURE:
<223> OTHER INFORMATION: Synthetic Construct

<400> SEQUENCE: 124

Met His Val Ala Gln Pro Ala Val Val Leu Ala Ser Ser Arg Gly Ile
1               5                   10                  15

-continued

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Ala Gln Ile
            100                 105                 110

Tyr Val Ile Asp Pro Glu
        115
```

<210> SEQ ID NO 125
<211> LENGTH: 118
<212> TYPE: PRT
<213> ORGANISM: Artificial Sequence
<220> FEATURE:
<223> OTHER INFORMATION: Synthetic Construct

<400> SEQUENCE: 125

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu
        115
```

<210> SEQ ID NO 126
<211> LENGTH: 115
<212> TYPE: PRT
<213> ORGANISM: Artificial Sequence
<220> FEATURE:
<223> OTHER INFORMATION: Synthetic Construct

<400> SEQUENCE: 126

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Ile Cys
    50                  55                  60

Thr Gly Thr Ser Ser Gly Asn Gln Val Asn Leu Thr Ile Gln Gly Leu
65                  70                  75                  80
```

```
Arg Ala Met Asp Thr Gly Leu Tyr Ile Cys Lys Val Glu Leu Met Tyr
                85                  90                  95

Pro Pro Pro Tyr Tyr Leu Gly Ile Gly Asn Gly Thr Gln Ile Tyr Val
            100                 105                 110

Ile Asp Pro
        115


<210> SEQ ID NO 127
<211> LENGTH: 114
<212> TYPE: PRT
<213> ORGANISM: Artificial Sequence
<220> FEATURE:
<223> OTHER INFORMATION: Synthetic Construct

<400> SEQUENCE: 127

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Asp Ser Ile
    50                  55                  60

Cys Thr Gly Thr Ser Ser Gly Asn Gln Val Asn Leu Thr Ile Gln Gly
65                  70                  75                  80

Leu Arg Ala Met Asp Thr Gly Leu Tyr Ile Cys Lys Val Glu Leu Met
                85                  90                  95

Tyr Pro Pro Pro Tyr Tyr Leu Gly Ile Gly Asn Gly Thr Gln Ile Tyr
            100                 105                 110

Val Ile


<210> SEQ ID NO 128
<211> LENGTH: 120
<212> TYPE: PRT
<213> ORGANISM: Homo sapiens

<400> SEQUENCE: 128

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu
        115                 120


<210> SEQ ID NO 129
<211> LENGTH: 120
<212> TYPE: PRT
```

<213> ORGANISM: Mus musculus

<400> SEQUENCE: 129

```
Glu Ala Ile Gln Val Thr Gln Pro Ser Val Val Leu Ala Ser Ser His
1               5                   10                  15

Gly Val Ala Ser Phe Pro Cys Glu Tyr Ser Pro Ser His Asn Thr Asp
            20                  25                  30

Glu Val Arg Val Thr Val Leu Arg Gln Thr Asn Asp Gln Met Thr Glu
        35                  40                  45

Val Cys Ala Thr Thr Phe Thr Glu Lys Asn Thr Val Gly Phe Leu Asp
    50                  55                  60

Tyr Pro Phe Cys Ser Gly Thr Phe Asn Glu Ser Arg Val Asn Leu Thr
65                  70                  75                  80

Ile Gln Gly Leu Arg Ala Val Asp Thr Gly Leu Tyr Leu Cys Lys Val
                85                  90                  95

Glu Leu Met Tyr Pro Pro Pro Tyr Phe Val Gly Met Gly Asn Gly Thr
            100                 105                 110

Gln Ile Tyr Val Ile Asp Pro Glu
        115                 120
```

<210> SEQ ID NO 130
<211> LENGTH: 31
<212> TYPE: PRT
<213> ORGANISM: Artificial Sequence
<220> FEATURE:
<223> OTHER INFORMATION: Synthetic Construct

<400> SEQUENCE: 130

```
Glu Val Gly Ser Tyr Pro Asn Pro Ser Ser Asp Cys Val Pro Tyr Tyr
1               5                   10                  15

Tyr Ala Cys Ala Tyr Ser Gly Arg Ser Ala Pro Leu Gly Leu Ala
            20                  25                  30
```

<210> SEQ ID NO 131
<211> LENGTH: 22
<212> TYPE: PRT
<213> ORGANISM: Artificial Sequence
<220> FEATURE:
<223> OTHER INFORMATION: Synthetic Construct

<400> SEQUENCE: 131

```
Glu Asp Cys Val Pro Tyr Tyr Tyr Ala Cys Ala Tyr Ser Gly Arg Ser
1               5                   10                  15

Ala Pro Leu Gly Leu Ala
            20
```

<210> SEQ ID NO 132
<211> LENGTH: 17
<212> TYPE: PRT
<213> ORGANISM: Artificial Sequence
<220> FEATURE:
<223> OTHER INFORMATION: Synthetic Construct

<400> SEQUENCE: 132

```
Glu Asp Cys Val Pro Tyr Tyr Tyr Ala Cys Ala Tyr Ser Gly Arg Ser
1               5                   10                  15

Ala
```

<210> SEQ ID NO 133
<211> LENGTH: 17
<212> TYPE: PRT

-continued

```
<213> ORGANISM: Artificial Sequence
<220> FEATURE:
<223> OTHER INFORMATION: Synthetic Construct

<400> SEQUENCE: 133

Glu Asp Cys Val Pro Tyr Tyr Tyr Ala Cys Ala Tyr Pro Leu Gly Leu
1               5                   10                  15

Ala
```

MASKED ACTIVATABLE CD137 ANTIBODIES

CROSS REFERENCE TO RELATED APPLICATIONS

This application is a national stage application under 35 U.S.C. § 371 of International Application No. PCT/CN2019/074581, filed internationally on Feb. 2, 2019, which claims the priority benefit of International Application No. PCT/CN2018/075065, filed on Feb. 2, 2018, each of which is incorporated herein by reference in entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 695402000600SUBSEQLIST.TXT, date recorded: Dec. 20, 2020, size: 55,524 bytes.

FIELD OF THE INVENTION

The present disclosure relates to polynucleotides and polynucleotide libraries useful for screening for and/or identifying one or more precision/context-dependent activatable binding polypeptides (e.g., activatable antibodies), as well as polypeptides and polypeptide libraries useful for screening for and/or identifying precision/context-dependent activatable binding polypeptides (e.g., activatable antibodies capable of binding to CTLA4 or CD137 when in active form), cells, methods, and kits related thereto.

BACKGROUND

Activatable binding polypeptides exhibit an "activatable" conformation such that an antigen binding moiety contained therein is less accessible to bind to its target when uncleaved than after cleavage in the presence of one or more specific proteases. These activatable binding polypeptides thus provide antigen-specific binding proteins that are only capable of binding their targets in certain contexts (e.g., in the protease-rich tumor microenvironment). While a number of interesting activatable binding polypeptides have been developed, the process of developing such proteins is slow, labor intensive, and costly. Accordingly, there exists a need for improved methods and products useful for identifying self-blocking peptides for activatable binding polypeptides.

All references cited herein, including patent applications, patent publications, non-patent literature, and UniProtKB/Swiss-Prot/GenBank Accession numbers are herein incorporated by reference in their entirety, as if each individual reference were specifically and individually indicated to be incorporated by reference.

BRIEF SUMMARY

To meet the above and other needs, disclosed herein are libraries of polynucleotides e.g., that are useful for screening for and/or identifying activatable binding polypeptides (i.e., activatable antibodies). The present disclosure is based, at least in part, on the finding that polypeptides described herein show a significantly improved masking efficiency before activation, allowing for better design, screening and/or identification of activatable binding polypeptides (i.e., activatable antibodies) with superior therapeutic indexes and safety profiles. The present disclosure is further based, at least in part, on the surprising finding that the polynucleotide libraries described herein may be successfully constructed and screened to identify activatable binding polypeptides, (see Examples 1 and 2 below). Disclosed herein are precision/context-dependent activatable binding polypeptides that bind to human CTLA4 (see Example 3) or human CD137 (see Example 5) when in active form but not in inactive form, i.e., they bind their target (when in active form) only after cleavage of the cleavable moiety (CM) to remove the first peptide (FP) (i.e., a masking moiety (MM) or self-blocking peptide). The discovered first peptides (FPs) (e.g., masking moieties) described herein are capable of efficiently masking antibody activity and/or reducing or completely inhibiting antigen binding, while in some embodiments being devoid of the chemically labile residues methionine and/or tryptophan. Furthermore, activatable antibodies identified using the polynucleotide libraries described herein are as efficient at treating multiple cancer types as their parental antibody, while having significantly reduced cytotoxicity even in susceptible animals (NOD mice, see Example 4).

Accordingly, in one aspect, provided herein is a library comprising polynucleotides, wherein at least one of the polynucleotides encodes a polypeptide comprising, from N-terminus to C-terminus, a first peptide (FP), a cleavable moiety (CM), and a target binding moiety (TBM), wherein the FP comprises an amino acid sequence according to Formula (XIII): $X_mCX_nCX_o$ (SEQ ID NO: 86), wherein m is from 2-10 (e.g., from 3-10), n is from 3-10, and o is from 1-10, and wherein each X is independently an amino acid selected from the group consisting of A, C, D, E, F, G, H, I, K, L, M, N, P, Q, R, S, T, V, W, and Y; wherein the CM comprises at least a first cleavage site; and wherein the TBM comprises an antibody light chain variable region and/or an antibody heavy chain variable region. In some embodiments, the polynucleotides in the library encode at least two, at least three, at least four, at least five, at least ten, at least 50, at least 100, at least 500, at least 1000 unique polypeptides and each unique polypeptide comprise, from N-terminus to C-terminus, a first peptide (FP), a cleavable moiety (CM), and a target binding moiety (TBM), wherein the FP comprises an amino acid sequence according to Formula (XIII): $X_mCX_nCX_o$ (SEQ ID NO: 86), wherein m is from 2-10 (e.g., from 3-10), n is from 3-10, and o is from 1-10, and wherein each X is independently an amino acid selected from the group consisting of A, C, D, E, F, G, H, I, K, L, M, N, P, Q, R, S, T, V, W, and Y; wherein the CM comprises at least a first cleavage site; and wherein the TBM comprises an antibody light chain variable region and/or an antibody heavy chain variable region. In some embodiments that may be combined with any of the preceding embodiments, each of the polynucleotides in the library encodes a polypeptide comprising, from N-terminus to C-terminus, a first peptide (FP), a cleavable moiety (CM), and a target binding moiety (TBM), wherein the FP comprises an amino acid sequence according to Formula (XIII): $X_mCX_nCX_o$ (SEQ ID NO: 86), wherein m is from 2-10 (e.g., from 3-10), n is from 3-10, and o is from 1-10, and wherein each X is independently an amino acid selected from the group consisting of A, C, D, E, F, G, H, I, K, L, M, N, P, Q, R, S, T, V, W, and Y; wherein the CM comprises at least a first cleavage site; and wherein the TBM comprises an antibody light chain variable region and/or an antibody heavy chain variable region. In some embodiments that may be combined with any of the preceding embodiments, the FP is encoded by a polynucleotide sequence comprising a nucleic acid sequence according to Formula (XIV): $(NNK)_m TGY(NNK)_n TGY(NNK)_o$ (SEQ ID NO: 87), wherein each N is independently A, G, T, or C, wherein each K is independently T or G, and wherein each Y is independently T or C.

In some embodiments that may be combined with any of the preceding embodiments, each X is not M, W, or C. In some embodiments that may be combined with any of the preceding embodiments, each X in $X_m$ of Formula (XIII) is independently an amino acid selected from the group consisting of D, A, Y, S, T, N, I, L, F, V, H, and P. In some embodiments that may be combined with any of the preceding embodiments, each X in $X_n$ of Formula (XIII) is independently an amino acid selected from the group consisting of D, A, Y, S, T, N, I, L, F, V, H, and P. In some embodiments that may be combined with any of the preceding embodiments, each X in $X_o$ of Formula (XIII) is independently an amino acid selected from the group consisting of D, A, Y, S, T, N, I, L, F, V, H, and P. In some embodiments that may be combined with any of the preceding embodiments, m is 6. In some embodiments that may be combined with any of the preceding embodiments, m is 2-5, e.g., 2, 3, 4, or 5. In some embodiments that may be combined with any of the preceding embodiments, n is from 6-8. In some embodiments that may be combined with any of the preceding embodiments, n is 6. In some embodiments that may be combined with any of the preceding embodiments, o is from 1-2. In some embodiments that may be combined with any of the preceding embodiments, o is 2. In some embodiments that may be combined with any of the preceding embodiments, the FP further comprises, at its N-terminus, an additional amino acid sequence. In some embodiments, the additional amino acid sequence comprises the amino acid sequence of SEQ ID NO: 16.

In some embodiments that may be combined with any of the preceding embodiments, the first cleavage site is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments that may be combined with any of the preceding embodiments, the CM further comprises a first linker ($L_1$) C-terminal to the first cleavage site. In some embodiments, the $L_1$ comprises an amino acid sequence selected from the group consisting of SEQ ID NOS: 17-24. In some embodiments that may be combined with any of the preceding embodiments, the CM further comprises a second cleavage site. In some embodiments, the second cleavage site is C-terminal to the $L_1$. In some embodiments, the second cleavage site is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the first and second cleavage sites are different. In some embodiments that may be combined with any of the preceding embodiments, the CM further comprises a second linker ($L_2$)C-terminal to the second cleavage site. In some embodiments, the $L_2$ comprises an amino acid sequence selected from the group consisting of SEQ ID NOS: 17-24. In some embodiments that may be combined with any of the preceding embodiments, the CM further comprises a linker N-terminal to the first cleavage site.

In some embodiments that may be combined with any of the preceding embodiments, the polypeptide encoded by one or more polynucleotides in the library comprises a first peptide (FP) and a cleavable moiety (CM) comprising an amino acid sequence according to Formula (III): $EVGSYX_1X_2X_3X_4X_5X_6CX_7X_8X_9X_{10}X_{11}X_{12}CX_{13}X_{14}SGRSAGGGGTENLYFQGS$ (SEQ ID NO: 3), wherein $X_1$ is A, D, I, N, P, or Y, $X_2$ is A, F, N, S, or V, $X_3$ is A, H, L, P, S, V, or Y, $X_4$ is A, H, S, or Y, $X_5$ is A, D, P, S, V, or Y, $X_6$ is A, D, L, S, or Y, $X_7$ is D, P, or V, $X_8$ is A, D, H, P, S, or T, $X_9$ is A, D, F, H, P, or Y, $X_{10}$ is L, P, or Y, $X_{11}$ is F, P, or Y, $X_{12}$ is A, P, S, or Y, $X_{13}$ is A, D, N, S, T, or Y, and $X_{14}$ is A, S, or Y. In some embodiments, each of the polynucleotides in the library encodes a polypeptide comprising an amino acid sequence according to Formula (III). In some embodiments that may be combined with any of the preceding embodiments, the polypeptide comprises an amino acid sequence selected from the group consisting of SEQ ID NOS: 25-46.

In some embodiments that may be combined with any of the preceding embodiments, the TBM comprises an antibody light chain variable region. In some embodiments, the TBM further comprises a heavy chain variable region C-terminal to the light chain variable region. In some embodiments, the library further comprises polynucleotides that encode one or more antibody heavy chain variable regions. In some embodiments, the heavy chain variable region and light chain variable region forms an antigen binding site that is capable of binding to a target in the absence of a masking moiety (MM).

In some embodiments that may be combined with any of the preceding embodiments, the TBM comprises an antibody heavy chain variable region. In some embodiments, the TBM further comprises a light chain variable region C-terminal to the heavy chain variable region. In some embodiments, the library further comprises polynucleotides that encode one or more antibody light chain variable regions. In some embodiments, the heavy chain variable region and light chain variable region forms an antigen binding site that is capable of binding to a target in the absence of a masking moiety (MM).

In some embodiments that may be combined with any of the preceding embodiments, at least one of the polynucleotides encoding the polypeptide is in a vector. In some embodiments, the vector is an expression vector or a display vector. In some embodiments that may be combined with any of the preceding embodiments, at least one of the polynucleotides encoding the polypeptide is in a cell. In some embodiments, the cell is a bacterial cell, a yeast cell, an insect cell, or a mammalian cell.

Other aspects of the present disclosure relate to a method of producing an activatable antibody comprising culturing any of the cells described herein under conditions suitable for producing the activatable antibody. In some embodiments, the method further comprises recovering the activatable antibody produced by the cell. In some embodiments, the method further comprises testing the activatable antibody for the ability to maintain an activatable phenotype while soluble.

Other aspects of the present disclosure relate to a method of using any of the libraries described herein to screen for an activatable antibody that binds to a target, comprising the steps of a) contacting the expression products of the library with the target before the CM is cleaved, b) contacting the expression products of the library with the target after the CM is cleaved, and c) isolating one or more of the expression products that binds to the target after the CM is cleaved, but does not bind to the target before the CM is cleaved. Also provided here is a method using any of the libraries described herein to screen for an activatable antibody that binds to a target, comprising the steps of a) contacting the expression products of the library with the target before the CM is cleaved, b) contacting the expression products of the library with the target after the CM is cleaved, and c) isolating one or more of the expression products that binds to the target after the CM is cleaved, but has reduced binding affinity to the target before the CM is cleaved as compared to the binding affinity after the CM is cleaved. In some embodiments, an expression product is isolated if the $K_D$ of the expression product before the CM is cleaved is at least 2-fold (e.g., at least 5-fold, at least 10-fold, at least 15-fold, or higher) of the $K_D$ of the expression product after the CM is cleaved. In some embodiments, the CM comprises at least a first protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the target is CTLA4, CD137, PD-1, PD-L1, PD-L2, LAG3, TIM3, B7-H3, OX40, CD3, CD19, CD20, CD40, CD95, CD120a, BTLA, VISTA, ICOS, BCMA, Her1, Her2, Her3, and/or B7-H4. In some embodiments, the target is CTLA4 or CD137.

Other aspects of the present disclosure relate to a polypeptide encoded by one or more polynucleotides of any of the libraries described herein or a library of the polypeptides encoded by one or more polynucleotides of any of the libraries described herein.

Other aspects of the present disclosure relate to a kit comprising any of the libraries described herein.

Other aspects of the present disclosure relate to a library comprising antigen binding domains, wherein at least one of the antigen binding domains comprises a polypeptide comprising, from N-terminus to C-terminus, a first peptide (FP), a cleavable moiety (CM), and a target binding moiety (TBM), wherein the FP comprises an amino acid sequence according to Formula (XIII): $X_mCX_nCX_o$ (SEQ ID NO: 86), wherein m is from 2-10 (e.g., from 3-10), n is from 3-10, and o is from 1-10, and wherein each X is independently an amino acid selected from the group consisting of A, C, D, E, F, G, H, I, K, L, M, N, P, Q, R, S, T, V, W, and Y; wherein the CM comprises at least a first cleavage site; and wherein the TBM comprises an antibody light chain variable region and/or an antibody heavy chain variable region. In some embodiments, at least two, at least three, at least four, at least five, at least ten, at least 50, at least 100, at least 1000 of the antigen binding domains comprise a unique polypeptide comprising, from N-terminus to C-terminus, a first peptide (FP), a cleavable moiety (CM), and a target binding moiety (TBM), wherein the FP comprises an amino acid sequence according to Formula (XIII): $X_mCX_nCX_o$ (SEQ ID NO: 86), wherein m is from 2-10 (e.g., from 3-10), n is from 3-10, and o is from 1-10, and wherein each X is independently an amino acid selected from the group consisting of A, C, D, E, F, G, H, I, K, L, M, N, P, Q, R, S, T, V, W, and Y; wherein the CM comprises at least a first cleavage site; and wherein the TBM comprises an antibody light chain variable region and/or an antibody heavy chain variable region. In some embodiments that may be combined with any of the preceding embodiments, each of the antigen binding domains comprises a unique polypeptide comprising, from N-terminus to C-terminus, a first peptide (FP), a cleavable moiety (CM), and a target binding moiety (TBM), wherein the FP comprises an amino acid sequence according to Formula (XIII): $X_mCX_nCX_o$ (SEQ ID NO: 86), wherein m is from 2-10 (e.g., from 3-10), n is from 3-10, and o is from 1-10, and wherein each X is independently an amino acid selected from the group consisting of A, C, D, E, F, G, H, I, K, L, M, N, P, Q, R, S, T, V, W, and Y; wherein the CM comprises at least a first cleavage site; and wherein the TBM comprises an antibody light chain variable region and/or an antibody heavy chain variable region. In some embodiments that may be combined with any of the preceding embodiments, the TBM comprises an antibody light chain variable region and the antigen binding domain further comprises an antibody heavy chain variable region. In some embodiments that may be combined with any of the preceding embodiments, the TBM comprises an antibody heavy chain variable region and the antigen binding domain further comprises an antibody light chain variable region. In some embodiments that may be combined with any of the preceding embodiments, each X is not M, W, or C. In some embodiments that may be combined with any of the preceding embodiments, each X in $X_m$ in formula (XIII) is independently an amino acid selected from the group consisting of D, A, Y, S, T, N, I, L, F, V, H, and P. In some embodiments that may be combined with any of the preceding embodiments, each X in $X_n$ of Formula (XIII) is independently an amino acid selected from the group consisting of D, A, Y, S, T, N, I, L, F, V, H, and P. In some embodiments that may be combined with any of the preceding embodiments, each X in $X_o$ of Formula (XIII) is independently an amino acid selected from the group consisting of D, A, Y, S, T, N, I, L, F, V, H, and P. In some embodiments, each of the antigen binding domains in the library is displayed on a phage or a cell (e.g., a yeast cell).

Other aspects of the present disclosure relate to an antibody light chain comprising a polypeptide comprising, from N-terminus to C-terminus, a first peptide (FP), a cleavable moiety (CM), and a target binding moiety (TBM), wherein the FP comprises an amino acid sequence according to Formula (I): $X_mCX_nCZ_o$ (SEQ ID NO: 1), wherein m is from 2-10 (e.g., from 3-10), n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the CM comprises at least a first cleavage site; and wherein the TBM comprises an antibody light chain variable region. Other aspects of the present disclosure relate to an antibody comprising a heavy chain and a light chain, wherein the light chain is any of the antibody light chains described herein. In some embodiments that may be combined with any of the preceding embodiments, each X is not M, W, or C. In some embodiments that may be combined with any of the preceding embodiments, each X in $X_m$ in formula (XIII) is independently an amino acid selected from the group consisting of D, A, Y, S, T, N, I, L, F, V, H, and P.

Other aspects of the present disclosure relate to an antibody heavy chain comprising a polypeptide comprising, from N-terminus to C-terminus, a first peptide (FP), a cleavable moiety (CM), and a target binding moiety (TBM), wherein the FP comprises an amino acid sequence according to Formula (I): $X_mCX_nCZ_o$ (SEQ ID NO: 1), wherein m is from 2-10 (e.g., from 3-10), n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the CM comprises at least a first cleavage site; and wherein the TBM comprises an antibody heavy chain variable region. Other aspects of the present disclosure relate to an antibody comprising a heavy chain and a light chain, wherein the heavy chain is any of the antibody heavy chains described herein. In some embodiments that may be combined with any of the preceding embodiments, each X is not M, W, or C. In some embodiments that may be combined with any of the preceding embodiments, each X in $X_m$ in formula (XIII) is independently an amino acid selected from the group consisting of D, A, Y, S, T, N, I, L, F, V, H, and P.

Other aspects of the present disclosure relate to a cell comprising at least one polypeptide displayed on its surface, wherein the at least polypeptide comprises, from N-terminus to C-terminus, a first peptide (FP), a cleavable moiety (CM), and a target binding moiety (TBM), wherein the FP comprises an amino acid sequence according to Formula (I): $X_mCX_nCX_o$ (SEQ ID NO: 1), wherein m is from 2-10 (e.g., from 3-10), n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the CM comprises at least a first cleavage site; and wherein the TBM comprises an antibody light chain variable region and/or an antibody heavy chain variable region. In some embodiments, the cell is a bacterial cell, a yeast cell, an insect cell, or a mammalian cell. In some embodiments that may be combined with any of the preceding embodiments, each X is not M, W, or C. In some embodiments that may be combined with any of the preceding embodiments, each X in $X_m$ of formula (I) is independently an amino acid selected from the group consisting of D, A, Y, S, T, N, I, L, F, V, H, and P. In some embodiments that may be combined with any of the preceding embodiments, each X in $X_n$ of formula (I) is independently an amino acid selected from the group consisting of D, A, Y, S, T, N, I, L, F, V, H, and P.

Other aspects of the present disclosure relate to an activatable antibody comprising: a polypeptide comprising, from N-terminus to C-terminus, a masking moiety (MM), a cleavable moiety (CM), and a target binding moiety (TBM), wherein the MM comprises an amino acid sequence according to Formula (I): $X_mCX_nCZ_o$ (SEQ ID NO: 1), wherein m is from 2-10 (e.g., from 3-10), n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the MM inhibits the binding of the activatable antibody to human CTLA4 when the CM is not cleaved; wherein the CM comprises at least a first cleavage site; and wherein the TBM comprises an antibody light chain variable region (VL) and/or an antibody heavy chain variable region (VH); and wherein the activatable antibody binds to human CTLA4 via the VH and VL when the CM is cleaved. In some embodiments, the TBM comprises the VL and the activatable antibody further comprises a VH. In some embodiments, the TBM comprises the VH and the activatable antibody further comprises a VL. In some embodiments, the TBM comprises, from N-terminus to C-terminus, VH and VL or VL and VH. In some embodiments, the CM comprises at least a first protease cleavage site and is cleaved with one or more proteases selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments that may be combined with any of the preceding embodiments, each X is not M, W, or C. In some embodiments that may be combined with any of the preceding embodiments, each X in $X_m$ of formula (I) is independently an amino acid selected from the group consisting of D, A, Y, S, T, N, I, L, F, V, H, and P. In some embodiments that may be combined with any of the preceding embodiments, each X in $X_n$ of formula (I) is independently an amino acid selected from the group consisting of D, A, Y, S, T, N, I, L, F, V, H, and P. In some embodiments that may be combined with any of the preceding embodiments, the MM comprises an amino acid sequence selected from the group consisting of SEQ ID NO: 72-78. In some embodiments that may be combined with any of the preceding embodiments, the VL comprises an HVR-L1 comprising the amino acid sequence of SEQ ID NO: 62, an HVR-L2 comprising the amino acid sequence of SEQ ID NO: 63, and an HVR-L3 comprising the amino acid sequence of SEQ ID NO: 64. In some embodiments that may be combined with any of the preceding embodiments, the VL comprises the amino acid sequence of SEQ ID NO: 48. In some embodiments that may be combined with any of the preceding embodiments, the VH comprises an HVR-H1 comprising the amino acid sequence of SEQ ID NO: 59, an HVR-H2 comprising the amino acid sequence of SEQ ID NO: 60, and an HVR-H3 comprising the amino acid sequence of SEQ ID NO: 61. In some embodiments that may be combined with any of the preceding embodiments, the VH comprises the amino acid sequence of SEQ ID NO: 47. In some embodiments, m is 3-10.

Other aspects of the present disclosure relate to an activatable antibody comprising: a polypeptide comprising, from N-terminus to C-terminus, a masking moiety (MM), a cleavable moiety (CM), and a target binding moiety (TBM), wherein the MM comprises an amino acid sequence according to Formula (I): $X_mCX_nCZ_o$ (SEQ ID NO: 1), wherein m is from 2-10 (e.g., from 3-10), n is from 3-10, and o is from 1-10, wherein each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; wherein the MM inhibits the binding of the activatable antibody to human CD137 when the CM is not cleaved; wherein the CM comprises at least a first cleavage site; and wherein the TBM comprises an antibody light chain variable region (VL) and/or an antibody heavy chain variable region (VH); and wherein the activatable antibody binds to human CD137 via the VH and VL when the CM is cleaved. In some embodiments, the TBM comprises the VL and the activatable antibody further comprises a VH. In some embodiments, the TBM comprises the VH and the activatable antibody further comprises a VL. In some embodiments, the TBM comprises, from N-terminus to C-terminus, VH and VL or VL and VH. In some embodiments, the CM comprises at least a first protease cleavage site and is cleaved with one or more proteases selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments that may be combined with any of the preceding embodiments, each X is not M, W, or C. In some embodiments that may be combined with any of the preceding embodiments, each X in $X_m$ of formula (I) is independently an amino acid selected from the group consisting of D, A, Y, S, T, N, I, L, F, V, H, and P. In some embodiments that may be combined with any of the preceding embodiments, each X in $X_n$ of formula (I) is independently an amino acid selected from the group consisting of D, A, Y, S, T, N, I, L, F, V, H, and P. In some embodiments that may be combined with any of the preceding embodiments, the MM comprises an amino acid sequence selected from the group consisting of SEQ ID NO: 79-85 and 88-94. In some embodiments that may be combined with any of the preceding embodiments, the VL comprises an HVR-L1 comprising the amino acid sequence of SEQ ID NO: 68, an HVR-L2 comprising the amino acid sequence of SEQ ID NO: 69, and an HVR-L3 comprising the amino acid sequence of SEQ ID NO: 70. In some embodiments that may be combined with any of the preceding embodiments, the VL comprises the amino acid sequence of SEQ ID NO: 50. In some embodiments that may be combined with any of the preceding embodiments, the VH comprises an HVR-H1 comprising the amino acid sequence of SEQ ID NO: 65, an HVR-H2 comprising the amino acid sequence of SEQ ID NO: 66, and an HVR-H3 comprising the amino acid sequence of SEQ ID NO: 67. In some embodiments that may be combined with any of the preceding embodiments, the VH comprises the amino acid sequence of SEQ ID NO: 49. In some embodiments, m is 3-10.

Other aspects of the present disclosure relate to a polynucleotide encoding any of the activatable antibodies described herein. In other aspects, the present disclosure relates to a vector comprising any of the polynucleotides described herein (e.g., a polynucleotide encoding an activatable antibody). In some embodiments, the vector is an expression vector and/or a display vector. In other aspects, the present disclosure relates to a host cell comprising any of the polynucleotides and/or vectors described herein (e.g., a polynucleotide and/or vector encoding an activatable antibody). In some embodiments, the host cell is a eukaryotic cell. In some embodiments, the host cell is a Chinese Hamster Ovary (CHO) cell. In other aspects, the present disclosure relates to a method of making an activatable antibody comprising culturing any of the host cells described herein under conditions suitable for producing the antibody or activatable antibody. In some embodiments, the method further comprises recovering the antibody or activatable antibody produced by the cell.

Other aspects of the present disclosure relate to a method of treating or delaying progression of cancer in a subject in need thereof, the method comprising administering to the subject an effective amount of a polypeptide encoded by one or more polynucleotides from any of the libraries described herein and/or any of the activatable antibodies (e.g., activatable antibody to human CTLA4 or activatable antibody to human CD137) described herein. In some embodiments, the method further comprises administering to the subject an effective amount of at least one additional therapeutic agent. In some embodiments, the at least one additional therapeutic agent is selected from the group consisting of viral gene therapy, immune checkpoint inhibitors, target therapies, radiation therapies, and chemotherapies. In some embodiments, the at least one additional therapeutic agent is selected from the group consisting of pomalyst, revlimid, lenalidomide, pomalidomide, thalidomide, a DNA-alkylating platinum-containing derivative, cisplatin, 5-fluorouracil, cyclophosphamide, an anti-CD137 antibody, an anti-CTLA4 antibody, an anti-PD-1 antibody, an anti-PD-L1 antibody, an anti-CD20 antibody, an anti-CD40 antibody, an anti-DR5 antibody, an anti-CD1d antibody, an anti-TIM3 antibody, an anti-SLAMF7 antibody, an anti-MR receptor antibody, an anti-OX40 antibody, an anti-HER2 antibody, an anti-ErbB-2 antibody, an anti-EGFR antibody, cetuximab, rituximab, trastuzumab, pembrolizumab, radiotherapy, single dose radiation, fractionated radiation, focal radiation, whole organ radiation, IL-12, IFNα, GM-CSF, a chimeric antigen receptor, adoptively transferred T cells, an anti-cancer vaccine, and an oncolytic virus.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIG. 3A shows functional display of Fabs targeting CTLA4 on the surface of yeast. FIG. 3B shows functional display of scFvs targeting CTLA4 on the surface of yeast.

FIG. 5A shows binding affinity of CTLA4 activatable antibody clones in the scFv format, including the CTLA4 activatable antibody clone B13287 with the masking peptide intact, or with the masking peptide cleaved by the TEV protease, as compared to the scFv fragment of the target antibody with no masking peptide.

FIG. 5B shows CTLA4 binding affinity of CTLA4 activatable antibody clones in the Fab format, including the CTLA4 activatable antibody clone B13189 with the masking peptide intact, or with the masking peptide cleaved by the TEV protease, as compared to the Fab fragment of the target antibody with no masking peptide.

FIG. 6A shows the association and dissociation curves of the indicated activatable antibodies as compared to the parental antibody TY21580, as determined by the ForteBio system. FIG. 6B shows a graph of the relative ratio of bound activatable antibodies, as compared to the parental antibody TY21580.

FIG. 7A shows a first batch of ELISA data indicating binding of CTLA4 activatable antibodies TY22401, TY22402, TY22403, TY22404 to recombinant human CTLA4-Fc, as compared to the parental antibody TY21580. FIG. 7B shows a second batch of ELISA data indicating binding of CTLA4 activatable antibodies TY22401, TY22402, TY22403, TY22404 to recombinant human CTLA4-Fc, as compared to the parental antibody TY21580. FIG. 7C shows binding of CTLA4 activatable antibodies TY22563, TY22564, TY22565, TY22566 to recombinant human CTLA4-Fc, as compared to the parental antibody TY21580.

FIG. 8A shows SDS-PAGE results of activatable antibody TY22404 with no treatment, treated with the protease uPA, or treated with 5 or 10 units of the protease MMP-9. FIG. 8B shows binding of activatable antibody TY22404 with no treatment, treated with the protease uPA, or treated with the protease MMP-9, as compared to the parental antibody TY21580, determined by ELISA.

FIG. 9A shows the SEC profiles of activatable antibody TY22402 after six cycles of freezing and thawing, as compared to the control condition. FIG. 9B shows the SEC profiles of activatable antibody TY22402 after seven days at 50° C., as compared to the control condition. FIG. 9C shows the percentages of SEC main peak area of the exemplary activatable antibodies after seven days at 50° C., after storage at 40° C. for up to 28 days, or after six cycles of freezing and thawing, as compared to the control condition.

FIG. 12A shows the effect on IL-2 secretion from CD3-primed human PBMCs stimulated with isotype control antibody, parental antibody TY21580, and exemplary CTLA4 activatable antibodies TY22401, TY22402, or TY22404. FIG. 12B shows the effect on IFNγ secretion from CD3-primed human PBMCs stimulated with isotype control antibody, parental antibody TY21580, and exemplary CTLA4 activatable antibodies TY22401, TY22402, or TY22404.

FIG. 14A shows the tumor growth curves of different treatment groups of female C57BL/6 mice bearing MC38-established tumors. Data points represent group mean; error bars represent SEM. FIG. 14B shows individual tumor growth curves for the groups treated with TY21580, TY22401, TY22402, and TY22566.

FIG. 17A shows the tumor growth curves of different treatment groups of female C57BL/6 mice bearing 3LL-established tumors. Data points represent group mean; error bars represent SEM. FIG. 17B shows individual tumor growth curves for the groups treated with TY21580, TY22401, TY22402, and TY22566.

FIG. 18A shows a time course of the blood concentrations of the activatable antibody TY22401 intravenously administered at a concentration of 10 mg/kg to female BALB/c mice, as compared to the parental antibody TY21580. FIG. 18B shows a time course of the blood concentrations of the activatable antibody TY22402 intravenously administered at a concentration of 10 mg/kg to female BALB/c mice, as compared to the parental antibody TY21580. FIG. 18C shows a time course of the blood concentrations of the activatable antibody TY22404 intravenously administered at a concentration of 10 mg/kg to female BALB/c mice, as compared to the parental antibody TY21580.

FIG. 20A shows scFvs targeting CD137 on the surface of yeast. FIG. 20B shows Fabs targeting CD137 on the surface of yeast.

FIG. 22A shows binding affinity of CD137 activatable antibody clones in the scFv format, including the CD137 activatable antibody clone B13428 with the masking peptide intact, or with the masking peptide cleaved by the TEV protease, as compared to the scFv fragment of the target antibody with no masking peptide.

Figure 22A:
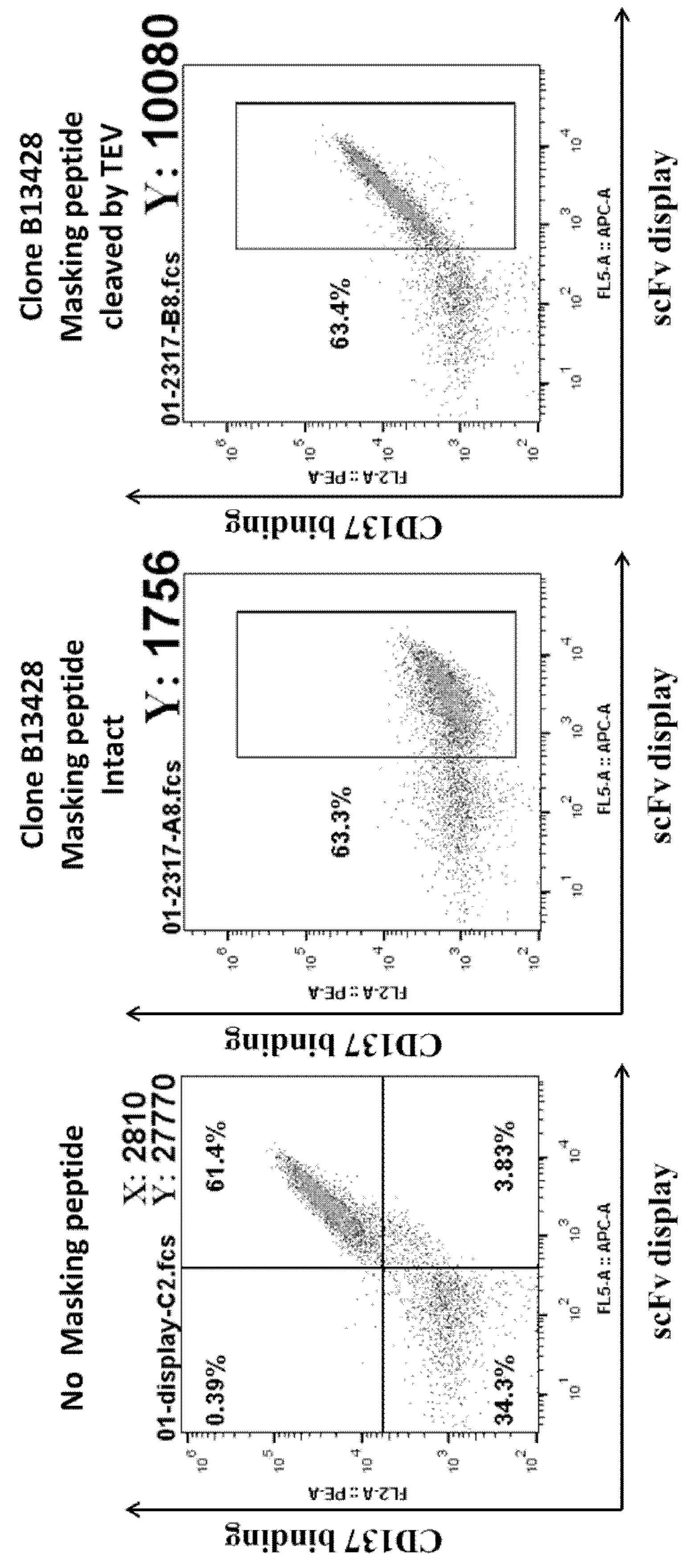
FIGS. 22A-B show CD137 binding affinity of exemplary CD137 activatable antibody clones, as determined by flow cytometry.
Figure 22B:
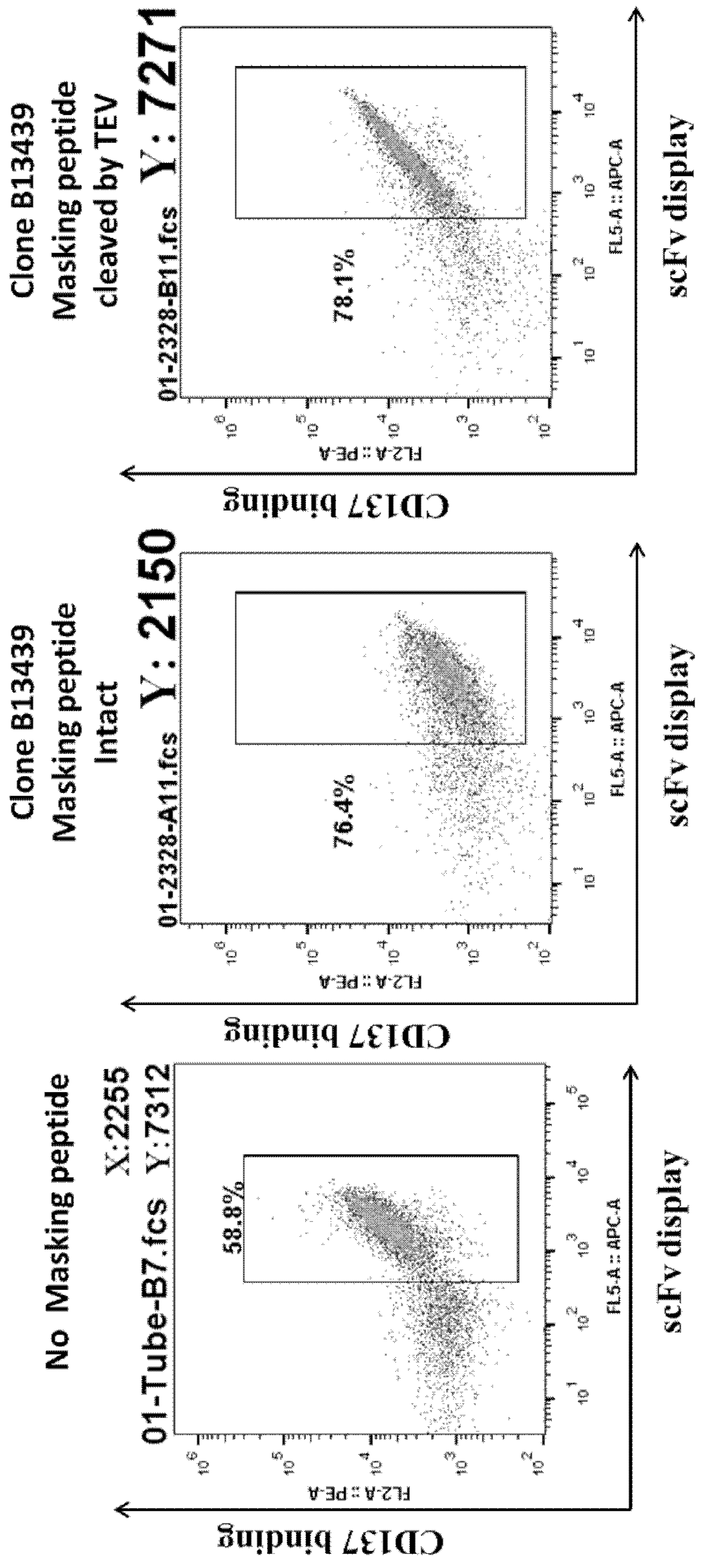

FIG. 22B shows CD137 binding affinity of CD137 activatable antibody clones in the scFv format, including the CD137 activatable antibody clone B13439 with the masking peptide intact, or with the masking peptide cleaved by the TEV protease, as compared to the scFv fragment of the target antibody with no masking peptide.

Figure 23:
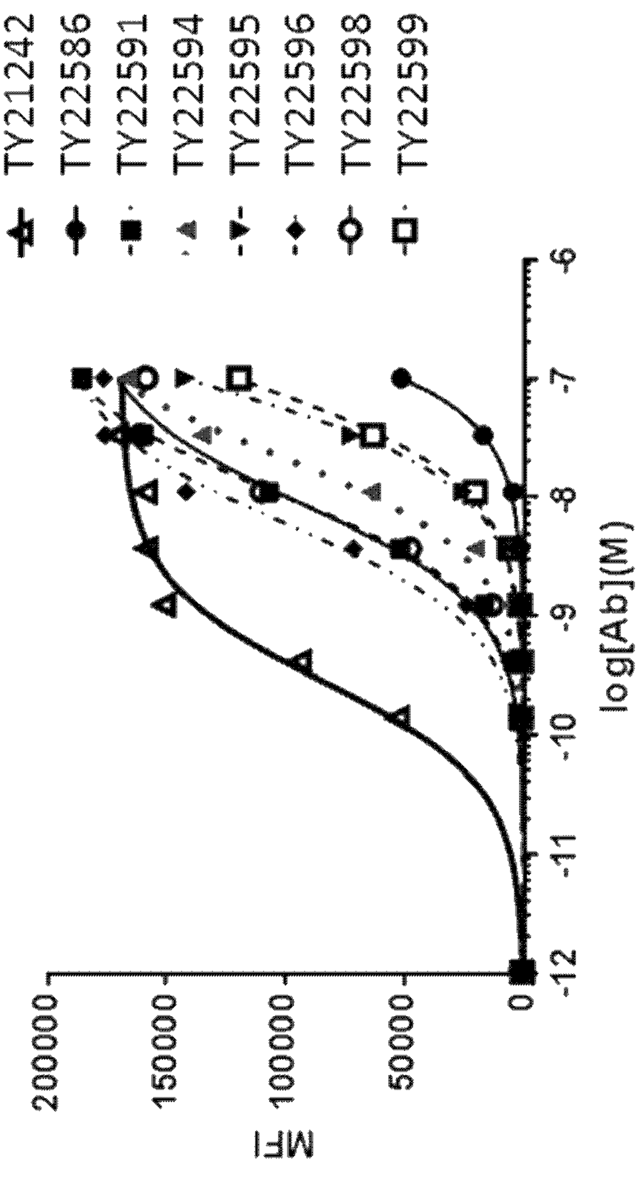

FIG. 23 shows masking efficiency of exemplary activatable antibodies against human CD137, as compared to the parental antibody TY21242, determined by flow cytometry.

Figure 24B:
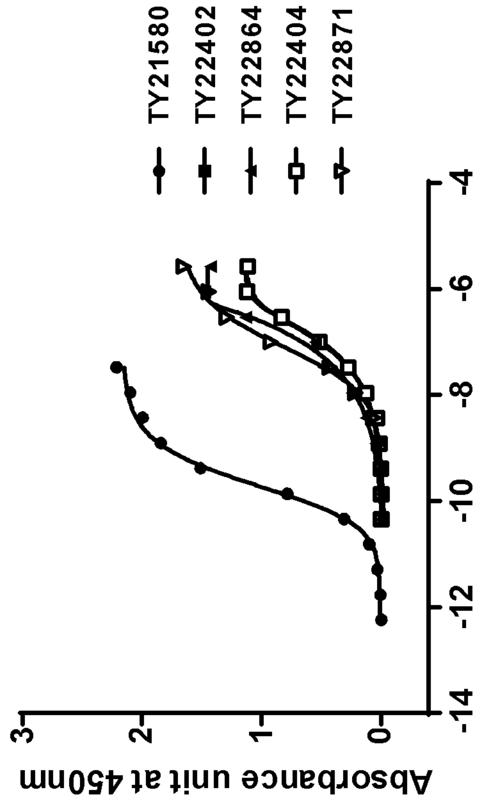
Figure 24A:
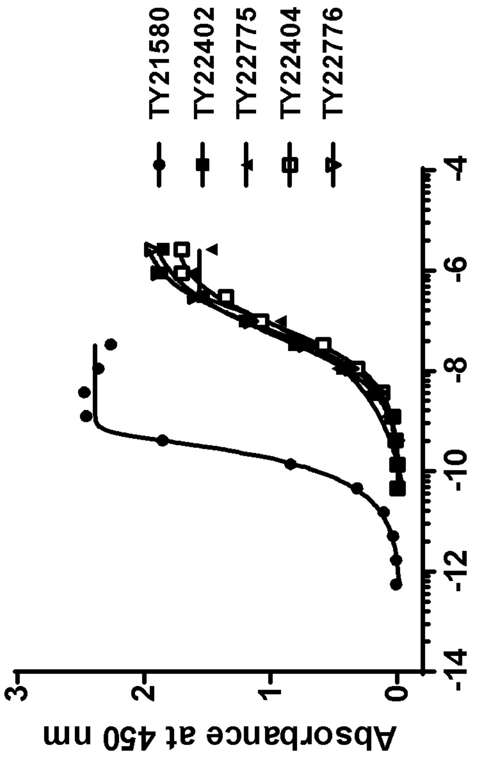

FIGS. 24A and 24B depict masking efficiencies of exemplary activatable antibodies containing masking peptides of variable lengths, as compared to the parental antibody TY21580. Masking efficiencies were determined using ELISA-based methods. FIGS. 24A and 24B represent two experiments set up using the same experimental methods to test various activatable anti-CTLA4 antibodies.

Figure 25:
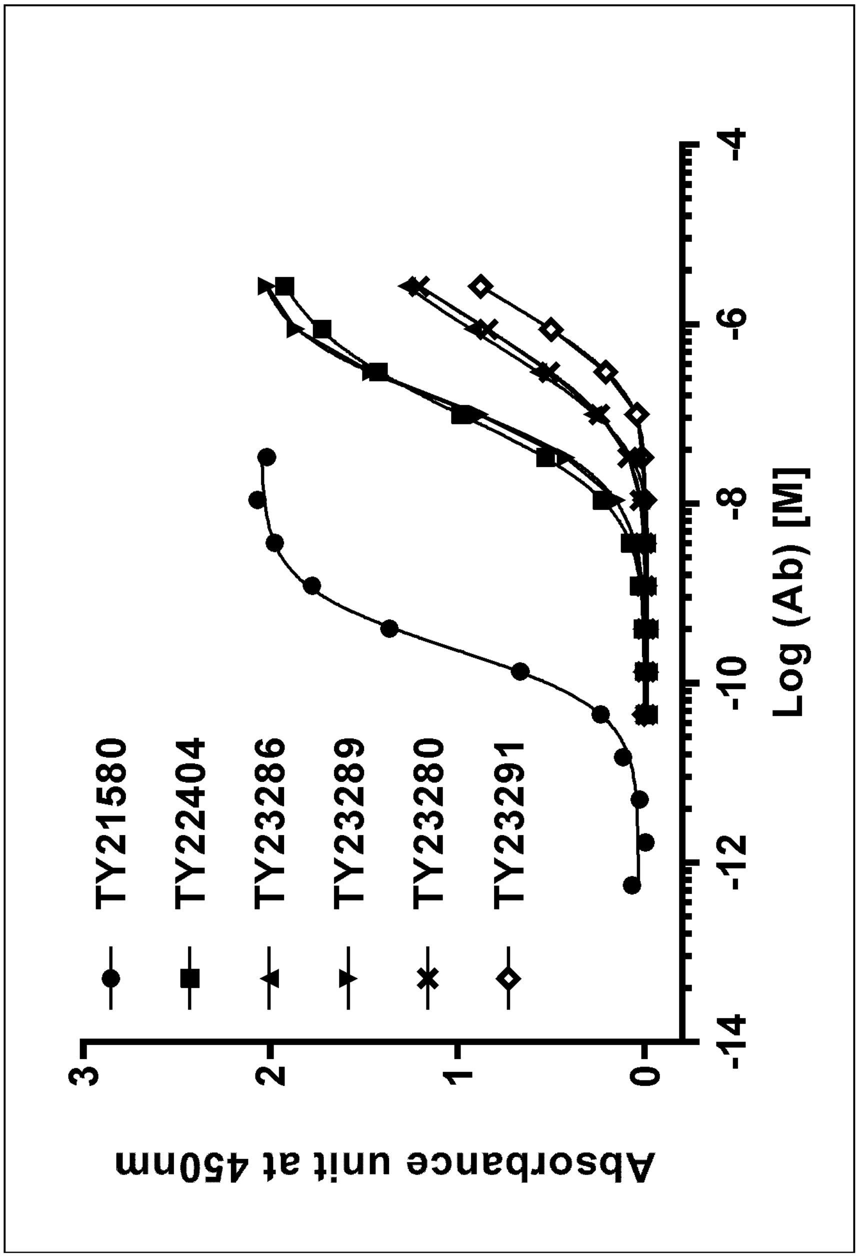

FIG. 25 depicts the masking efficiency of exemplary activatable antibodies containing cleavage peptides of varying lengths, as compared to the parental antibody TY21580. Masking efficiencies were determined using ELISA-based methods.

DETAILED DESCRIPTION

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (RI. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

Before describing the present disclosure in detail, it is to be understood that this present disclosure is not limited to particular compositions or biological systems, which can, of course, vary. It is also to be understood that the terminology used herein is for the purpose of describing particular embodiments only, and is not intended to be limiting.

As used herein, the singular forms “a”, “an” and “the” include plural referents unless the content clearly dictates otherwise. Thus, for example, reference to “a molecule” optionally includes a combination of two or more such molecules, and the like.

The term “about” as used herein refers to the usual error range for the respective value readily known to the skilled person in this technical field. Reference to “about” a value or parameter herein includes (and describes) embodiments that are directed to that value or parameter per se.

It is understood that aspects and embodiments of the present disclosure described herein include “comprising,” “consisting,” and “consisting essentially of” aspects and embodiments.

The term “and/or” as used herein a phrase such as “A and/or B” is intended to include both A and B; A or B; A (alone); and B (alone). Likewise, the term “and/or” as used herein a phrase such as “A, B, and/or C” is intended to encompass each of the following embodiments: A, B, and C; A, B, or C; A or C; A or B; B or C; A and C; A and B; B and C; A (alone); B (alone); and C (alone).

The term “amino acid” refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. The term “amino acid analogs” refers to compounds that have the same basic chemical structure as a naturally occurring amino acid but the C-terminal carboxy group, the N-terminal amino group, or side chain functional group has been chemically modified to another functional group. The term “amino acid mimetics” refers to chemical compounds that have a structure that is different from the general chemical structure of an amino acid, but that functions similarly to a naturally occurring amino acid.

As used herein, the twenty conventional amino acids and their abbreviations follow conventional usage. See e.g., *Immunology—A Synthesis* (2nd Edition, E. S. Golub and D. R. Gren, Eds., Sinauer Associates, Sunderland, Mass. (1991)).

The terms “polypeptide,” “protein,” and “peptide” are used interchangeably herein and may refer to polymers of two or more amino acids.

“Polynucleotide,” or “nucleic acid,” as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "isolated nucleic acid" refers to a nucleic acid molecule of genomic, cDNA, or synthetic origin, or a combination thereof, which is separated from other nucleic acid molecules present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid of interest.

As used herein, "library" refers to a set of two or more entities having a shared class. For example, a library containing polynucleotides may refer to a set of two or more polynucleotides. The term "library" is used herein in the broadest sense and specifically covers sub-libraries that may or may not be combined.

As used herein, "unique" refers to a member of a set that is different from other members of the set. For example, a unique activatable antibody in a library may refer to an activatable antibody having a particular sequence not shared by other activatable antibodies in the library. As a practical matter, it is to be understood that a "unique" member of a physical realization of a library may be present in more than one copy. For example, a library may contain a plurality of "unique" activatable antibodies, with one or more of the "unique" activatable antibody molecules occurring in more than one copy.

As used herein, "diversity" refers to a variety and/or heterogeneity. For example, a diversity of antibodies in a library may refer to a variety of antibodies with unique sequences present in the library.

The term "antibody" is used herein in the broadest sense and specifically covers monoclonal antibodies (including full length monoclonal antibodies), polyclonal antibodies, multispecific antibodies (e.g., bispecific antibodies, trispecific antibodies), and antibody fragments (e.g., Fab, Fab', Fab'-SH, F(ab')2, Fv and/or a single-chain variable fragment or scFv) so long as they exhibit the desired biological activity.

In some embodiments, the term "antibody" refers to an antigen-binding protein (i.e., immunoglobulin) having a basic four-polypeptide chain structure consisting of two identical heavy (H) chains and two identical light (L) chains. Each L chain is linked to an H chain by one covalent disulfide bond, while the two H chains are linked to each other by one or more disulfide bonds depending on the H chain isotype. Each heavy chain has, at the N-terminus, a variable region (abbreviated herein as $V_H$) followed by a constant region. The heavy chain constant region is comprised of three domains, $C_{H1}$, $C_{H2}$ and $C_{H3}$. Each light chain has, at the N-terminus, a variable region (abbreviated herein as $V_L$) followed by a constant region at its other end. The light chain constant region is comprised of one domain, $C_L$. The $V_L$ is aligned with the $V_H$ and the $C_L$ is aligned with the first constant domain of the heavy chain (CH1). The pairing of a $V_H$ and $V_L$ together forms a single antigen-binding site. An IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain.

The $V_H$ and $V_L$ regions can be further subdivided into regions of hypervariability, termed hyper-variable regions (HVR) based on structural and sequence analysis. HVRs are interspersed with regions that are more conserved, termed framework regions (FW) (see e.g., Chen et al. (1999) J. Mol. Biol. (1999) 293, 865-881). Each $V_H$ and $V_L$ is composed of three HVRs and four FWs, arranged from amino-terminus to carboxy-terminus in the following order: FW-1_HVR-1_FW-2_HVR-2_FW-3_HVR-3_FW4. Throughout the present disclosure, the three HVRs of the heavy chain are referred to as HVR-H1, HVR-H2, and HVR-H3. Similarly, the three HVRs of the light chain are referred to as HVR-L1, HVR-L2, and HVR-L3.

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 or more amino acids (see e.g., Fundamental Immunology Ch. 7 (Paul, W., ed., 2nd ed. Raven Press, N.Y). (1989)).

The L chain from any vertebrate species can be assigned to one of two clearly distinct types, called kappa and lambda, based on the amino acid sequences of their constant domains. Depending on the amino acid sequence of the constant domain of their heavy chains (CH), antibodies can be assigned to different classes or isotypes. There are five classes of antibodies: IgA, IgD, IgE, IgG, and IgM, having heavy chains designated a (alpha), δ (delta), (epsilon), γ (gamma), and μ (mu), respectively. The IgG class of antibody can be further classified into four subclasses IgG1, IgG2, IgG3, and IgG4 by the gamma heavy chains, Y1-Y4, respectively.

The term "antigen-binding fragment" or "antigen binding portion" of an antibody refers to one or more portions of an antibody that retain the ability to bind to the antigen that the antibody bonds to. Examples of "antigen-binding fragments" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., *Nature* 341:544-546 (1989)), which consists of a $V_H$ domain; and (vi) an isolated complementarity determining region (CDR).

The term "CTLA4" is used in the present application, and includes the human CTLA4 (e.g., UniProt accession number P16410), as well as variants, isoforms, and species homologs thereof (e.g., mouse CTLA4 (UniProt accession number P09793), rat CTLA4 (UniProt accession number Q9Z1A7), dog CTLA4 (UniProt accession number Q9XSI1), cynomolgus monkey CTLA4 (UniProt accession number G7PL88), etc.). Accordingly, a binding molecule (e.g., an activatable antibody) may also bind CTLA4 from species other than human. In other cases, a binding molecule may be completely specific for the human CTLA4 and may not exhibit species or other types of cross-reactivity.

The term "CD137" is used in the present application, and includes the human CD137 (e.g., GenBank Accession No. NM 001561; NP 001552), as well as variants, isoforms, and species homologs thereof (e.g., mouse CD137 (GenBank Gene ID 21942), rat CD137 (GenBank Gene ID 500590), dog CD137 (GenBank Gene ID 608274), cynomolgus monkey CTLA4 (GenBank Gene ID 102127961), etc.). Accordingly, a binding molecule (e.g., an activatable antibody) may also bind CD137 from species other than human. In other cases, a binding molecule may be completely specific for the human CD137 and may not exhibit species or other types of cross-reactivity.

The term "chimeric antibody" refers to an antibody that comprises amino acid sequences derived from different animal species, such as those having a variable region derived from a human antibody and a murine immunoglobulin constant region.

The term "compete for binding" refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The term "epitope" refers to a part of an antigen to which an antibody (or antigen-binding fragment thereof) binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope can include various numbers of amino acids in a unique spatial conformation. Methods of determining spatial conformation of epitopes include, for example, x-ray crystallography, 2-dimensional nuclear magnetic resonance, deuterium and hydrogen exchange in combination with mass spectrometry, or site-directed mutagenesis, or all methods used in combination with computational modeling of antigen and its complex structure with its binding antibody and its variants (see e.g., Epitope Mapping Protocols in Methods in Molecular Biology, Vol. 66, G. E. Morris, Ed. (1996)). Once a desired epitope of an antigen is determined, antibodies to that epitope can be generated, e.g., using the techniques described herein. The generation and characterization of antibodies may also elucidate information about desirable epitopes. From this information, it is then possible to competitively screen antibodies for binding to the same epitope. An approach to achieve this is to conduct cross-competition studies to find antibodies that competitively bind with one another, i.e., the antibodies compete for binding to the antigen. A high throughput process for "binning" antibodies based upon their cross-competition is described in PCT Publication No. WO 03/48731.

The term "germline" refers to the nucleotide sequences of the antibody genes and gene segments as they are passed from parents to offspring via the germ cells. The germline sequence is distinguished from the nucleotide sequences encoding antibodies in mature B cells which have been altered by recombination and hypermutation events during the course of B cell maturation.

The term "glycosylation sites" refers to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. The specific site of attachment is typically signaled by a sequence of amino acids, referred to herein as a "glycosylation site sequence". The glycosylation site sequence for N-linked glycosylation is: -Asn-X-Ser- or -Asn-X-Thr-, where X may be any of the conventional amino acids, other than proline. The terms "N-linked" and "O-linked" refer to the chemical group that serves as the attachment site between the sugar molecule and the amino acid residue. N-linked sugars are attached through an amino group; 0-linked sugars are attached through a hydroxyl group. The term "glycan occupancy" refers to the existence of a carbohydrate moiety linked to a glycosylation site (i.e., the glycan site is occupied). Where there are at least two potential glycosylation sites on a polypeptide, either none (0-glycan site occupancy), one (1-glycan site occupancy) or both (2-glycan site occupancy) sites can be occupied by a carbohydrate moiety.

The term "host cell" refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; human cells (e.g., HEK293F cells, HEK293T cells; or human tissues or hybridoma cells, yeast cells, insect cells (e.g., S2 cells), bacterial cells (e.g., *E. coli* cells) and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "humanized antibody" refers to a chimeric antibody that contains amino acid residues derived from human antibody sequences. A humanized antibody may contain some or all of the CDRs or HVRs from a non-human animal or synthetic antibody while the framework and constant regions of the antibody contain amino acid residues derived from human antibody sequences.

The term "illustrative antibody" refers to any one of the antibodies described herein. These antibodies may be in any class (e.g., IgA, IgD, IgE, IgG, and IgM). Thus, each antibody identified above encompasses antibodies in all five classes that have the same amino acid sequences for the $V_L$ and $V_H$ regions. Further, the antibodies in the IgG class may be in any subclass (e.g., IgG1 IgG2, IgG3, and IgG4). Thus, each antibody identified above in the IgG subclass encompasses antibodies in all four subclasses that have the same amino acid sequences for the $V_L$ and $V_H$ regions. The amino acid sequences of the heavy chain constant regions of human antibodies in the five classes, as well as in the four IgG subclasses, are known in the art. The amino acid sequence of the full length heavy chain and light chain for the IgG4 subclass of each of the illustrative antibodies shown in in Table 1b is provided in the disclosure.

An "isolated" antibody or binding molecule is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see e.g., Flatman et al., J. Chromatogr. B 848:79-87 (2007).

The term "$k_a$" refers to the association rate constant of a particular antibody-antigen interaction, whereas the term "$k_d$" refers to the dissociation rate constant of a particular antibody-antigen interaction.

The term "$K_D$" refers to the equilibrium dissociation constant of a particular antibody-antigen interaction. It is obtained from the ratio of $k_d$ to $k_a$ (i.e., $k_d/k_a$) and is expressed as a molar concentration (M). $K_D$ is used as a measure for the affinity of an antibody's binding to its binding partner. The smaller the $K_D$, the more tightly bound the antibody is, or the higher the affinity between antibody and the antigen. For example, an antibody with a nanomolar (nM) dissociation constant binds more tightly to a particular antigen than an antibody with a micromolar (μM) dissociation constant. $K_D$ values for antibodies can be determined using methods well established in the art. One method for determining the $K_D$ of an antibody is by using an ELISA. For example, an assay procedure using an ELISA is described in at least Example 3 of the present disclosure.

The term "mammal" refers to any animal species of the Mammalia class. Examples of mammals include: humans; laboratory animals such as rats, mice, hamsters, rabbits, non-human primates, and guinea pigs; domestic animals such as cats, dogs, cattle, sheep, goats, horses, and pigs; and captive wild animals such as lions, tigers, elephants, and the like.

The term "prevent" or "preventing," with reference to a certain disease condition in a mammal, refers to preventing or delaying the onset of the disease, or preventing the manifestation of clinical or subclinical symptoms thereof.

As used herein, "sequence identity" between two polypeptide sequences indicates the percentage of amino acids that are identical between the sequences. The amino acid sequence identity of polypeptides can be determined conventionally using known computer programs such as Bestfit, FASTA, or BLAST (see e.g., Pearson, *Methods Enzymol.* 183:63-98 (1990); Pearson, *Methods Mol. Biol.* 132:185-219 (2000); Altschul et al., *J. Mol. Biol.* 215:403-410 (1990); Altschul et al., *Nucleic Acids Res.* 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

As used herein, the term "binds", "binds to", "specifically binds" "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "treat", "treating", or "treatment", with reference to a certain disease condition in a mammal, refers causing a desirable or beneficial effect in the mammal having the disease condition. The desirable or beneficial effect may include reduced frequency or severity of one or more symptoms of the disease (i.e., tumor growth and/or metastasis, or other effect mediated by the numbers and/or activity of immune cells, and the like), or arrest or inhibition of further development of the disease, condition, or disorder. In the context of treating cancer in a mammal, the desirable or beneficial effect may include inhibition of further growth or spread of cancer cells, death of cancer cells, inhibition of reoccurrence of cancer, reduction of pain associated with the cancer, or improved survival of the mammal. The effect can be either subjective or objective. For example, if the mammal is human, the human may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to treatment include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

The term "vector" refers to a nucleic acid molecule capable of transporting a foreign nucleic acid molecule. The foreign nucleic acid molecule is linked to the vector nucleic acid molecule by a recombinant technique, such as ligation or recombination. This allows the foreign nucleic acid molecule to be multiplied, selected, further manipulated or expressed in a host cell or organism. A vector can be a plasmid, phage, transposon, cosmid, chromosome, virus, or virion. One type of vectors can be integrated into the genome of a host cell upon introduction into the host cell, and thereby are replicated along with the host genome (e.g., non-episomal mammalian vectors). Another type of vector is capable of autonomous replication in a host cell into which it is introduced (e.g., bacterial vectors having a bacterial origin of replication and episomal mammalian vectors). Another specific type of vector capable of directing the expression of expressible foreign nucleic acids to which they are operatively linked is commonly referred to as "expression vectors." Expression vectors generally have control sequences that drive expression of the expressible foreign nucleic acids. Simpler vectors, known as "transcription vectors," are only capable of being transcribed but not translated: they can be replicated in a target cell but not expressed. The term "vector" encompasses all types of vectors regardless of their function. Vectors capable of directing the expression of expressible nucleic acids to which they are operatively linked are commonly referred to "expression vectors." Other examples of "vectors" may include display vectors (e.g., vectors that direct expression and display of an encoded polypeptide on the surface of a virus or cell (such as a bacterial cell, yeast cell, insect cell, and/or mammalian cell).

As used herein, a "subject", "patient", or "individual" may refer to a human or a non-human animal. A "non-human animal" may refer to any animal not classified as a human, such as domestic, farm, or zoo animals, sports, pet animals (such as dogs, horses, cats, cows, etc.), as well as animals used in research. Research animals may refer without limitation to nematodes, arthropods, vertebrates, mammals, frogs, rodents (e.g., mice or rats), fish (e.g., zebrafish or pufferfish), birds (e.g., chickens), dogs, cats, and non-human primates (e.g., rhesus monkeys, cynomolgus monkeys, chimpanzees, etc.). In some embodiments, the subject, patient, or individual is a human.

An "effective amount" refers to at least an amount effective, at dosages and for periods of time necessary, to achieve one or more desired or indicated effects, including a therapeutic or prophylactic result. An effective amount can be provided in one or more administrations. For purposes of the present disclosure, an effective amount of antibody, drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition (e.g., an effective amount as administered as a monotherapy or combination therapy). Thus, an "effective amount" may be considered in the context of administering one or more therapeutic agents, and a single agent may be considered to be given in an effective amount if, in conjunction with one or more other agents, a desirable result may be or is achieved.

III. Activatable Binding Polypeptide Libraries and Generation of Libraries

Certain aspects of the present disclosure relate to polynucleotides (e.g., encoding any of the polypeptides described herein) and/or libraries of polynucleotides e.g., that encode polypeptides useful for screening for and/or identifying one or more activatable binding polypeptides (i.e., one or more activatable antibodies), including activatable antibodies, activatable antigen binding fragments thereof, or derivatives of activatable antibodies.

The term "activatable binding polypeptide", "ABP", or "activatable antibody" includes a polypeptide that comprises a target binding moiety (TBM), a cleavable moiety (CM), and a masking moiety (MM). In some embodiments, the TBM comprises an amino acid sequence that binds to a target. In some embodiments, the TBM comprises an antigen binding domain (ABD) of an antibody or antibody fragment thereof. In some embodiments, the TBM comprises an antibody light chain variable region (VL) and an antibody heavy chain variable region (VH), wherein the VH and VL forms a binding domain that binds to the target in the absence of the MM. In some embodiments, the VH and VL are covalently linked, e.g., in an scFv. In some embodiments, the VH and VL form a Fab fragment. In some embodiments, the VH is linked to an antibody heavy chain constant region, and the VL is linked to an antibody light chain constant region.

In some embodiments, the activatable antibody comprises a polypeptide comprising the structure, from N-terminus to C-terminus, of: masking moiety (MM)-cleavable moiety (CM)-VL, and the activatable antibody further comprises a second polypeptide comprising a VH (e.g., a Fab fragment). In some embodiments, the activatable antibody comprises a polypeptide comprising the structure, from N-terminus to C-terminus, of: masking moiety (MM)-cleavable moiety (CM)-VL-VH (e.g., an scFv). In some embodiments, the activatable antibody comprises a polypeptide comprising the structure, from N-terminus to C-terminus, of: masking moiety (MM)-cleavable moiety (CM)-VH, and the activatable antibody further comprises a second polypeptide comprising a VL (e.g., a Fab fragment). In some embodiments, the activatable antibody comprises a polypeptide comprising the structure, from N-terminus to C-terminus, of: masking moiety (MM)-cleavable moiety (CM)-VH-VL (e.g., an scFv).

In some embodiments, the activatable antibody comprises a polypeptide comprising the structure, from N-terminus to C-terminus, of: masking moiety (MM)-$L_1$-cleavable moiety (CM)-$L_2$-VL, and the activatable antibody further comprises a second polypeptide comprising a VH (e.g., a Fab fragment). In some embodiments, the activatable antibody comprises a polypeptide comprising the structure, from N-terminus to C-terminus, of: masking moiety (MM)-$L_1$-cleavable moiety (CM)-$L_2$-VL-$L_3$-VH (e.g., an scFv). In some embodiments, the activatable antibody comprises a polypeptide comprising the structure, from N-terminus to C-terminus, of: masking moiety (MM)-cleavable moiety (CM)-$L_1$-VH, and the activatable antibody further comprises a second polypeptide comprising a VL (e.g., a Fab fragment). In some embodiments, the activatable antibody comprises a polypeptide comprising the structure, from N-terminus to C-terminus, of: masking moiety (MM)-$L_1$-cleavable moiety (CM)-$L_2$-VH-$L_3$-VL (e.g., an scFv). In some embodiments, $L_1$, $L_2$, and/or $L_3$ are linkers. In some embodiments, each of $L_1$, $L_2$, and $L_3$ is a linker that can have an independently selected length that is either 0 amino acids or 1 or more, 2 or more, 3 or more, 4 or more, 5 or more, 6 or more, 7 or more, 8 or more, 9 or more, or 10 or more amino acids.

The CM generally includes an amino acid sequence that is cleavable, for example, serves as the substrate for an enzyme and/or a cysteine-cysteine pair capable of forming a reducible disulfide bond. As such, when the terms "cleavage," "cleavable," "cleaved" and the like are used in connection with a CM, the terms encompass enzymatic cleavage, e.g., by a protease, as well as disruption of a disulfide bond between a cysteine-cysteine pair via reduction of the disulfide bond that can result from exposure to a reducing agent.

The MM refers to an amino acid sequence that, when the CM of the activatable antibody is intact (e.g., uncleaved by a corresponding enzyme, and/or containing an unreduced cysteine-cysteine disulfide bond), the MM interferes with or inhibits binding of the TBM to its target. In some embodiments, the MM interferes with or inhibits binding of the TBM to its target so efficiently that binding of the TBM to its target is extremely low and/or below the limit of detection (e.g., binding cannot be detected in an ELISA or flow cytometry assay). The amino acid sequence of the CM may overlap with or be included within the MM. It should be noted that for sake of convenience "ABP" or "activatable antibody" are used herein to refer to an ABP or activatable antibody in both their uncleaved (or "native") state, as well as in their cleaved state. It will be apparent to the ordinarily skilled artisan that in some embodiments a cleaved ABP may lack an MM due to cleavage of the CM, e.g., by a protease, resulting in release of at least the MM (e.g., where the MM is not joined to the ABP by a covalent bond (e.g., a disulfide bond between cysteine residues)). Exemplary ABPs are described in more detail below.

A library of the present disclosure may contain one or more polynucleotides encoding any of the polypeptides described herein (e.g., one or more of the activatable binding polypeptides described herein). In some embodiments, one or more (i.e., one, some, or all) of the polynucleotides of a library described herein encode(s) a polypeptide comprising full length antibody light and/or heavy chain(s). In some embodiments, one or more (i.e., one, some, or all) of the polynucleotides of a library described herein encode(s) a polypeptide comprising light and/or heavy chain Fab fragment(s). In some embodiments, one or more (i.e., one, some, or all) of the polynucleotides of a library described herein encode(s) a polypeptide comprising single-chain variable fragment(s) (scFvs).

Other aspects of the present disclosure relate to polypeptides (e.g., any of the polypeptides described herein) and/or libraries of polypeptides useful for screening for and/or identifying one or more activatable binding polypeptides (i.e., one or more activatable antibodies), including activatable antibodies, activatable antigen binding fragments thereof, or derivatives of activatable antibodies. A library of the present disclosure may contain one or more of the polypeptides described herein (e.g., one or more activatable binding polypeptides). In some embodiments, one or more (e.g., one, some, or all) of the polypeptides of a library described herein comprise full length antibody light and/or heavy chain(s). In some embodiments, one or more (e.g., one, some, or all) of the polypeptides of a library described herein comprise light and/or heavy chain Fab fragment(s). In some embodiments, one or more (e.g., one, some, or all) of the polypeptides of a library described herein comprise single-chain variable fragment(s) (scFvs). In some embodiments, the polypeptides are expressed on a cell surface (e.g., yeast or mammalian cell display).

In some embodiments, a polypeptide of the present disclosure comprises: (a) a first peptide (FP); (b) a cleavable moiety (CM); and (c) a target binding moiety (TBM). In some embodiments, the FP is any of the first peptides described herein (e.g., a first peptide (FP) comprising an amino acid sequence according to Formula (XIII): $X_mCX_nCX_o$ (SEQ ID NO: 86), where m is from 2-10, n is from 3-10, and o is from 1-10, and each X is independently an amino acid selected from A, C, D, E, F, G, H, I, K, L, M, N, P, Q, R, S, T, V, W, and Y). In some embodiments, X is not W, M, and/or C. In some embodiments, each X in $X_m$ of formula (XIII) is independently an amino acid selected from the group consisting of D, A, Y, S, T, N, I, L, F, V, H, and P, each X in $X_n$ of formula (XIII) is independently an amino acid selected from the group consisting of D, A, Y, S, T, N, I, L, F, V, H, and P, and/or each X in $X_o$ of formula (XIII) is independently an amino acid selected from the group consisting of D, A, Y, S, T, N, I, L, F, V, H, and P. In some embodiments m is from 3-10. In some embodiments, the FP is any of the first peptides described herein (e.g., a first peptide (FP) comprising an amino acid sequence according to Formula (I): $X_mCX_nCZ_o$ (SEQ ID NO: 1), where m is from 2-10, n is from 3-10, and o is from 1-10, each X is independently an amino acid selected from A, C, D, E, F, G, H, I, K, L, M, N, P, Q, R, S, T, V, W, and Y, and each Z is independently an amino acid selected from the group consisting of D, A, Y, S, T, N, I, L, F, V, H, and P). In some embodiments m is from 3-10. In some embodiments, X is not W, M, and/or C. In some embodiments, each X in $X_m$ of formula (I) is independently an amino acid selected from the group consisting of D, A, Y, S, T, N, I, L, F, V, H, and P and/or each X in $X_n$ of formula (I) is independently an amino acid selected from the group consisting of D, A, Y, S, T, N, I, L, F, V, H, and P. In some embodiments, the FP is any of the first peptides described herein (e.g., a first peptide (FP) comprising an amino acid sequence according to Formula (XII): $Z_mCZ_nCZ_o$ (SEQ ID NO: 71), where m is from 2-10, n is from 3-10, and o is from 1-10, and each Z is independently an amino acid selected from the group consisting of D, A, Y, S, T, N, I, L, F, V, H, and P). In some embodiments m is from 3-10. In some embodiments, the CM is any of the cleavable moieties described herein (e.g., a cleavable moiety (CM) comprising at least a first protease cleavage site). In some embodiments, the CM is any of the cleavable moieties described herein (e.g., a cleavable moiety (CM) comprising at least a first protease cleavage site). In some embodiments, the TBM is any of the target binding moieties described herein (e.g., a target binding moiety (TBM) comprising an antibody light chain variable region and/or an antibody heavy chain variable region).

In some embodiments, the first peptide (FP) interferes with, obstructs, reduces the ability of, prevents, inhibits, or competes with the target binding moiety for binding to its target (e.g., an "inactive activatable antibody). In some embodiments, the first peptide (FP) interferes with, obstructs, reduces, prevents, inhibits, or competes with the target binding moiety for binding to its target only when the polypeptide has not been activated (e.g., activated by a change in pH (increased or decreased), activated by a temperature shift (increased or decreased), activated after being contacted with a second molecule (such as a small molecule or a protein ligand), etc.). In some embodiments, activation induces cleavage of the polypeptide within the cleavage moiety. In some embodiments, activation induces conformation changes in the polypeptide (e.g., displacement of the first peptide (FP)), leading to the first peptide no longer preventing the activatable antibody from binding to its target. In some embodiments, the first peptide (FP) interferes with, obstructs, reduces the ability of, prevents, inhibits, or competes with the target binding moiety for binding to its target only when the cleavable moiety (CM) has not been cleaved by one or more proteases that cleave within the cleavable moiety (CM). In some embodiments, the first peptide (FP) has a masking efficiency of at least about 2.0 (e.g., at least about 2.0, at least about 3.0, at least about 4.0, at least about 5.0, at least about 6.0, at least about 7.0, at least about 8.0, at least about 9.0, at least about 10, at least about 25, at least about 50, at least about 75, at least about 100, at least about 150, at least about 200, at least about 300, at least about 400, at least about 500, etc.) prior to activation. In some embodiments, masking efficiency is measured as the difference in affinity of an activatable antibody comprising the first peptide (FP) for binding its target (before activation) relative to the affinity of a polypeptide lacking the first peptide for binding its target (e.g., the difference in affinity for a target antigen (such as CTLA4) of an activatable antibody comprising a first peptide (FP) (before activation) relative to a parental antibody lacking the first peptide (FP), or the difference in affinity for a target antigen (such as CTLA4) of an activatable antibody comprising a first peptide (FP) (before activation) relative to the affinity for the target antigen of the activatable antibody after activation). In some embodiments, the masking efficiency is measured by dividing the $EC_{50}$ for binding of an activatable antibody comprising a first peptide (FP) (before activation) by the $EC_{50}$ of the parental antibody (e.g., by measuring $EC_{50}$ by ELISA; see e.g., the methods of Example 3). In some embodiments, masking efficiency is measured as the difference in affinity of an activatable antibody comprising the first peptide (FP) for binding its target before activation relative to the affinity of the activatable antibody comprising the first peptide (FP) for binding its target after activation (e.g., the difference in affinity for a target antigen (such as CTLA4) of an activatable antibody before activation relative to the activatable antibody after activation). In some embodiments, the first peptide (FP) binds to the target binding moiety (TBM), and prevents the activatable antibody from binding to its target (e.g., an "inactive" activatable antibody). In some embodiments, the first peptide (FP) has a dissociation constant for binding to the target binding moiety (TBM) that is greater than the dissociation constant of the target binding moiety (TBM) for its target. In some embodiments, the first peptide (FP) is a masking moiety (MM). Dissociation constants can be measured, e.g., by techniques such as ELISA, surface plasmon resonance or Bio-Layer Interferometry (BLI), or flow cytometry.

In some embodiments, the first peptide (FP) does not interfere with, obstruct, reduce the ability of, prevent, inhibit, or compete with the target binding moiety (TBM) for binding to its target after the polypeptide has been activated (e.g., activated by treatment with one or more proteases that cleave within the cleavable moiety (CM), activated by a change in pH (increased or decreased), activated by a temperature shift (increased or decreased), activated after being contacted with a second molecule (such as an enzyme), etc.). In some embodiments, the first peptide (FP) does not interfere with, obstruct, reduce the ability of, prevent, inhibit, or compete with the target binding moiety (TBM) for binding to its target after the cleavable moiety (CM) has been cleaved by one or more proteases that cleave within the cleavable moiety (CM). In some embodiments, the first peptide (FP) has a masking efficiency of at most about 1.75 (e.g., at most about 1.75, at most about 1.5, at most about 1.4, at most about 1.3, at most about 1.2, at most about 1.1, at most about 1.0, at most about 0.9, at most about 0.8, at most about 0.7, at most about 0.6, or at most about 0.5, etc.) after to activation (e.g., the relative affinity of the activatable antibody after activation as compared to the affinity of a parental antibody).

In some embodiments, a polypeptide of the present disclosure comprises the structure, from N-terminus to C-terminus, of: the first peptide (FP)—the cleavable moiety (CM)—the target binding moiety (TBM). Libraries of the present disclosure may be used to screen for one or more activatable binding polypeptides (i.e., activatable antibodies) that, when in active form, bind to any target of interest, including, for example, CTLA4, CD137, PD-1, PD-L1, PD-L2, LAG3, TIM3, B7-H3, OX40, CD3, CD19, CD20, CD40, CD95, CD120a, BTLA, VISTA, ICOS, BCMA, Her1, Her2, Her3, and/or B7-H4.

In some embodiments, a library of the present disclosure contains a plurality of polynucleotides that encodes at least one, at least 2, at least 3, at least 4, at least 5, at least 6, at least 7, at least 8, at least 9, at least 10, at least 20, at least 30, at least 40, at least 50, at least 100, at least 250, at least 500, at least $10^3$, at least $10^4$, at least $10^5$, at least $10^6$, at least $10^7$, at least $10^8$, at least $10^9$ at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$ unique polypeptides comprising: (a) a first peptide (FP); (b) a cleavable moiety (CM); and (c) a target binding moiety (TBM), as described herein.

In some embodiments, a library of the present disclosure contains a plurality of polynucleotides that encodes at least one, at least 2, at least 3, at least 4, at least 5, at least 6, at least 7, at least 8, at least 9, at least 10, at least 20, at least 30, at least 40, at least 50, at least 100, at least 250, at least 500, at least $10^3$, at least $10^4$, at least $10^5$, at least $10^6$, at least $10^7$, at least $10^8$, at least $10^9$ at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$ polypeptides comprising: (a) a unique first peptide (FP); (b) a cleavable moiety (CM); and (c) a target binding moiety (TBM), as described herein.

In some embodiments, a library of the present disclosure: 1) encodes and/or contains a smaller number of unique peptides (e.g., FPs comprising an amino acid sequence according to Formula (XIII): $X_mCX_nCX_o$ (SEQ ID NO: 86) or Formula (I): $X_mCX_nCZ_o$ (SEQ ID NO: 1)) than are found in typical random peptide libraries; 2) encodes and/or contains peptides (e.g., FPs comprising an amino acid sequence according to Formula (XIII): $X_mCX_nCX_o$ (SEQ ID NO: 86) or Formula (I): $X_mCX_nCZ_o$ (SEQ ID NO: 1)) comprising a pair of cysteine residues at fixed positions to ensure that the display peptides had constrained conformations; and/or 3) encodes and/or contains peptides (e.g., FPs comprising an amino acid sequence according to Formula (XIII): $X_mCX_nCX_o$ (SEQ ID NO: 86) or Formula (I): $X_mCX_nCZ_o$ (SEQ ID NO: 1)) harboring few or no chemically labile residues (such as methionine or tryptophan). Advantageously, libraries of the present disclosure have dramatically reduced library size relative to random peptide libraries, enabling the construction of libraries with much better coverage of the peptides (e.g., FPs comprising an amino acid sequence according to Formula (XIII): $X_mCX_nCX_o$ (SEQ ID NO: 86) or Formula (I): $X_mCX_nCZ_o$ (SEQ ID NO: 1)). Moreover, the inclusion of a pair of cysteine residues at fixed positions ensured that the display peptides had constrained conformations, tending to exhibit increased binding affinity and/or specificity. Furthermore, libraries of the present disclosure have peptides (e.g., FPs comprising an amino acid sequence according to Formula (XIII): $X_mCX_nCX_o$ (SEQ ID NO: 86) or Formula (I): $X_mCX_nCZ_o$ (SEQ ID NO: 1)) including few to no unfavorable residues for manufacturing processes, such as methionine or tryptophan.

In some embodiments, a library of the present disclosure contains a plurality of polynucleotides, with at least one of the polynucleotides in the library encoding a polypeptide comprising: (a) a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y; (b) a cleavable moiety (CM) comprising at least a first cleavage site (e.g., at least a first protease cleavage site); and c) a target binding moiety (TBM) comprising an antibody light chain variable region and/or an antibody heavy chain variable region. In some embodiments m is from 3-10. In some embodiments, at least one of the polynucleotides in the library encodes an activatable binding polypeptide (i.e., an activatable antibody). In some embodiments, one or more polynucleotides of the library are in a vector (e.g., an expression vector or display vector). In some embodiments, a library of the present disclosure contains a plurality of polynucleotides, with at least one of the polynucleotides in the library encoding a polypeptide comprising: (a) a first peptide (FP) comprising an amino acid sequence according to Formula (I): $X_mCX_nCZ_o$ (SEQ ID NO: 1), where m is from 2-10, n is from 3-10, and o is from 1-10, where each X is independently an amino acid selected from A, C, D, E, F, G, H, I, K, L, M, N, P, Q, R, S, T, V, W, and Y, and where each Z is independently an amino acid selected from D, A, Y, S, T, N, I, L, F, V, H, and P; (b) a cleavable moiety (CM) comprising at least a first cleavage site (e.g., at least a first protease cleavage site); and c) a target binding moiety (TBM) comprising an antibody light chain variable region and/or an antibody heavy chain variable region. In some embodiments m is from 3-10. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, at least one of the polynucleotides in the library encodes a polypeptide comprising an amino acid sequence according to Formula (III), $EVGSYX_1X_2X_3X_4X_5X_6CX_7X_8X_9X_{10}X_{11}X_{12}CX_{13}X_{14}$ SGRSAGGGGTENLYFQGSGGS (SEQ ID NO: 3), where $X_1$ is A, D, I, N, P, or Y, $X_2$ is A, F, N, S, or V, $X_3$ is A, H, L, P, S, V, or Y, $X_4$ is A, H, S, or Y, $X_5$ is A, D, P, S, V, or Y, $X_6$ is A, D, L, S, or Y, $X_7$ is D, P, or V, $X_8$ is A, D, H, P, S, or T, $X_9$ is A, D, F, H, P, or Y, $X_{10}$ is L, P, or Y, $X_{11}$ is F, P, or Y, $X_{12}$ is A, P, S, or Y, $X_{13}$ is A, D, N, S, T, or Y, and $X_{14}$ is A, S, or Y. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, at least one of the polynucleotides in the library encodes a polypeptide comprising an amino acid sequence selected from SEQ ID NOS: 25-46. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 250, at least 500, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$ of the polynucleotides in the library encodes a polypeptide comprising: (a) a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y; (b) a cleavable moiety (CM) comprising at least a first cleavage site (e.g., at least a first protease cleavage site); and c) a target binding moiety (TBM) comprising an antibody light chain variable region and/or an antibody heavy chain variable region. In some embodiments m is from 3-10. In some embodiments, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 250, at least 500, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$ of the polynucleotides in the library encodes a polypeptide comprising: (a) a first peptide (FP) comprising an amino acid sequence according to Formula (I): $X_mCX_nCZ_o$ (SEQ ID NO: 1), where m is from 2-10, n is from 3-10, and o is from 1-10, where each X is independently an amino acid selected from A, C, D, E, F, G, H, I, K, L, M, N, P, Q, R, S, T, V, W, and Y, and where each Z is independently an amino acid selected from D, A, Y, S, T, N, I, L, F, V, H, and P; (b) a cleavable moiety (CM) comprising at least a first cleavage site (e.g., at least a first protease cleavage site); and c) a target binding moiety (TBM) comprising an antibody light chain variable region and/or an antibody heavy chain variable region. In some embodiments m is from 3-10. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 250, at least 500, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$ of the polynucleotides in the library encodes a polypeptide comprising an amino acid sequence according to Formula (III), $EVGSYX_1X_2X_3X_4X_5X_6CX_7X_8X_9X_{10}X_{11}X_{12}CX_{13}X_{14}$ SGRSAGGGGTENLYFQGSGGS (SEQ ID NO: 3), where $X_1$ is A, D, I, N, P, or Y, $X_2$ is A, F, N, S, or V, $X_3$ is A, H, L, P, S, V, or Y, $X_4$ is A, H, S, or Y, $X_5$ is A, D, P, S, V, or Y, $X_6$ is A, D, L, S, or Y, $X_7$ is D, P, or V, $X_8$ is A, D, H, P, S, or T, $X_9$ is A, D, F, H, P, or Y, $X_{10}$ is L, P, or Y, $X_{11}$ is F, P, or Y, $X_{12}$ is A, P, S, or Y, $X_{13}$ is A, D, N, S, T, or Y, and $X_{14}$ is A, S, or Y. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 250, at least 500, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$ of the polynucleotides in the library encodes a polypeptide comprising an amino acid sequence selected from SEQ ID NOS: 25-46. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, each of the polynucleotides in the library encode a polypeptide comprising: (a) a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y; (b) a cleavable moiety (CM) comprising at least a first cleavage site (e.g., at least a first protease cleavage site); and c) a target binding moiety (TBM) comprising an antibody light chain variable region and/or an antibody heavy chain variable region. In some embodiments m is from 3-10. In some embodiments, each of the polynucleotides in the library encode a polypeptide comprising: (a) a first peptide (FP) comprising an amino acid sequence according to Formula (I): $X_mCX_nCZ_o$ (SEQ ID NO: 1), where m is from 2-10, n is from 3-10, and o is from 1-10, where each X is independently an amino acid selected from A, C, D, E, F, G, H, I, K, L, M, N, P, Q, R, S, T, V, W, and Y, and where each Z is independently an amino acid selected from D, A, Y, S, T, N, I, L, F, V, H, and P; (b) a cleavable moiety (CM) comprising at least a first cleavage site (e.g., at least a first protease cleavage site); and c) a target binding moiety (TBM) comprising an antibody light chain variable region and/or an antibody heavy chain variable region. In some embodiments m is from 3-10. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, each of the polynucleotides in the library encode a polypeptide comprising an amino acid sequence according to Formula (III), $EVGSYX_1X_2X_3X_4X_5X_6CX_7X_8X_9X_{10}X_{11}X_{12}CX_{13}X_{14}$ SGRSAGGGGTENLYFQGSGGS (SEQ ID NO: 3), where X1 is A, D, I, N, P, or Y, X2 is A, F, N, S, or V, X3 is A, H, L, P, S, V, or Y, X4 is A, H, S, or Y, X5 is A, D, P, S, V, or Y, X6 is A, D, L, S, or Y, X7 is D, P, or V, X8 is A, D, H, P, S, or T, X9 is A, D, F, H, P, or Y, X10 is L, P, or Y, X11 is F, P, or Y, X12 is A, P, S, or Y, X13 is A, D, N, S, T, or Y, and X14 is A, S, or Y. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, each of the polynucleotides in the library encodes a polypeptide comprising an amino acid sequence selected from SEQ ID NOS: 25-46. In some embodiments, at least one of the polynucleotides in the library encodes an activatable binding polypeptide (i.e., an activatable antibody). In some embodiments, one or more polynucleotides of the library are in a vector (e.g., an expression vector or display vector).

In some embodiments, a library of the present disclosure contains at least one (e.g., at least one, at least two, at least 5, at least 10, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y; (b) a cleavable moiety (CM) comprising at least a first cleavage site (e.g., at least a first protease cleavage site); c) a target binding moiety (TBM) comprising an antibody light chain variable region; and d) an antibody heavy chain variable region. In some embodiments m is from 3-10. In some embodiments, a library of the present disclosure contains at least one (e.g., at least one, at least two, at least 5, at least 10, at least 100, at least $10^3$, at least $10^4$, at least $10^5$, at least $10^6$, at least $10^7$, at least $10^8$, at least $10^9$ at least $10^{10}$ at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (I): $X_mCX_nCZ_o$ (SEQ ID NO: 1), where m is from 2-10, n is from 3-10, and o is from 1-10, where each X is independently an amino acid selected from A, C, D, E, F, G, H, I, K, L, M, N, P, Q, R, S, T, V, W, and Y, and where each Z is independently an amino acid selected from D, A, Y, S, T, N, I, L, F, V, H, and P; (b) a cleavable moiety (CM) comprising at least a first cleavage site (e.g., at least a first protease cleavage site); c) a target binding moiety (TBM) comprising an antibody light chain variable region; and d) an antibody heavy chain variable region. In some embodiments m is from 3-10. In some embodiments, the polypeptide comprising the structure, from N-terminus to C-terminus, of: first peptide (FP)-cleavable moiety (CM)-VL-VH. In some embodiments, at least one of the polypeptides is an activatable binding polypeptide (i.e., an activatable antibody). In some embodiments, a linker sequence separates the VL and VH (i.e., the structure VL-linker-VH). The inker sequence may be any linker sequence known in the art, e.g., any of the linker sequences described herein. In some embodiments, the linker sequence is any copy number of GGGGS (SEQ ID NO: 17) (e.g., repeated 2 times, repeated 3 times, etc.).

In some embodiments, a library of the present disclosure contains at least one (e.g., at least one, at least two, at least 5, at least 10, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y; (b) a cleavable moiety (CM) comprising at least a first cleavage site (e.g., at least a first protease cleavage site); c) a target binding moiety (TBM) comprising an antibody light chain variable region, and the library further comprises one or more polynucleotides encoding an antibody heavy chain variable region. In some embodiments m is from 3-10. In some embodiments, a library of the present disclosure contains at least one (e.g., at least one, at least two, at least 5, at least 10, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (I): $X_mCX_nCZ_o$ (SEQ ID NO: 1), where m is from 2-10, n is from 3-10, and o is from 1-10, where each X is independently an amino acid selected from A, C, D, E, F, G, H, I, K, L, M, N, P, Q, R, S, T, V, W, and Y, and where each Z is independently an amino acid selected from D, A, Y, S, T, N, I, L, F, V, H, and P; (b) a cleavable moiety (CM) comprising at least a first cleavage site (e.g., at least a first protease cleavage site); c) a target binding moiety (TBM) comprising an antibody light chain variable region, and the library further comprises one or more polynucleotides encoding an antibody heavy chain variable region. In some embodiments m is from 3-10. In some embodiments, the polynucleotide encoding the polypeptide comprising a target binding moiety (TBM) comprising an antibody light chain variable region, and the polynucleotide encoding an antibody heavy chain variable region are on the same vector (e.g., expressed from their own promoters) or on different vectors. In some embodiments, at least one of the polypeptides forms an activatable binding polypeptide (i.e., an activatable antibody) when coupled with the antibody heavy chain variable region.

In some embodiments, a library of the present disclosure contains at least one (e.g., at least one, at least two, at least 5, at least 10, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y; (b) a cleavable moiety (CM) comprising at least a first cleavage site (e.g., at least a first protease cleavage site); c) a target binding moiety (TBM) comprising an antibody heavy chain variable region; and d) an antibody light chain variable region. In some embodiments m is from 3-10. In some embodiments, the activatable binding polypeptide comprises a polypeptide comprising the structure, from N-terminus to C-terminus, of: first peptide (FP)-cleavable moiety (CM)-VH-VL In some embodiments, a library of the present disclosure contains at least one (e.g., at least one, at least two, at least 5, at least 10, at least 100, at least $10^3$, at least $10^4$, at least $10^5$, at least $10^6$, at least $10^7$ at least $10^8$ at least $10^9$ at least $10^{10}$ at least $10^{11}$ at least $10^{12}$ at least $10^{13}$ at least $10^{14}$ at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (I): $X_mCX_nCZ_o$ (SEQ ID NO: 1), where m is from 2-10, n is from 3-10, and o is from 1-10, where each X is independently an amino acid selected from A, C, D, E, F, G, H, I, K, L, M, N, P, Q, R, S, T, V, W, and Y, and where each Z is independently an amino acid selected from D, A, Y, S, T, N, I, L, F, V, H, and P; (b) a cleavable moiety (CM) comprising at least a first cleavage site (e.g., at least a first protease cleavage site); c) a target binding moiety (TBM) comprising an antibody heavy chain variable region; and d) an antibody light chain variable region. In some embodiments m is from 3-10. In some embodiments, the activatable binding polypeptide comprises a polypeptide comprising the structure, from N-terminus to C-terminus, of: first peptide (FP)-cleavable moiety (CM)-VH-VL. In some embodiments, at least one of the polypeptides is an activatable binding polypeptide (i.e., an activatable antibody). In some embodiments, a linker sequence separates the VH and VL (i.e., the structure VH-linker-VL). The inker sequence may be any linker sequence known in the art, e.g., any of the linker sequences described herein. In some embodiments, the linker sequence is any copy number of GGGGS (SEQ ID NO: 17) (e.g., repeated 2 times, repeated 3 times, etc.).

In some embodiments, a library of the present disclosure contains at least one (e.g., at least one, at least two, at least 5, at least 10, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y; (b) a cleavable moiety (CM) comprising at least a first cleavage site (e.g., at least a first protease cleavage site); c) a target binding moiety (TBM) comprising an antibody heavy chain variable region, and the library further comprises one or more polynucleotides encoding an antibody light chain variable region. In some embodiments m is from 3-10. In some embodiments, a library of the present disclosure contains at least one (e.g., at least one, at least two, at least 5, at least 10, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) polynucleotide encoding a polypeptide comprising: (a) a first peptide (FP) comprising an amino acid sequence according to Formula (I): $X_mCX_nCZ_o$ (SEQ ID NO: 1), where m is from 2-10, n is from 3-10, and o is from 1-10, where each X is independently an amino acid selected from A, C, D, E, F, G, H, I, K, L, M, N, P, Q, R, S, T, V, W, and Y, and where each Z is independently an amino acid selected from D, A, Y, S, T, N, I, L, F, V, H, and P; (b) a cleavable moiety (CM) comprising at least a first cleavage site (e.g., at least a first protease cleavage site); c) a target binding moiety (TBM) comprising an antibody heavy chain variable region, and the library further comprises one or more polynucleotides encoding an antibody light chain variable region. In some embodiments m is from 3-10. In some embodiments, the polynucleotide encoding the polypeptide comprising a target binding moiety (TBM) comprising an antibody heavy chain variable region, and the polynucleotide encoding an antibody light chain variable region are on the same vector (e.g., expressed from their own promoters) or on different vectors. In some embodiments, at least one of the polypeptides forms an activatable binding polypeptide (i.e., an activatable antibody) when coupled with the antibody light chain variable region.

Polynucleotides and/or polynucleotide libraries described herein may incorporate any of the HVR sequences (e.g., one, two, or three of the heavy chain variable region HVR sequences, and/or one, two, or three of the light chain variable region HVR sequences), heavy chain variable region sequences, and/or light chain variable region sequences of any of the antibodies described herein (e.g., an anti-CTLA4 antibody, an anti-CD137 antibody). Polynucleotides and/or polynucleotide libraries described herein may also incorporate any of the HVR sequences (e.g., one, two, or three of the heavy chain variable region HVR sequences, and/or one, two, or three of the light chain variable region HVR sequences), heavy chain variable region sequences, light chain variable region sequences, heavy chains, and/or light chains described in PCT application number PCT/CN2017/098333 (incorporated herein by reference in its entirety), and/or PCT application number PCT/CN2017/098299 (incorporated herein by reference in its entirety).

In some embodiments, a library of the present disclosure includes one or more vectors (e.g., an expression vector and/or display vector) encoding one or more polynucleotides (e.g., synthetic polynucleotides) of the present disclosure.

Further provided herein is a method of preparing a library, e.g., by providing and assembling the polynucleotide sequences (e.g., synthetic polynucleotide(s)) of a library of the present disclosure. Also provided herein is a method of making a library, e.g., by selecting multiple (e.g., at least one, at least two, at least 5, at least 10, at least 100, at least $10^3$, at least $10^4$, at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, at least $10^{15}$, at least $10^{16}$, at least $10^{17}$, at least $10^{18}$, or at least $10^{19}$) first peptide (FP) sequences, cleavable moiety (CM) sequences, and/or target binding moiety (TBM) sequences (e.g., any one or more of the FP, CM, and TBM sequences described herein), and assembling polynucleotide sequences encoding these sequences to produce a library of polynucleotides (e.g., synthetic polynucleotides) encoding a plurality of polypeptides. In some embodiments, at least one of the polypeptides encoded by the assembled library is an activatable binding polypeptide (i.e., an activatable antibody).

Polynucleotides encoding polypeptides as described herein can be cloned into any suitable vector for expression of a portion or the entire polypeptide sequence. In some embodiments, the polynucleotide is cloned into a vector allowing for production of a portion or the entire polypeptide fused to all or a portion of a protein (e.g., a viral coat protein, a bacterial surface protein, a yeast surface protein, an insect cell surface protein, a mammalian cell surface protein) (i.e., creating a fusion protein) and displayed on the surface of a particle or cell. Several types of vectors are available and may be used to practice the present disclosure, for example, phagemid vectors. Phagemid vectors generally contain a variety of components including promoters, signal sequences, phenotypic selection genes, origin of replication sites, and other necessary components as are known to those of ordinary skill in the art. In some embodiments, the polynucleotides encoding the polypeptide regions can be cloned into vectors for expression in bacterial cells for bacterial display or in yeast cells for yeast display. Exemplary vectors are described in US PG Pub. No. US20160145604. In some embodiments, the vector is a display vector comprising, from 5' to 3', a polynucleotide encoding an amino acid sequence to be displayed on a surface (e.g., a surface of phage, bacteria, yeast, insect, or mammalian cells), a restriction site, a second polynucleotide encoding a surface peptide capable of being displayed on the surface, and a second restriction site. In some embodiments, the second polynucleotide encodes a phage coat protein, a yeast outer wall protein (such as Aga2), a bacterial outer membrane protein, a cell surface tether domain, or an adapter, or a truncation or derivative thereof. In some embodiments, the surface peptide is for phage display, yeast display, bacterial display, insect display, or mammalian display, or shuttling display there between. In some embodiments, when expressed, the amino acid sequence and the surface peptide are displayed as a fusion protein on the surface. In some embodiments, the vector further comprises a fusion tag 5' to the first restriction site or 3' to the second restriction site.

Certain aspects of the present disclosure relate to a population of cells containing vector(s) described herein. Polypeptides encoded by polynucleotides generated by any of the techniques described herein, or other suitable techniques, can be expressed and screened to identify activatable binding polypeptides having desired structure and/or activity. Expression of the polypeptides can be carried out, for example, using cell-free extracts (e.g., ribosome display), phage display, prokaryotic cells (e.g., bacterial display), or eukaryotic cells (e.g., yeast display). In some embodiments, the cells are bacterial cells, yeast cells, insect cells, or mammalian cells (such as Chinese Hamster Ovary (CHO) cells). Methods for transfecting bacterial cells, yeast cells, or mammalian cells are known in the art and described in the references cited herein. Expression (e.g., from a library of the present disclosure) of polypeptides (e.g., one or more activatable binding polypeptides) in these cell types, as well as screening for activatable binding polypeptides of interest, are described in more detail below.

Alternatively, the polynucleotides can be expressed in an *E. coli* expression system, such as that described by Pluckthun and Skerra. (Meth. Enzymol., 1989, 178: 476; Biotechnology, 1991, 9: 273). The mutant proteins can be expressed for secretion in the medium and/or in the cytoplasm of the bacteria, as described by Better and Horwitz, Meth. Enzymol., 1989, 178: 476. In some embodiments, the polypeptides are attached to the 3' end of a sequence encoding a signal sequence, such as the ompA, phoA or pelB signal sequence (Lei et al., J. Bacteriol., 1987, 169: 4379). These gene fusions are assembled in a dicistronic construct, so that they can be expressed from a single vector and secreted into the periplasmic space of *E. coli* where they will refold and can be recovered in active form. (Skerra et al., Biotechnology, 1991, 9: 273). For example, a gene encoding a polypeptide comprising a first peptide (FP), a cleavable moiety (CM), and a target binding moiety (TBM) comprising an antibody light chain can be concurrently expressed with an antibody heavy chain gene to produce a polypeptide of interest.

In other embodiments, the polypeptide sequences of the present disclosure are expressed on the membrane surface of a prokaryote, e.g., *E. coli*, using a secretion signal and lipidation moiety as described, e.g., in US20040072740; US20030100023; and US20030036092.

Alternatively, polypeptide sequences of the present disclosure can be expressed and screened by anchored periplasmic expression (APEx 2-hybrid surface display), as described, for example, in Jeong et al., PNAS, 2007, 104: 8247 or by other anchoring methods as described, for example, in Mazor et al., Nature Biotechnology, 2007, 25: 563.

Higher eukaryotic cells, such as mammalian cells, for example myeloma cells (e.g., NS/0 cells), hybridoma cells, Chinese hamster ovary (CHO) cells, and human embryonic kidney (HEK) cells, can also be used for expression of the polypeptides of the present disclosure. Polypeptides (e.g., activatable binding polypeptides) expressed in mammalian cells may be designed to be secreted into the culture medium, or expressed on the surface of the cell.

In other embodiments, polypeptides (e.g., activatable binding polypeptides) can be selected using mammalian cell display (Ho et al., PNAS, 2006, 103: 9637). In some embodiments, as described above and exemplified below, polypeptides (e.g., activatable binding polypeptides) can be selected after production of a portion or the entire polypeptide sequence fused to all or a portion of a viral coat protein (i.e., creating a fusion protein) and displayed on the surface of a particle or cell, e.g., using phage display.

Certain aspects of the present disclosure relate to a non-human animal comprising a polynucleotide or polynucleotide library of the present disclosure. For example, a non-human animal of the present disclosure may be modified such that its genome includes a polynucleotide encoding a polypeptide (e.g., an activatable binding polypeptide) of the present disclosure. In some embodiments, the transgenic animal (e.g., mouse) expresses polypeptides encoded by the polynucleotides. Techniques for modifying the genome of a non-human animal are known in the art (e.g., methods used to generate Xenomouse™).

The screening for activatable binding polypeptides derived from the libraries of the present disclosure can be carried out by any appropriate means (e.g., determining target binding before and after activation (such as treatment of a polypeptide with one or more proteases that cleave a sequence within the cleavable moiety (CM))). For example, binding activity can be evaluated by standard immunoassay and/or affinity chromatography. Screening of the polypeptides of the present disclosure for catalytic function, e.g., proteolytic function can be accomplished using a standard assays, e.g., a hemoglobin plaque assay. Determining binding affinity of a polypeptide (e.g., an activatable binding polypeptide) to a target can be assayed in vitro using a variety of well-known techniques, e.g., an ELISA, a BIACORE™ instrument, which measures binding rates of an protein to a given target based on surface plasmon resonance, or Bio-Layer Interferometry (BLI), as exemplified below using the ForteBio Octet® RED96 platform (Pall Life Sciences). In vivo assays can be conducted using any of a number of animal models and then subsequently tested, as appropriate, in humans. Cell-based biological assays are also contemplated. The polypeptides (e.g., activatable binding polypeptides) can be further selected for functional activity, for example, antagonist or agonist activity. For example, in some embodiments, affinity of binding between a polypeptide comprising fab fragment(s) and one or more target(s) is measured using BLI by tagging antigens with human IgG1-Fc tag and capture by Anti-hIgG-Fc Capture (AHC) Biosensor (e.g., before and after activation). Polypeptides can be tagged at the C-terminus of the CH1 domain with a His6 tag, over-expressed in a host cell such as *E. coli*, and purified, e.g., using a Ni-NTA resin. Affinity can then be measured using AHC sensors (anti-human IgG-Fc capture dip and read biosensors) dipped into wells containing the purified polypeptides comprising the Fabs diluted, e.g., to 5-10 μg/mL with kinetic buffer (e.g., before and after activation).

After binders are identified (e.g., by determining that the polypeptide is capable of binding to a target or antigen when "active" (e.g., after treatment with protease), but not when "inactive" (e.g., before treatment with protease)), the nucleic acid can be extracted. Extracted DNA can then be used directly to transform *E. coli* host cells or alternatively, the encoding sequences can be amplified, for example using PCR with suitable primers, and sequenced by any typical sequencing method. DNA sequences of the binders can be restriction enzyme digested and then inserted into a vector for protein expression.

First Peptides (FPs)

In some embodiments, the present disclosure relates to polynucleotides and/or polynucleotide libraries encoding one or more polypeptides comprising a first peptide (FP). In some embodiments, the present disclosure relates to polypeptides and/or polypeptide libraries comprising at least one polypeptide comprising a first peptide (FP). In some embodiments, the first peptide (FP) comprises an amino acid sequence according to Formula (XIII): $X_mCX_nCX_o$ (SEQ ID NO: 86), where m is from 2-10 (e.g., from 3-10), n is from 3-10, and o is from 1-10, and where each X is independently an amino acid selected from the group consisting of A, C, D, E, F, G, H, I, K, L, M, N, P, Q, R, S, T, V, W, and Y. In some embodiments m is from 3-10. In some embodiments, X is not W, M, and/or C. In some embodiments, each X in $X_m$ of formula (XIII) is independently an amino acid selected from the group consisting of D, A, Y, S, T, N, I, L, F, V, H, and P, each X in $X_n$ of formula (XIII) is independently an amino acid selected from the group consisting of D, A, Y, S, T, N, I, L, F, V, H, and P, and/or each X in $X_o$ of formula (XIII) is independently an amino acid selected from the group consisting of D, A, Y, S, T, N, I, L, F, V, H, and P. In some embodiments, the FP comprises a polypeptide encoded by a polynucleotide sequence according to Formula (XIV): $(NNK)_mTGY(NNK)_nTGY(NNK)_o$ (SEQ ID NO: 87), where each N is independently A, G, T, or C, where each K is independently T or G, and where each Y is independently T or C, and wherein each H is independently A, T, or C.

In some embodiments, the first peptide (FP) comprises an amino acid sequence according to Formula (I): $X_mCX_nCZ_o$ (SEQ ID NO: 1), where m is from 2-10 (e.g., from 3-10), n is from 3-10, and o is from 1-10, where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P. In some embodiments m is from 3-10. In some embodiments, X is not W, M, and/or C. In some embodiments, each X in $X_m$ of formula (I) is independently an amino acid selected from the group consisting of D, A, Y, S, T, N, I, L, F, V, H, and P and each X in $X_n$ of formula (I) is independently an amino acid selected from the group consisting of D, A, Y, S, T, N, I, L, F, V, H, and P. In some embodiments, the FP comprises a polypeptide encoded by a polynucleotide sequence according to Formula (II): $(NNK)_mTGY(NNK)_nTGY(NHC)_o$ (SEQ ID NO: 2), wherein each N is independently A, G, T, or C, wherein each K is independently T or G, wherein each Y is independently T or C, and wherein each H is independently A, T, or C.

In some embodiments, the first peptide (FP) comprises an amino acid sequence according to Formula (XII): $Z_mCZ_nCZ_o$ (SEQ ID NO: 71), where m is from 2-10 (e.g., from 3-10), n is from 3-10, and o is from 1-10, and each Z is independently an amino acid selected from the group consisting of D, A, Y, S, T, N, I, L, F, V, H, and P. In some embodiments m is from 3-10.

In some embodiments, m is from 2-5, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, m is from 6-8. In some embodiments, m is 2, 3, 4, 5, 6, 7, 8, 9, or 10. In some embodiments, m is 6.

In some embodiments, n is from 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10. In some embodiments, n is from 6-8. In some embodiments, n is 3, 4, 5, 6, 7, 8, 9, or 10. In some embodiments, n is 6. In some embodiments, n is 8.

In some embodiments, o is from 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5- 9, 5-8, 5-7, 5-6, 6-10, 6-9, 6-8, 6-7, 7-10, 7-9, 7-8, 8-10, 8-9, or 9-10. In some embodiments, o is from 1-2. In some embodiments, o is 1, 2, 3, 4, 5, 6, 7, 8, 9, or 10. In some embodiments, o is 2.

In some embodiments, the first peptide (FP) comprises an amino acid sequence according to Formula (IV): $Z_6CX_6CZ_2$ (SEQ ID NO: 55), where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, the first peptide (FP) comprises an amino acid sequence according to Formula (V): $Z_6CX_8CZ_2$ (SEQ ID NO: 56) where each X is independently an amino acid selected from the group consisting of A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, the first peptide (FP) comprises an amino acid sequence according to Formula (VI): $(Z_6)C(Z_6)C(Z_2)$ (SEQ ID NO: 57), where each Z is independently an amino acid selected from the group consisting of D, A, Y, S, T, N, I, L, F, V, H, and P.

In some embodiments, the first peptide (FP) comprises an amino acid sequence according to Formula (VII): $(Z_6)C(Z_8)C(Z_2)$ (SEQ ID NO: 58), where each Z is independently an amino acid selected from the group consisting of D, A, Y, S, T, N, I, L, F, V, H, and P.

In some embodiments, the first peptide (FP) comprises an amino acid sequence selected from the group consisting of (SEQ ID NO: 88)
$X_m$CADAPNHCXX, (SEQ ID NO: 89)
$X_m$CHHSPANCXX, (SEQ ID NO: 90)
$X_m$CPILRHRCXX, (SEQ ID NO: 91)
$X_m$CKWRPSRCXX, -continued (SEQ ID NO: 92)
$X_m$CRVLPRRCXX, (SEQ ID NO: 93)
$X_m$CLWRHRSCXX,
and (SEQ ID NO: 94)
$X_m$CPRLRRKCXX, where m is from 2-10, and where each X is independently an amino acid selected from the group consisting of A, C, D, E, F, G, H, I, K, L, M, N, P, Q, R, S, T, V, W, and Y. In some embodiments, each X is not M, W, or C. In some embodiments, each X is independently an amino acid selected from the group consisting of D, A, Y, S, T, N, I, L, F, V, H, and P. In some embodiments, m is 2. In some embodiments, the first peptide (FP) comprises the amino acid sequence (SEQ ID NO: 95)
EVGSYPTDLDACADAPNHCHF, (SEQ ID NO: 96)
EVGSYSSTHAHCHHSPANCIS, (SEQ ID NO: 97)
EVGSYDTDYDFCPILRHRCDS, (SEQ ID NO: 98)
EVGSYNDYNYHCKWRPSRCHN, (SEQ ID NO: 99)
EVGSYYHDYDDCRVLPRRCFN, (SEQ ID NO: 100)
EVGSYSNNFASCLWRHRSCAD,
or (SEQ ID NO: 101)
EVGSYTDNYDYCPRLRRKCYH.

In some embodiments, the target binding moiety (TBM) comprises a sequence of one or more of the anti-CD137 antibodies described herein, including antibodies described with reference to specific amino acid sequences of HVRs, variable regions (VL, VH), and/or light and heavy chains (e.g., IgG1, IgG2, IgG4). In some embodiments, the target binding moiety (TBM) comprises a full length antibody light chain of one or more of the anti-CD137 antibodies described herein.

In some embodiments, the first peptide (FP) comprises an amino acid sequence selected from the group consisting of (SEQ ID NO: 102)
$X_m$CPDHPYPCXX, (SEQ ID NO: 103)
$X_m$CDAFYPYCXX, (SEQ ID NO: 104)
$X_m$CDSHYPYCXX,
and (SEQ ID NO: 105)
$X_m$CVPYYYACXX, where m is from 2-10, and where each X is independently an amino acid selected from the group consisting of A, C, D, E, F, G, H, I, K, L, M, N, P, Q, R, S, T, V, W, and Y. In some embodiments, the first peptide (FP) comprises the amino acid sequence (SEQ ID NO: 110)
EVGSYNFVADSCPDHPYPCSA, (SEQ ID NO: 111)
EVGSYIVHHSDCDAFYPYCDS, (SEQ ID NO: 112)
EVGSYYSAYPACDSHYPYCNS, (SEQ ID NO: 113)
EVGSYPNPSSDCVPYYYACAY, (SEQ ID NO: 114)
EVGSYYSAYPACDSHYPYCQS, (SEQ ID NO: 115)
EVGSYYSAYPACDSHYPYCNS, (SEQ ID NO: 116)
EVGSYPQPSSDCVPYYYACAY,
or (SEQ ID NO: 117)
EVGSYPNPASDCVPYYYACAY.

In some embodiments, the target binding moiety (TBM) comprises a sequence of one or more of the anti-CTLA4 antibodies described herein, including antibodies described with reference to specific amino acid sequences of HVRs, variable regions (VL, VH), and/or light and heavy chains (e.g., IgG1, IgG2, IgG4). In some embodiments, the target binding moiety (TBM) comprises a full length antibody light chain of one or more of the anti-CTLA4 antibodies described herein.

In some embodiments, the first peptide (FP) comprises an amino acid sequence selected from SEQ ID NOS: 72-85.

In some embodiments, any of the first peptides (FPs) described herein may further comprise one or more additional amino acid sequences (e.g., one or more polypeptide tags). Examples of suitable additional amino acid sequence may include, without limitation, purification tags (such as his-tags, flag-tags, maltose binding protein and glutathione-S-transferase tags), detection tags (such as tags that may be detected photometrically (e.g., red or green fluorescent protein, etc.)), tags that have a detectable enzymatic activity (e.g., alkaline phosphatase, etc.), tags containing secretory sequences, leader sequences, and/or stabilizing sequences, protease cleavage sites (e.g., furin cleavage sites, TEV cleavage sites, Thrombin cleavage sites), and the like. In some embodiments, the one or more additional amino acid sequences are at the N-terminus of the first peptide (FP). In some embodiments, the additional amino acid sequence comprises or consists of the sequence EVGSY (SEQ ID NO: 16).

In some embodiments, the first peptide is a masking peptide that binds to the target binding moiety (TBM) and inhibits the polypeptide from binding to its target before activation (e.g., before treatment with one or more proteases that cleave within the cleavable moiety (CM), before undergoing a (local) change in pH (increased or decreased), before a temperature shift (increased or decreased), before being contacted with a second molecule (such as a small molecule or a protein ligand), etc.), but does not bind to the TBM and/or inhibit the polypeptide from binding to its target after activation (e.g., after treatment with one or more proteases that cleave within the cleavable moiety (CM), after undergoing a (local) change in pH (increased or decreased), after a temperature shift (increased or decreased), after being contacted with a second molecule (such as a small molecule or a protein ligand), etc.). In some embodiments, the first peptide (FP) (e.g., a masking moiety) inhibits binding of a polypeptide (e.g., an activatable binding polypeptide (i.e., an activatable antibody)) to its target when the CM is not cleaved, but does not inhibit binding of a polypeptide (e.g., an activatable binding polypeptide (i.e., an activatable antibody)) to its target when the CM is cleaved. In some embodiments, the first peptide (FP) (e.g., a masking moiety) has a dissociation constant for binding to the TBM that is greater (e.g., at least about 1.5-fold greater, at least about 2-fold greater, at least about 2.5-fold greater, at least about 3-fold greater, at least about 3.5-fold greater, at least about 4-fold greater, at least about 4.5-fold greater, at least about 5-fold greater, at least about 10-fold greater, at least about 100-fold greater, at least about 500-fold greater, etc.) than the dissociation constant of the polypeptide (e.g., an activatable polypeptide (i.e., activatable antibody)) for its target.

Cleavable Moieties (CMs)

In some embodiments, the present disclosure relates to polynucleotides and/or polynucleotide libraries encoding one or more polypeptides comprising a cleavable moiety (CM). In some embodiments, the present disclosure relates to polypeptides and/or polypeptide libraries comprising at least one polypeptide comprising a cleavable moiety (CM).

In some embodiments, the cleavable moiety (CM) comprises at least a first cleavage site ($CS_1$) (e.g., a first protease cleavage site). In some embodiments, the first cleavage site is a first protease cleavage site. Any suitable protease cleavage site recognized and/or cleaved by any protease (e.g., a protease that is known to be co-localized with a target of a polypeptide comprising the CM) known in the art may be used, including, for example, a protease cleavage site recognized and/or cleaved by urokinase-type plasminogen activator (uPA); matrix metalloproteinases (e.g., MMP-1, MMP-2, MMP-3, MMP-7, MMP-8, MMP-9, MMP-10, MMP-11, MMP-12, MMP-13, MMP-14, MMP-15, MMP-16, MMP-17, MMP-19, MMP-20, MMP-23, MMP-24, MMP-26, and/or MMP-27); Tobacco Etch Virus (TEV) protease; plasmin; Thrombin; PSA; PSMA; ADAMS/ADAMTS (e.g., ADAM 8, ADAM 9, ADAM10, ADAM12, ADAM15, ADAM17/TACE, ADAMDEC1, ADAMTS1, ADAMTS4, and/or ADAMTS5); caspases (e.g., Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, and/or Caspase-14); aspartate proteases (e.g., RACE and/or Renin); aspartic cathepsins (e.g., Cathepsin D and/or Cathepsin E); cysteine cathepsins (e.g., Cathepsin B, Cathepsin C, Cathepsin K, Cathepsin L, Cathepsin S, Cathepsin V/L2, and/or Cathepsin X/Z/P); cysteine proteinases (e.g., Cruzipain, Legumain, and/or Otubain-2); KLKs (e.g., KLK4, KLK5, KLK6, KLK7, KLK8, KLK10, KLK11, KLK13, and/or KLK14); metallo proteainases (e.g., Meprin, Neprilysin, PSMA, and/or BMP-1); serine proteases (e.g., activated protein C, Cathepsin A, Cathepsin G, Chymase, and/or coagulation factor proteases (such as FVIIa, FIXa, FXa, FXIa, FXIIa)); elastase; granzyme B; guanidinobenzoatase; HtrA1; human neutrophil elastase; lactoferrin; marapsin; NS3/4A; PACE4; tPA; tryptase; type II transmembrane serine proteases (TTSPs) (e.g., DESC1, DPP-4, FAP, Hepsin, Matriptase-2, MT-SP1/Matriptase, TMPRSS2, TMPRSS3 and/or TMPRSS4); etc. In some embodiments, the first protease cleavage site is a cleavage site for a protease selected from uPA, MMP-1, MMP-2, MMP-3, MMP-8, MMP-9, MMP-14, TEV protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In some embodiments, the first protease cleavage site is a cleavage site for a protease selected from uPA, MMP-2, MMP-9, and/or TEV protease. In some embodiments, the protease cleavage comprises an amino acid sequence selected from SGRSA (SEQ ID NO: 13), PLGLAG (SEQ ID NO: 14), and ENLYFQG (SEQ ID NO: 15).

In some embodiments, a polypeptide comprising a first peptide (FP) and a cleavable moiety (CM) comprises an amino acid sequence according to Formula (VIII): EVGSY (Z6)C(Z6)C(Z2)SGRSA (SEQ ID NO: 4), where each Z is independently an amino acid selected from D, A, Y, S, T, N, I, L, F, V, H, and P.

In some embodiments, a polypeptide comprising a first peptide (FP) and a cleavable moiety (CM) comprises an amino acid sequence according to Formula (IX): EVGSY (Z6)C(X6)C(Z2)SGRSA (SEQ ID NO: 5), where each X is independently an amino acid selected from A, C, D, E, F, G, H, I, K, L, M, N, P, Q, R, S, T, V, W, and Y, and where each Z is independently an amino acid selected from the group consisting of D, A, Y, S, T, N, I, L, F, V, H, and P.

In some embodiments, a polypeptide comprising a first peptide (FP) and a cleavable moiety (CM) comprises an amino acid sequence according to Formula (X): EVGSY (Z6)C(Z8)C(Z2)SGRSA (SEQ ID NO: 6), where each Z is independently an amino acid selected from D, A, Y, S, T, N, I, L, F, V, H, and P.

In some embodiments, a polypeptide comprising a first peptide (FP) and a cleavable moiety (CM) comprises an amino acid sequence according to Formula (XI): EVGSY (Z6)C(X8)C(Z2)SGRSA (SEQ ID NO: 7), where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P.

In some embodiments, the cleavable moiety (CM) further comprises a first linker ($L_1$). In some embodiments, the first linker ($L_1$) is C-terminal to the first cleavage site ($CS_1$) (e.g., a first protease cleavage site). In some embodiments, the cleavable moiety (CM) comprises a structure, from N-terminus to C-terminus, of: ($CS_1$)-$L_1$.

Any suitable linker (e.g., a flexible linker) known in the art may be used, including, for example: glycine polymers (G)n, where n is an integer of at least 1 (e.g., at least one, at least 2, at least 3, at least 4, at least 5, at least 6, at least 7, at least 8, at least 9, at least 10, etc.); glycine-serine polymers (GS)n, where n is an integer of at least 1 (e.g., at least one, at least 2, at least 3, at least 4, at least 5, at least 6, at least 7, at least 8, at least 9, at least 10, etc.) such as GGGGS (SEQ ID NO: 17), SGGS (SEQ ID NO: 18), GGSG (SEQ ID NO: 19), GGSGG (SEQ ID NO: 20), GSGSG (SEQ ID NO: 21), GSGGG (SEQ ID NO: 22), GGGSG (SEQ ID NO: 23), and/or GSSSG (SEQ ID NO: 24)); glycine-alanine polymers; alanine-serine polymers; and the like. Linker sequences may be of any length, such as from about 1 amino acid (e.g., glycine or serine) to about 20 amino acids (e.g., 20 amino acid glycine polymers or glycine-serine polymers), about 1 amino acid to about 15 amino acids, about 3 amino acids to about 12 amino acids, about 4 amino acids to about 10 amino acids, about 5 amino acids to about 9 amino acids, about 6 amino acids to about 8 amino acids, etc. In some embodiments, the linker is any of about 1, 2, 3, 4, 5, 6, 7, 8, 9, 10, 11, 12, 13, 14, 15, 16, 17, 18, 19, or 20 amino acids in length. In some embodiments, the linker comprises an amino acid sequence selected from SEQ ID NOS: 17-24. In some embodiments, the linker comprises an amino acid sequence of SEQ ID NO: 17 or 18.

In some embodiments, the cleavable moiety (CM) further comprises at least a second cleavage site (e.g., at least a second, at least a third, at least a fourth, at least a fifth, etc.). In some embodiments, the cleavable moiety (CM) further comprises a second cleavage site ($CS_2$). In some embodiments, the second cleavage site is a second protease cleavage site. The second protease cleavage site may be any suitable protease cleavage site recognized and/or cleaved by any of the proteases described above. In some embodiments, the first ($CS_1$) and second ($CS_2$) cleavage sites are protease cleavage sites recognized and/or cleaved by the same protease. In some embodiments, the first ($CS_1$) and second ($CS_2$) cleavage sites are protease cleavage sites recognized and/or cleaved by different proteases (e.g., the first protease cleavage site is recognized and/or cleaved by uPA, and the second protease cleavage site is recognized and/or cleaved by MMP-2; the first protease cleavage site is recognized and/or cleaved by uPA, and the second protease cleavage site is recognized and/or cleaved by MMP-9; the first protease cleavage site is recognized and/or cleaved by uPA, and the second protease cleavage site is recognized and/or cleaved by TEV protease; etc.). In some embodiments, the at least second cleavage site ($CS_2$) is C-terminal to the first linker ($L_1$). In some embodiments, the cleavable moiety (CM) comprises a structure, from N-terminus to C-terminus, of: ($CS_1$)-$L_1$-($CS_2$).

In some embodiments, the cleavable moiety (CM) further comprises at least a second linker (e.g., at least a second, at least a third, at least a fourth, at least a fifth, etc.). In some embodiments, the cleavable moiety (CM) further comprises a second linker ($L_2$). The second linker ($L_2$) may be any suitable linker described above. In some embodiments, the second linker comprises an amino acid sequence selected from SEQ ID NO: 17-24. In some embodiments, the first ($L_1$) and second ($L_2$) linkers are the same (e.g., both linkers comprise the sequence of SEQ ID NO: 17 or 18). In some embodiments, the first ($L_1$) and second ($L_2$) linkers are different (e.g., the first linker ($L_1$) comprises the amino acid sequence of SEQ ID NO: 17, and the second linker ($L_2$) comprises the amino acid sequence of SEQ ID NO: 18, etc.). In some embodiments, the at least second linker ($L_2$) is C-terminal to the second cleavage site ($CS_2$). In some embodiments, the cleavable moiety (CM) comprises a structure, from N-terminus to C-terminus, of: ($CS_1$)-$L_1$-($CS_2$)-$L_2$.

Exemplary FP-CM Sequences

In some embodiments, a polypeptide of the present disclosure comprises the structure, from N-terminus to C-terminus, of: (FP)-($PCS_1$)-$L_1$-($PCS_2$)-$L_2$. In some embodiments, a polypeptide of the present disclosure comprises the amino acid sequence of:

(SEQ ID NO: 25)
EVGSYDALHYACPPDYYACYYSGRSAGGGGTENLYFQGSGGS;

(SEQ ID NO: 26)
EVGSYNSYHAYCPHPLYPCTASGRSAGGGGTENLYFQGSGGS;

(SEQ ID NO: 27)
EVGSYASSAVLCVTAYFSCNSSGRSAGGGGTENLYFQGSGGS;

(SEQ ID NO: 28)
EVGSYNFVADSCPDHPYPCSASGRSAGGGGSPLGLAGSGGS;

(SEQ ID NO: 29)
EVGSYNFVADSCPDHPYPCSASGRSAGGGGTENLYFQGSGGS;

(SEQ ID NO: 30)
EVGSYIVHHSDCDAFYPYCDSSGRSAGGGGSPLGLAGSGGS;

-continued (SEQ ID NO: 31)
EVGSYIVHHSDCDAFYPYCDSSGRSAGGGGTENLYFQGSGGS;

(SEQ ID NO: 32)
EVGSYYSAYPACDSHYPYCNSSGRSAGGGGSPLGLAGSGGS;

(SEQ ID NO: 33)
EVGSYYSAYPACDSHYPYCNSSGRSAGGGGTENLYFQGSGGS;

(SEQ ID NO: 34)
EVGSYPNPSSDCVPYYYACAYSGRSAGGGGSPLGLAGSGGS;

(SEQ ID NO: 35)
EVGSYPNPSSDCVPYYYACAYSGRSAGGGGTENLYFQGSGGS;

(SEQ ID NO: 36)
EVGSYYSAYPACDSHYPYCQSSGRSAGGGGSPLGLAGSGGS;

(SEQ ID NO: 37)
EVGSYYSAYPACDSHYPYCNSAGRSAGGGGSPLGLAGSGGS;

(SEQ ID NO: 38)
EVGSYPQPSSDCVPYYYACAYSGRSAGGGGSPLGLAGSGGS;

(SEQ ID NO: 39)
EVGSYPNPASDCVPYYYACAYSGRSAGGGGSPLGLAGSGGS;

(SEQ ID NO: 40)
EVGSYPTDLDACADAPNHCHFSGRSAGGGGSPLGLAGSGGS;

(SEQ ID NO: 41)
EVGSYSSTHAHCHHSPANCISSGRSAGGGGSPLGLAGSGGS;

(SEQ ID NO: 42)
EVGSYDTDYDFCPILRHRCDSSGRSAGGGGSPLGLAGSGGS;

(SEQ ID NO: 43)
EVGSYNDYNYHCKWRPSRCHNSGRSAGGGGSPLGLAGSGGS;

(SEQ ID NO: 44)
EVGSYYHDYDDCRVLPRRCFNSGRSAGGGGSPLGLAGSGGS;

(SEQ ID NO: 45)
EVGSYSNNFASCLWRHRSCADSGRSAGGGGSPLGLAGSGGS;
and/or (SEQ ID NO: 46)
EVGSYTDNYDYCPRLRRKCYHSGRSAGGGGSPLGLAGSGGS.

In some embodiments, a polypeptide of the present disclosure comprises the structure, from N-terminus to C-terminus, of: (FP)-($PCS_1$)-$L_1$-($PCS_2$)-$L_2$-(TBM).

Target Binding Moieties (TBMs)

In some embodiments, the present disclosure relates to polynucleotides and/or polynucleotide libraries encoding one or more polypeptides comprising a target binding moiety (TBM). In some embodiments, the present disclosure relates to polypeptides and/or polypeptide libraries comprising at least one polypeptide comprising a target binding moiety (TBM). In some embodiments, the target binding moiety (TBM) comprises an antibody light chain variable region and/or an antibody heavy chain variable region. In some embodiments, the target binding moiety (TBM) comprises an antibody light chain variable region. In some embodiments, the target binding moiety (TBM) comprises an antibody heavy chain variable region. In some embodiments, the target binding moiety (TBM) comprises an antibody light chain variable region and an antibody heavy chain variable region. In some embodiments, the antibody heavy chain variable region is C-terminal to the antibody light chain variable region. In some embodiments, the antibody light chain variable region is C-terminal to the antibody heavy chain variable region. In some embodiments, a target binding moiety (TBM) of the present disclosure comprises an antibody light chain variable region and/or an antibody heavy chain variable region with specificity for any target of interest, including, for example, CTLA4, CD137, PD-1, PD-L1, PD-L2, LAG3, TIM3, B7-H3, OX40, CD3, CD19, CD20, CD40, CD95, CD120a, BTLA, VISTA, ICOS, BCMA, Her 1, Her2, Her3, and/or B7-H4.

In some embodiments, the target binding moiety (TBM) comprises a full length antibody light chain and/or a full length antibody heavy chain. The antibody light chain may be a kappa or lambda light chain. The antibody heavy chain may be in any class, such as IgG, IgM, IgE, IgA, or IgD. In some embodiments, the antibody heavy chain is in the IgG class, such as IgG1, IgG2, IgG3, or IgG4 subclass. An antibody heavy chain described herein may be converted from one class or subclass to another class or subclass using methods known in the art.

Any one or more of the target binding moieties (TBMs) described herein may incorporate any of the HVR sequences (e.g., one, two, or three of the heavy chain variable region HVR sequences, and/or one, two, or three of the light chain variable region HVR sequences), heavy chain variable region sequences, and/or light chain variable region sequences of any of the antibodies described in PCT application number PCT/CN2017/098333 (incorporated herein by reference in its entirety), PCT application number PCT/CN2017/098299 (incorporated herein by reference in its entirety), PCT application number PCT/CN2017/098332 (incorporated herein by reference in its entirety), and/or the PCT application titled "Compositions Comprising Cross-reactive Anti-CTLA4 Antibodies, and Methods of Making and Using the Same", (incorporated herein by reference in its entirety).

Any one or more of the target binding moieties (TBMs) described herein may incorporate any of the HVR sequences (e.g., one, two, or three of the heavy chain variable region HVR sequences, and/or one, two, or three of the light chain variable region HVR sequences), heavy chain variable region sequences, and/or light chain variable region sequences of any of the antibodies described herein (e.g., an anti-CTLA4 antibody, an anti-CD137 antibody).

In some embodiments, the target binding moiety (TBM) comprises a sequence of one or more of the anti-CTLA4 antibodies described herein, including antibodies described with reference to specific amino acid sequences of HVRs, variable regions (VL, VH), and/or light and heavy chains (e.g., IgG1, IgG2, IgG4). In some embodiments, the target binding moiety (TBM) comprises an antibody light chain variable region comprising an HVR-L1 comprising the amino acid sequence RASQSVRGRFLA (SEQ ID NO: 62), an HVR-L2 comprising the amino acid sequence DASNRATGI (SEQ ID NO: 63), and/or an HVR-L3 comprising the amino acid sequence YCQQSSSWPPT (SEQ ID NO: 64). In some embodiments, the target binding moiety (TBM) comprises an antibody light chain variable region comprising the amino acid sequence of SEQ ID NO: 48. In some embodiments, the target binding moiety (TBM) comprises an antibody heavy chain variable region comprising an HVR-H1 comprising the amino acid sequence YSISSGYHWSWI (SEQ ID NO: 59), an HVR-H2 comprising the amino acid sequence LARIDWDDDKYYSTSLKSRL (SEQ ID NO: 60), and/or an HVR-H3 comprising the amino acid sequence ARSYVYYFDY (SEQ ID NO: 61). In some embodiments, the target binding moiety (TBM) comprises an antibody heavy chain variable region comprising the amino acid sequence of SEQ ID NO: 47. In some embodiments, the target binding moiety (TBM) comprises: a) an antibody light chain variable region comprising an HVR-L1 comprising the amino acid sequence RASQSVRGRFLA (SEQ ID NO: 62), an HVR-L2 comprising the amino acid sequence DASNRATGI (SEQ ID NO: 63), and/or an HVR-L3 comprising the amino acid sequence YCQQSSSWPPT (SEQ ID NO: 64); and b) an antibody heavy chain variable region comprising an HVR-H1 comprising the amino acid sequence YSISSGYHWSWI (SEQ ID NO: 59), an HVR-H2 comprising the amino acid sequence LARIDWDDDKYYSTSLKSRL (SEQ ID NO: 60), and/or an HVR-H3 comprising the amino acid sequence ARSYVYFDY (SEQ ID NO: 61). In some embodiments, the target binding moiety (TBM) comprises an antibody light chain variable region comprising the amino acid sequence of SEQ ID NO: 48, and an antibody heavy chain variable region comprising the amino acid sequence of SEQ ID NO: 47.

In some embodiments, the target binding moiety (TBM) comprises a sequence of one or more of the anti-CD137 antibodies described herein, including antibodies described with reference to specific amino acid sequences of HVRs, variable regions (VL, VH), and/or light and heavy chains (e.g., IgG1, IgG2, IgG4). In some embodiments, the target binding moiety (TBM) comprises an antibody light chain variable region comprising an HVR-L1 comprising the amino acid sequence RASQSIGSYLA (SEQ ID NO: 68), an HVR-L2 comprising the amino acid sequence DASNLETGV (SEQ ID NO: 69), and/or an HVR-L3 comprising the amino acid sequence YCQQGYYLWT (SEQ ID NO: 70). In some embodiments, the target binding moiety (TBM) comprises an antibody light chain variable region comprising the amino acid sequence of SEQ ID NO: 50. In some embodiments, the target binding moiety (TBM) comprises an antibody heavy chain variable region comprising an HVR-H1 comprising the amino acid sequence FSLSTGGVGVGWI (SEQ ID NO: 65), an HVR-H2 comprising the amino acid sequence LALIDWADDKYYSPSLKSRL (SEQ ID NO: 66), and/or an HVR-H3 comprising the amino acid sequence ARGGSDTVIGDWFAY (SEQ ID NO: 67). In some embodiments, the target binding moiety (TBM) comprises an antibody heavy chain variable region comprising the amino acid sequence of SEQ ID NO: 49. In some embodiments, the target binding moiety (TBM) comprises: a) an antibody light chain variable region comprising an HVR-L1 comprising the amino acid sequence RASQSIGSYLA (SEQ ID NO: 68), an HVR-L2 comprising the amino acid sequence DASNLETGV (SEQ ID NO: 69), and/or an HVR-L3 comprising the amino acid sequence YCQQGYYLWT (SEQ ID NO: 70); and b) an antibody heavy chain variable region comprising an HVR-H1 comprising the amino acid sequence FSLSTGGVGVGWI (SEQ ID NO: 65), an HVR-H2 comprising the amino acid sequence LALIDWADDKYYSPSLKSRL (SEQ ID NO: 66), and/or an HVR-H3 comprising the amino acid sequence ARGGSDTVIGDWFAY (SEQ ID NO: 67). In some embodiments, the target binding moiety (TBM) comprises an antibody light chain variable region comprising the amino acid sequence of SEQ ID NO: 50, and an antibody heavy chain variable region comprising the amino acid sequence of SEQ ID NO: 49.

V. Polypeptides and Polypeptide Libraries

Other aspects of the present disclosure relate to polypeptides (e.g., any of the polypeptides described herein) and/or libraries of polypeptides useful for screening for, identifying, and/or selecting one or more activatable binding polypeptides (i.e., one or more activatable antibodies), including activatable antibodies, activatable antigen binding fragments thereof, or derivatives of activatable antibodies. A library of the present disclosure may contain one or more of the polypeptides described herein (e.g., one or more activatable binding polypeptides). In some embodiments, one or more (e.g., one, some, or all) of the polypeptides of a library described herein comprise antigen binding domain(s). In some embodiments, one or more (e.g., one, some, or all) of the polypeptides of a library described herein comprise full length antibody light and/or heavy chain(s). In some embodiments, one or more (e.g., one, some, or all) of the polypeptides of a library described herein comprise light and/or heavy chain Fab fragment(s). In some embodiments, one or more (e.g., one, some, or all) of the polypeptides of a library described herein comprise single-chain variable fragment(s) (scFvs). In some embodiments, the polypeptides are expressed on a cell surface (e.g., yeast or mammalian cell display).

In some embodiments, a polypeptide of the present disclosure (e.g., in a library) comprises: (a) a first peptide (FP); (b) a cleavable moiety (CM); and (c) a target binding moiety (TBM). In some embodiments, the FP is any of the first peptides described herein (e.g., a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y). In some embodiments, the FP is any of the first peptides described herein (e.g., a first peptide (FP) comprising an amino acid sequence according to Formula (I): $X_mCX_nCZ_o$ (SEQ ID NO: 1), where m is from 2-10, n is from 3-10, and o is from 1-10, each X is independently an amino acid selected from A, C, D, E, F, G, H, I, K, L, M, N, P, Q, R, S, T, V, W, and Y, and each Z is independently an amino acid selected from the group consisting of D, A, Y, S, T, N, I, L, F, V, H, and P. In some embodiments m is from 3-10. In some embodiments, the CM is any of the cleavable moieties described herein (e.g., a cleavable moiety (CM) comprising at least a first protease cleavage site). In some embodiments, the TBM is any of the target binding moieties described herein (e.g., a target binding moiety (TBM) comprising an antibody light chain variable region and/or an antibody heavy chain variable region).

In some embodiments, provided herein is an antigen binding domain and/or a library comprising antigen binding domains, wherein at least one (e.g., one, some, or all) of the antigen binding domains comprises a polypeptide of the present disclosure. In some embodiments, at least one (e.g., one, some, or all) of the antigen binding domains comprises a polypeptide comprising, from N-terminus to C-terminus: (a) a first peptide (FP) (e.g., a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y); (b) a cleavable moiety (e.g., a cleavable moiety (CM) comprising at least a first protease cleavage site); and (c) a target binding moiety comprising an antibody light chain variable region. In some embodiments m is from 3-10. In some embodiments, at least one (e.g., one, some, or all) of the antigen binding domains comprises a polypeptide comprising, from N-terminus to C-terminus: (a) a first peptide (FP) (e.g., a first peptide (FP) comprising an amino acid sequence according to Formula (I): $X_mCX_nCZ_o$ (SEQ ID NO: 1), where m is from 2-10, n is from 3-10, and o is from 1-10, each X is independently an amino acid selected from A, C, D, E, F, G, H, I, K, L, M, N, P, Q, R, S, T, V, W, and Y, and each Z is independently an amino acid selected from the group consisting of D, A, Y, S, T, N, I, L, F, V, H, and P); (b) a cleavable moiety (e.g., a cleavable moiety (CM) comprising at least a first protease cleavage site); and (c) a target binding moiety comprising an antibody light chain variable region. In some embodiments, the antigen binding domain further comprises an antibody heavy chain variable region. In some embodiments m is from 3-10. In some embodiments, at least one (e.g., one, some, or all) of the antigen binding domains comprises a polypeptide comprising, from N-terminus to C-terminus: (a) a first peptide (FP) (e.g., a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y); (b) a cleavable moiety (e.g., a cleavable moiety (CM) comprising at least a first protease cleavage site); and (c) a target binding moiety comprising an antibody heavy chain variable region. In some embodiments m is from 3-10. In some embodiments, at least one (e.g., one, some, or all) of the antigen binding domains comprises a polypeptide comprising, from N-terminus to C-terminus: (a) a first peptide (FP) (e.g., a first peptide (FP) comprising an amino acid sequence according to Formula (I): $X_mCX_nCZ_o$ (SEQ ID NO: 1), where m is from 2-10, n is from 3-10, and o is from 1-10, each X is independently an amino acid selected from A, C, D, E, F, G, H, I, K, L, M, N, P, Q, R, S, T, V, W, and Y, and each Z is independently an amino acid selected from the group consisting of D, A, Y, S, T, N, I, L, F, V, H, and P); (b) a cleavable moiety (e.g., a cleavable moiety (CM) comprising at least a first protease cleavage site); and (c) a target binding moiety comprising an antibody heavy chain variable region. In some embodiments m is from 3-10. In some embodiments, the antigen binding domain further comprises an antibody light chain variable region.

In some embodiments, further provided herein is an antibody fragment or scFv comprising any of the polypeptides described herein. In some embodiments, the antibody fragment or scFv comprises a polypeptide comprising a target binding moiety (TBM) comprising an antibody light chain variable region. In some embodiments, the antibody fragment or scFv comprises a polypeptide comprising a target binding moiety (TBM) comprising an antibody heavy chain variable region. In some embodiments, provided herein is a library of antibody fragments or scFvs, wherein at least one of the antibody fragments or scFvs comprises any of the polypeptides described herein. In some embodiments, at least one (e.g., one, some, or all) of the antibody fragments or scFvs in the library comprises a polypeptide comprising a target binding moiety (TBM) comprising an antibody light chain variable region. In some embodiments, at least one (e.g., one, some, or all) of the antibody fragments or scFvs in the library comprises a polypeptide comprising a target binding moiety (TBM) comprising an antibody heavy chain variable region. Further provided herein are cells and/or a library of cells expressing one or more of the antibody fragments and/or scFvs described herein on their surface.

In some embodiments, the present disclosure relates to an antibody light chain comprising a polypeptide of the present disclosure. In some embodiments, the antibody light chain comprises a polypeptide comprising, from N-terminus to C-terminus: (a) a first peptide (FP) (e.g., a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y); (b) a cleavable moiety (e.g., a cleavable moiety (CM) comprising at least a first protease cleavage site); and (c) a target binding moiety (TBM) comprising an antibody light chain variable region. In some embodiments m is from 3-10. In some embodiments, the antibody light chain comprises a polypeptide comprising, from N-terminus to C-terminus: (a) a first peptide (FP) (e.g., a first peptide (FP) comprising an amino acid sequence according to Formula (I): $X_mCX_nCZ_o$ (SEQ ID NO: 1), where m is from 2-10, n is from 3-10, and o is from 1-10, each X is independently an amino acid selected from A, C, D, E, F, G, H, I, K, L, M, N, P, Q, R, S, T, V, W, and Y, and each Z is independently an amino acid selected from the group consisting of D, A, Y, S, T, N, I, L, F, V, H, and P); (b) a cleavable moiety (e.g., a cleavable moiety (CM) comprising at least a first protease cleavage site); and (c) a target binding moiety (TBM) comprising an antibody light chain variable region. In some embodiments m is from 3-10. In some embodiments, the present disclosure relates to a library comprising antibody light chains, where at least one (e.g., one, some, or all) of the antibody light chains in the library are antibody light chains as described above). In some embodiments, the present disclosure relates to an antibody comprising an antibody light chain and an antibody heavy chain, wherein the antibody light chain is an antibody light chain as described above. In some embodiments, the antibody heavy chain is any antibody heavy chain known in the art (including any of the antibody heavy chains described herein). In some embodiments, the present disclosure relates to a library comprising antibodies, where at least one (e.g., one, some, or all) of the antibodies are antibodies as described above).

In some embodiments, the present disclosure relates to an antibody heavy chain comprising a polypeptide of the present disclosure. In some embodiments, the antibody heavy chain comprises a polypeptide comprising, from N-terminus to C-terminus: (a) a first peptide (FP) (e.g., a first peptide (FP) comprising an amino acid sequence according to Formula (XIII): $X_mCX_nCX_o$ (SEQ ID NO: 86), where m is from 2-10, n is from 3-10, and o is from 1-10, and where each X is independently an amino acid selected from A, C, D, E, F, G, H, I, K, L, M, N, P, Q, R, S, T, V, W, and Y); (b) a cleavable moiety (e.g., a cleavable moiety (CM) comprising at least a first protease cleavage site); and (c) a target binding moiety (TBM) comprising an antibody heavy chain variable region. In some embodiments m is from 3-10. In some embodiments, the antibody heavy chain comprises a polypeptide comprising, from N-terminus to C-terminus: (a) a first peptide (FP) (e.g., a first peptide (FP) comprising an amino acid sequence according to Formula (I): $X_mCX_nCZ_o$ (SEQ ID NO: 1), where m is from 2-10, n is from 3-10, and o is from 1-10, each X is independently an amino acid selected from A, C, D, E, F, G, H, I, K, L, M, N, P, Q, R, S, T, V, W, and Y, and each Z is independently an amino acid selected from the group consisting of D, A, Y, S, T, N, I, L, F, V, H, and P); (b) a cleavable moiety (e.g., a cleavable moiety (CM) comprising at least a first protease cleavage site); and (c) a target binding moiety (TBM) comprising an antibody heavy chain variable region. In some embodiments m is from 3-10. In some embodiments, the present disclosure relates to a library comprising antibody heavy chains, where at least one (e.g., one, some, or all) of the antibody heavy chains in the library are antibody heavy chains as described above). In some embodiments, the present disclosure relates to an antibody comprising an antibody heavy chain and an antibody light chain, wherein the antibody heavy chain is an antibody heavy chain as described above. In some embodiments, the antibody light chain is any antibody light chain known in the art (including any of the antibody light chains described herein). In some embodiments, the present disclosure relates to a library comprising antibodies, where at least one (e.g., one, some, or all) of the antibodies are antibodies as described above).

Polypeptides (e.g., any of the antibodies described above) of the present disclosure may be produced using recombinant methods and compositions, e.g., as described in U.S. Pat. No. 4,816,567. In some embodiments, isolated nucleic acids encoding any or the polypeptides (e.g., any of the antibodies described above) are provided. Such nucleic acids may encode an amino acid sequence comprising the $V_L$ and/or an amino acid sequence comprising the $V_H$ of the antibodies (e.g., the light and/or heavy chains of the antibodies). In some embodiments, one or more vectors (e.g., expression vectors) comprising such nucleic acids are provided herein. In some embodiments, a host cell comprising such nucleic acids is provided. In one such embodiment, a host cell comprises (e.g., has been transformed with): (1) a vector comprising a nucleic acid that encodes an amino acid sequence comprising a polypeptide of the present disclosure comprising a $V_L$ and an amino acid sequence comprising a $V_H$ (e.g., an activatable binding polypeptide (i.e., an activatable antibody)), (2) a vector comprising a nucleic acid that encodes an amino acid sequence comprising a polypeptide of the present disclosure comprising a $V_H$ and an amino acid sequence comprising the $V_L$ (e.g., an activatable binding polypeptide (i.e., an activatable antibody)), (3) a first vector comprising a nucleic acid that encodes an amino acid sequence comprising a polypeptide of the present disclosure comprising a $V_L$ and a second vector comprising a nucleic acid that encodes an amino acid sequence comprising the $V_H$ (e.g., an activatable binding polypeptide (i.e., an activatable antibody)), or (4). a first vector comprising a nucleic acid that encodes an amino acid sequence comprising a polypeptide of the present disclosure comprising a $V_H$ and a second vector comprising a nucleic acid that encodes an amino acid sequence comprising the $V_L$ (e.g., an activatable binding polypeptide (i.e., an activatable antibody)). In some embodiments, the host cell is eukaryotic, e.g. a yeast cell, an insect cell, a Chinese Hamster Ovary (CHO) cell or lymphoid cell (e.g., Y0, NS0, Sp20 cell). In some embodiments, a method of making a polypeptide (e.g., an activatable binding polypeptide (i.e., an activatable antibody)) is provided, wherein the method comprises culturing a host cell comprising a nucleic acid encoding the polypeptide (e.g., an activatable binding polypeptide (i.e., an activatable antibody)), as provided above, under conditions suitable for expression of the polypeptide, and optionally recovering the polypeptide (e.g., an activatable binding polypeptide (i.e., an activatable antibody)) from the host cell (or host cell culture medium).

For recombinant production of polypeptides (e.g., activatable binding polypeptides (i.e., activatable antibodies)) of the present disclosure, nucleic acid encoding a polypeptide (e.g., an activatable binding polypeptide (i.e., an activatable antibody)), e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the polypeptide(s)).

Suitable host cells for cloning or expression of polypeptide-encoding (e.g., activatable binding polypeptide (i.e., an activatable antibody)-encoding) vectors include prokaryotic or eukaryotic cells. For example, polypeptides (e.g., an activatable binding polypeptide (i.e., an activatable antibody)) may be produced in bacteria, in particular when glycosylation and Fc effector function are not needed (see, e.g., U.S. Pat. Nos. 5,648,237, 5,789,199, and 5,840,523; See also Charlton, *Methods in Molecular Biology*, Vol. 248 (B. K. C. Lo, ed., Humana Press, Totowa, N.J., 2003), pp. 245-254, describing expression of antibody fragments in *E. coli*.). After expression, the polypeptide may be isolated from the bacterial cell paste in a soluble fraction and may be further purified.

In addition to prokaryotes, eukaryotic microbes such as filamentous fungi or yeast are suitable cloning or expression hosts for polypeptide-encoding (e.g., activatable binding polypeptide (i.e., activatable antibody)-encoding) vectors, including fungi and yeast strains whose glycosylation pathways have been "humanized," resulting in the production of a polypeptide with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including $DHFR^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

VI. Activatable Binding Polypeptides and their Production

In some embodiments, provided herein are activatable binding polypeptides (e.g., activatable antibodies) screened for, identified and/or selected from any of the polynucleotide and/or polypeptide libraries described herein.

In some embodiments, activatable antibodies of the present disclosure are context-dependent (e.g., are activated (are only capable of binding their targets) in certain contexts (such as in the protease-rich tumor microenvironment)). In some embodiments, the activatable antibodies of the present disclosure provide improved safety over more traditional, non-activatable antibodies (e.g., show reduced toxicity, do not induce significant alterations to the weights of many organs, do not alter liver histopathology, hematology, and/or blood biochemistry, etc.). In some embodiments, activatable antibodies of the present disclosure have improved pharmacokinetic properties as compared to more traditional, non-activatable antibodies (e.g., have longer in vivo half-lives).

In some embodiments, an activatable binding polypeptide of the present disclosure comprises: (a) a first peptide (FP) (e.g., a masking moiety), (b) a cleavable moiety, and (c) a target binding moiety. In some embodiments, the first peptide (FP) binds to the target binding moiety (TBM) of the activatable binding domain and reduces or inhibits binding of the activatable binding moiety to its target (e.g., human CTLA4 or human CD137), as compared to the binding of a corresponding binding polypeptide lacking the masking moiety to the target and/or as compared to the binding of a parental antibody to the target. In some embodiments, the masking moiety (MM) has a masking efficiency of at least about 2.0 (e.g., at least about 2.0, at least about 3.0, at least about 4.0, at least about 5.0, at least about 6.0, at least about 7.0, at least about 8.0, at least about 9.0, at least about 10, at least about 25, at least about 50, at least about 75, at least about 100, at least about 150, at least about 200, at least about 300, at least about 400, at least about 500, etc.) prior to activation. In some embodiments, masking efficiency is measured as the difference in affinity of an activatable antibody comprising the masking moiety (MM) for binding its target (before activation) relative to the affinity of a polypeptide lacking the masking moiety for binding its target (e.g., the difference in affinity for a target antigen (such as CTLA4 or CD137) of an activatable antibody comprising a masking moiety (MM) (before activation) relative to a parental antibody lacking the masking moiety (MM), or the difference in affinity for a target antigen (such as CTLA4 or CD137) of an activatable antibody comprising a masking moiety (MM) (before activation) relative to the affinity for the target antigen of the activatable antibody after activation). In some embodiments, the masking efficiency is measured by dividing the $EC_{50}$ for binding of an activatable antibody comprising a masking moiety (MM) (before activation) by the $EC_{50}$ of the parental antibody (e.g., by measuring $EC_{50}$ by ELISA; see e.g., the methods of Example 3). In some embodiments, masking efficiency is measured as the difference in affinity of an activatable antibody comprising the masking moiety (MM) for binding its target before activation relative to the affinity of the activatable antibody comprising the masking moiety (MM) for binding its target after activation (e.g., the difference in affinity for a target antigen of an activatable antibody before activation relative to the activatable antibody after activation). In some embodiments, the masking moiety (MM) binds to the target binding moiety (TBM), and prevents the activatable antibody from binding to its target (e.g., an "inactive" activatable antibody).

In some embodiments, an "activatable" binding polypeptides refers to a binding polypeptide that exhibits a first level of binding to a target when in an inhibited, masked, and/or uncleaved state, and exhibits a second level of binding to the target in an uninhibited, unmasked, and/or cleaved state, where the second level of target binding is greater than the first level of target binding. In some embodiments, access to the target by the activatable binding polypeptide is greater after cleavage within the cleavable moiety (e.g., by one or more proteases).

In some embodiments, a polypeptide of the present disclosure is generally considered to be an "activatable" binding polypeptide when binding affinity of the polypeptide to its target (e.g., human CTLA4 or CD137) increases by at least about 2-fold (e.g., at least about 2-fold, at least about 2.5-fold, at least about 3, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 25-fold, at least about 50-fold, at least about 75-fold, at least about 100-fold, at least about 250-fold, at least about 500-fold, at least about 750-fold, or at least about 1000-fold, or more) after activation of the polypeptide as compared to prior to activation of the polypeptide (e.g., after activation by treatment with one or more proteases that cleave within the cleavable moiety (CM), after activation by a change in pH (increased or decreased), after activation by a temperature shift (increased or decreased), after activation by being contacted with a second molecule (such as a small molecule or a protein ligand), etc.). In some embodiments, a polypeptide of the present disclosure is generally considered "activatable" if the $EC_{50}$ of the polypeptide decreases by at least about 2-fold (e.g., at least about 2-fold, at least about 2.5-fold, at least about 3, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 25-fold, at least about 50-fold, at least about 75-fold, at least about 100-fold, at least about 250-fold, at least about 500-fold, at least about 750-fold, or at least about 1000-fold, or more) after "activation" (e.g., as measured by an ELISA or FACS assay; see the examples below). In some embodiments, a polypeptide of the present disclosure is generally considered "activatable" if the $EC_{50}$ of the polypeptide decreases by at least about 2-fold after treatment with a protease that cleaves within the cleavable moiety (e.g., as measured by an ELISA or FACS assay; see the examples below).

In some embodiments, when the masking moiety is bound to the target binding moiety of the activatable binding polypeptide, the $K_D$ of the activatable binding polypeptide for its target is about 2 (e.g., about 2, about 2.5, about 3, about 3.5 about 4, about 4.5, about 5, about 5.5, about 6, about 6.5, about 7, about 7.5, about 8, about 8.5, about 9, about 9.5, about 10, about 25, about 50, about 75, about 100, about 250, about 500, about 750, or about 1000 or more) times greater than when the masking moiety is not bound to the target binding moiety (e.g., after "activation" of the activatable binding polypeptide (such as after protease treatment to cleave within the cleavable moiety)) and/or than the $K_D$ of the parental antibody for the target. Methods of measuring affinity are known in the art, including, for example, by the methods described in Example 3 below).

In some embodiments, when the masking moiety is bound to the target binding moiety of the activatable binding polypeptide, the $K_D$ of the activatable binding polypeptide for its target is reduced by at least about 25% (e.g., at least about 25%, at least about 30%, at least about 40%, at least about 50%, at least about 60%, at least about 70%, at least about 80%, at least about 90%, at least about 95%, at least about 99%) relative to when the masking moiety is not bound to the target binding moiety (e.g., after "activation" of the activatable binding polypeptide (such as after protease treatment to cleave within the cleavable moiety)) and/or relative to the $K_D$ of the parental antibody for the target. Methods of measuring affinity are known in the art, including, for example, by the methods described in Example 3 below).

In some embodiments, the masking moiety sterically hinders binding of the activatable binding polypeptide to its target and/or allosterically hinders binding of the activatable binding polypeptide to its target. In some embodiments, the masking moiety does not comprise an amino acid sequence of a natural binding partner of activatable binding polypeptide.

In some embodiments, the dissociation constant of the masking moiety for the target binding moiety is greater than the dissociation constant for the activatable binding polypeptide for the target (when in active activate form). In some embodiments, the dissociation constant of the masking moiety for the target binding moiety is about 2 (e.g., about 2, about 2.5, about 3, about 3.5 about 4, about 4.5, about 5, about 5.5, about 6, about 6.5, about 7, about 7.5, about 8, about 8.5, about 9, about 9.5, about 10, about 25, about 50, about 75, about 100, about 250, about 500, about 750, or about 1000 or more) times greater than the dissociation constant for the activatable binding polypeptide for the target (when in activate form). In some embodiments, the dissociation constant of the masking moiety for the target binding moiety is about equal to the dissociation constant for the activatable binding polypeptide for the target (when in activate form). In some embodiments, the first peptide (FP) binds to the target binding moiety (TBM), and prevents the polypeptide from binding to its target only when the polypeptide has not been activated (e.g., activated by treatment with one or more proteases that cleave within the cleavable moiety (CM), activated by a change in pH (increased or decreased), activated by a temperature shift (increased or decreased), activated after being contacted with a second molecule (such as a small molecule or a protein ligand), etc.). In some embodiments, activation induces cleavage of the polypeptide within the cleavage moiety. In some embodiments, activation induces conformation changes in the polypeptide (e.g., displacement of the first peptide (FP)), leading to the first peptide no longer preventing the polypeptide from binding to its target.

The activatable binding polypeptides (i.e., activatable antibodies) described herein may be further modified. In some embodiments, the activatable binding polypeptides are linked to an additional molecular entity. Examples of additional molecular entities include pharmaceutical agents, peptides or proteins, detection agent or labels, and antibodies.

In some embodiments, an activatable binding polypeptide of the present disclosure is linked to a pharmaceutical agent. Examples of pharmaceutical agents include cytotoxic agents or other cancer therapeutic agents, and radioactive isotopes. Specific examples of cytotoxic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Examples of radioactive isotopes that can be conjugated to antibodies for use diagnostically or therapeutically include, but are not limited to, $iodine^{131}$, $indium^{111}$, $yttrium^{90}$ and $lutetium^{177}$. Methods for linking a polypeptide to a pharmaceutical agent are known in the art, such as using various linker technologies. Examples of linker types include hydrazones, thioethers, esters, disulfides and peptide-containing linkers. For further discussion of linkers and methods for linking therapeutic agents to antibodies see e.g., Saito et al., *Adv. Drug Deliv. Rev.* 55:199-215 (2003); Trail, et al., *Cancer Immunol. Immunother.* 52:328-337 (2003); Payne, *Cancer Cell* 3:207-212 (2003); Allen, *Nat. Rev. Cancer* 2:750-763 (2002); Pastan and Kreitman, *Curr. Opin. Investig. Drugs* 3:1089-1091 (2002); Senter and Springer (2001) *Adv. Drug Deliv. Rev.* 53:247-264.

Activatable Binding Polypeptides Targeting CTLA4

In some embodiments, the present disclosure relates to activatable binding polypeptides (i.e., activatable antibodies) that bind to human CTLA4, including activatable anti-CTLA4 antibodies, antigen binding fragments of the activatable anti-CTLA4 antibodies, and/or derivatives of the activatable anti-CTLA4 antibodies. In some embodiments, the activatable antibody comprises: (a) a polypeptide comprising, from N-terminus to C-terminus, a masking moiety (MM), a cleavable moiety (CM), and a target binding moiety (TBM), where the MM comprises an amino acid sequence according to Formula (I): $X_mCX_nCZ_o$ (SEQ ID NO: 1), where m is from 2-10, n is from 3-10, and o is from 1-10, where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; where the CM comprises at least a first cleavage site (e.g., at least a first protease cleavage site); and where the TBM comprises an antibody light chain variable region (VL); and (b) an antibody heavy chain variable region (VH). In some embodiments m is from 3-10. In some embodiments, the MM inhibits the binding of the activatable antibody to human CTLA4 when the CM is not cleaved. In some embodiments, the activatable antibody is capable of binding to human CTLA4 when the CM is cleaved. In some embodiments, the MM comprises an amino acid sequence selected from SEQ ID NOS: 72-78, as listed in Table A.

TABLE A

| Masking peptide sequences for activatable antibodies | |
|---|---|
| Masking peptide sequences | SEQ ID NOS |
| NFVADSCPDHPYPCSA | SEQ ID NO: 72 |
| IVHHSDCDAFYPYCDS | SEQ ID NO: 73 |
| YSAYPACDSHYPYCNS | SEQ ID NO: 74 |
| PNPSSDCVPYYYACAY | SEQ ID NO: 75 |
| YSAYPACDSHYPYCQS | SEQ ID NO: 76 |

TABLE A-continued

| Masking peptide sequences for activatable antibodies | |
|---|---|
| Masking peptide sequences | SEQ ID NOS |
| PQPSSDCVPYYYACAY | SEQ ID NO: 77 |
| PNPASDCVPYYYACAY | SEQ ID NO: 78 |

In some embodiments, the activatable binding polypeptides comprise any of the anti-CTLA4 antibodies described herein, including antibodies described with reference to specific amino acid sequences of HVRs, variable regions (VL, VH), and/or light and heavy chains (e.g., IgG1, IgG2, IgG4). In some embodiments, the anti-CTLA4 antibodies are human antibodies. In some embodiments, the anti-CTLA4 antibodies are humanized antibodies and/or chimeric antibodies.

In some embodiments, the activatable binding polypeptide comprises: a) an HVR-H1 comprising the amino acid sequence YSISSGYHWSWI (SEQ ID NO: 59), an HVR-H2 comprising the amino acid sequence LARIDWDDDKYYSTSLKSRL (SEQ ID NO: 60), and an HVR-H3 comprising the amino acid sequence ARSYVYFDY (SEQ ID NO: 61); and/or b) an HVR-L1 comprising the amino acid sequence RASQSVRGRFLA (SEQ ID NO: 62), an HVR-L2 comprising the amino acid sequence DASNRATGI (SEQ ID NO: 63), and an HVR-L3 comprising the amino acid sequence YCQQSSSWPPT (SEQ ID NO: 64). In some embodiments, the activatable binding polypeptide comprises: a) a heavy chain variable region comprising the amino acid sequence of SEQ ID NO: 47; and/or b) a light chain variable region comprising the amino acid sequence of SEQ ID NO: 48.

In some embodiments, the present disclosure relates to activatable binding polypeptides that bind to human CTLA4 when in active form (e.g., the activatable binding polypeptides are active after cleavage in the cleavable moiety (e.g., with one or more proteases), but inactive prior to cleavage in the cleavable moiety (e.g., with one or more proteases)), and have at least one (e.g., at least one, at least two, at least three, at least four, at least five, at least six, at least seven, at least eight, or all nine) of the following functional properties: (a) bind to human, cynomolgus monkey, mouse, rat, and/or dog CTLA4 with a $K_D$ of 500 nM or less; (b) have antagonist activity on human CTLA4; (c) do not bind to human PD-1, PD-L1, PD-L2, LAG3, TIM3, B7-H3, CD95, CD120a, OX40, CD40, BTLA, VISTA, ICOS, and/or B7-H4 at concentration up to 100 nM; (d) are cross-reactive with monkey, mouse, rat, and/or dog CTLA4; (e) induces ADCC effects (e.g., on Tregs); (f) activates human PBMCs (e.g., stimulates secretion of IL-2 and/or IFNγ); (g) are capable of inhibiting tumor cell growth; (h) have therapeutic effect on a cancer; and (i) inhibit binding of human CTLA4 to human CD80 and/or human CD86. Also provided herein are one or more activatable binding polypeptides that cross-compete for binding to human CTLA4 with one or more of the CTLA4-targeting activatable binding polypeptides and/or anti-CTLA4 antibodies described herein.

In some embodiments, the activatable binding polypeptides bind to human, cynomolgus monkey, mouse, rat, and/or dog CTLA4 with a $K_D$ of about 500 nM or more when in inactive form. In some embodiments, the activatable binding polypeptides bind to human, cynomolgus monkey, mouse, rat, and/or dog CTLA4 with a $K_D$ of about 500 nM or less when in active form (e.g., about 500 nM or less, about 450 nM or less, about 400 nM or less, about 350 nM or less, about 300 nM or less, about 250 nM or less, about 200 nM or less, about 150 nM or less, about 100 nM or less, about 90 nM or less, about 80 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.) In some embodiments, the activatable binding polypeptides bind to human, cynomolgus monkey, mouse, rat, and/or dog CTLA4 with a $K_D$ of about 350 nM or less when in active form. In some embodiments, the activatable binding polypeptides bind to human CTLA4 with a $K_D$ of about 100 nM or less when in active form. In some embodiments, the activatable binding polypeptides bind to human CTLA4 with a $K_D$ of about 50 nM or less when in active form. In some embodiments, the activatable binding polypeptides bind to human CTLA4 with a $K_D$ of about 10 nM or less when in active form. Methods of measuring the $K_D$ of an activatable binding polypeptide may be carried out using any method known in the art, including for example, by surface plasmon resonance, an ELISA, isothermal titration calorimetry, a filter binding assay, an EMSA, etc. In some embodiments, the $K_D$ is measured by an ELISA (see e.g., Example 3 below).

In some embodiments, the activatable binding polypeptides do not have antagonist activity on human CTLA4 when in inactive form. In some embodiments, the activatable binding polypeptides have antagonist activity on human CTLA4 when in active form (e.g., induces ADCC effects (such as on Tregs), activates PBMCs (such as by activating, inducing, and/or stimulating IL-2 and/or IFNγ secretion), blocks binding of human CTLA4 to human CD80 and/or human CD86, etc.). In some embodiments, the activatable binding polypeptides repress one or more activities of human CTLA4 when in active form (e.g., repress one or more activities of human CTLA4 when a cell (such as a human cell) expressing human CTLA4 is contacted by an activated activatable binding polypeptide).

In some embodiments, when in inactive form, the activatable binding polypeptides are not cross-reactive with monkey (e.g., cynomolgus monkey), mouse, rat, and/or dog CTLA4. In some embodiments, when in active form, the activatable binding polypeptides are cross-reactive with monkey (e.g., cynomolgus monkey), mouse, rat, and/or dog CTLA4. In some embodiments, when in active form, the activatable binding polypeptides are cross-reactive with monkey CTLA4. In some embodiments, when in active form, the activatable binding polypeptides are cross-reactive with mouse CTLA4. In some embodiments, when in active form, the activatable binding polypeptides are cross-reactive with rat CTLA4. In some embodiments, when in active form, the activatable binding polypeptides are cross-reactive with dog CTLA4. In some embodiments, when in active form, the activatable binding polypeptides are cross reactive with monkey and mouse CTLA4; monkey and rat CTLA4; monkey and dog CTLA4; mouse and rat CTLA4; mouse and dog CTLA4; rat and dog CTLA4; monkey, mouse, and rat CTLA4; monkey, mouse, and dog CTLA4; monkey, rat, and dog CTLA4; mouse, rat, and dog CTLA4; or monkey, mouse, rat, and dog CTLA4. In some embodiments, when in active form, the activatable binding polypeptides are cross-reactive at about 350 nM (e.g., at about 1 nM, at about 10 nM, at about 25 nM, at about 50 nM, at about 75 nM, at about 100 nM, at about 150 nM, at about 200 nM, at about 250 nM, at about 300 nM, at about 350 nM). Methods of measuring cross-reactivity are known in the art, including, without limitation, surface plasmon resonance, an ELISA, isothermal titration calorimetry, a filter binding assay, an EMSA, etc.

In some embodiments, the activatable binding polypeptides do not induce ADCC effects (e.g., on human cells such as Tregs) when in inactive form. In some embodiments, the activatable binding polypeptides have reduced ADCC effects (e.g., on human cells such as Tregs) when in inactive form as compared to a control binding polypeptide (e.g., a parental antibody lacking the first peptide (FP) and cleavable moiety (CM)). In some embodiments, the activatable antibodies induce ADCC effects (e.g., on human cells such as Tregs) when in active form. Methods of measuring ADCC effects (e.g., in vitro methods) are known in the art, including, without limitation, via the methods described in Example 4 below. In some embodiments, when in inactive form, the activatable binding polypeptides induce ADCC effects by less than about 10% (e.g., induce ADCC by less than about 10%, less than about 5%, less than about 1%, etc.) relative to a control (e.g., a parental antibody lacking the first peptide (FP) and cleavable moiety (CM)). In some embodiments, when in active form, the activatable binding polypeptides induce ADCC effects by more than about 10% (e.g., induce ADCC by more than about 10%, more than about 15%, more than about 20%, more than about 25%, more than about 30%, more than about 35%, more than about 40%, etc.) relative to a control (e.g., an isotype control).

In some embodiments, the activatable binding polypeptides are capable of inhibiting tumor cell growth and/or proliferation. In some embodiments, the tumor cell growth and/or proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the activatable binding polypeptides relative to corresponding tumor cells not contacted with the activatable binding polypeptides (or relative to corresponding tumor cells contacted with an isotype control antibody). In some embodiments, the activatable binding polypeptides are capable of reducing tumor volume in a subject when the subject is administered the activatable binding polypeptides. In some embodiments, the activatable binding polypeptides are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the activatable binding polypeptides; as compared to a corresponding tumor in a subject administered an isotype control antibody). Methods of monitoring tumor cell growth/proliferation, tumor volume, and/or tumor inhibition are known in the art, including, for example, via the methods described in Example 4 below.

In some embodiments, the activatable binding polypeptides have therapeutic effect on a cancer. In some embodiments, the activatable binding polypeptides reduce one or more signs or symptoms of a cancer. In some embodiments, a subject suffering from a cancer goes into partial or complete remission when administered the activatable binding polypeptides.

In some embodiments, the present disclosure provides isolated activatable binding polypeptides that, when in active form, compete or cross-compete for binding to human CTLA4 with an antibody comprising: a) an HVR-H1 comprising the amino acid sequence of SEQ ID NO: 59; an HVR-H2 comprising the amino acid sequence of SEQ ID NO: 60; and an HVR-H3 comprising the amino acid sequence of SEQ ID NO: 61; and/or b) an HVR-L1 comprising the amino acid sequence of SEQ ID NO: 62; an HVR-L2 comprising the amino acid sequence of SEQ ID NO: 63; and an HVR-L3 comprising the amino acid sequence of SEQ ID NO: 54. In some embodiments, the present disclosure provides isolated activatable binding polypeptides that, when in active form, compete or cross-compete for binding to human CTLA4 with an antibody comprising: a) a heavy chain variable region comprising the amino acid sequence of SEQ ID NO: 47; and/or b) a light chain variable region comprising the amino acid sequence of SEQ ID NO: 48. The ability of an activatable binding polypeptide to compete or cross-compete for binding with an antibody can be determined using standard binding assays known in the art, such as BIAcore analysis, ELISA assays, or flow cytometry. For example, one can allow an antibody (e.g., as described above) to bind to human CTLA4 under saturating conditions and then measure the ability of the test activatable binding polypeptide (when in active form) to bind to the CTLA4. If the test activatable binding polypeptide is able to bind to the CTLA4 at the same time as the antibody, then the test activatable binding polypeptide binds to a different epitope then the antibody. However, if the test activatable binding polypeptide is not able to bind to the CTLA4 at the same time, then the test activatable binding polypeptide binds to the same epitope, an overlapping epitope, or an epitope that is in close proximity to the epitope bound by the antibody. This experiment can be performed using various methods, such as ELISA, RIA, FACS or surface plasmon resonance.

In some embodiments, the activatable binding polypeptides (when in inactive form) do not inhibit the binding between CTLA4 and one or more of its binding partners (e.g., human CTLA4 and human CD80, human CTLA4 and human CD86). In some embodiments, the activatable binding polypeptides (when in active form) inhibit the binding between CTLA4 and one or more of its binding partners (e.g., human CTLA4 and human CD80, human CTLA4 and human CD86). In some embodiments, the activatable binding polypeptides inhibit the binding between CTLA4 and its ligand in vitro. In some embodiments, the activatable binding polypeptides have a half maximal inhibitory concentration ($IC_{50}$) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for inhibiting binding of CTLA4 to CD80 and/or CD86. In some embodiments, the activatable binding polypeptides have a half maximal inhibitory concentration ($IC_{50}$) of about 100 nM or less for inhibiting binding of CTLA4 to CD80 and/or CD86. In some embodiments, the activatable binding polypeptides completely inhibit binding of human CTLA4 to CD80 and/or CD86 when provided at a concentration of about 100 nM or greater (e.g., about 100 nM or greater, about 500 nM or greater, about 1 μM or greater, about 10 μM or greater, etc.). As used herein, the term "complete inhibiting" or "completely inhibits" refers to the activatable binding polypeptide's ability to reduce binding between a first protein and a second protein by at least about 80% (e.g., at least about 80%, at least about 85%, at least about 90%, at least about 95%, at least about 99%, etc.). Methods of measuring the ability of an a polypeptide to inhibit binding of a first protein (e.g., human CTLA4) and a second protein (e.g., human CD80 or human CD86) are known in the art, including, without limitation, via BIAcore analysis, ELISA assays, and flow cytometry.

Activatable Binding Polypeptides Targeting CD137

In some embodiments, the present disclosure relates to activatable binding polypeptides (i.e., activatable antibodies) that bind to human CD137, including activatable anti-CD137 antibodies, antigen binding fragments of the activatable anti-CD137 antibodies, and/or derivatives of the activatable anti-CD137 antibodies. In some embodiments, the activatable antibody comprises: (a) a polypeptide comprising, from N-terminus to C-terminus, a masking moiety (MM), a cleavable moiety (CM), and a target binding moiety (TBM), where the MM comprises an amino acid sequence according to Formula (I): $X_mCX_nCZ_o$ (SEQ ID NO: 1), where m is from 2-10, n is from 3-10, and o is from 1-10, where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; where the CM comprises at least a first cleavage site (e.g., at least a first protease cleavage site); and where the TBM comprises an antibody light chain variable region (VL); and (b) an antibody heavy chain variable region (VH). In some embodiments, the activatable antibody comprises: (a) a polypeptide comprising, from N-terminus to C-terminus, a masking moiety (MM), a cleavable moiety (CM), and a target binding moiety (TBM), where the MM comprises an amino acid sequence according to Formula (I): $X_mCX_nCZ_o$ (SEQ ID NO: 1), where m is from 2-10, n is from 3-10, and o is from 1-10, where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; where the CM comprises at least a first cleavage site (e.g., at least a first protease cleavage site); and where the TBM comprises an antibody light chain variable region (VH); and (b) an antibody heavy chain variable region (VL). In some embodiments, the activatable antibody comprises: (a) a polypeptide comprising, from N-terminus to C-terminus, a masking moiety (MM), a cleavable moiety (CM), and a target binding moiety (TBM), where the MM comprises an amino acid sequence according to Formula (I): $X_mCX_nCZ_o$ (SEQ ID NO: 1), where m is from 2-10, n is from 3-10, and o is from 1-10, where each X is independently an amino acid selected from the group consisting of A, C, D, E, F, G, H, I, K, L, M, N, P, Q, R, S, T, V, W, and Y, and wherein each Z is independently an amino acid selected from the group consisting of D, A, Y, S, T, N, I, L, F, V, H, and P; where the CM comprises at least a first cleavage site (e.g., at least a first protease cleavage site); and where the TBM comprises an antibody light chain variable region (VL) and an antibody heavy chain variable region (VH). In some embodiments, m is 2, 3, 4, 5, 6, 7, 8, 9, or 10. In some embodiments, n is 3, 4, 5, 6, 7, 8, 9, or 10. In some embodiments, o is 1, 2, 3, 4, 5, 6, 7, 8, 9, or 10.

In some embodiments, the MM inhibits the binding of the activatable antibody to human CD137 when the CM is not cleaved. In some embodiments, the activatable antibody is capable of binding to human CD137 when the CM is cleaved. In some embodiments, the MM comprises an amino acid sequence selected from SEQ ID NOS: 79-85 and 88-94, as listed in Table B.

TABLE B

Masking peptide sequences for activatable antibodies

| Masking peptide sequences | SEQ ID NOS |
|---|---|
| PTDLDACADAPNHCHF | SEQ ID NO: 79 |
| SSTHAHCHHSPANCIS | SEQ ID NO: 80 |
| DTDYDFCPILRHRCDS | SEQ ID NO: 81 |
| NDYNYHCKWRPSRCHN | SEQ ID NO: 82 |
| YHDYDDCRVLPRRCFN | SEQ ID NO: 83 |
| NNFASCLWRHRSCAD | SEQ ID NO: 84 |
| TDNYDYCPRLRRKCYH | SEQ ID NO: 85 |
| $X_m$CADAPNHCXX | SEQ ID NO: 88 |
| $X_m$CHHSPANCXX | SEQ ID NO: 89 |
| $X_m$CPILRHRCXX | SEQ ID NO: 90 |
| $X_m$CKWRPSRCXX | SEQ ID NO: 91 |
| $X_m$CRVLPRRCXX | SEQ ID NO: 92 |
| $X_m$CLWRHRSCXX | SEQ ID NO: 93 |
| $X_m$CPRLRRKCXX | SEQ ID NO: 94 |

*m* is from 2-10; and each X is independently an amino acid selected from the group consisting of A, C, D, E, F, G, H, I, K, L, M, N, P, Q, R, S, T, V, W, and Y.

In some embodiments, the activatable binding polypeptides comprise any of the anti-CD137 antibodies described herein, including antibodies described with reference to specific amino acid sequences of HVRs, variable regions (VL, VH), and/or light and heavy chains (e.g., IgG1, IgG2, IgG4). In some embodiments, the anti-CD137 antibodies are human antibodies. In some embodiments, the anti-CD137 antibodies are humanized antibodies and/or chimeric antibodies.

In some embodiments, the activatable binding polypeptide comprises: a) an HVR-H1 comprising the amino acid sequence FSLSTGGVGVGWI (SEQ ID NO: 65), an HVR-H2 comprising the amino acid sequence LALIDWADDKYYSPSLKSRL (SEQ ID NO: 66), and an HVR-H3 comprising the amino acid sequence ARGGSDTVIGDWFAY (SEQ ID NO: 67); and/or b) an HVR-L1 comprising the amino acid sequence RASQSIGSYLA (SEQ ID NO: 68), an HVR-L2 comprising the amino acid sequence DASNLETGV (SEQ ID NO: 69), and an HVR-L3 comprising the amino acid sequence YCQQGYYLWT (SEQ ID NO: 70). In some embodiments, the activatable binding polypeptide comprises: a) a heavy chain variable region comprising the amino acid sequence of SEQ ID NO: 49 or a sequence having at least 90% (e.g., 91%, 92%, 93%, 94%, 95%, 96%, 97%, 98%, or 99%) sequence identity to SEQ ID NO: 49; and/or b) a light chain variable region comprising the amino acid sequence of SEQ ID NO: 50 or a sequence having at least 90% (e.g., 91%, 92%, 93%, 94%, 95%, 96%, 97%, 98%, or 99%) sequence identity to SEQ ID NO: 50.

In some embodiments, the present disclosure relates to activatable binding polypeptides that bind to human CD137 when in active form (e.g., the activatable binding polypeptides are active after cleavage in the cleavable moiety (e.g., with one or more proteases), but inactive prior to cleavage in the cleavable moiety (e.g., with one or more proteases)) and have at least one (e.g., at least one, at least two, at least three, at least four, at least five, at least six, at least seven, or all eight) of the following functional properties: (a) bind to human CD137 with a $K_D$ of 500 nM or less; (b) have agonist activity on human CD137; (c) do not bind to human OX40, CD40, GITR and/or CD27 receptor at concentration up to 1000 nM; (d) are cross-reactive with monkey, mouse, rat, and/or dog CD137; (e) do not induce ADCC effects; (f) are capable of inhibiting tumor cell growth; (g) have therapeutic effect on a cancer; and (h) inhibit binding between CD137 and CD137L. In some embodiments, the activatable binding polypeptides disclosed herein can also inhibit, e.g., completely inhibit, the binding between CD137 and its ligand CD137L. Also provided herein are one or more activatable binding polypeptides anti-CD137 antibodies or antigen-binding fragments that cross-compete for binding to human CD137 with one or more of the CD137-targeting activatable binding polypeptides and/or anti-CD137 antibodies described herein.

In some embodiments, the activatable binding polypeptides (when in inactive form) bind to human CD137 with a $K_D$ of about 500 nM or more. In some embodiments, the activatable binding polypeptides (when in active form) bind to human CD137 with a $K_D$ of about 500 nM or less (e.g., about 500 nM or less, about 400 nM or less, about 300 nM or less, about 200 nM or less, about 150 nM or less, about 100 nM or less, about 90 nM or less, about 80 nM or less, about 75 nM or less, about 70 nM or less, about 60 nM or less, about 50 nM or less, about 40 nM or less, about 30 nM or less, about 25 nM or less, about 20 nM or less, about 10 nM or less, about 1 nM or less, about 0.1 nM or less, etc.). In some embodiments, the activatable binding polypeptides bind to human CD137 with a $K_D$ of about 100 nM or less. In some embodiments, the activatable binding polypeptides bind to human CD137 with a $K_D$ of about 50 nM or less. Methods of measuring the $K_D$ of an activatable binding polypeptide may be carried out using any method known in the art, including for example, by surface plasmon resonance, an ELISA, isothermal titration calorimetry, a filter binding assay, an EMSA, etc. In some embodiments, the $K_D$ is measured by an ELISA (see e.g., Example 5 below).

In some embodiments, the activatable binding polypeptides (when in active form) described herein have agonist activity on human CD137. In some embodiments, the activatable binding polypeptides induce one or more (e.g., one or more, two or more, three or more, etc.) activities of human CD137 when a cell (e.g., a human cell) expressing human CD137 is contacted by the (active) activatable binding polypeptide. Various CD137 activities are known in the art and may include, without limitation, induction of NF-κB-dependent transcription, induction of T cell proliferation, prolonging T cell survival, co-stimulation of activated T cells, induction of cytokine secretion (such as IL-2), and induction of monocyte activation. In some embodiments, the one or more CD137 activities is not CD137 binding to its ligand. Methods of measuring CD137 activity (e.g., the induction of NF-κB-dependent transcription and/or T cell proliferation, etc.) are known in the art. In some embodiments, the activatable binding polypeptides increase NF-κB dependent transcription in cells (e.g., human cells) expressing human CD137. In some embodiments, NF-κB dependent transcription is increased by about 10% or more, about 20% or more, about 30% or more, about 40% or more, about 50% or more, about 60% or more, about 70% or more, about 80% or more, about 90% or more, or about 99% or more in cells (e.g., human cells) expressing CD137 contacted with the (active) activatable binding polypeptide, relative to a corresponding cell not contacted with the activatable binding polypeptide (e.g., a corresponding cell contacted with an isotype control antibody), or contacted with the activatable binding polypeptide when in inactive form. In some embodiments, NF-κB dependent transcription is increased by about 2-fold, 3-fold, 4-fold, 5-fold, 6-fold, 7-fold, 8-fold, 9-fold, 10-fold, 100-fold, 1000-fold or more in cells (e.g., human cells) expressing CD137 contacted with the activatable binding polypeptide (when in active form), relative to a corresponding cell not contacted with the activatable binding polypeptide (e.g., a corresponding cell contacted with an isotype control antibody), or contacted with the activatable binding polypeptide when in inactive form.

In some embodiments, the activatable binding polypeptides (when in inactive form) are not cross-reactive with monkey (e.g., cynomolgus monkey), mouse, rat, and/or dog CD137. In some embodiments, the activatable binding polypeptides (when in active form) are cross-reactive with monkey (e.g., cynomolgus monkey), mouse, rat, and/or dog CD137. In some embodiments, the activatable binding polypeptides are cross-reactive with monkey CD137. In some embodiments, the activatable binding polypeptides are cross-reactive with mouse CD137. In some embodiments, the activatable binding polypeptides are cross-reactive with rat CD137. In some embodiments, the activatable binding polypeptides are cross-reactive with dog CD137. In some embodiments, the activatable binding polypeptides are cross reactive with monkey and mouse CD137; monkey and rat CD137; monkey and dog CD137; mouse and rat CD137; mouse and dog CD137; rat and dog CD137; monkey, mouse, and rat CD137; monkey, mouse, and dog CD137; monkey, rat, and dog CD137; mouse, rat, and dog CD137; or monkey, mouse, rat, and dog CD137. In some embodiments, the activatable binding polypeptides are cross-reactive at about 100 nM (e.g., at about 1 nM, at about 10 nM, at about 25 nM, at about 50 nM, at about 75 nM, at about 100 nM). Methods of measuring cross-reactivity are known in the art, including, without limitation, surface plasmon resonance, an ELISA, isothermal titration calorimetry, a filter binding assay, an EMSA, etc.

In some embodiments, the activatable binding polypeptides do not induce ADCC effects. Methods of measuring ADCC effects are known in the art. In some embodiments, the activatable binding polypeptides (when in active form or inactive form) do not ADCC effects by more than about 10% (do not induce ADCC by more than about 10%, more than about 5%, more than about 1%, more than about 0.1%, more than about 0.01%) relative to a control.

In some embodiments, the activatable binding polypeptides are capable of inhibiting tumor cell growth and/or proliferation. In some embodiments, the tumor cell growth and/or proliferation is inhibited by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) when contacted with the activatable binding polypeptides relative to corresponding tumor cells not contacted with the activatable binding polypeptides (or relative to corresponding tumor cells contacted with an isotype control antibody). In some embodiments, the activatable binding polypeptides are capable of reducing tumor volume in a subject when the subject is administered the activatable binding polypeptides. In some embodiments, the activatable binding polypeptides are capable of reducing tumor volume in a subject by at least about 5% (e.g., at least about 5%, at least about 10%, at least about 20%, at least about 30%, at least about 40%, at least about 50%, at least about 60%, at least about 70%, at least about 80%, at least about 90%, or at least about 99%) relative to the initial tumor volume in the subject (e.g., prior to administration of the activatable binding polypeptides; as compared to a corresponding tumor in a subject administered an isotype control antibody). Methods of monitoring tumor cell growth/proliferation, tumor volume, and/or tumor inhibition are known in the art.

In some embodiments, the activatable binding polypeptides have therapeutic effect on a cancer. In some embodiments, the activatable binding polypeptides reduce one or more signs or symptoms of a cancer. In some embodiments, a subject suffering from a cancer goes into partial or complete remission when administered the activatable binding polypeptides.

In some embodiments, the present disclosure provides isolated activatable binding polypeptides that, when in active form, compete or cross-compete for binding to human CD137 with an antibody comprising: a) an HVR-H1 comprising the amino acid sequence of SEQ ID NO: 65; an HVR-H2 comprising the amino acid sequence of SEQ ID NO: 66; and an HVR-H3 comprising the amino acid sequence of SEQ ID NO: 67; and/or b) an HVR-L1 comprising the amino acid sequence of SEQ ID NO: 68; an HVR-L2 comprising the amino acid sequence of SEQ ID NO: 69; and an HVR-L3 comprising the amino acid sequence of SEQ ID NO: 70. In some embodiments, the present disclosure provides isolated activatable binding polypeptides that, when in active form, compete or cross-compete for binding to human CD137 with an antibody comprising: a) a heavy chain variable region comprising the amino acid sequence of SEQ ID NO: 49; and/or b) a light chain variable region comprising the amino acid sequence of SEQ ID NO: 50. The ability of an activatable binding polypeptide to compete or cross-compete for binding with an antibody can be determined using standard binding assays known in the art, such as BIAcore analysis, ELISA assays, or flow cytometry. For example, one can allow an antibody (e.g., as described above) to bind to human CD137 under saturating conditions and then measure the ability of the test activatable binding polypeptide (when in active form) to bind to the CD137. If the test activatable binding polypeptide is able to bind to the CD137 at the same time as the antibody, then the test activatable binding polypeptide binds to a different epitope then the antibody. However, if the test activatable binding polypeptide is not able to bind to the CD137 at the same time, then the test activatable binding polypeptide binds to the same epitope, an overlapping epitope, or an epitope that is in close proximity to the epitope bound by the antibody. This experiment can be performed using various methods, such as ELISA, RIA, FACS or surface plasmon resonance.

In some embodiments, the activatable binding polypeptides (when in inactive form) do not inhibit the binding between CD137 and its ligand (e.g., human CD137 and human CD137L). In some embodiments, the activatable binding polypeptides (when in active form) inhibit the binding between CD137 and its ligand (e.g., human CD137 and human CD137L). In some embodiments, the activatable binding polypeptides inhibit the binding between CD137 and its ligand in vitro. In some embodiments, the activatable binding polypeptide (when in active form) has a half maximal inhibitory concentration ($IC_{50}$) of about 500 nM or less (e.g., about 500 nM or less, about 400 nM or less, about 300 nM or less, about 200 nM or less, about 100 nM or less, about 50 nM or less, about 25 nM or less, about 10 nM or less, about 1 nM or less, etc.) for inhibiting binding of CD137 to its ligand. In some embodiments, the activatable binding polypeptide has a half maximal inhibitory concentration ($IC_{50}$) of about 100 nM or less for inhibiting binding of CD137 to its ligand. In some embodiments, the activatable binding polypeptide completely inhibits binding of human CD137 to its ligand when provided at a concentration of about 100 nM or greater (e.g., about 100 nM or greater, about 500 nM or greater, about 1 μM or greater, about 10 μM or greater, etc.). Methods of measuring the ability of a polypeptide to inhibit binding of a first protein (e.g., CD137) and a second protein (e.g., CD137L) are known in the art, including, without limitation, via BIAcore analysis, ELISA assays, and flow cytometry.

Antibodies

In some embodiments, the present disclosure relates to an activatable binding polypeptide comprising an antibody described herein (e.g., a CTLA4 or CD137 antibody described above). The antibodies described herein (e.g., a CTLA4 or CD137 antibody) may be in any class, such as IgG, IgM, IgE, IgA, or IgD. In some embodiments, the antibodies described herein (e.g., a CTLA4 or CD137 antibody) are in the IgG class, such as IgG1, IgG2, IgG3, or IgG4 subclass. An antibody described herein (e.g., a CTLA4 or CD137 antibody) antibody can be converted from one class or subclass to another class or subclass using methods known in the art. An exemplary method for producing an antibody in a desired class or subclass comprises the steps of isolating a nucleic acid encoding a heavy chain of an antibody described herein (e.g., a CTLA4 or CD137 antibody) and a nucleic acid encoding a light chain of an antibody described herein (e.g., a CTLA4 or CD137 antibody), isolating the sequence encoding the $V_H$ region, ligating the $V_H$ sequence to a sequence encoding a heavy chain constant region of the desired class or subclass, expressing the light chain gene and the heavy chain construct in a cell, and collecting the antibody.

Antigen Binding Fragments

In some embodiments, the present disclosure relates to an activatable binding polypeptide comprising an antigen-binding fragment (e.g., an antigen binding fragment of an antibody described herein (e.g., a CTLA4 or CD137 antibody)).

The antigen-binding fragment may comprise any sequences of any of the antibodies described herein. In some embodiments, the antigen-binding fragment comprises the amino acid sequence of: (1) a light chain of an antibody described herein (e.g., a CTLA4 or CD137 antibody); (2) a heavy chain of an antibody described herein (e.g., a CTLA4 or CD137 antibody); (3) a variable region from the light chain of an antibody described herein (e.g., a CTLA4 or CD137 antibody); (4) a variable region from the heavy chain of an antibody described herein (e.g., a CTLA4 or CD137 antibody); (5) one or more HVRs (e.g., one, two, three, four, five, or six HVRs) of an antibody described herein (e.g., a CTLA4 or CD137 antibody); or (6) three HVRs from the light chain and three HVRs from the heavy chain of an antibody described herein (e.g., a CTLA4 or CD137 antibody).

In some embodiments, the present disclosure provides an antigen-binding fragment of an antibody (that binds to human CTLA4) comprising a heavy chain variable region comprising: an HVR-H1 comprising the amino acid sequence YSISSGYHWSWI (SEQ ID NO: 59), an HVR-H2 comprising the amino acid sequence LARIDWDDDKYYSTSLKSRL (SEQ ID NO: 60), and an HVR-H3 comprising the amino acid sequence ARSYVYFDY (SEQ ID NO: 61); and/or a light chain variable region comprising: an HVR-L1 comprising the amino acid sequence RASQSVRGRFLA (SEQ ID NO: 62), an HVR-L2 comprising the amino acid sequence DASNRATGI (SEQ ID NO: 63), and an HVR-L3 comprising the amino acid sequence YCQQSSSWPPT (SEQ ID NO: 64). In some embodiments, the present disclosure provides an antigen-binding fragment of an antibody comprising: a) a heavy chain variable region comprising the amino acid sequence of SEQ ID NO: 47; and/or b) a light chain variable region comprising the amino acid sequence of SEQ ID NO: 48.

In some embodiments, the present disclosure provides an antigen-binding fragment of an antibody (that binds to human CD137) comprising a heavy chain variable region comprising: an HVR-H1 comprising the amino acid sequence FSLSTGGVGVGWI (SEQ ID NO: 65), an HVR-H2 comprising the amino acid sequence LALIDWADDKYYSPSLKSRL (SEQ ID NO: 66), and an HVR-H3 comprising the amino acid sequence ARGGSDTVIGDWFAY (SEQ ID NO: 67); and/or a light chain variable region comprising: an HVR-L1 comprising the amino acid sequence RASQSIGSYLA (SEQ ID NO: 68), an HVR-L2 comprising the amino acid sequence DASNLETGV (SEQ ID NO: 69), and an HVR-L3 comprising the amino acid sequence YCQQGYYLWT (SEQ ID NO: 70). In some embodiments, the present disclosure provides an antigen-binding fragment of an antibody comprising: a) a heavy chain variable region comprising the amino acid sequence of SEQ ID NO: 49; and/or b) a light chain variable region comprising the amino acid sequence of SEQ ID NO: 50.

In some embodiments, the antigen-binding fragments of an antibody described herein (e.g., a CTLA4 or CD137 antibody) include: (i) a Fab fragment, which is a monovalent fragment consisting of the $V_L$, $V_H$, $C_L$ and $C_H1$ domains; (ii) a $F(ab')_2$ fragment, which is a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated CDR, and (vii) single chain antibody (scFv), which is a polypeptide comprising a $V_L$ region of an antibody linked to a $V_H$ region of an antibody (see e.g., Bird et al. (1988) Science 242:423-426; Huston et al. (1988) Proc. Natl. Acad. Sci. USA 85:5879-5883).

Antibody Derivatives

In some embodiments, the present disclosure provides an activatable binding polypeptide comprising a derivative of an antibody described herein (e.g., a CTLA4 or CD137 antibody).

In some embodiments, the antibody derivative is derived from modifications of the amino acid sequences of the parent antibody while conserving the overall molecular structure of the parent antibody amino acid sequence. Amino acid sequences of any regions of the parent antibody chains may be modified, such as framework regions, HVR regions, or constant regions. Types of modifications include substitutions, insertions, deletions, or combinations thereof, of one or more amino acids of the parent antibody.

In some embodiments, the antibody derivative comprises a $V_L$ or $V_H$ region that is at least 65%, at least 75%, at least 85%, at least 90%, at least 91%, at least 92%, at least 93%, at least 94%, at least 95%, at least 96%, at least 97%, at least 98%, or at least 99% identical to the amino acid sequence as set forth in any of SEQ ID NOS: 47-50. In some embodiments, the antibody derivative comprises an HVR-H1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 59 or 65. In some embodiments, the antibody derivative comprises an HVR-H2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 60 or 66. In some embodiments, the antibody derivative comprises an HVR-H3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 61 or 67. In some embodiments, the antibody derivative comprises an HVR-L1 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 62 or 68. In some embodiments, the antibody derivative comprises an HVR-L2 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 63 or 69. In some embodiments, the antibody derivative comprises an HVR-L3 amino acid sequence region that is at least 65%, at least 75%, at least 85%, at least 90%, at least 91%, at least 92%, at least 93%, at least 94%, at least 95%, at least 96%, at least 97%, at least 98%, or at least 99% identical to an amino acid sequence as set forth in any of SEQ ID NOS: 64 or 70.

In some particular embodiments, the derivative comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to an amino acid sequence of an antibody described herein (e.g., a CTLA4 or CD137 antibody).

Amino acid substitutions encompass both conservative substitutions and non-conservative substitutions. The term "conservative amino acid substitution" means a replacement of one amino acid with another amino acid where the two amino acids have similarity in certain physico-chemical properties such as polarity, charge, solubility, hydrophobicity, hydrophilicity, and/or the amphipathic nature of the residues involved. For example, substitutions typically may be made within each of the following groups: (a) nonpolar (hydrophobic) amino acids, such as alanine, leucine, isoleucine, valine, proline, phenylalanine, tryptophan, and methionine; (b) polar neutral amino acids, such as glycine, serine, threonine, cysteine, tyrosine, asparagine, and glutamine; (c) positively charged (basic) amino acids, such as arginine, lysine, and histidine; and (d) negatively charged (acidic) amino acids, such as aspartic acid and glutamic acid.

The modifications may be made in any positions of the amino acid sequences of the antibody, including the HVRs, framework regions, or constant regions. In one embodiment, the present disclosure provides an antibody derivative that contains the $V_H$ and $V_L$ HVR sequences of an illustrative antibody described herein (e.g., a CTLA4 or CD137 antibody), yet contains framework sequences different from those of the illustrative antibody. Such framework sequences can be obtained from public DNA databases or published references that include germline antibody gene sequences. For example, germline DNA sequences for human heavy and light chain variable region genes can be found in the Genbank database or in the "VBase" human germline sequence database (Kabat et al., Sequences of Proteins of Immunological Interest, Fifth Edition, U.S. Department of Health and Human Services, NIH Publication No. 91-3242 (1991); Tomlinson et al., *J. Mol. Biol.* 227:776-798 (1992); and Cox et al., *Eur. J. Immunol.* 24:827-836 (1994)). Framework sequences that may be used in constructing an antibody derivative include those that are structurally similar to the framework sequences used by illustrative antibodies of the disclosure For example, the HVR-H1, HVR-H2, and HVR-H3 sequences, and the HVR-L1, HVR-L2, and HVR-L3 sequences of an illustrative antibody can be grafted onto framework regions that have the identical sequence as that found in the germline immunoglobulin gene from which the framework sequence derive, or the HVR sequences can be grafted onto framework regions that contain one or more mutations as compared to the germline sequences.

In some embodiments, the antibody derivative is a chimeric antibody which comprises an amino acid sequence of an illustrative antibody described herein (e.g., a CTLA4 or CD137 antibody). In one example, one or more HVRs from one or more illustrative antibodies are combined with HVRs from an antibody from a non-human animal, such as mouse or rat. In another example, all of the HVRs of the chimeric antibody are derived from one or more illustrative antibodies. In some particular embodiments, the chimeric antibody comprises one, two, or three HVRs from the heavy chain variable region and/or one, two, or three HVRs from the light chain variable region of an illustrative antibody. Chimeric antibodies can be generated using conventional methods known in the art.

Another type of modification is to mutate amino acid residues within the HVR regions of the $V_H$ and/or $V_L$ chain. Site-directed mutagenesis or PCR-mediated mutagenesis can be performed to introduce the mutation(s) and the effect on antibody binding, or other functional property of interest, can be evaluated in in vitro or in vivo assays known in the art. Typically, conservative substitutions are introduced. The mutations may be amino acid additions and/or deletions. Moreover, typically no more than one, two, three, four or five residues within an HVR region are altered. In some embodiments, the antibody derivative comprises 1, 2, 3, or 4 amino acid substitutions in the heavy chain HVRs and/or in the light chain HVRs. In another embodiment, the amino acid substitution is to change one or more cysteines in an antibody to another residue, such as, without limitation, alanine or serine. The cysteine may be a canonical or non-canonical cysteine. In one embodiment, the antibody derivative has 1, 2, 3, or 4 conservative amino acid substitutions in the heavy chain HVR regions relative to the amino acid sequences of an illustrative antibody.

Modifications may also be made to the framework residues within the $V_H$ and/or $V_L$ regions. Typically, such framework variants are made to decrease the immunogenicity of the antibody. One approach is to "back mutate" one or more framework residues to the corresponding germline sequence. An antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back mutated" to the germline sequence by, for example, site-directed mutagenesis or PCR-mediated mutagenesis.

In addition, modifications may also be made within the Fc region of an illustrative antibody, typically to alter one or more functional properties of the antibody, such as serum half-life, complement fixation, Fc receptor binding, and/or antigen-dependent cellular cytotoxicity. In one example, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody. In another case, the Fc hinge region of an antibody is mutated to decrease the biological half-life of the antibody.

Furthermore, an antibody of the present disclosure may be modified to alter its potential glycosylation site or pattern in accordance with routine experimentation known in the art. In another aspect, the present disclosure provides a derivative of an antibody described herein (e.g., a CTLA4 or CD137 antibody) that contains at least one mutation in a variable region of a light chain or heavy chain that changes the pattern of glycosylation in the variable region. Such an antibody derivative may have an increased affinity and/or a modified specificity for binding an antigen. The mutations may add a novel glycosylation site in the V region, change the location of one or more V region glycosylation site(s), or remove a pre-existing V region glycosylation site. In one embodiment, the present disclosure provides a derivative of an antibody described herein (e.g., a CTLA4 or CD137 antibody) having a potential N-linked glycosylation site at asparagine in the heavy chain variable region, wherein the potential N-linked glycosylation site in one heavy chain variable region is removed. In another embodiment, the present disclosure provides a derivative of an antibody described herein (e.g., a CTLA4 or CD137 antibody) having a potential N-linked glycosylation site at asparagine in the heavy chain variable region, wherein the potential N-linked glycosylation site in both heavy chain variable regions is removed. Method of altering the glycosylation pattern of an antibody is known in the art, such as those described in U.S. Pat. No. 6,933,368, the disclosure of which incorporated herein by reference.

Examples of other antibody derivatives provided by the present disclosure include single chain antibodies, diabodies, domain antibodies, nanobodies, and unibodies. A "single-chain antibody" (scFv) consists of a single polypeptide chain comprising a $V_L$ domain linked to a $V_H$ domain wherein $V_L$ domain and $V_H$ domain are paired to form a monovalent molecule. Single chain antibody can be prepared according to method known in the art (see e.g., Bird et al., (1988) Science 242:423-426 and Huston et al., (1988) Proc. Natl. Acad. Sci. USA 85:5879-5883). A "diabody" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (see e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see e.g., U.S. Pat.

Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609). Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (see e.g., U.S. Pat. Nos. 6,765,087, 6,838,254, WO 06/079372). Unibodies consist of one light chain and one heavy chain of an IgG4 antibody. Unibodies may be made by the removal of the hinge region of IgG4 antibodies. Further details of unibodies and methods of preparing them may be found in WO2007/059782.

VII. Compositions

In other aspects, the present disclosure provides a composition comprising one or more of the polypeptides (e.g., activatable binding polypeptides) described herein. In some embodiments, the composition is a pharmaceutical composition comprising a polypeptide (e.g., an activatable binding polypeptide) and a pharmaceutically acceptable carrier. The compositions can be prepared by conventional methods known in the art.

The term "pharmaceutically acceptable carrier" refers to any inactive substance that is suitable for use in a formulation for the delivery of a polypeptide (e.g., an activatable binding polypeptide). A carrier may be an anti-adherent, binder, coating, disintegrant, filler or diluent, preservative (such as antioxidant, antibacterial, or antifungal agent), sweetener, absorption delaying agent, wetting agent, emulsifying agent, buffer, and the like. Examples of suitable pharmaceutically acceptable carriers include water, ethanol, polyols (such as glycerol, propylene glycol, polyethylene glycol, and the like) dextrose, vegetable oils (such as olive oil), saline, buffer, buffered saline, and isotonic agents such as sugars, polyalcohols, sorbitol, and sodium chloride.

The compositions may be in any suitable forms, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering a polypeptide (e.g., an activatable binding polypeptide) is a sterile liquid, such as a solution, suspension, or dispersion, for injection or infusion. Sterile solutions can be prepared by incorporating the polypeptide (e.g., an activatable binding polypeptide) in the required amount in an appropriate carrier, followed by sterilization microfiltration. Dispersions may be prepared by incorporating the polypeptide (e.g., an activatable binding polypeptide) into a sterile vehicle that contains a basic dispersion medium and other carriers. In the case of sterile powders for the preparation of sterile liquid, methods of preparation include vacuum drying and freeze-drying (lyophilization) to yield a powder of the active ingredient plus any additional desired ingredient from a previously sterile-filtered solution thereof. The various dosage forms of the compositions can be prepared by conventional techniques known in the art.

The relative amount of a polypeptide (e.g., an activatable binding polypeptide) included in the composition will vary depending upon a number of factors, such as the specific polypeptide and carriers used, dosage form, and desired release and pharmacodynamic characteristics. The amount of a polypeptide (e.g., an activatable binding polypeptide) in a single dosage form will generally be that amount which produces a therapeutic effect, but may also be a lesser amount. Generally, this amount will range from about 0.01 percent to about 99 percent, from about 0.1 percent to about 70 percent, or from about 1 percent to about 30 percent relative to the total weight of the dosage form.

In addition to the polypeptide (e.g., an activatable binding polypeptide), one or more additional therapeutic agents may be included in the composition. Examples of additional therapeutic agents are described herein below. The suitable amount of the additional therapeutic agent to be included in the composition can be readily selected by a person skilled in the art, and will vary depending on a number of factors, such as the particular agent and carriers used, dosage form, and desired release and pharmacodynamic characteristics. The amount of the additional therapeutic agent included in a single dosage form will generally be that amount of the agent which produces a therapeutic effect, but may be a lesser amount as well.

Any of the polypeptides (e.g., activatable binding polypeptides) and/or compositions (e.g., pharmaceutical compositions) described herein may be used in the preparation of a medicament (e.g., a medicament for use in treating or delaying progression of cancer in a subject in need thereof).

VIII. Use of the Activatable Binding Polypeptides and Pharmaceutical Compositions Polypeptides (e.g., activatable binding polypeptides) and pharmaceutical compositions thereof provided by the present disclosure are useful for therapeutic, diagnostic, or other purposes, such as modulating an immune response, treating cancer, enhancing efficacy of other cancer therapy, enhancing vaccine efficacy, or treating autoimmune diseases. Thus, in other aspects, the present disclosure provides methods of using the polypeptides (e.g., activatable binding polypeptides) or pharmaceutical compositions thereof. In one aspect, the present disclosure provides a method of treating a disorder in a mammal, which comprises administering to the mammal in need of treatment an effective amount of a polypeptide (e.g., an activatable binding polypeptide) or composition thereof provided by the present disclosure. In some embodiments, the polypeptide is an activatable binding polypeptide that binds CTLA4 (e.g., human CTLA4) or CD137 (e.g., human CD137) when in active form. In some embodiments, the mammal is a human.

In some embodiments, the disorder is a cancer. A variety of cancers may be treated or prevented with a method, use, or medicament provided by the present disclosure. Examples of such cancers include lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblastic, myelomonocytic) leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas.

In another aspect, the present disclosure provides a method of enhancing an immune response in a mammal, which comprises administering to the mammal an effective amount of a polypeptide (e.g., an activatable binding polypeptide) or composition thereof provided by the present disclosure. In some embodiments, the polypeptide is an activatable binding polypeptide that binds CTLA4 (e.g., human CTLA4) or CD137 (e.g., human CD137), and the mammal is a human. The term "enhancing immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated), and may be a primary or secondary immune response. Examples of enhancement of immune response include activation of PBMCs and/or T cells (including increasing secretion of one or more cytokines such as IL-2 and/or IFNγ). The enhancement of immune response can be assessed using a number of in vitro or in vivo measurements known to those skilled in the art, including, but not limited to, cytotoxic T lymphocyte assays, release of cytokines, regression of tumors, survival of tumor bearing animals, antibody production, immune cell proliferation, expression of cell surface markers, and cytotoxicity. Typically, methods of the present disclosure enhance the immune response by a mammal when compared to the immune response by an untreated mammal or a mammal not treated using the recited methods.

In practicing the therapeutic methods, the polypeptides (e.g., activatable binding polypeptides) may be administered alone as monotherapy, or administered in combination with one or more additional therapeutic agents or therapies. Thus, in another aspect, the present disclosure provides a combination therapy, which comprises a polypeptide (e.g., an activatable binding polypeptide) in combination with one or more additional therapies or therapeutic agents for separate, sequential or simultaneous administration. The term "additional therapeutic agent" may refer to any therapeutic agent other than a polypeptide (e.g., an activatable binding polypeptide) provided by the disclosure. In one particular aspect, the present disclosure provides a combination therapy for treating cancer in a mammal, which comprises administering to the mammal an effective amount of a polypeptide (e.g., an activatable binding polypeptide) provided herein in combination with one or more additional therapeutic agents. In a further embodiment, the mammal is a human.

A wide variety of cancer therapeutic agents may be used in combination with a polypeptide (e.g., an activatable binding polypeptide) provided by the present disclosure. One of ordinary skill in the art will recognize the presence and development of other cancer therapies which can be used in combination with the methods and polypeptides of the present disclosure, and will not be restricted to those forms of therapy set forth herein. Examples of categories of additional therapeutic agents that may be used in the combination therapy for treating cancer include (1) chemotherapeutic agents, (2) immunotherapeutic agents, and (3) hormone therapeutic agents. In some embodiments, the additional therapeutic is a viral gene therapy, an immune checkpoint inhibitor, a target therapy, a radiation therapies, and/or a chemotherapeutic.

The term "chemotherapeutic agent" refers to a chemical or biological substance that can cause death of cancer cells, or interfere with growth, division, repair, and/or function of cancer cells. Examples of chemotherapeutic agents include those that are disclosed in WO 2006/129163, and US 20060153808, the disclosures of which are incorporated herein by reference. Examples of particular chemotherapeutic agents include: (1) alkylating agents, such as chlorambucil (LEUKERAN), mcyclophosphamide (CYTOXAN), ifosfamide (IFEX), mechlorethamine hydrochloride (MUSTARGEN), thiotepa (THIOPLEX), streptozotocin (ZANOSAR), carmustine (BICNU, GLIADEL WAFER), lomustine (CEENU), and dacarbazine (DTIC-DOME); (2) alkaloids or plant vinca alkaloids, including cytotoxic antibiotics, such as doxorubicin (ADRIAMYCIN), epirubicin (ELLENCE, PHARMORUBICIN), daunorubicin (CERUBIDINE, DAUNOXOME), nemorubicin, idarubicin (IDAMYCIN PFS, ZAVEDOS), mitoxantrone (DHAD, NOVANTRONE). dactinomycin (actinomycin D, COSMEGEN), plicamycin (MITHRACIN), mitomycin (MUTAMYCIN), and bleomycin (BLENOXANE), vinorelbine tartrate (NAVELBINE)), vinblastine (VELBAN), vincristine (ONCOVIN), and vindesine (ELDISINE); (3) antimetabolites, such as capecitabine (XELODA), cytarabine (CYTOSAR-U), fludarabine (FLUDARA), gemcitabine (GEMZAR), hydroxyurea (HYDRA), methotrexate (FOLEX, MEXATE, TREXALL), nelarabine (ARRANON), trimetrexate (NEUTREXIN), and pemetrexed (ALIMTA); (4) Pyrimidine antagonists, such as 5-fluorouracil (5-FU); capecitabine (XELODA), raltitrexed (TOMUDEX), tegafur-uracil (UFTORAL), and gemcitabine (GEMZAR); (5) taxanes, such as docetaxel (TAXOTERE), paclitaxel (TAXOL); (6) platinum drugs, such as cisplatin (PLATINOL) and carboplatin (PARAPLATIN), and oxaliplatin (ELOXATIN); (7) topoisomerase inhibitors, such as irinotecan (CAMPTOSAR), topotecan (HYCAMTIN), etoposide (ETO- POPHOS, VEPESSID, TOPOSAR), and teniposide (VUMON); (8) epipodophyllotoxins (podophyllotoxin derivatives), such as etoposide (ETOPOPHOS, VEPESSID, TOPOSAR); (9) folic acid derivatives, such as leucovorin (WELLCOVORIN); (10) nitrosoureas, such as carmustine (BiCNU), lomustine (CeeNU); (11) inhibitors of receptor tyrosine kinase, including epidermal growth factor receptor (EGFR), vascular endothelial growth factor (VEGF), insulin receptor, insulin-like growth factor receptor (IGFR), hepatocyte growth factor receptor (HGFR), and platelet-derived growth factor receptor (PDGFR), such as gefitinib (IRESSA), erlotinib (TARCEVA), bortezomib (VELCADE), imatinib mesylate (GLEEVEC), genefitinib, lapatinib, sorafenib, thalidomide, sunitinib (SUTENT), axitinib, rituximab (RITUXAN, MABTHERA), trastuzumab (HERCEPTIN), cetuximab (ERBITUX), bevacizumab (AVASTIN), and ranibizumab (LUCENTIS), lym-1 (ONCOLYM), antibodies to insulin-like growth factor-1 receptor (IGF-1R) that are disclosed in WO2002/053596); (12) angiogenesis inhibitors, such as bevacizumab (AVASTIN), suramin (GERMANIN), angiostatin, SU5416, thalidomide, and matrix metalloproteinase inhibitors (such as batimastat and marimastat), and those that are disclosed in WO2002055106; and (13) proteasome inhibitors, such as bortezomib (VELCADE).

The term "immunotherapeutic agents" refers to a chemical or biological substance that can enhance an immune response of a mammal. Examples of immunotherapeutic agents include: bacillus Calmette-Guerin (BCG); cytokines such as interferons; vaccines such as MyVax personalized immunotherapy, Onyvax-P, Oncophage, GRNVAC1, Favld, Provenge, GVAX, Lovaxin C, BiovaxlD, GMXX, and NeuVax; and antibodies such as alemtuzumab (CAMPATH), bevacizumab (AVASTIN), cetuximab (ERBITUX), gemtuzunab ozogamicin (MYLOTARG), ibritumomab tiuxetan (ZEVALIN), panitumumab (VECTIBIX), rituximab (RITUXAN, MABTHERA), trastuzumab (HERCEPTIN), tositumomab (BEXXAR), ipilimumab (YERVOY) tremelimumab, CAT-3888, agonist antibodies to OX40 receptor (such as those disclosed in WO2009/079335), agonist antibodies to CD40 receptor (such as those disclosed in WO2003/040170, and TLR-9 agonists (such as those disclosed in WO2003/015711, WO2004/016805, and WO2009/022215).

The term "hormone therapeutic agent" refers to a chemical or biological substance that inhibits or eliminates the production of a hormone, or inhibits or counteracts the effect of a hormone on the growth and/or survival of cancerous cells. Examples of such agents suitable for the methods herein include those that are disclosed in US20070117809. Examples of particular hormone therapeutic agents include tamoxifen (NOLVADEX), toremifene (Fareston), fulvestrant (FASLODEX), anastrozole (ARIMIDEX), exemestane (AROMASIN), letrozole (FEMARA), megestrol acetate (MEGACE), goserelin (ZOLADEX), and leuprolide (LUPRON). The binding molecules of this disclosure may also be used in combination with non-drug hormone therapies such as (1) surgical methods that remove all or part of the organs or glands which participate in the production of the hormone, such as the ovaries, the testicles, the adrenal gland, and the pituitary gland, and (2) radiation treatment, in which the organs or glands of the patient are subjected to radiation in an amount sufficient to inhibit or eliminate the production of the targeted hormone.

In some embodiments, the additional therapeutic agent is one or more of pomalyst, revlimid, lenalidomide, pomalidomide, thalidomide, a DNA-alkylating platinum-containing derivative, cisplatin, 5-fluorouracil, cyclophosphamide, an anti-CD137 antibody, an anti-CTLA4 antibody, an anti-PD-1 antibody, an anti-PD-L1 antibody, an anti-CD20 antibody, an anti-CD40 antibody, an anti-DR5 antibody, an anti-CD1d antibody, an anti-TIM3 antibody, an anti-SLAMF7 antibody, an anti-MR receptor antibody, an anti-OX40 antibody, an anti-HER2 antibody, an anti-ErbB-2 antibody, an anti-EGFR antibody, cetuximab, rituximab, trastuzumab, pembrolizumab, radiotherapy, single dose radiation, fractionated radiation, focal radiation, whole organ radiation, IL-12, IFN$\alpha$, GM-CSF, a chimeric antigen receptor, adoptively transferred T cells, an anti-cancer vaccine, and an oncolytic virus.

The combination therapy for treating cancer also encompasses the combination of a binding molecule with surgery to remove a tumor. The binding molecule may be administered to the mammal before, during, or after the surgery.

The combination therapy for treating cancer also encompasses combinations of a polypeptide (e.g., an activatable binding polypeptide) with radiation therapy, such as ionizing (electromagnetic) radiotherapy (e.g., X-rays or gamma rays) and particle beam radiation therapy (e.g., high linear energy radiation). The source of radiation can be external or internal to the mammal. The polypeptide may be administered to the mammal before, during, or after the radiation therapy.

The polypeptides (e.g., activatable binding polypeptides) and compositions thereof provided by the present disclosure can be administered via any suitable enteral route or parenteral route of administration. The term "enteral route" of administration refers to the administration via any part of the gastrointestinal tract. Examples of enteral routes include oral, mucosal, buccal, and rectal route, or intragastric route. "Parenteral route" of administration refers to a route of administration other than enteral route. Examples of parenteral routes of administration include intravenous, intramuscular, intradermal, intraperitoneal, intratumor, intravesical, intraarterial, intrathecal, intracapsular, intraorbital, intracardiac, transtracheal, intraarticular, subcapsular, subarachnoid, intraspinal, epidural and intrasternal, subcutaneous, or topical administration. The polypeptides (e.g., activatable binding polypeptides) and compositions of the present disclosure can be administered using any suitable method, such as by oral ingestion, nasogastric tube, gastrostomy tube, injection, infusion, implantable infusion pump, and osmotic pump. The suitable route and method of administration may vary depending on a number of factors such as the specific polypeptide being used, the rate of absorption desired, specific formulation or dosage form used, type or severity of the disorder being treated, the specific site of action, and conditions of the patient, and can be readily selected by a person skilled in the art.

The term "effective amount" of a binding molecule may refer to an amount that is effective for an intended therapeutic purpose. For example, in the context of enhancing an immune response, an "effective amount" may be any amount that is effective in stimulating, evoking, increasing, improving, or augmenting any response of a mammal's immune system. In the context of treating a disease, an "effective amount" may be any amount that is sufficient to cause any desirable or beneficial effect in the mammal being treated. Specifically, in the treatment of cancer, examples of desirable or beneficial effects include inhibition of further growth or spread of cancer cells, death of cancer cells, inhibition of reoccurrence of cancer, reduction of pain associated with the cancer, or improved survival of the mammal. The effective amount of a polypeptide (e.g., an activatable binding polypeptide) described herein may range from about 0.001 to about 500 mg/kg, or about 0.01 to about 100 mg/kg, of the body weight of the mammal. For example, the amount can be about 0.3 mg/kg, 1 mg/kg, 3 mg/kg, 5 mg/kg, 10 mg/kg, 50 mg/kg, or 100 mg/kg of body weight of the mammal. In some embodiments, the effective amount of a polypeptide (e.g., an activatable binding polypeptide) of the present disclosure is in the range of about 0.01-30 mg/kg of body weight of the mammal. In some other embodiments, the effective amount of a polypeptide (e.g., an activatable binding polypeptide) of the present disclosure is in the range of about 0.05-15 mg/kg of body weight of the mammal. The precise dosage level to be administered can be readily determined by a person skilled in the art and will depend on a number of factors, such as the type, and severity of the disorder to be treated, the particular polypeptide employed, the route of administration, the time of administration, the duration of the treatment, the particular additional therapy employed, the age, sex, weight, condition, general health and prior medical history of the patient being treated, and like factors well known in the medical arts.

A polypeptide (e.g., an activatable binding polypeptide) or composition thereof may be administered on multiple occasions. Intervals between single doses can be, for example, daily, weekly, monthly, every three months or yearly. An exemplary treatment regimen entails administration once per week, once every two weeks, once every three weeks, once every four weeks, once a month, once every three months or once every three to six months. Dosage regimens for a polypeptide (e.g., an activatable binding polypeptide) of the present disclosure may include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks.

IX. Kits

In another aspect, provided herein is a kit comprising a library of polynucleotides of the present disclosure. In some embodiments, the kit further comprises a package insert comprising instructions for expressing, modifying, screening, or otherwise using the library, e.g., to identify an activatable binding polypeptide of interest. In some embodiments, the kit further comprises one or more buffers, e.g., for storing, transferring, transfecting, or otherwise using one or more of the polynucleotides (e.g., synthetic polynucleotides). In some embodiments, the kit further comprises one or more containers for storing one or more of the polynucleotides. In some embodiments, the kit further comprises one or more vectors, e.g., for transfection of a host cell with one or more of the polynucleotides.

In another aspect, provided herein is a kit comprising activatable binding polypeptides and/or compositions described herein. In some embodiments, the kit further comprises a package insert comprising instructions for use of the activatable binding polypeptides and/or compositions. In some embodiments, the kit further comprises one or more buffers, e.g., for storing, transferring, administering, or otherwise using the activatable binding polypeptides and/or compositions. In some embodiments, the kit further comprises one or more containers for storing or administering (e.g., syringes, etc.) the activatable binding polypeptides and/or compositions.

The foregoing written description is considered to be sufficient to enable one skilled in the art to practice the present disclosure. The following Examples are offered for illustrative purposes only, and are not intended to limit the scope of the present disclosure in any way. Indeed, various modifications of the present disclosure in addition to those shown and described herein will become apparent to those skilled in the art from the foregoing description and fall within the scope of the appended claims.

Examples

Figure 1:
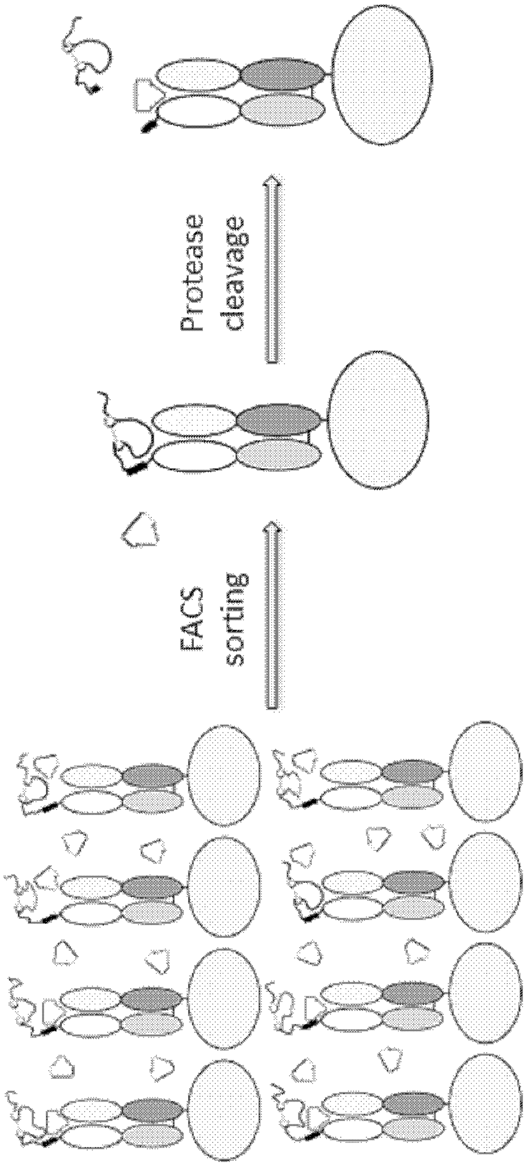
FIG. 1 shows a schematic of an exemplary selection process for self-blocking peptides using the Fab fragment of the target antibody displayed on yeast surface.
Figure 2:
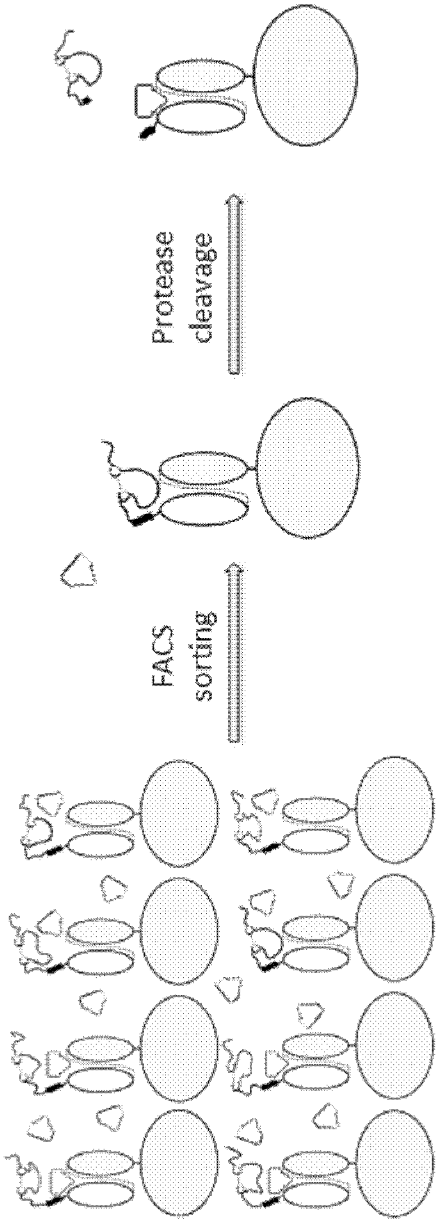
FIG. 2 shows a schematic of an exemplary selection process for self-blocking peptide using the scFv fragment of the target antibody displayed on yeast surface.

Example 1: Methods of Identifying Self-Blocking Peptides for Activatable Binding Polypeptides As described above, there exists a need for improved methods and products useful for identifying self-blocking peptides for activatable binding polypeptides. Accordingly, described herein is a new system that has been designed and executed for efficient discovery of masking moieties with good developability. In this system, the target antibody fragments, either Fab (FIG. 1) or scFv (FIG. 2), were first displayed on the yeast surface, and were confirmed to be functional in binding to its antigen. Then the improved peptide libraries were directly fused to the N-terminus of the light chain, and a yeast library was constructed that displays the fusion protein on the yeast surface. The yeast library then underwent several rounds of FACS-based screening: first the yeast clones that have low binding to antigen were enriched, then the enriched yeast clones were treated with a protease to remove the N-terminal peptide, and the clones with high binding to antigen were selected (FIGS. 1 and 2). After 4-5 rounds of sorting, the plasmids were extracted from these clones and the masking peptide sequences were confirmed through DNA sequencing.

There are several unique features built into this new system that make it powerful in identifying masking peptides for target antibodies with good developability:

1) The peptide libraries were directly fused to the N-terminus of the target antibody fragments instead of any foreign scaffold proteins, and the masking peptides were discovered in the same context as the final product. This eliminated the contamination with false positive peptide sequences, and dramatically reduced the amount of work for their downstream characterizations.
2) A protease cleavage-mediated activation mechanism was integrated into the screening processes. This was to ensure that the discovered peptides not only masked antigen binding before activation, but no longer blocked antigen binding after protease cleavage. These were the prerequisites considered for qualifying as a good masking peptide for any activatable antibody.
3) Improved designs of peptide libraries were employed. In contrast to the random peptide libraries commonly used, a pair of cysteine residues was introduced into fixed positions in the peptide libraries, to ensure that the display peptides had constrained conformations. It was observed that constrained peptides tend to exhibit increased binding affinity and specificity (Uchiyama et al. (2005) 99(5):448-56). In contrast to the widely used NNK (or NNS) codons that encode all 20 residues, including the chemically labile residues such as M and W, NHC codons were employed in part or all of the peptide libraries. The NHC codon encodes 12 amino acid residues (D, A, Y, S, T, N, I, L, F, V, H, and P), and does not include unfavorable residues for manufacturing processes, such as methionine, tryptophan, or cysteine. In addition, use of the NHC codon also dramatically reduced the theoretical peptide library size relative to an NNK (or NNS) codon, and therefore, enabled the construction of libraries with much better coverage. These libraries performed well when tested against different target antibodies.

Example 2: Design of Constrained Peptide Libraries (CPLs)

Four exemplary constrained peptide libraries (CPLs) were designed (Table 1).

TABLE 1

| Designed CPLs | | |
|---|---|---|
| CPL name: | Amino Acid Sequence: | Nucleic Acid sequence: |
| CPL010 | EVGSY(Z6)C(Z6)C(Z2)SGRSA (SEQ ID NO: 4) | gaggttggatcctac(NHC)6tgt(NHC)6tgc(NHC)2tca ggtcgttccgct (SEQ ID NO: 8) |
| CPL011 | EVGSY(Z6)C(X6)C(Z2)SGRSA (SEQ ID NO: 5) | gaggttggatcctac(NHC)6tgt(NNK)6tgc(NHC)2tca ggtcgttccgct (SEQ ID NO: 9) |
| CPL012 | EVGSY(Z6)C(Z8)C(Z2)SGRSA (SEQ ID NO: 6) | gaggttggatcctac(NHC)6tgt(NHC)8tgc(NHC)2tca ggtcgttccgct (SEQ ID NO: 10) |
| CPL013 | EVGSY(Z6)C(X8)C(Z2)SGRSA (SEQ ID NO: 7) | gaggttggatcctac(NHC)6tgt(NNK)8tgc(NHC)2tca ggtcgttccgct (SEQ ID NO: 11) |

Each X is independently an amino acid selected from the group consisting of A, C, D, E, F, G, H, I, K, L, M, N, P, Q, R, S, T, V, W, and Y; each Z is independently an amino acid selected from the group consisting of D, A, Y, S, T, N, I, L, F, V, H, and P At their cores were the sequences Z6CX6CZ2 (SEQ ID NO: 55) or Z6CX8CZ2 (SEQ ID NO: 56), and the two fixed cysteine residues formed a disulfide bond to constrain the peptide conformations. In the synthesized oligonucleotides, the degenerate codon NHC was adopted in all places except inside the loop, where an NNK codon was also employed in CPL011 and CPL013. In contrast to the NNK or NNS codon, NHC codon encodes 12 residues (Table 2), encompassing significant diversity, but lacking the chemically labile residues methionine, tryptophan, and cysteine. In addition, the reduced theoretical diversity compared with the NNK or NNS codon enabled the construction of libraries with better coverage.

TABLE 2

| NHC codons | | | | | | | | | | | | |
|---|---|---|---|---|---|---|---|---|---|---|---|---|
| | NHC: | | | | | | | | | | | |
| | AAC | ACC | ATC | TAC | TCC | TTC | GAC | GCC | GTC | CAC | CCC | CTC |
| Amino acid: | N | T | I | Y | S | F | D | A | V | H | P | L |

Following these masking peptide sequences was an invariant cleavage peptide sequence (SGRSAGGGGSPLGLAGSGGS, SEQ ID NO: 12) containing two protease recognition sites: SGRSA (SEQ ID NO: 13) for the protease urokinase-type plasminogen activator (uPA), and PLGLAG (SEQ ID NO: 14) for the proteases matrix metalloproteinase-2 (MMP-2) and matrix metalloproteinase-9 (MMP-9). These recognition sites have been used by many group in in vivo tumor cell-specific activation of targeting agents (see e.g., Ke et al. (1997) J Biol Chem 272(33):20456-62; Gerspach et al. (2006) Cancer Immunol Immunother 55(12):1590-600; and Jiang et al. (2004) Proc Natl Acad Sci USA 101(51):17867-72). During yeast-based screening, the MMP-9 recognition sequence was replaced with the Tobacco Etch Virus (TEV) protease recognition sequence (ENLYFQG, SEQ ID NO: 15) due to the availability and specificity of the TEV protease.

The CPLs and the invariant cleavage peptide were fused to the N-terminus of light chain of the target antibody, in the form of either scFv or Fab, that is connected to the yeast surface displayed Aga2 protein. The inclusion of the surrogate TEV protease recognition site was important in identifying the right type of masking peptide sequences, i.e, the antigen binding is blocked before protease cleavage, and antigen binding is enabled after protease cleavage. The examples described below demonstrated that the cleavage-activation mechanism of activatable antibodies initially shown in yeast was replicated in full IgG molecules expressed in mammalian cells.

Example 3: Construction and Validation of Activatable Antibodies Targeting CTLA4

Display of the Functional Target Antibody on the Yeast Surface

A low copy number, CEN/ARS-based vector was used to express the target antibody (antibody TY21580, targeting human CTLA4) under the control of the inducible GAL1-10 promoter in the yeast *S. cerevisiae*. The surface display of scFvs was achieved through the Aga2 protein fused at its C-terminus under the control of the GAL1 promoter, similar to previously published arrangements (Boder and Wittrup (1997) Nat Biotechnol 15(6):553-7). For Fabs, their surface display was achieved through the Aga2 protein fused to the N-terminus of the heavy chain (fusion of VH and CH1), under the control of the GAL1 promoter, while the light chain (fusion of VL and CL) was under the control of the GAL10 promoter. The Fabs were displayed on the yeast surface through its association with the membrane anchored heavy chain.

Figure 3A:
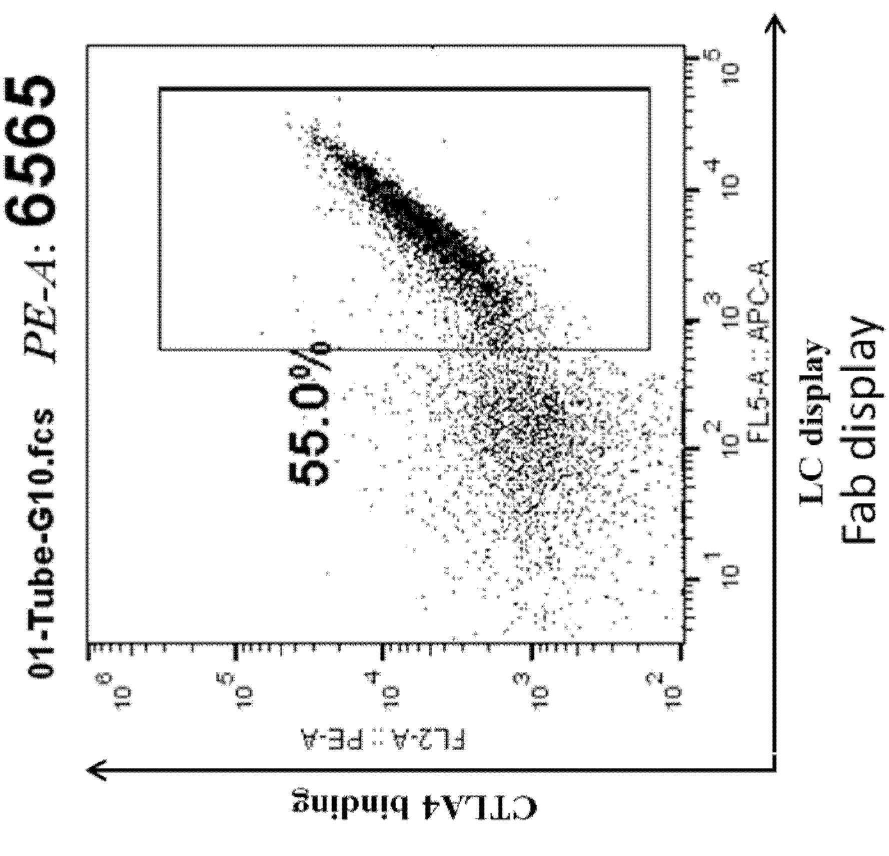
FIGS. 3A-B show functional display of Fabs and scFvs targeting CTLA4 on yeast, as determined by flow cytometry.
Figure 3B:
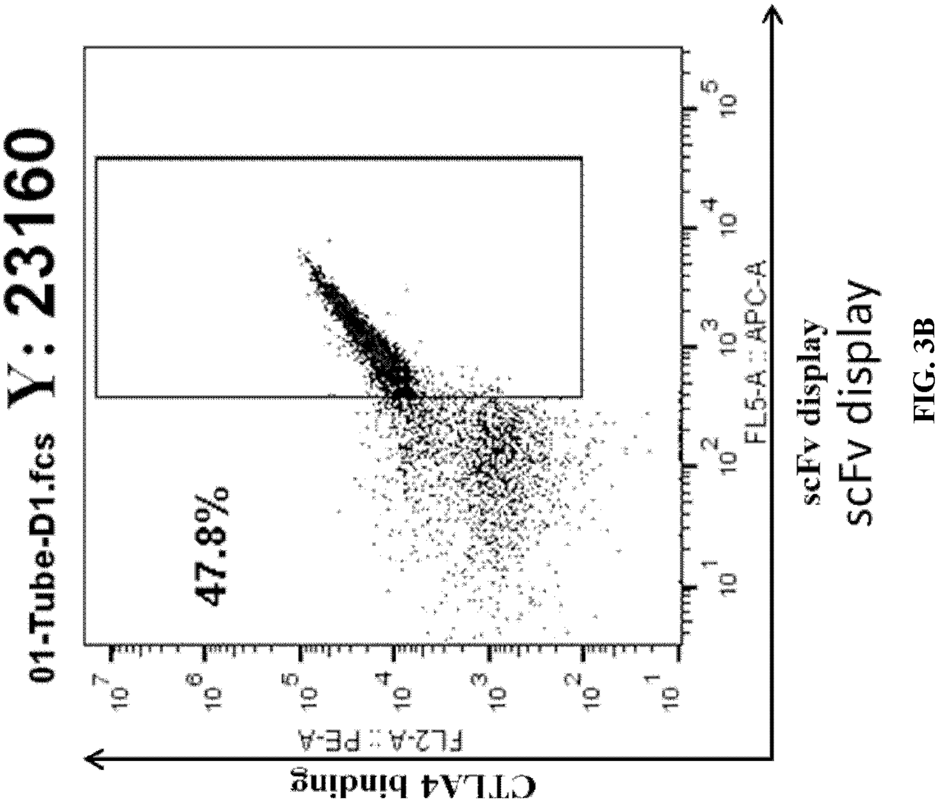

The surface display of the Fab or scFv was verified by staining with antibodies recognizing the fused affinity tag, and the functionality of the Fabs or scFvs displayed on yeast was examined using biotinylated human CTLA4. Briefly, 48 hours after induction in galactose medium, yeast cells (1×10^6) were harvested, washed once with PBSA buffer, and then incubated with 10 nM of biotinylated antigen for 1 hour at room temperature. The yeast cells were then washed twice with PBSA buffer, and incubated with PE conjugated streptavidin (1:500 dilution) (eBioscience #2-4317-87) for 30 minutes at 4° C. The yeast cells were then analyzed by flow cytometry. As shown in FIGS. 3A-B, both Fabs (FIG. 3A) and scFvs (FIG. 3B) targeting CTLA4 were successfully displayed on the yeast surface, and were both capable of binding strongly to their antigens.

Construction of Yeast Libraries Containing CPLs

Synthesized oligonucleotides encoding the CPLs were fused with the oligonucleotides encoding the cleavage peptides through 5 cycles of PCR. The primers used (F-primer and R-primer) are listed in Table 3. The compositions of PCR reactions were: 1× PrimeSTAR buffer, 2.5 mM dNTP, 100 μM of F-primer and R-primer each, and 100 μM each of template 1 (CPL oligonucleotide) and template 2 (oligonucleotide encoding the cleavage peptide), and 2.5 U of PrimeSTAR HS DNA Polymerase. The PCR program used was: a) 1 cycle of 96° C. for 5 minutes; 2) 5 cycles of 96° C. (15 sec), 60° C. (15 sec), 72° C. (6 sec); and 3) 1 cycle of 72° C. for 3 minutes. Exonuclease I was used to digest the single-stranded DNA before purification of the PCR product through gel electrophoresis. The purified PCR product was then digested with BamHI and KpnI, and cloned into a bacterial filter vector digested with the same two restriction enzymes. In the filter vector, the CPL and the cleavage peptides were placed downstream of a bacterial secretion signal peptide, and upstream of a beta-lactamase lacking signal sequence. The functional beta-lactamase, selected on ampicillin plates, indicated in-frame fusions of CPLs and the cleavage peptides, thereby eliminating any out-of-frame errors (N−1 or N−2) introduced into the synthesized degenerate oligonucleotides. In addition, some poorly folded sequences were also reduced from the pool. The ligation product was transformed into electro-competent bacterial cells, and the diversity of CPL libraries was generally between 5×10^9 and 1×10^10. Sequencing of individual clones indicated that very high in-frame rate (in many cases, almost 100%) were achieved through this approach.

TABLE 3

PCR primers

| Primer name: | Sequence: | SEQ ID NO: |
|---|---|---|
| F-primer | Tcgggtgaggttggatcctac | 51 |
| R-primer | gtacaggttctcggtaccacc | 52 |
| PL0009_F | tggagacacagacaggatcactggagactgggt cagcaggatatcggatcctgaaccgcctgaac | 53 |
| BL1024_R | cttcgctgttttcaatattttctgttattgct tcagttttagcaggatccgaggttggatcctac | 54 |

To make yeast libraries containing CPLs, the plasmids were extracted from the bacterial libraries, and used as templates for PCR amplification of the DNA fragments encoding the CPLs and cleavage peptide. The primers used (PL0009_F and BL1024_R) are listed in Table 3. The amplified PCR fragments were purified through gel-electrophoresis, and together with a linearized plasmid that expressed the target antibody fused to Aga2, were transformed into electro-competent yeast cells. The homologous sequences on both ends of the PCR fragments and the plasmids ensured efficient homologous recombination inside yeast cells. The diversity of the constructed yeast libraries was generally between 1×10^9 to 2×10^9.

FACS-Based Screening of Masking Peptides Against a CTLA4 Antibody

Figure 4:
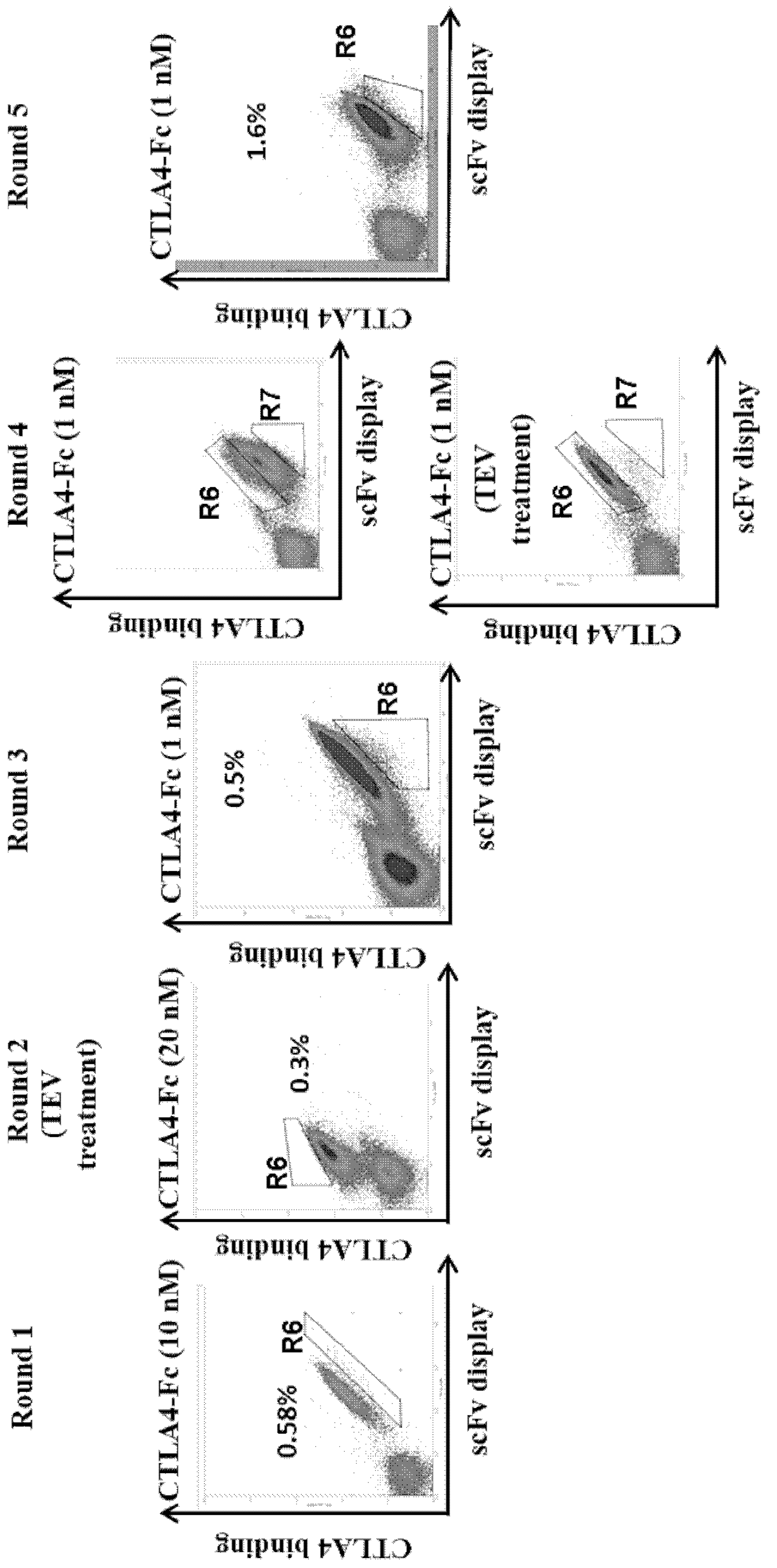
FIG. 4 shows an exemplary selection process for activatable antibodies targeting human CTLA4. A yeast library displaying fusion proteins were subjected to several rounds of FACS-based screening.

A total of 1×10^8 yeast cells from a CPL yeast library were used to screen for masking peptides against the target antibody. For each round of sorting through MoFlo XDP, yeast cells induced in galactose medium were harvested, washed once with PBSA buffer, and then incubated with 10 nM (decreased to 1 nM in the later rounds) of biotinylated antigen for 1 hour at room temperature. The yeast cells were then washed twice with PBSA buffer, and incubated with PE conjugated streptavidin (1:500 dilution) (eBioscience #2-4317-87) for 30 minutes at 4° C. After two more washes with PBSA buffer, the yeast cells were adjusted to 2-3 OD/mL, and subject to sorting. As shown in FIG. 4, in round 1, 10 nM of biotinylated CTLA4-Fc was used, and the weak binders were enriched. The yeast cells from round 1, after growth in glucose medium, were induced in galactose medium and treated with AcTEV protease (6U/OD cell) (Thermo Fisher Scientific #12575015) for 2 hours at 30° C., and the strong binders were purified. Starting from the 3rd round of sorting, the concentration of the biotinylated CTLA4-Fc was reduced to 1 nM, and the weak binders were collected. At the 4th round, fractions of the yeast cells were also treated with AcTEV in parallel, to verify the protease cleavage mediated activation of the target antibody. As shown in FIG. 4, it was apparent that AcTEV cleavage resulted in a dramatic increase of the population of cells that bound strongly to antigen, suggesting that the screening strategy was effective. The single clones from the 5th round of sorting were plated on selective media, and grown individually for further confirmation of cleavage mediated activated antigen binding.

Figure 5A:
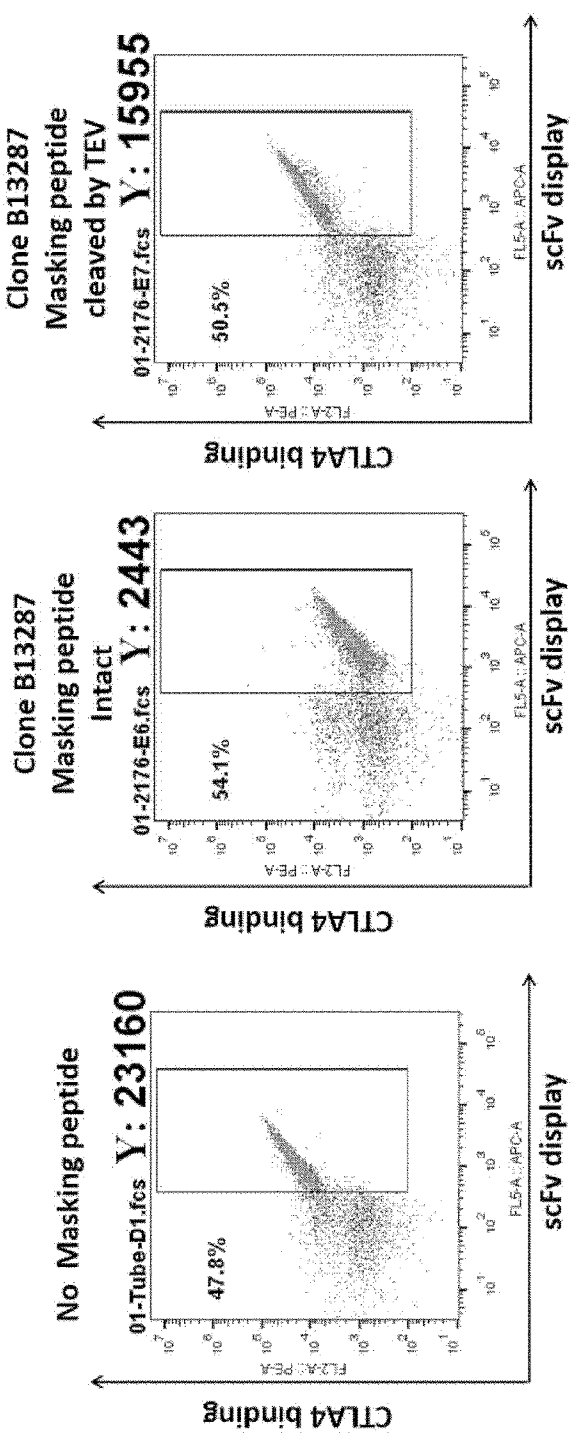
FIGS. 5A-B show CTLA4 binding affinity of exemplary CTLA4 activatable antibody clones, as determined by flow cytometry.
Figure 5B:
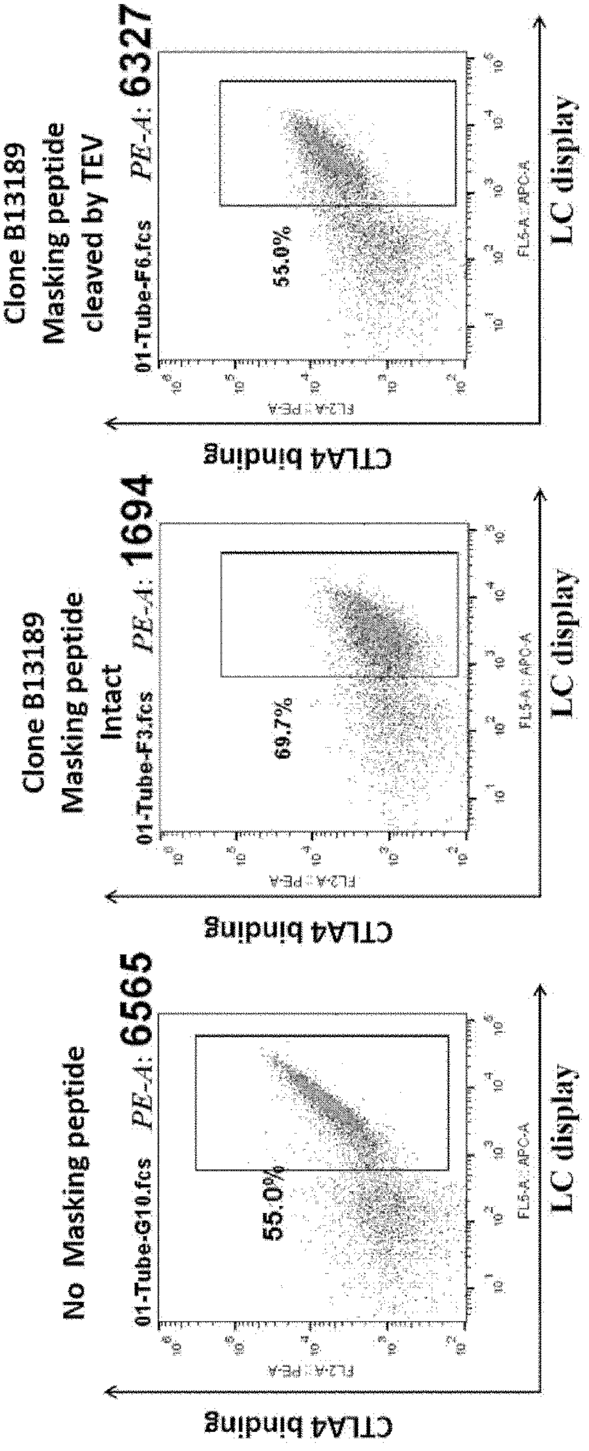

As shown in FIGS. 5A-B, the selected CTLA4 activatable antibody clones, either in scFv (FIG. 5A) or Fab (FIG. 5B) format, exhibited little binding to antigen in the presence of masking peptide. However, binding to antigen was dramatically increased when the yeast cells were treated with TEV protease to remove the masking peptide. The incorporation of the TEV recognition site in the cleavage peptide, combined with the application of TEV protease to verify the selected clones, significantly increased the success rate of masking peptide selection.

To identify the masking peptide sequences, the shuttle plasmids were extracted from the selected yeast clones (Generay #GK2002-200), and transformed into competent E. coli cells. The plasmids were prepared, and the regions encoding the masking peptides were sequenced and aligned. As anticipated, these sequences could be separated into several groups, indicating clear enrichment through rounds of sorting. Four groups of masking peptide sequences, together with the invariant cleavage peptide sequences, are listed in Table 4.

TABLE 4

Masking peptide sequences

| Sample ID: | Peptide name: | Masking + cleavage peptide sequences: |
|---|---|---|
| TY22401 | B13189 | EVGSYNFVADSCPDHPYPCSASGRSAGGGGS PLGLAGSGGS (SEQ ID NO: 28) |
| TY22402 | B13180 | EVGSYIVHHSDCDAFYPYCDSSGRSAGGGGS PLGLAGSGGS SEQ ID NO: 30) |

TABLE 4-continued

| Masking peptide sequences | | |
|---|---|---|
| Sample ID: | Peptide name: | Masking + cleavage peptide sequences: |
| TY22403 | B13192 | EVGSYYSAYPACDSHYPYCNSSGRSAGGGGS PLGLAGSGGS (SEQ ID NO: 32) |
| TY22404 | B13197 | EVGSYPNPSSDCVPYYYACAYSGRSAGGGGS PLGLAGSGGS (SEQ ID NO: 34) |

IgG Conversion and Expression

The four groups of masking peptides listed in Table 4, as well as additional four masking peptide sequences (Table 5) derived from two of them (B13192 and B13197) to eliminate a potential glycosylation site, were converted into IgG1 s.

TABLE 5

| additional masking peptide sequences | |
|---|---|
| Sample ID: | Masking + cleavage peptide sequences: |
| TY22563 | EVGSYYSAYPACDSHYPYCQSSGRSAGGGGSPLGLAGSGGS (SEQ ID NO: 36) |
| TY22564 | EVGSYYSAYPACDSHYPYCNSAGRSAGGGGSPLGLAGSGGS (SEQ ID NO: 37) |
| TY22565 | EVGSYPQPSSDCVPYYYACAYSGRSAGGGGSPLGLAGSGGS (SEQ ID NO: 38) |
| TY22566 | EVGSYPNPASDCVPYYYACAYSGRSAGGGGSPLGLAGSGGS (SEQ ID NO: 39) |

The heavy and light chains were cloned into the mammalian expression vector pCDNA3.3 (Thermo Fisher Scientific, cat #K830001) separately, and the masking peptides and the invariant cleavage peptide were fused to the N-terminus of the light chain in the same manner as displayed on yeast surface. The VH and VL sequences for the parental CTLA4 antibody (TY21580) are listed below (See also PCT International Application titled “Compositions Comprising Cross-reactive Anti-CTLA4 Antibodies, and Methods of Making and Using the Same”, incorporated herein by reference in its entirety):

Anti-CTLA4 heavy chain variable region

Anti-CTL4 heavy chain variable region
(SEQ ID NO: 47):
EVQLVESGGGLVQPGGSLRLSCAASGYSISSGYHWSWIRQAPGKGLEWLA

RIDWDDDKYYSTSLKSRLTISRDNSKNTLYLQLNSLRAEDTAVYYCARSY

VYFDYWGQGTLVTVSS

Anti-CTLA4 light chain variable region

Anti-CTL4 light chain variable region
(SEQ ID NO: 48):
DIQLTQSPSSLSASVGDRVTITCRASQSVRGRFLAWYQQKPGKAPKLLIY

DASNRATGIPSRFSGSGSGTDFTLTISSLQPEDFATYYCQQSSSWPPTFG

QGTKVEIKR.

Pairs of plasmids were transiently transfected into HEK293F cells. After six days, the supernatants were harvested, cleared by centrifugation and filtration, and IgGs were purified with standard protein A affinity chromatography (MabSelect SuRe, GE Healthcare). The IgGs were eluted and neutralized, and buffer exchanged into PB buffer (20 mM sodium phosphate, 150 mM NaCl, pH 7.0). Protein concentrations were determined by UV-spectrophotometry, and IgG purity was analyzed under denaturing, reducing and non-reducing conditions by SDS-PAGE or SEC-HPLC. Importantly, the expression levels of the activatable antibodies in HEK293 cells were similar to their parental antibody, and their purification yields after protein A resin were also similar, suggesting that the presence of the masking and cleavage peptides do not have a negative impact on antibody expression in mammalian cells.

Measurement of Masking Efficiency

Figure 6A:
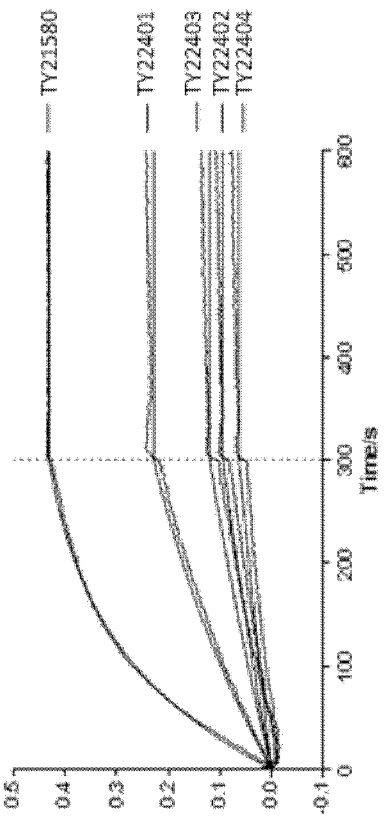
FIGS. 6A-B show the masking efficiency of exemplary CTLA4 activatable antibodies TY22401, TY22403, TY22402, and TY22404, as compared to the parental antibody TY21580.
Figure 6B:
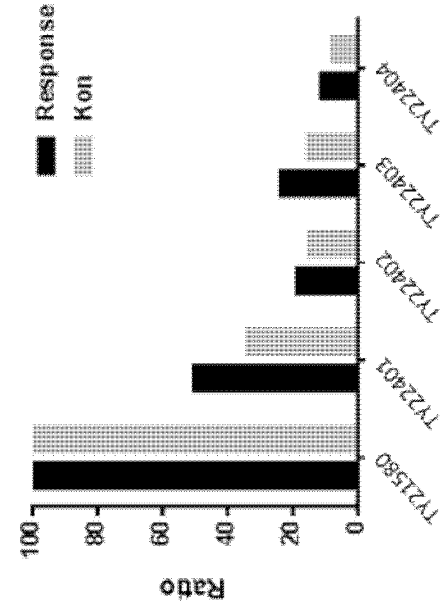

The ForteBio Octet RED96 system (Pall, USA) was used to quickly assess the efficiency of the masking peptides. Briefly, activatable antibodies (and their parent antibody, TY21580) were diluted to 30 μg/mL in KB buffer (PBS buffer supplemented with 0.02% Tween 20 and 0.1% BSA), and captured by anti-Human IgG Capture (AHC) Biosensors (Pall, USA) in parallel. The sensors were then allowed to associate with His-tagged CTLA4 protein (25 nM) for 300 seconds, and then dissociate in KB buffer for another 300 seconds. The association and dissociation curves were fitted to a 1:1 Langmuir binding model using ForteBio Data Analysis 7.1 (Pall, USA) according to the manufacturer’s guidelines. As shown in FIGS. 6A-B, the responses achieved with the activatable antibodies were significantly lower than that for the parent antibody, suggesting that masking peptides effectively blocked the binding of the antibody to its antigen. Among the four activatable antibodies, however, TY22401 was less effective, consistent with the results from the ELISA assay discussed below.

Figure 7A:
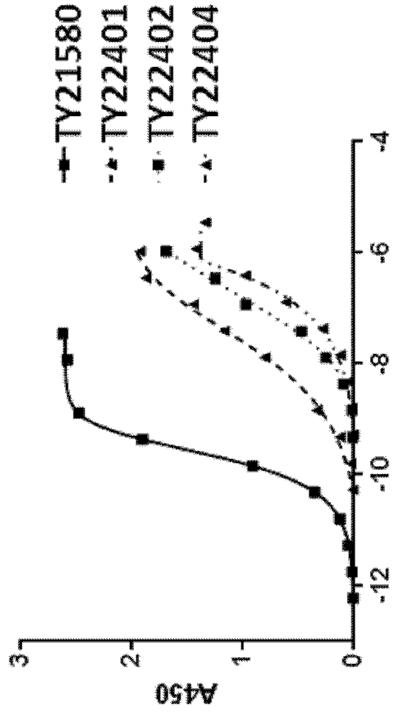
FIGS. 7A-C show the masking efficiency of exemplary CTLA4 activatable antibodies against recombinant human CTLA4-Fc, as determined by ELISA.
Figure 7B:
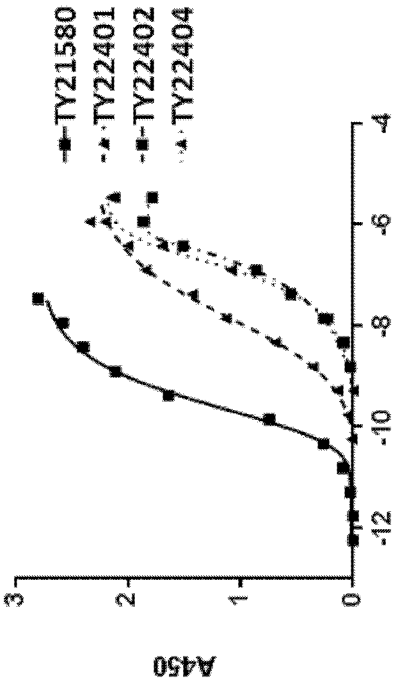
Figure 7C:
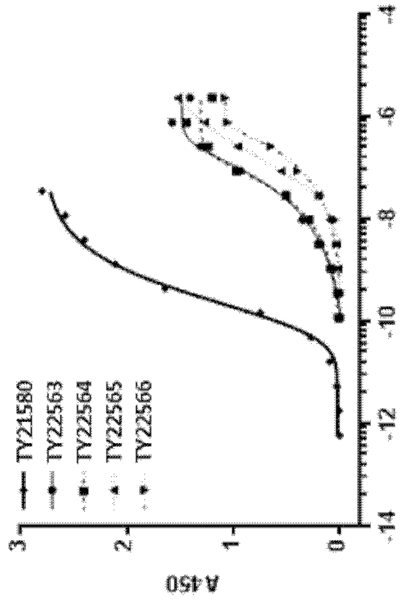

Recombinant human CTLA4-Fc was diluted to 1 μg/mL in PBS and coated on a Maxisorp plate at 4° C. overnight. Plates were blocked with PBS supplemented with 3% non-fat milk at 37° C. for 1 hour. After washing, 100 μL of 3-fold serial dilutions of antibodies were added to each well. After incubation at 37° C. for 1 hour, plates were washed four times, and 100 μL HRP conjugated anti-human IgG (Fab specific) (1:6000 dilution) was added to each well. Plates were incubated at 37° C. for 1 hour, washed four times, and then 50 μL TMB substrate solution was added to each well, and the plate was incubated at room temperature. Absorbance at 450 nm was measured after the reactions were stopped with 50 μL $H_2SO_4$ per well. The $EC_{50}$ was evaluated by fitting the ELISA data using the asymmetrical sigmoidal (five-parameter logistic equation) model of GraphPad Prism 6 software. Experiments for activatable antibodies TY22401, TY22402, and TY22404 were performed twice, leading to two calculated masking efficiencies being obtained for each of these activatable antibodies. Masking efficiencies for each activatable antibody were calculated by dividing the $EC_{50}$ for binding of the activatable antibody by the $EC_{50}$ of the parental antibody (TY21580). As shown in FIGS. 7A-C and Table 6, compared with the parental antibody, all of the activatable antibodies showed dramatically reduced binding to its antigen, and the calculated masking efficiency ranged from 48 to 2213. Differences in masking efficiency likely resulted from variation in measurement and data fitting for the $EC_{50}$ values, and the masking efficiency for each activatable antibody likely falls within the calculated ranges (e.g., the masking efficiency for activatable antibody TY22402 is between 377 and 2213). These results indicated that multiple masking peptides identified from the CPLs maintained their masking efficiency when expressed in mammalian cells, and as part of a full IgG molecule.

TABLE 6

| Activatable antibody ELISAs prior to protease cleavage | | | | | |
|---|---|---|---|---|---|
| | | $EC_{50}$ | | | Masking |
| Sample ID: | $LogEC_{50}$: | M: | nM: | $R^2$: | efficiency: |
| Data Batch 1 | | | | | |
| TY21580 | −9.665 | 2.161E−10 | 0.216 | 0.999 | 1.0 |
| TY22401 | −7.623 | 2.382E−08 | 23.82 | 0.997 | 110 |
| TY22402 | −6.321 | 4.779E−07 | 477.9 | 0.997 | 2213 |
| TY22404 | −6.749 | 178.4E−07 | 178.4 | 0.998 | 826 |
| Data Batch 2 | | | | | |
| TY21580 | −9.478 | 3.324E−10 | 0.3324 | 0.998 | 1.0 |
| TY22401 | −7.800 | 1.586E−08 | 15.86 | 0.994 | 48 |
| TY22402 | −6.902 | 1.254E−07 | 125.4 | 0.998 | 377 |
| TY22404 | −6.892 | 1.281E−07 | 128.1 | 0.998 | 385 |
| TY21580 | −9.48 | 3.3E−10 | 0.33 | | 1.0 |
| TY22563 | −7.32 | 4.771E−08 | 47.71 | | 143.5 |
| TY22564 | −7.41 | 3.898E−08 | 38.98 | | 117.3 |
| TY22565 | −6.68 | 2.099E−07 | 209.9 | | 631.5 |
| TY22566 | −6.79 | 1.6264E−07 | 162.6 | | 489.2 |

Removal of the Masking Peptide Restores Antibody Activity

Figure 8A:
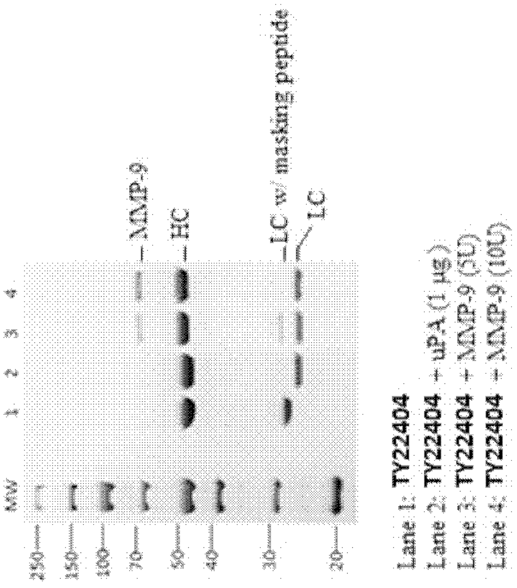
FIGS. 8A-B show activity of CTLA4 activatable antibody TY22404 upon removal of the masking peptide.
Figure 8B:
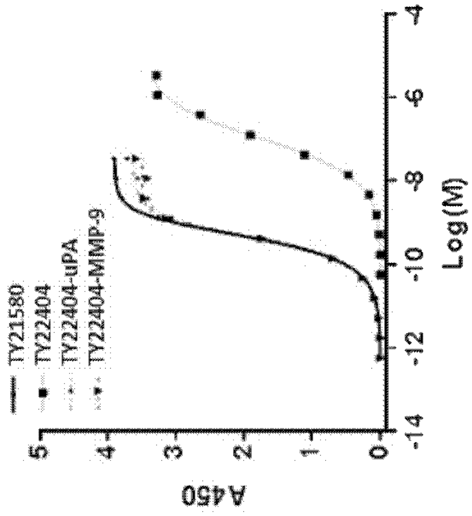

The purified activatable antibodies were treated with the proteases which recognize the cleavage sequences, and were then tested to determine whether removal of the masking peptide restored their activity. As an example, 20 μg of TY22404 (0.5 mg/mL) was treated with 1 μg of recombinant human uPA (Acrobiosystems, #PLU-H5229) in reaction buffer (50 mM Tris-HCl, 0.01% Tween 20, pH 8.5); or TY22404 was treated with 5 or 10 units of recombinant human MMP-9 (BioVision, #7867-500) in reaction buffer (50 mM Tris, 150 mM NaCl, 5 mM $CaCl_2$, 20 μM $ZnCl_2$, pH 7.5). The reactions were carried out at 37° C. for 21 hours. The masking peptides were confirmed to be removed from the light chain by SDS-PAGE analysis FIG. 8A. The masking efficiency was then measured by ELISA as described above. As shown in FIG. 8B and Table 7, after removal of masking peptide, the activatable antibody became indistinguishable from the parent antibody in its binding to the antigen.

TABLE 7

| Activatable antibody ELISAs after protease cleavage | | | |
|---|---|---|---|
| | | $EC_{50}$ | |
| Sample ID: | $LogEC_{50}$: | nM: | Masking efficiency: |
| TY21580 | −9.35 | 0.447 | 1.0 |
| TY22404 | −7.01 | 96.8 | 216 |
| TY22404-uPA | −9.40 | 0.402 | 0.9 |
| TY22404-MMP-9 | −9.39 | 0.412 | 0.9 |

Activatable Antibody Developability Profiles

For manufacturing purpose, it is critical that the discovered activatable antibodies have a good developability profile. Several different tests were performed with purified activatable antibodies that were expressed in mammalian cells. The activatable antibodies were adjusted to 1 mg/mL in 20 mM Histidine, pH 5.5, and antibody quality analysis was performed using analytical size-exclusion chromatography using a Waters 2695 with a Waters 2996 UV detector and aTSKgel g3000 SWXL column (300 mm×7.8 mm) (Tosoh Bioscience). For each assay, 10 μg of antibody was injected, and fractionation was performed at a flow rate of 0.5 mL/min in buffer (200 mM sodium phosphate at pH 7.0).

Figure 9A:
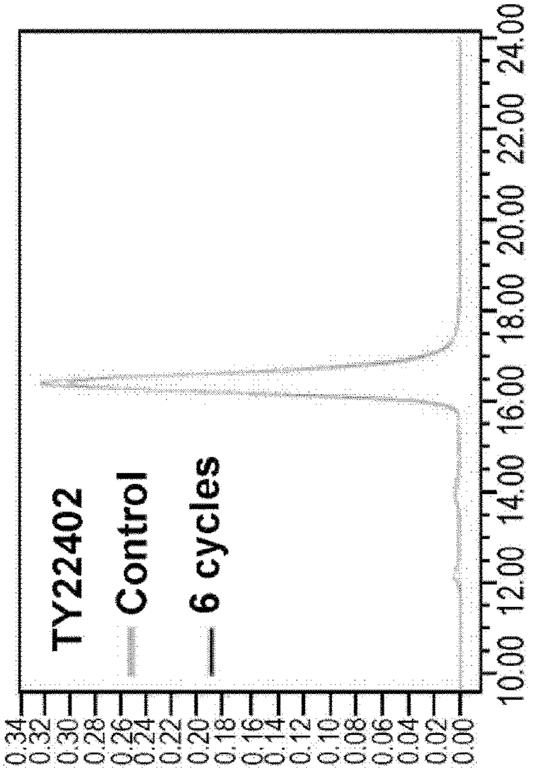
FIGS. 9A-C show the size-exclusion chromatography (SEC) profiles of exemplary activatable antibodies under accelerated stress conditions.
Figure 9B:
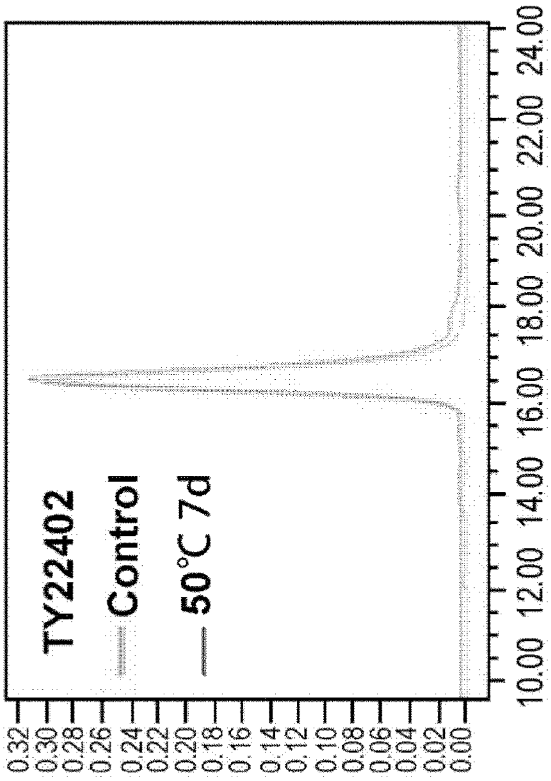
Figure 9C:
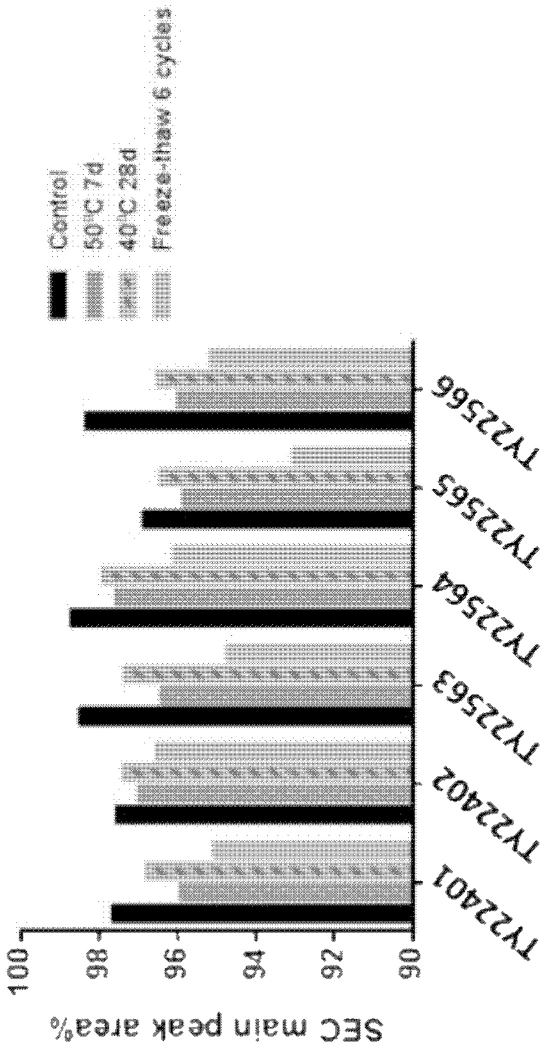

Three accelerated stress tests were conducted: incubation of the activatable antibodies at 50° C. for 7 days, incubation of the activatable antibodies at 40° C. for 28 days, and six cycles of freeze-thaw. The freeze-thaw tests were conducted by freezing 100 μL sample (1 mg/mL in 20 mM histidine, pH 5.5) at −80° C. for 30 minutes, followed by thawing at room temperature for 60 min. As shown in FIGS. 9A-C, all activatable antibodies remained stable, and exhibited little aggregation after storage at 50° C. for 7 days or 40° C. for 28 days. After six cycles of freeze-thaw, they showed slight deterioration; however, the main monomer peak remained around 95%, indicating that these activatable antibodies were very stable under these accelerated stress tests. Without wishing to be bound by theory, it is worth noting that the activatable antibodies had not yet gone through an extensive buffer optimization process, and therefore, the stability of the activatable antibodies may be further improved with optimized buffer and excipient.

Figure 10:
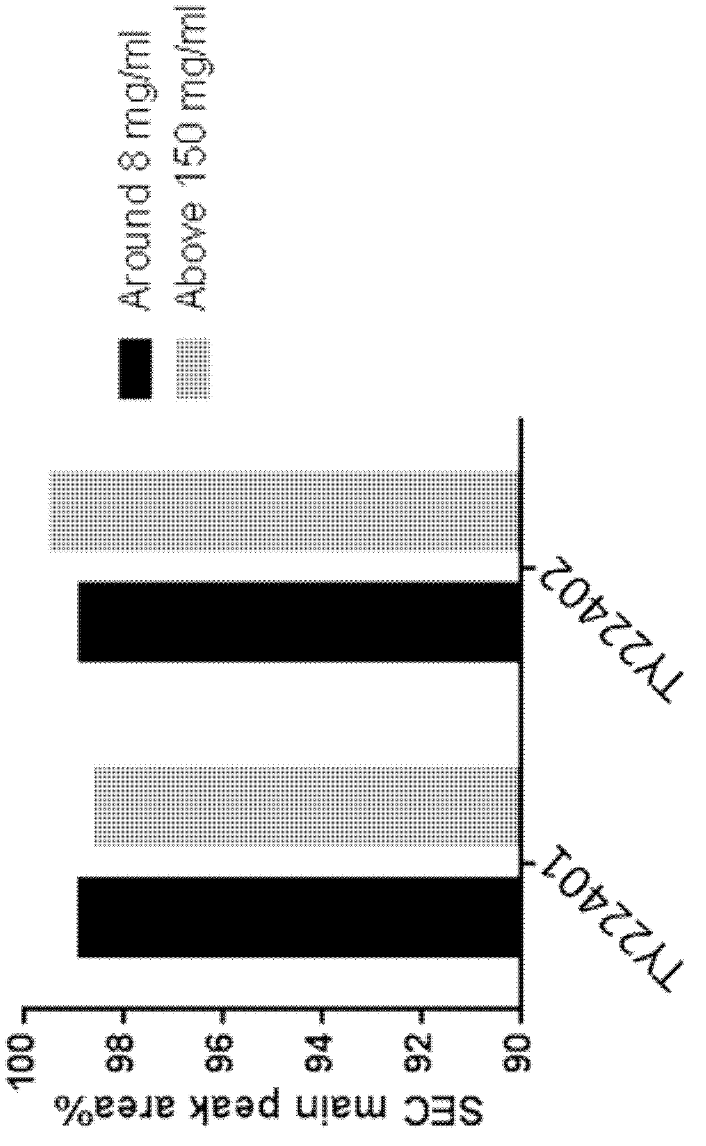
FIG. 10 shows the percentages of SEC main peak area of activatable antibodies TY22401 and TY22402 after storage at approximately 8 mg/mL or at >150 mg/mL.

Next, activatable antibodies were concentrated to more than 150 mg/mL in 20 mM histidine, pH 5.5 (Table 8). No activatable antibody precipitation was observed, and viscosity of the samples was quite manageable. The concentrated activatable antibodies were then diluted to either 20 mg/mL or 1 mg/mL for analysis of high molecular weight (HMW) species. As shown in FIG. 10 and Table 8, no apparent increase of the HMW species was observed, suggesting that these activatable antibodies were very soluble and stable in the buffer tested, up to high concentrations.

TABLE 8

| Concentration of activatable antibodies > 150 mg/mL | | |
|---|---|---|
| Sample ID: | Starting conc. (mg/mL): | High conc. (mg/mL): |
| TY22401 | 10.9 | 187.2 |
| TY22402 | 8.4 | 160.0 |

Figure 11:
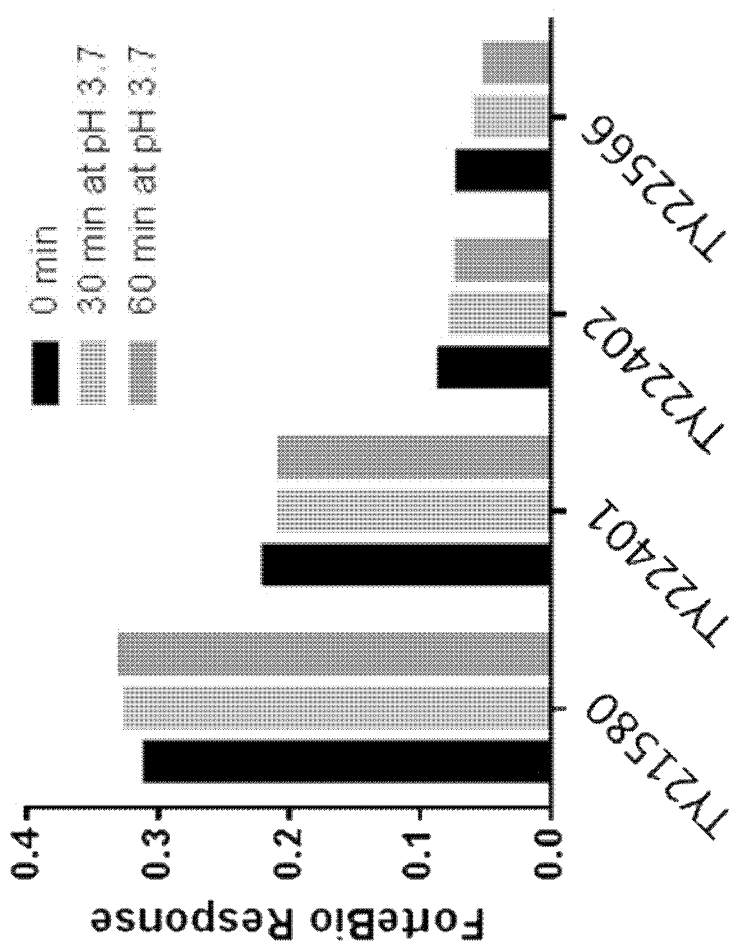
FIG. 11 shows the masking efficiency of untreated activatable antibodies TY21580, TY22401, TY22402 and TY22566 incubated at pH 3.7 for 30 minutes, or incubated at pH 3.7 for an hour, as determined by the ForteBio System.

To study the stability of the activatable antibodies at low pH, the purified activatable antibodies (at 10 mg/mL in 20 mM histidine, pH 5.5) were titrated to 1 mg/mL with citric acid, and the pH was adjusted to 3.7 and held at room temperature for 30 and 60 minutes. Afterwards, the samples were neutralized to pH 7.0 with 1 M Tris-base. The masking efficiency of the activatable antibodies was measured with ForteBio, as described above. As shown in FIG. 11, masking efficiency remained unchanged after low pH incubation for 30 or 60 minutes, suggesting that the masking peptides retained their blocking efficacy after low pH incubation.

Taken together, the data indicates that the discovered activatable antibodies remained stable under various stress conditions, and therefore, they have good developability profile.

Example 4: In Vitro and In Vivo Characterization of Activatable Antibodies Targeting CTLA4

It was previously shown that the parental antibody TY21580 alone does not stimulate human T cell activation or the activation of human PBMC cells (See PCT International Application titled "Compositions Comprising Cross-reactive Anti-CTLA4 Antibodies, and Methods of Making and Using the Same", incorporated herein by reference in its entirety). It is known that CTLA-4 activity on T cells is related to the first (TCR/CD3) and second signals involving B7-CD28/CTLA-4. Consistently, it was shown that, with low concentrations of anti-CD3, the parental antibody TY21580 significantly enhanced human PBMC cell activation.

In Vitro Functional Characterization

Figure 12A:
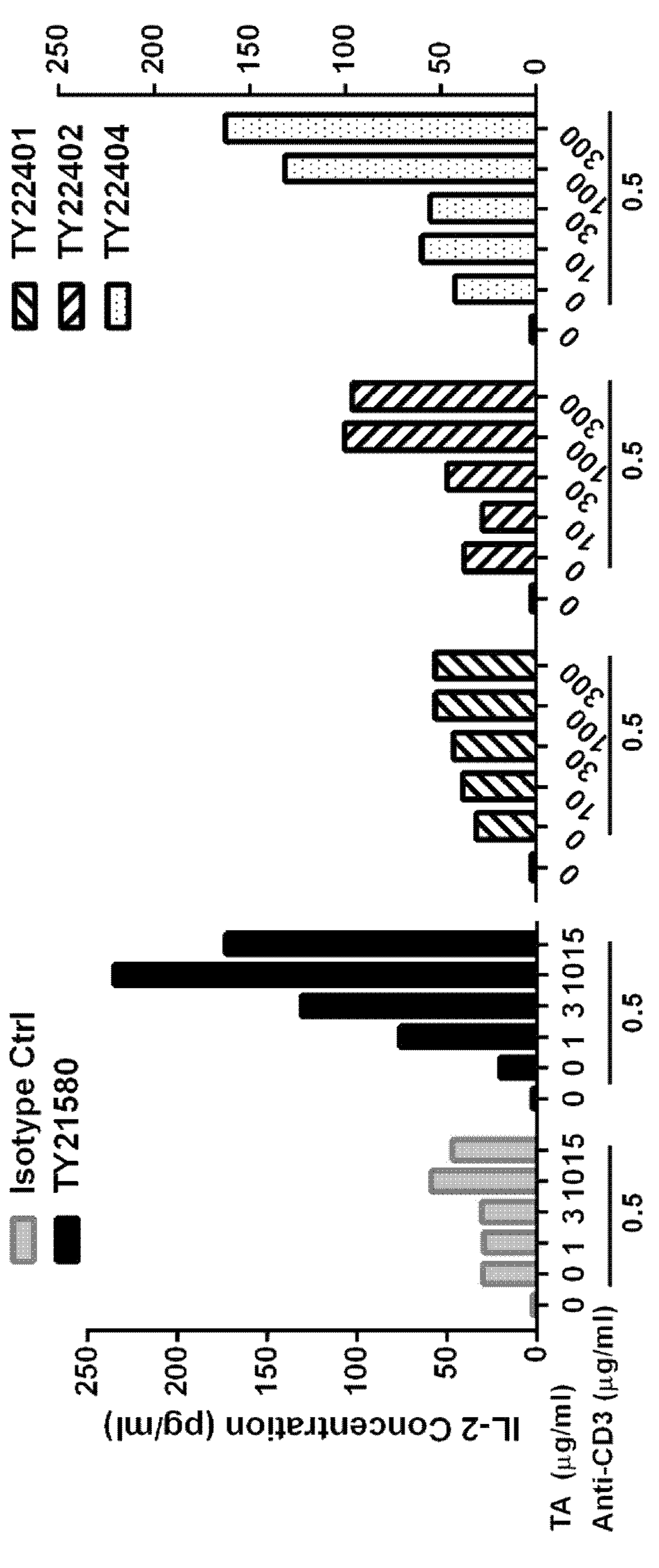
FIGS. 12A-B show human peripheral blood mononuclear cell (PBMC) activation by isotype control antibody, parental antibody TY21580, or exemplary CTLA4 activatable antibodies TY22401, TY22402, or TY22404, as measured by ELISA.
Figure 12B:
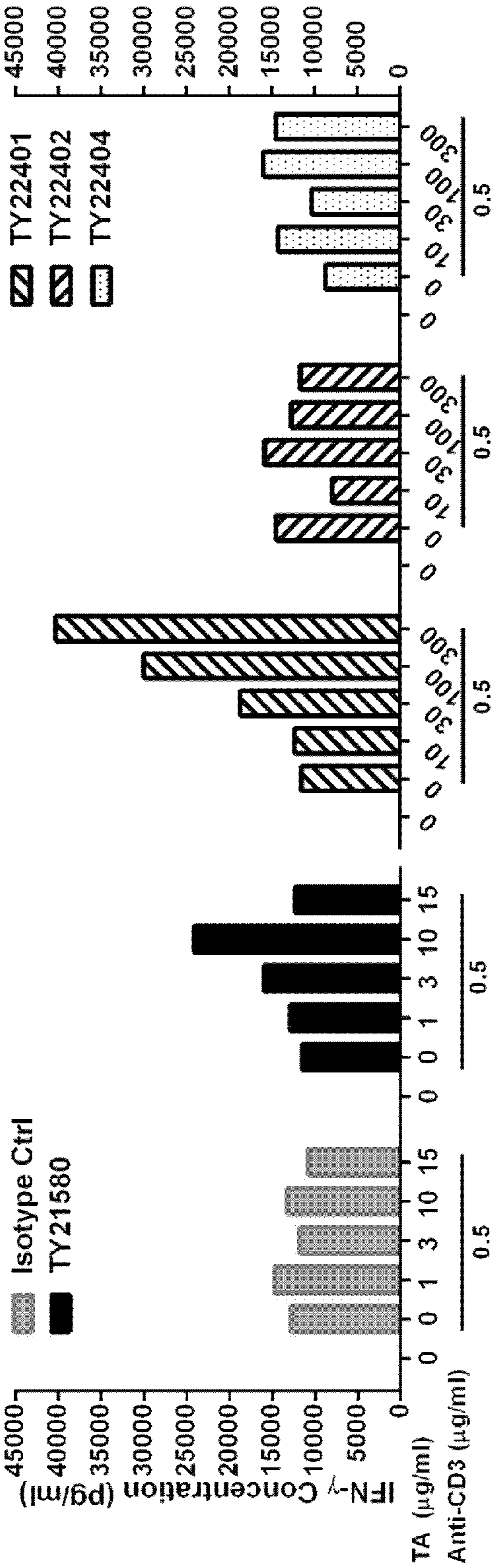

Here the activities of the activatable antibodies targeting CTLA4 were evaluated in the presence of a low concentration of anti-CD3 antibody on human PMBC activation. Human PBMCs were freshly isolated from the blood of a healthy donor (#44) by density gradient centrifugation using Histopaque-1077 (Sigma). Anti-CD3 (OKT-3) antibody was coated on a 96 well plate overnight at 4° C. After washing, 1×10^5 freshly isolated human PBMCs were added to each well, followed by the addition of the test articles at different concentrations. Induction of IL-2 was measured 48 hours after stimulation using a Human IL-2 ELISA Ready-SET-Go (Invitrogen) kit. IFN-γ in the supernatant was measured using a Human IFN-γ ELISA Ready-SET-Go (Invitrogen) kit. As demonstrated in FIGS. 12A-B, at high concentrations, TY22404 induced IL-2 production, and TY22401 induced IFN-γ production. Nevertheless, the activities of the activatable antibodies were significantly lower than that of the parental TY21580 antibody.

Figure 13:
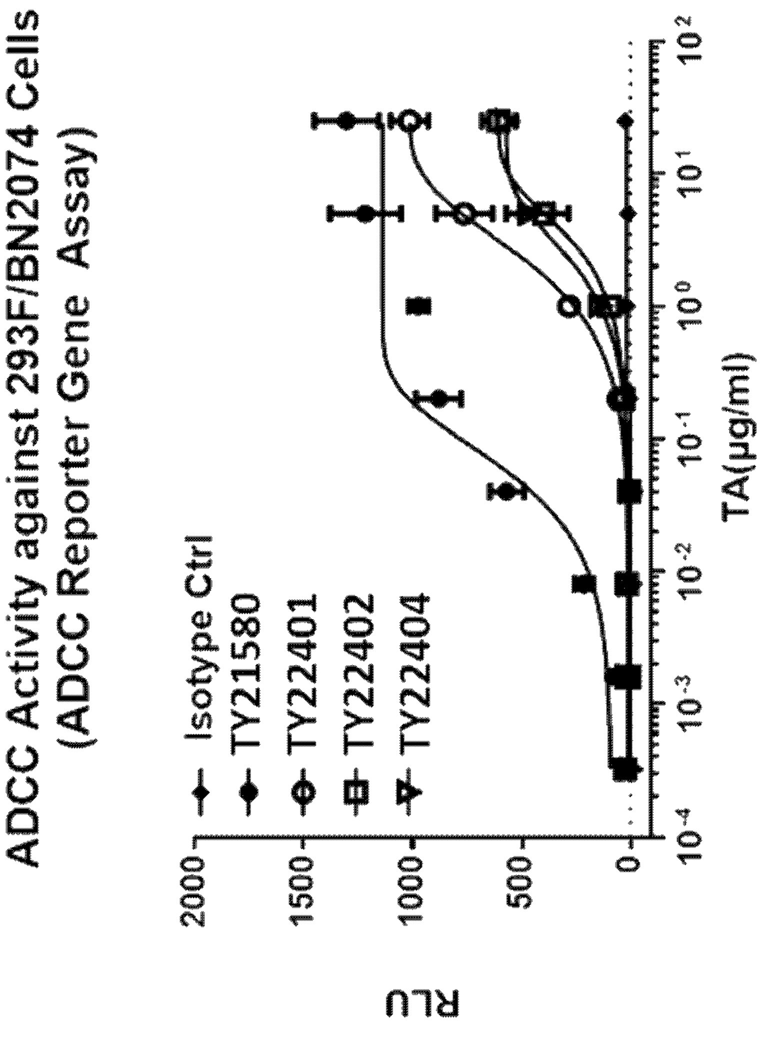
FIG. 13 shows the antibody-dependent cell-mediated cytotoxicity (ADCC) activity of isotype control antibody, the parental antibody TY21580, or exemplary activatable antibodies TY22401, TY21580, or TY22404 on HEK293F cells transiently overexpressing human CTLA4, as determined by an ADCC reporter gene assay.

Next, the antibody-dependent cell cytotoxicity activities of the activatable antibodies were tested and compared with that of the parental antibody TY21580. An ADCC reporter gene assay was used to evaluate the ADCC activities of the activatable antibodies. HEK293F cells overexpressing human CTLA4 (HEK293F/hCTLA-4 cells) were used as target cells; a Jurkat cell line overexpressing CD16a and NFAT-Luc (Jurkat/CD16a cells) was used as effector cells. 1×10^5 Jurkat/CD16a cells and 1×10^4 HEK293F/hCTLA-4 cells (E:T ratio 10:1) were mixed with different concentrations of antibody. After incubation for 6 hours, 100 μL of One-Glo reagent was added to the cells, and the cells were lysed for 10 min. Supernatants were removed for luminescence measurements using a SpectraMax i3x plate reader. As shown in FIG. 13, the activatable antibodies showed several log lower ADCC activities than the parental antibody TY21580. The ADCC activity of TY22401 was higher than that of TY22402 and TY22404. Taken together, the in vitro data indicates that the better masked activatable antibodies had less ADCC activity.

The anti-tumor activities of the activatable antibodies were next evaluated and compared with the anti-tumor activity of the parental antibody TY21580 in multiple syngeneic mouse tumor models, including an MC38 colorectal tumor model, a CT26 colorectal tumor models, an H22 liver tumor model, and a 3LL lung tumor model.

Anti-Tumor Efficacy in an MC38 Colorectal Tumor Model

Figure 14A:
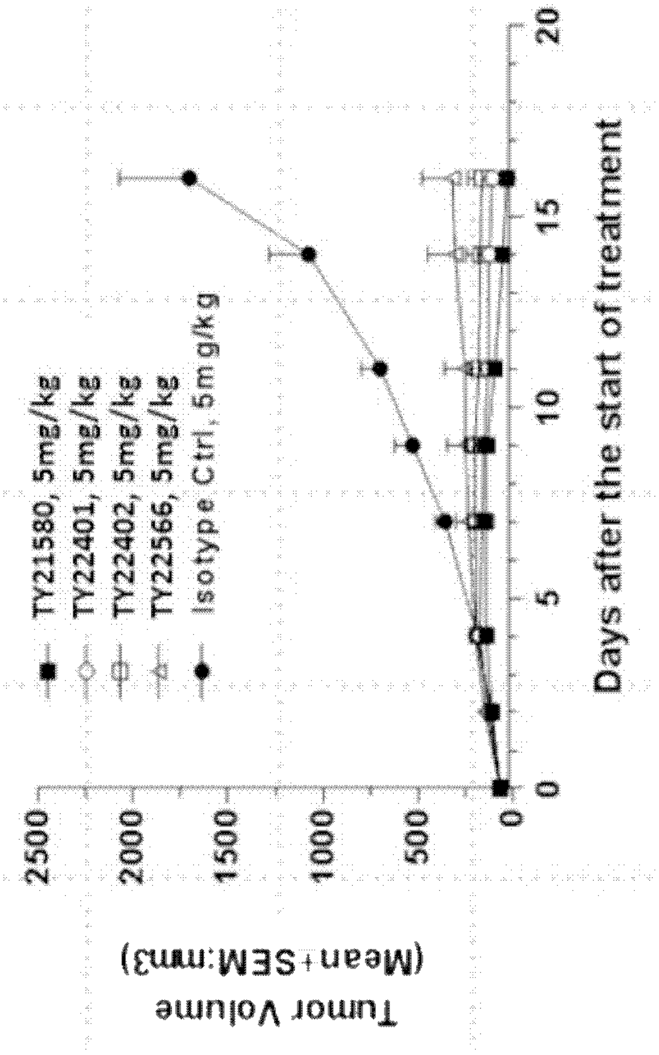
FIGS. 14A-B show the in vivo anti-tumor efficacy of parental antibody TY21580, isotype control antibody, or exemplary CTLA4 activatable antibodies TY22401, TY22402, or TY22566 in an MC38 syngeneic mouse colorectal tumor model.
Figure 14B:
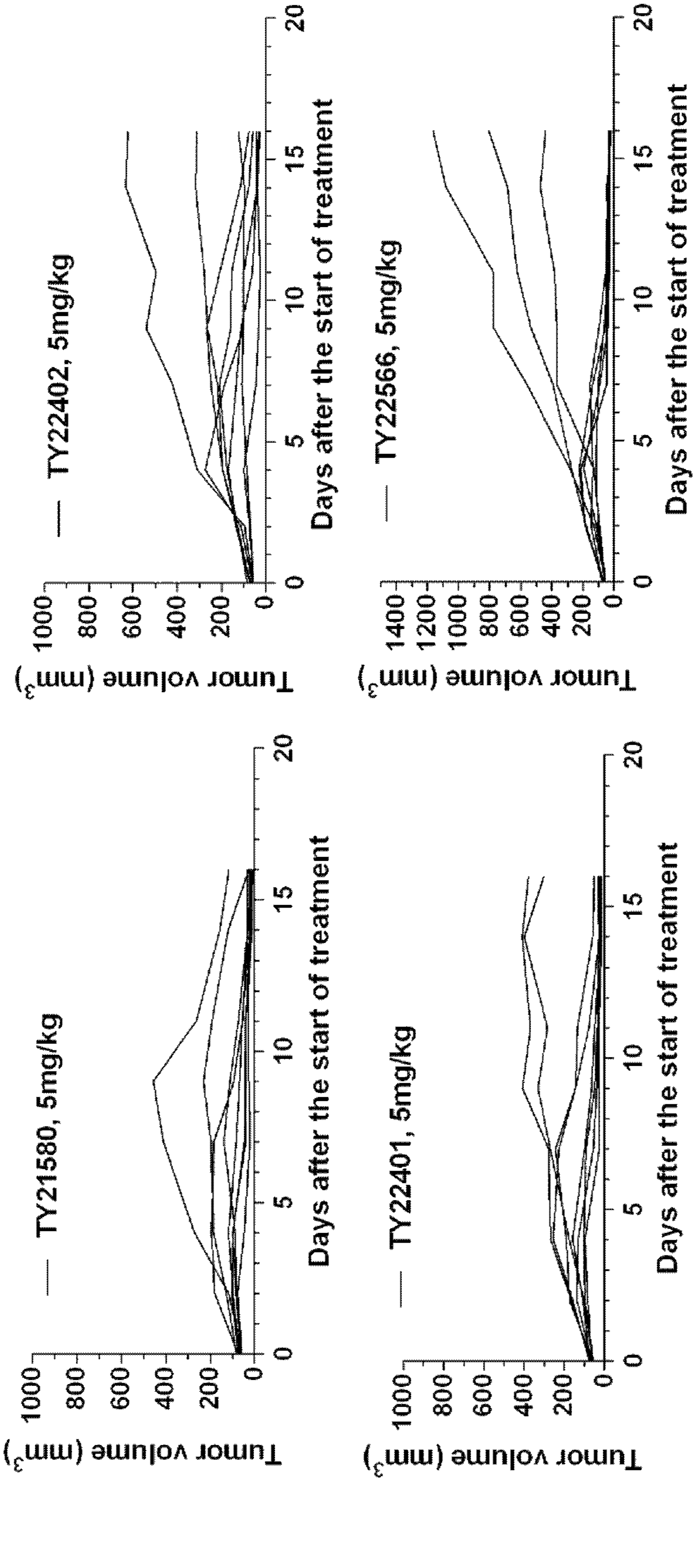

C57BL/6 mice (n=8 per group, female, 6-8 weeks old) were inoculated subcutaneously with MC38 (NTCC-MC38) murine colon cancer cells. When tumors were established (70 mm3), treatment began with isotype control antibody, parental antibody TY21580, or one of three activatable antibodies by intraperitoneal injection, twice a week. Tumor growth was monitored twice a week, the mean tumor volume±s.e.m. over time (FIG. 14A) and individual tumor growth curves (FIG. 14B) were assessed. As shown in FIGS. 14A-B, all three activatable antibodies showed potent anti-tumor activities, comparable to the parental antibody TY21580 in the MC38 syngeneic mouse tumor model.

Anti-Tumor Efficacy in a CT26 Colorectal Tumor Model

Figure 15:
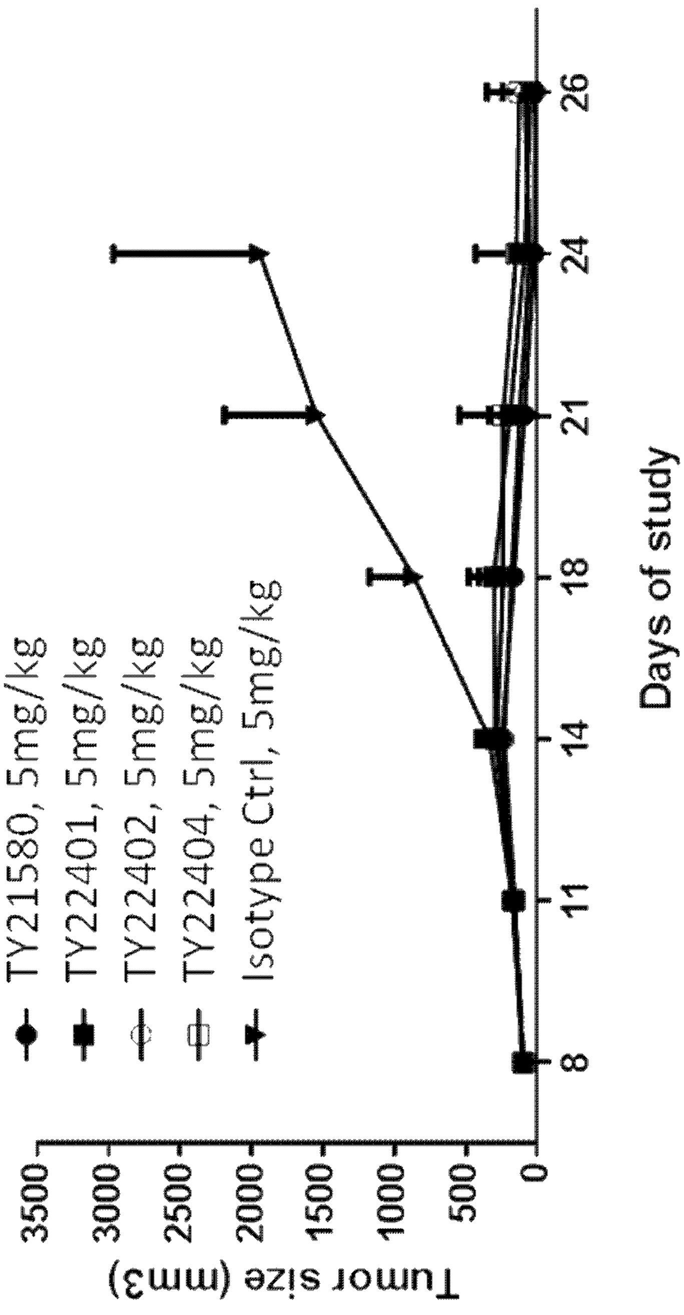
FIG. 15 shows the in vivo anti-tumor efficacy of isotype control antibody, parental antibody TY21580, or one of three activatable antibodies, in a CT26 syngeneic mouse colorectal tumor model. Tumor growth curves of different treatment groups of female C57BL/6 mice bearing CT26-established tumors are shown. Data points represent group mean; error bars represent SEM.

BALB/c mice (n=8 per group, female, 7-8 weeks old) were inoculated subcutaneously with CT26 (Shanghai Institutes for Biological Sciences) murine colon cancer cells. When tumors were established (100 mm3), treatment began with isotype control antibody, parental antibody TY21580, or one of three activatable antibodies at 5 mg/kg by intraperitoneal injection, twice a week. Tumor growth was monitored twice a week and reported as the mean tumor volume±s.e.m. over time. As shown in FIG. 15, all three activatable antibodies showed potent anti-tumor activities, comparable to the parental antibody TY21580 in CT26 syngeneic mouse tumor model.

Anti-Tumor Efficacy in an H22 Liver Tumor Model

Figure 16:
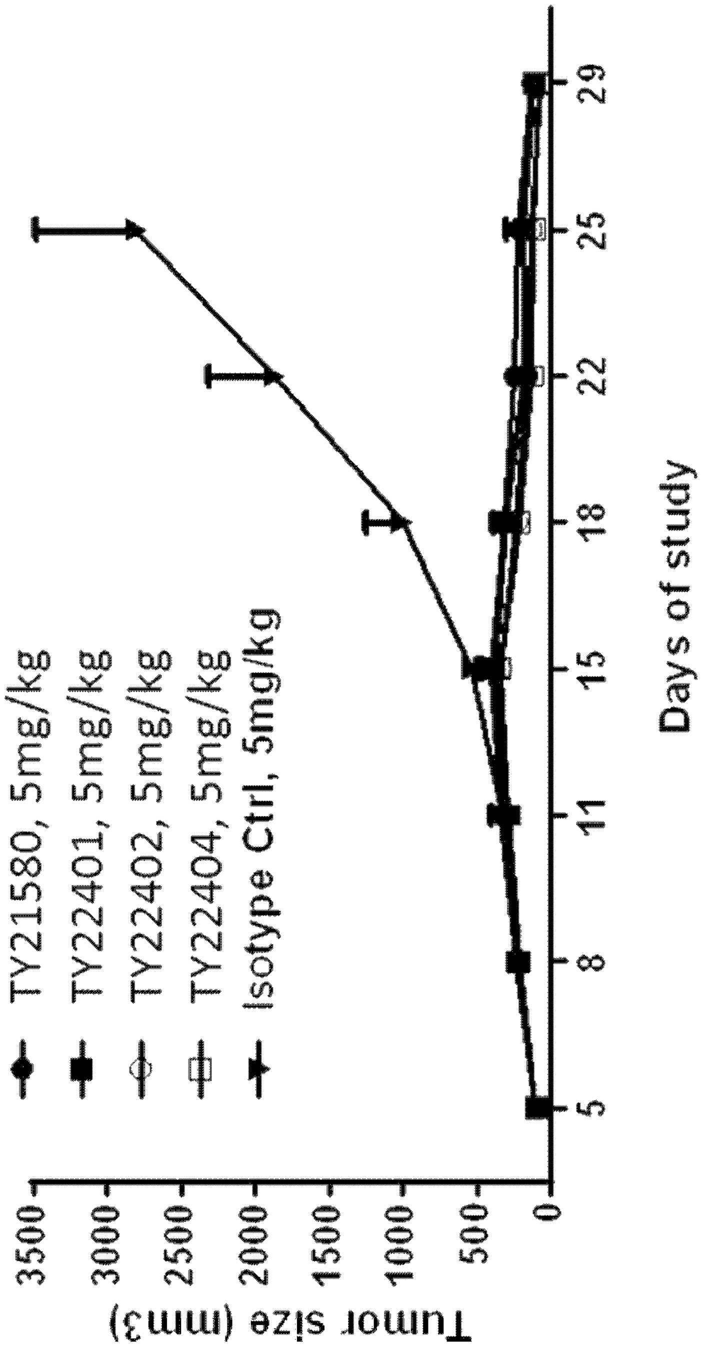
FIG. 16 shows the in vivo anti-tumor efficacy of isotype control antibody, parental antibody TY21580, or one of three activatable antibodies, in an H22 syngeneic mouse liver tumor model. Tumor growth curves of different treatment groups of female C57BL/6 mice bearing H22-established tumors are shown. Data points represent group mean; error bars represent SEM.

BALB/c mice (n=8 per group, female, 7-8 weeks old) were inoculated subcutaneously with H22 (China Center for Type Culture Collection) murine liver cancer cells. When tumors were established (100 mm3), treatment began with isotype control antibody, parental antibody TY21580, or one of three activatable antibodies at 5 mg/kg by intraperitoneal injection, twice a week. Tumor growth was monitored twice a week and reported as the mean tumor volume±s.e.m. over time. As shown in FIG. 16, all three activatable antibodies showed potent anti-tumor activities, comparable to the parental antibody TY21580 in H22 syngeneic mouse tumor model.

Anti-Tumor Efficacy in a 3LL Lung Cancer Model

Figure 17A:
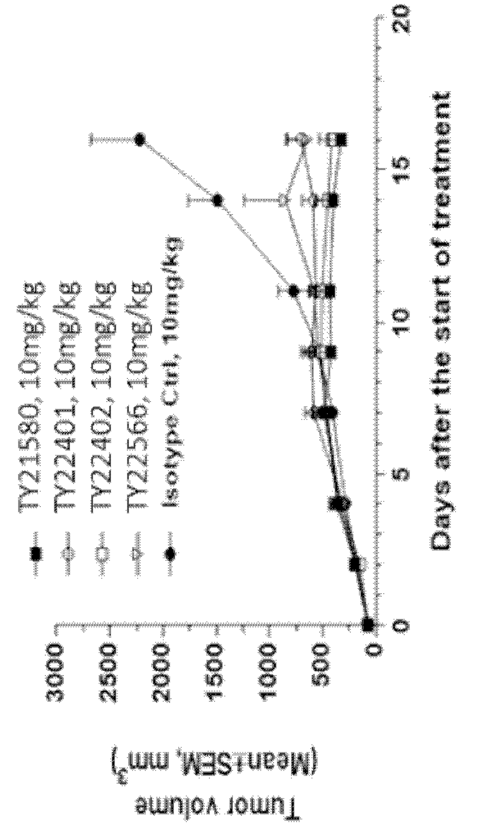
FIGS. 17A-B show the in vivo anti-tumor efficacy of parental antibody TY21580, isotype control antibody, and exemplary activatable antibodies TY22401, TY22402, or TY22566 in a 3LL syngeneic mouse lung tumor model.
Figure 17B:
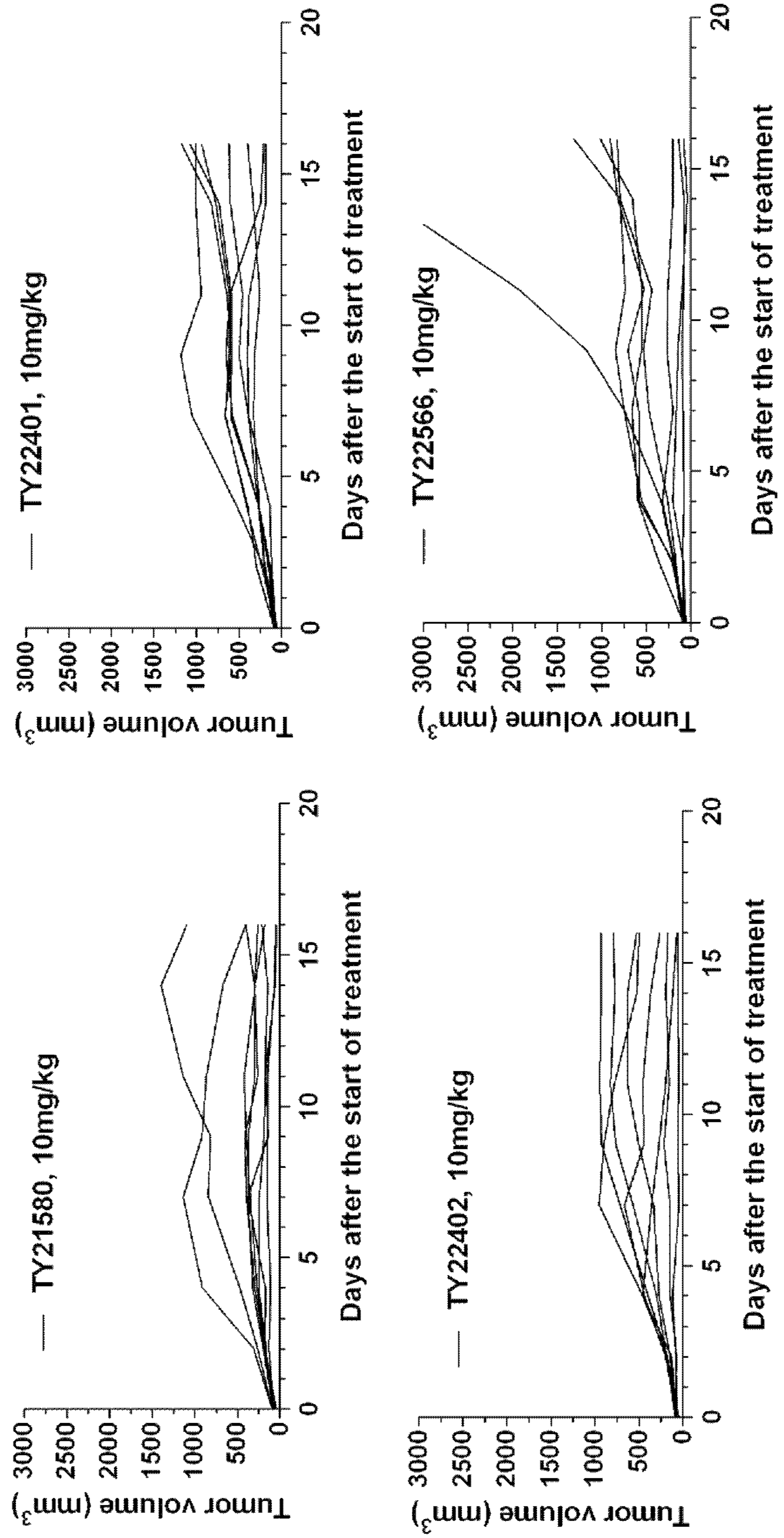

C57BL/6 mice (n=10 per group, female, 6-8 weeks old) were inoculated subcutaneously with 3LL (JCRB) murine lung cancer cells. When tumors were established (75 mm3), treatment began with isotype control antibody, parental antibody TY21580, or one of three activatable antibodies by intraperitoneal injection, twice a week. Tumor growth was monitored twice a week, the mean tumor volume±s.e.m. over time (FIG. 17A) and individual tumor growth curves (FIG. 17B) were assessed. As shown in FIGS. 17A-B, all three activatable antibodies showed potent anti-tumor activities, comparable to the parental antibody TY21580 in 3LL syngeneic mouse tumor model.

Pharmacokinetic Analysis

Figure 18B:
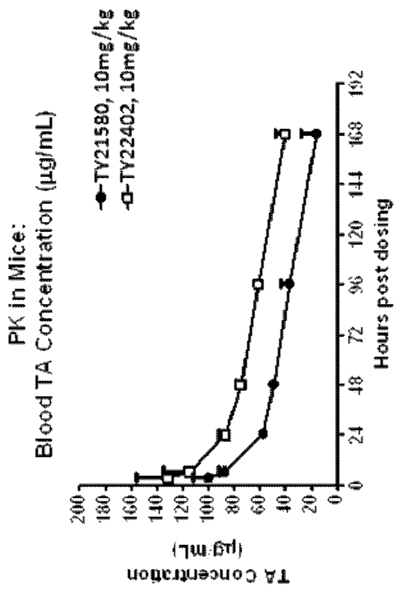
FIGS. 18A-C show time courses of the blood concentrations of the test articles (TAs) intravenously administered at a concentration of 10 mg/kg to female BALB/c mice, as determined by ELISA.
Figure 18A:
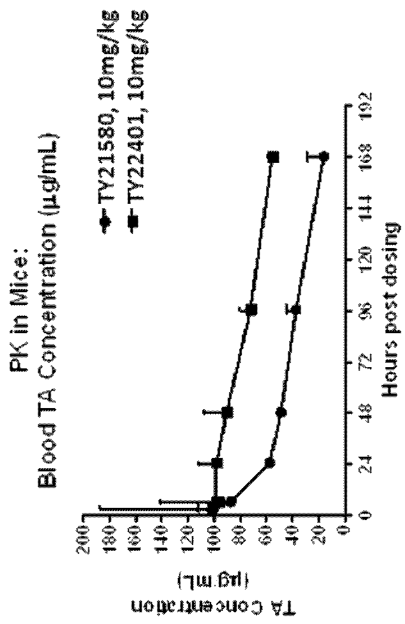
Figure 18C:
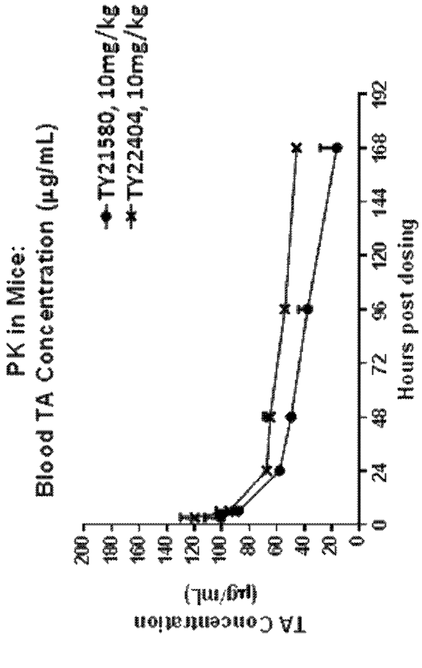

A pharmacokinetics study was conducted in BALB/c female mice at about eight weeks of age. Three mice per group were intraperitoneally injected with the test article at 10 mg/kg. Blood samples (~50 ul per sample) were collected at 3, 6, 24, 48, 96, and 168 hours post-dosing. Blank control blood was collected from three naïve female mice without antibody administration. Serum concentrations of each test antibody were determined by ELISA, in which anti-human IgG Fc was used for capture, and HRP-labeled anti-human IgG (Fab specific) antibody (Sigma) was used for detection (FIGS. 18A-C). As compared to the previous data collected for parental antibody TY21580, activatable antibodies TY22401 (FIG. 18A), TY22402 (FIG. 18B), and TY22404 (FIG. 18C) had a much slower clearance time and longer half-life. TY22401 has a half-life of 196 hours, and the drug concentration at 168 hours was about 55 μg/mL. TY22402 had a half-life of 134 hours, and the drug concentration at 168 hours was about 40 μg/mL. TY22404 had a half-life of 254 hours, and the drug concentration at 168 hours was about 45 μg/mL. In comparison, the parental antibody TY21580 had a half-life of 107 hours, and the drug concentration at 168 hours was about 17 μg/mL.

Repeated Dosing Toxicity Studies

Figure 19:
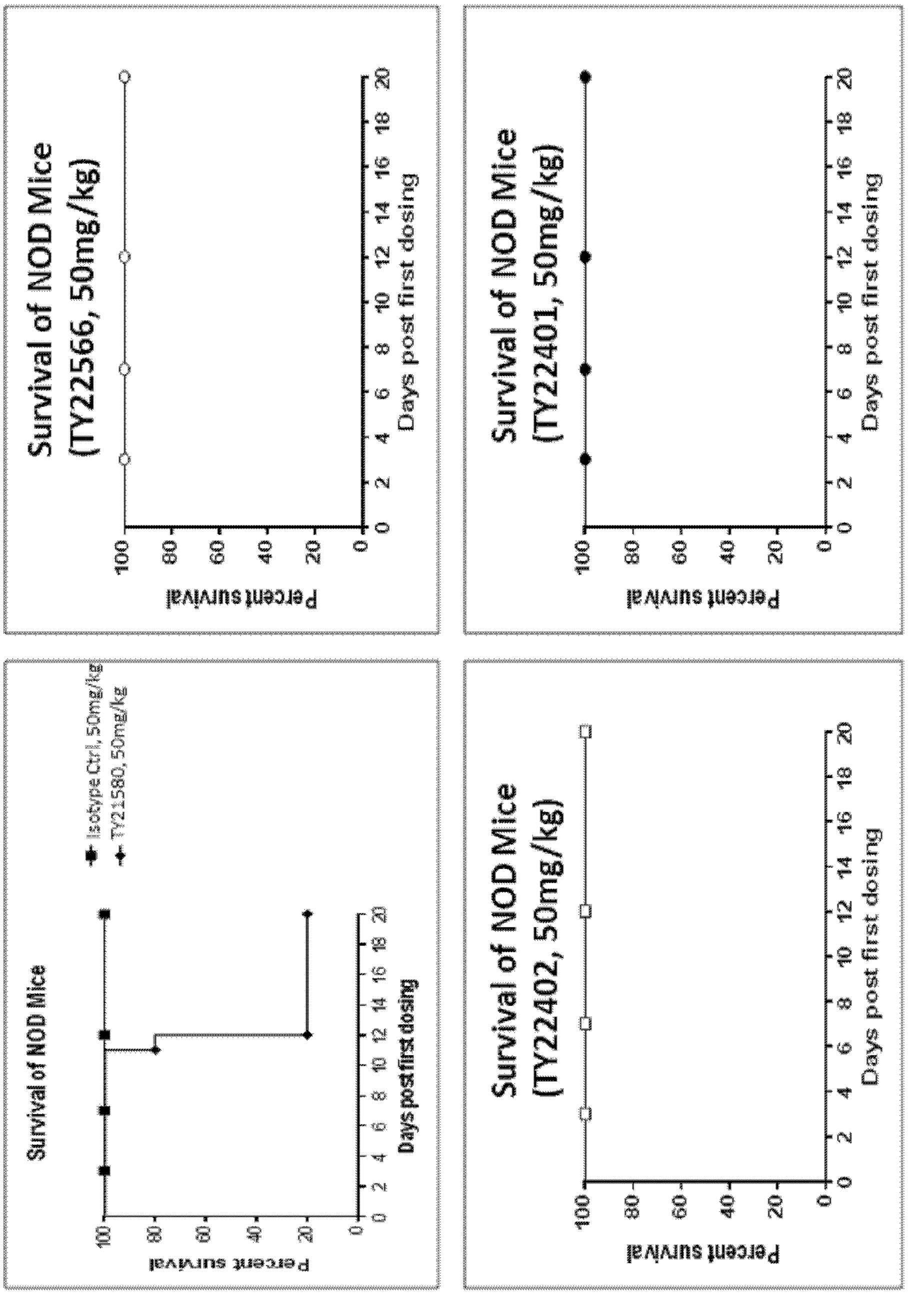
FIG. 19 shows the repeated dosing toxicity of isotype control antibody, parental antibody TY21580, and exemplary activatable antibodies TY22566, TY22401, and TY22402 using the NOD mouse model. Percent survival rate over 20 days were shown for each treatment group.

While evaluating the effect of TY21580 on diabetes onset age in NOD mice, it was found that high dosages of TY21580 could lead to animal death of NOD but not normal BALB/c mice. Here the NOD mouse model was used to evaluate the safety of the activatable antibodies, as compared to that of TY21580. NOD mice (n=5 per group, female, 6 weeks old) were treated with isotype control antibody, parental antibody TY21580, or one of three activatable antibodies by intraperitoneal injection at 50 mg/kg on days 0, 3, 7, and 12. In the TY21580 treatment group, 1 animal died after the third dosing, and 3 animals died after the fourth dosing. As shown in FIG. 19, all animals treated with the isotype control or any of the three activatable antibodies were alive and in good health at the termination of the study. These data indicated that the activatable antibodies have acceptable safety/toxicity profiles in mice, and, in NOD mice, the activatable antibodies are much safer than the parental antibody TY21580.

Example 5: Construction and Validation of Activatable Antibodies Targeting CD137

Figure 20A:
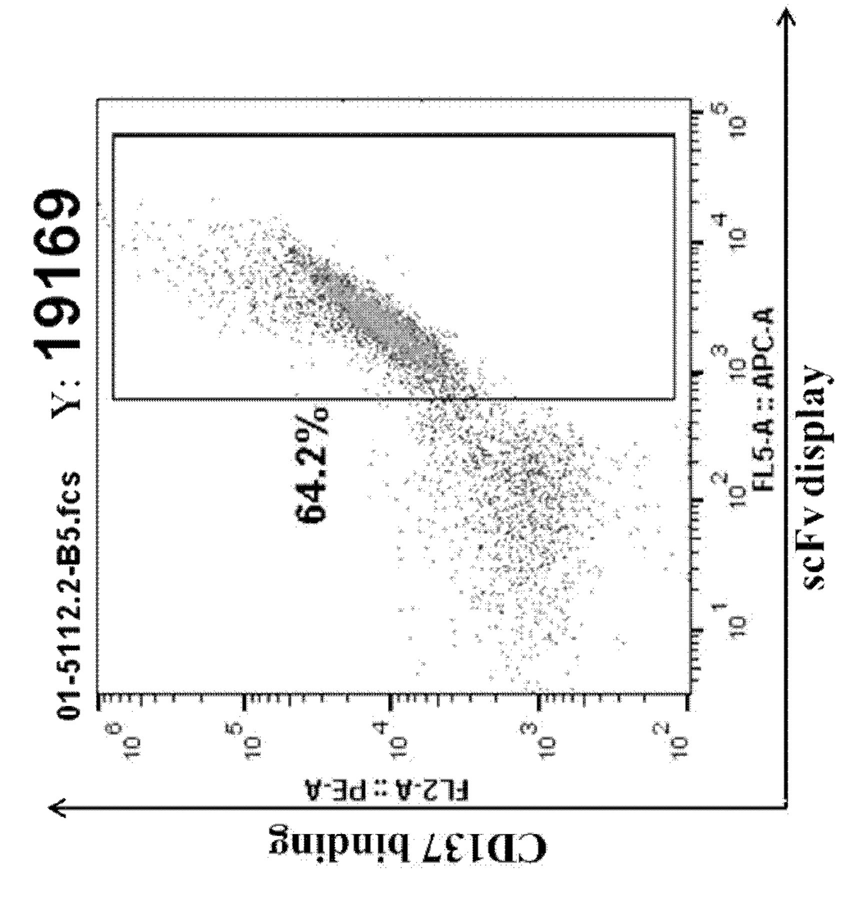
FIGS. 20A-B show functional display of Fabs and scFvs targeting human CD137 on yeast, as determined by flow cytometry.
Figure 20B:
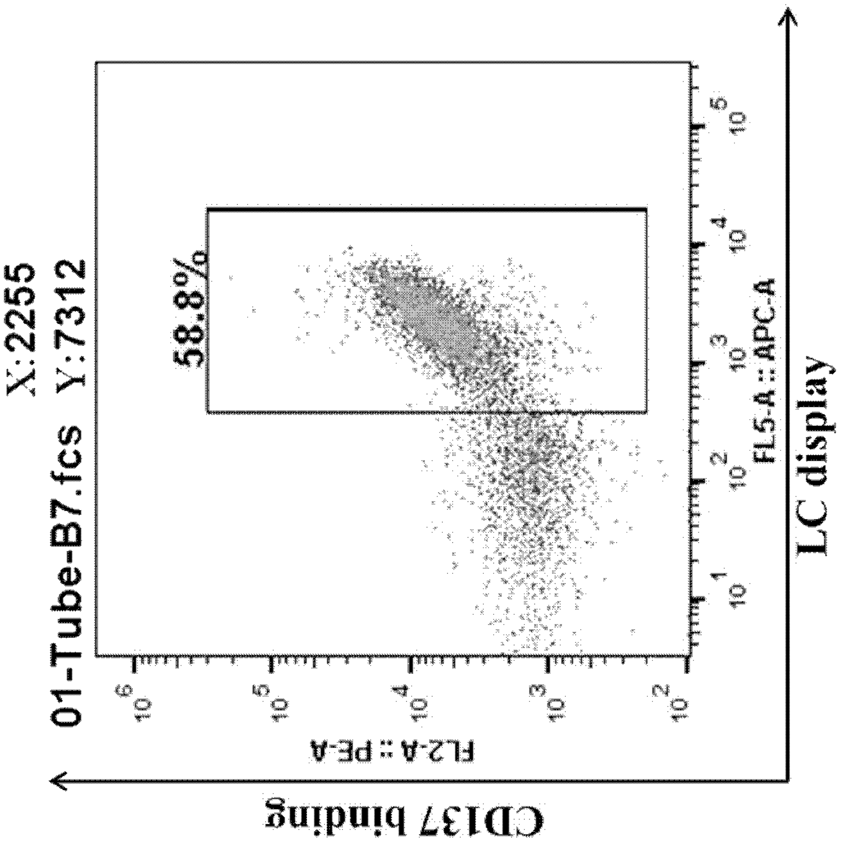

Activatable antibodies targeting human CD137 were developed similarly to the scheme used for the development of the anti-CTLA4 activatable antibodies described in Example 3 above. Fab fragments (FIG. 20A) or scFvs (FIG. 20B) of a parental CD137 antibody were displayed on the surface of yeast through fusion to the Aga2 protein, and their ability to bind to CD137 was confirmed by flow cytometry. The VH and VL sequences for the parental CD137 antibody (TY21242) are listed below (See also PCT International Application No. PCT/CN2017/098332, incorporated herein by reference in its entirety):

Anti-CD137 heavy chain variable region

```
Anti-CTL137 heavy chain variable region
(SEQ ID NO: 49):
EVQLVESGGGLVQPGGSLRLSCAASGFSLSTGGVGVGWIRQAPGKGLEWL

ALIDWADDKYYSPSLKSRLTISRDNSKNTLYLQLNSLRAEDTAVYYCARG

GSDTVIGDWFAYWGQGTLVTVSS
```

Anti-CD137 light chain variable region

```
Anti-CTL137 light chain variable region
(SEQ ID NO: 50):
DIQLTQSPSSLSASVGDRVTITCRASQSIGSYLAWYQQKPGKAPKLLIYD

ASNLETGVPSRFSGSGSGTDFTLTISSLQPEDFATYYCQQGYYLWTFGQG

TKVEIK.
```

Figure 21:
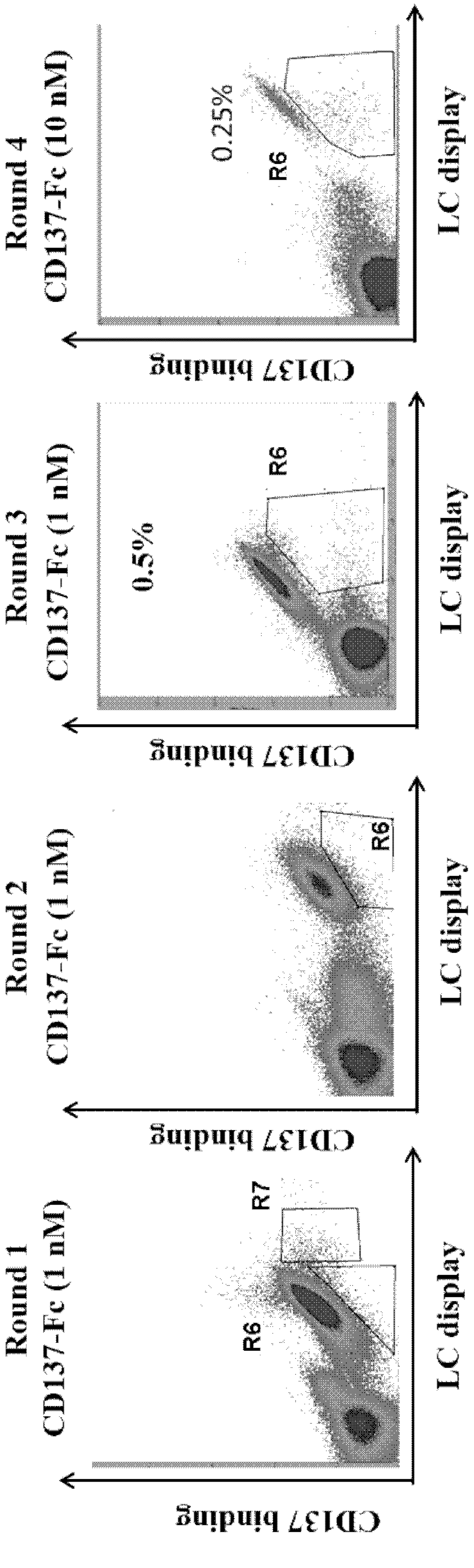
FIG. 21 shows an exemplary selection process for activatable antibodies targeting human CD137. A yeast library displaying fusion proteins were subjected to several rounds of FACS-based screening.

The yeast libraries were constructed with CPLs fused to the N-terminus of the light chain, and were subjected to a FACS-based screening processes. The single clones from the 4th or $5^{th}$ round of sorting (FIG. 21) were plated on selective media, and grown individually for confirmation of cleavage-mediated activated antigen binding. As shown in FIGS. 22A-B, the selected CD137 activatable antibody clones exhibited little binding to antigen in the presence of masking peptide; however, the binding to antigen was dramatically increased when the yeast cells were treated with TEV protease to remove the masking peptide.

As observed with CTLA4 activatable antibodies, the identified masking sequences could be separated into several groups, indicating clear enrichment through rounds of sorting. Seven groups of masking peptide sequences, together with the invariant cleavage peptide sequence, are listed in Table 9. Several of these sequence groups (TY22594, TY22595, TY22596, TY22598, TY22599) were derived from the CPL011 library, which contains NNK codons in the loop between the two fixed Cys residues. Interestingly, there are two or more Arg residues in the loop for all these sequence groups, suggesting that charge-charge interactions may be involved between the masking peptides and the CDRs of the parental antibody. Indeed, there are negatively charged Asp residues in the VH CDR2 and VH CDR3.

TABLE 9

Masking peptide sequences

| Sample ID: | Masking + cleavage peptide sequences: |
|---|---|
| TY22586 | EVGSYPTDLDACADAPNHCHFSGRSAGGGGSPLGLAGSGGS (SEQ ID NO: 40) |
| TY22591 | EVGSYSSTHAHCHHSPANCISSGRSAGGGGSPLGLAGSGGS (SEQ ID NO: 41) |
| TY22594 | EVGSYDTDYDFCPILRHRCDSSGRSAGGGGSPLGLAGSGGS (SEQ ID NO: 42) |
| TY22595 | EVGSYNDYNYHCKWRPSRCHNSGRSAGGGGSPLGLAGSGGS (SEQ ID NO: 43) |
| TY22596 | EVGSYYHDYDDCRVLPRRCFNSGRSAGGGGSPLGLAGSGGS (SEQ ID NO: 44) |
| TY22598 | EVGSYSNNFASCLWRHRSCADSGRSAGGGGSPLGLAGSGGS (SEQ ID NO: 45) |
| TY22599 | EVGSYTDNYDYCPRLRRKCYHSGRSAGGGGSPLGLAGSGGS (SEQ ID NO: 46) |

The masking sequences and the invariant cleavage sequences were then tested in full IgG4 molecules expressed in mammalian cells. Their expression levels were similar to their parental antibody, and their purification yields after protein A resin were also similar, suggesting that the presence of masking peptide and cleavage peptide did not have any negative impacts on antibody expression in mammalian cells.

The masking efficiency was then measured through flow cytometry. Briefly, yeast cells displaying human CD137 on their surface washed twice with PBSA buffer, and 50 μL (1×10^6) cells were dispensed into each well of a 96 well plate. Cells were then incubated with 3-fold serial dilutions of antibodies for 1 hour on ice, washed once with PBSA buffer, and then incubated with 100 μL of PE conjugated mouse anti-human Fc (1 μg/ml) for 30 minutes on ice. The cells were then washed once prior to analysis by flow cytometry (Beckman® CytoFlex). As shown in FIG. 23 and Table 10, compared with the parental antibody TY21242, all activatable antibodies showed dramatically reduced binding to human CD137 on the cell surface, and the calculated masking efficiency ranged from 20 fold for TY22596 to more than 300 fold for TY22586, TY22595 and TY22599. These results indicated that the masking peptides identified from the CPL libraries displayed on yeast maintained their masking efficiency when expressed in mammalian cells.

TABLE 10

Masking efficiency of CD137 activatable antibodies

| | $EC_{50}$ | |
|---|---|---|
| Sample ID: | $K_D$ (nM): | Masking efficiency: |
| TY21242 | 0.28 | 1.0 |
| TY22586 | Too low* | Very high |
| TY22591 | 10.8 | 38.3 |
| TY22594 | 23.6 | 83.7 |
| TY22595 | 106.8 | 378.7 |
| TY22596 | 5.86 | 20.8 |
| TY22598 | 8.61 | 30.5 |
| TY22599 | 98.1 | 347.9 |

Tow low = binding was so weak it was not detectable in this assay.

Taken together, the data indicated that multiple potent masking peptides were successfully discovered against each target antibody using the methods described herein.

Example 6: Effect of Masking Peptide Length on the Masking Efficiency of Activatable Antibodies Targeting CTLA4

Two activatable antibodies, TY22402 and TY22404, were chosen to test the dependence of masking efficiency on the length of masking peptides to suit their specific applications. The masking peptides of TY22402 and TY22404 were shortened from 21 residues to 16 or 12 residues by removing the residues from the N-terminus, leaving only 5 or 2 residues before the first cysteine residue in the masking peptide (Table 11). These activatable antibodies were expressed and purified from mammalian cells and their masking efficiencies were measured as described in Example 3 and compared to parent antibody TY21580. Results from two experiments indicated that these activatable antibodies can be made using different masking peptides with lengths ranging from 2 to 11 residues before the first cysteine residue to modulate antibody masking efficiency (FIGS. 24A and 24B; Tables 12 and 13). This seems to suggest that the core masking motif contains the cysteine loop and its immediately adjacent residues, and is sufficient to maintain masking efficiency.

TABLE 11

Masking peptides with varying peptide lengths

| Sample ID: | Masking + cleavage peptide sequences (underlined): |
|---|---|
| TY22402 | EVGSYIVHHSDCDAFYPYCDSSGRSAGGGGTPLGLAGSGGS (SEQ ID NO: 118) |
| TY22775 | EVGHSDCDAFYPYCDSSGRSAGGGGTPLGLAGSGGS (SEQ ID NO: 119) |
| TY22864 | EDCDAFYPYCDSSGRSAGGGGTPLGLAGSGGS (SEQ ID NO: 120) |
| TY22404 | EVGSYPNPSSDCVPYYYACAYSGRSAGGGGTPLGLAGSGGS (SEQ ID NO: 121) |
| TY22776 | EVGSSDCVPYYYACAYSGRSAGGGGTPLGLAGSGGS (SEQ ID NO: 122) |
| TY22871 | EDCVPYYYACAYSGRSAGGGGTPLGLAGSGGS (SEQ ID NO: 123) |

Table 12 shows the masking efficiencies of the antibodies in FIG. 24A. Table 13 shows the masking efficiencies of the antibodies in FIG. 24B.

TABLE 12

Masking efficiencies of antibodies with varying masking peptide lengths

| Sample ID | EC50(nM) | Masking efficiency |
|---|---|---|
| TY21580 | 0.2223 | |
| TY22402 | 53.99 | 243 |
| TY22775 | 37.31 | 168 |
| TY22404 | 68.40 | 308 |
| TY22776 | 65.90 | 296 |

TABLE 13

Masking efficiencies of antibodies with varying masking peptide lengths

| Sample ID | EC50(nM) | Masking efficiency |
|---|---|---|
| TY21580 | 0.2125 | |
| TY22402 | 115.6 | 554 |
| TY22864 | 117 | 550 |
| TY22404 | 121.5 | 572 |
| TY22871 | 88.09 | 414 |

Example 7: Effect of Cleavage Peptide Length on the Masking Efficiency of Activatable Antibodies Targeting CTLA4

TY22404 was chosen to test the dependence of masking efficiency on the length of the cleavage peptide to suit their specific applications. The cleavage peptide of TY22404 was shortened to various lengths (Table 14). Activatable antibodies were expressed and purified from mammalian cells and their masking efficiencies were measured as described in Example 3 and compared to parent antibody TY21580. As shown in FIG. 25 and Table 15, the results indicated that these activatable antibodies can be made using different cleavage peptides with their length ranging from 5 to 20 residues to modulate antibody masking efficiency. The strong correlation between masking and cleavage motifs is striking; the masking efficiency of TY23291 is enhanced least 30-fold compared to TY22404 when the peptide length is truncated from 41 to 17 amino acids. These results indicate that several novel masking peptides can be designed and engineered. In addition, the coupling between masking and cleavage motifs could be further explored.

TABLE 14

Masking peptides with varying cleavage peptide lengths

| Sample ID | Peptide name | Masking + cleavage peptide sequences (underlined): |
|---|---|---|
| TY22404 | | EVGSYPNPSSDCVPYYYACAYSGRSAGGGGTPLGLAGSGGS (SEQ ID NO: 121) |
| TY23286 | | EVGSYPNPSSDCVPYYYACAYSGRSAPLGLA (SEQ ID NO: 130) |
| TY23289 | | EDCVPYYYACAYSGRSAPLGLA (SEQ ID NO: 131) |
| TY23280 | | EDCVPYYYACAYSGRSA (SEQ ID NO: 132) |
| TY23291 | | EDCVPYYYACAYPLGLA (SEQ ID NO: 133) |

Table 15 shows the masking efficiencies of the antibodies in FIG. 25.

TABLE 15

Masking efficiencies of antibodies with varying cleavage peptide lengths

| Sample ID | EC50 (nM) | Masking efficiency |
|---|---|---|
| TY21580 | 0.2505 | |
| TY22404 | 117.4 | 469 |
| TY23286 | 1496 | 5972 |
| TY23289 | 133.2 | 532 |
| TY23280 | 2952 | 11784 |
| TY23291 | 3656 | 14595 |

What is claimed is:

1. An activatable antibody comprising:

a first polypeptide comprising, from N-terminus to C-terminus, a masking moiety (MM), a cleavable moiety (CM), and a target binding moiety (TBM), wherein the MM comprises an amino acid sequence selected from the group consisting of SEQ ID NOS: 79-85;

wherein the CM comprises at least a first cleavage site and a first flexible linker (L1); and wherein:

a) the TBM comprises an antibody light chain variable region (VL), and the activatable antibody further comprises a second polypeptide comprising an antibody heavy chain variable region (VH);

b) the TBM comprises an antibody heavy chain variable region (VH), and the activatable antibody further comprises a second polypeptide comprising an antibody light chain variable region (VL);

c) the TBM comprises from the N-terminus to the C-terminus, an antibody light chain variable region (VL) and an antibody heavy chain variable region (VH); or d) the TBM comprises from the N-terminus to the C-terminus, an antibody heavy chain variable region (VH) and an antibody light chain variable region (VL);

wherein:

(i) the VH comprises an HVR-H1 comprising the amino acid sequence of SEQ ID NO: 65, an HVR-H2 comprising the amino acid sequence of SEQ ID NO: 66, and an HVR-H3 comprising the amino acid sequence of SEQ ID NO: 67; and (ii) the VL comprises an HVR-L1 comprising the amino acid sequence of SEQ ID NO: 68, an HVR-L2 comprising the amino acid sequence of SEQ ID NO: 69, and an HVR-L3 comprising the amino acid sequence of SEQ ID NO: 70; and wherein the activatable antibody binds to human CD137 via the VH and the VL when the CM is cleaved.

2. The activatable antibody of claim 1, wherein the TBM comprises an antibody light chain variable region (VL), and the activatable antibody further comprises a second polypeptide comprising an antibody heavy chain variable region (VH).

3. The activatable antibody of claim 1, wherein the MM further comprises, at its N-terminus, an additional amino acid sequence.

4. The activatable antibody of claim 1, wherein the first cleavage site is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

5. The activatable antibody of claim 1, wherein the L1 comprises an amino acid sequence selected from the group consisting of SEQ ID NOS: 17-24.

6. The activatable antibody of claim 1, wherein the CM further comprises a second cleavage site.

7. The activatable antibody of claim 6, wherein the second cleavage site is a protease cleavage site for a protease selected from the group consisting of urokinase-type plasminogen activator (uPA), matrix metalloproteinase-1 (MMP-1), MMP-2, MMP-3, MMP-8, MMP-9, MMP-14, Tobacco Etch Virus (TEV) protease, plasmin, Thrombin, Factor X, PSA, PSMA, Cathepsin D, Cathepsin K, Cathepsin S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

8. The activatable antibody of claim 6, wherein the first and second cleavage sites are different.

9. The activatable antibody of claim 6, wherein the CM further comprises a second flexible linker (L2).

10. The activatable antibody of claim 9, wherein the L2 comprises an amino acid sequence selected from the group consisting of SEQ ID NOS: 17-24.

11. The activatable antibody of claim 1, wherein the first polypeptide comprises, from N-terminus to C-terminus, an amino acid sequence selected from the group consisting of SEQ ID NOS: 40-46 and the TBM, wherein the amino acid sequence selected from the group consisting of SEQ ID NOS: 40-46 comprises the MM and the CM.

12. The activatable antibody of claim 3, wherein the additional amino acid sequence comprises the amino acid sequence of SEQ ID NO: 16.

13. The activatable antibody of claim 6, wherein the second cleavage site is C-terminal to the $L_1$.

14. The activatable antibody of claim 1, wherein:

(a) the VH comprises the amino acid sequence of SEQ ID NO: 49; and (b) the VL comprises the amino acid sequence of SEQ ID NO: 50.

15. The activatable antibody of claim 1, wherein the MM comprises the amino acid sequence of SEQ ID NO: 79.

16. The activatable antibody of claim 15, wherein:

(a) the VH comprises the amino acid sequence of SEQ ID NO: 49; and (b) the VL comprises the amino acid sequence of SEQ ID NO: 50.

17. The activatable antibody of claim 15, wherein the CM comprises the amino acid sequence of SEQ ID NO: 12.

18. The activatable antibody of claim 1, wherein:

(a) the TBM comprises an antibody light chain variable region (VL), and the activatable antibody further comprises a second polypeptide comprising an antibody heavy chain variable region (VH);

(b) the MM comprises the amino acid sequence of SEQ ID NO: 79; and (c) the CM comprises the amino acid sequence of SEQ ID NO: 12.

19. The activatable antibody of claim 1, wherein:

(a) the TBM comprises an antibody light chain variable region (VL), and the activatable antibody further comprises a second polypeptide comprising an antibody heavy chain variable region (VH);

(b) the MM comprises the amino acid sequence of SEQ ID NO: 79;

(c) the CM comprises the amino acid sequence of SEQ ID NO: 12;

(d) the VH comprises the amino acid sequence of SEQ ID NO: 49; and (e) the VL comprises the amino acid sequence of SEQ ID NO: 50.

20. The activatable antibody of claim 1, wherein the first polypeptide comprises, from N-terminus to C-terminus, the amino acid sequence of SEQ ID NO: 40 and the TBM, and wherein:

(a) the TBM comprises an antibody light chain variable region (VL), and the activatable antibody further comprises a second polypeptide comprising an antibody heavy chain variable region (VH);

(b) the VH comprises the amino acid sequence of SEQ ID NO: 49; and (c) the VL comprises the amino acid sequence of SEQ ID NO: 50.

21. The activatable antibody of claim 1, wherein the MM comprises the amino acid sequence of SEQ ID NO: 82.

22. The activatable antibody of claim 21, wherein:

(a) the VH comprises the amino acid sequence of SEQ ID NO: 49; and (b) the VL comprises the amino acid sequence of SEQ ID NO: 50.

23. The activatable antibody of claim 21, wherein the CM comprises the amino acid sequence of SEQ ID NO: 12.

24. The activatable antibody of claim 1, wherein:

(a) the TBM comprises an antibody light chain variable region (VL), and the activatable antibody further comprises a second polypeptide comprising an antibody heavy chain variable region (VH);

(b) the MM comprises the amino acid sequence of SEQ ID NO: 82; and (c) the CM comprises the amino acid sequence of SEQ ID NO: 12.

25. The activatable antibody of claim 1, wherein:

(a) the TBM comprises an antibody light chain variable region (VL), and the activatable antibody further comprises a second polypeptide comprising an antibody heavy chain variable region (VH);

(b) the MM comprises the amino acid sequence of SEQ ID NO: 82;

(c) the CM comprises the amino acid sequence of SEQ ID NO: 12;

(d) the VH comprises the amino acid sequence of SEQ ID NO: 49; and (e) the VL comprises the amino acid sequence of SEQ ID NO: 50.

26. The activatable antibody of claim 1, wherein the first polypeptide comprises, from N-terminus to C-terminus, the amino acid sequence of SEQ ID NO: 43 and the TBM, and wherein:

(a) the TBM comprises an antibody light chain variable region (VL), and the activatable antibody further comprises a second polypeptide comprising an antibody heavy chain variable region (VH);

(b) the VH comprises the amino acid sequence of SEQ ID NO: 49; and (c) the VL comprises the amino acid sequence of SEQ ID NO: 50.

27. The activatable antibody of claim 1, wherein the MM comprises the amino acid sequence of SEQ ID NO: 85.

28. The activatable antibody of claim 27, wherein:

(a) the VH comprises the amino acid sequence of SEQ ID NO: 49; and (b) the VL comprises the amino acid sequence of SEQ ID NO: 50.

29. The activatable antibody of claim 27, wherein the CM comprises the amino acid sequence of SEQ ID NO: 12.

30. The activatable antibody of claim 1, wherein:

(a) the TBM comprises an antibody light chain variable region (VL), and the activatable antibody further comprises a second polypeptide comprising an antibody heavy chain variable region (VH);

(b) the MM comprises the amino acid sequence of SEQ ID NO: 85; and (c) the CM comprises the amino acid sequence of SEQ ID NO: 12.

31. The activatable antibody of claim 1, wherein:

(a) the TBM comprises an antibody light chain variable region (VL), and the activatable antibody further comprises a second polypeptide comprising an antibody heavy chain variable region (VH);

(b) the MM comprises the amino acid sequence of SEQ ID NO: 85;

(c) the CM comprises the amino acid sequence of SEQ ID NO: 12;

(d) the VH comprises the amino acid sequence of SEQ ID NO: 49; and (e) the VL comprises the amino acid sequence of SEQ ID NO: 50.

32. The activatable antibody of claim 1, wherein the first polypeptide comprises, from N-terminus to C-terminus, the amino acid sequence of SEQ ID NO: 46 and the TBM, and wherein:

(a) the TBM comprises an antibody light chain variable region (VL), and the activatable antibody further comprises a second polypeptide comprising an antibody heavy chain variable region (VH);

(b) the VH comprises the amino acid sequence of SEQ ID NO: 49; and (c) the VL comprises the amino acid sequence of SEQ ID NO: 50.

33. An activatable antibody comprising:

a first polypeptide comprising, from N-terminus to C-terminus, a masking moiety (MM), a cleavable moiety (CM), and an antibody light chain variable region (VL), and a second polypeptide comprising an antibody heavy chain variable region (VH);

wherein the MM comprises an amino acid sequence selected from the group consisting of SEQ ID NOS: 79-85;

wherein the CM comprises at least a first cleavage site and a first flexible linker (L1);

wherein:

(i) the VH comprises an HVR-H1 comprising the amino acid sequence of SEQ ID NO: 65, an HVR-H2 comprising the amino acid sequence of SEQ ID NO:

66, and an HVR-H3 comprising the amino acid sequence of SEQ ID NO: 67; and (ii) the VL comprises an HVR-L1 comprising the amino acid sequence of SEQ ID NO: 68, an HVR-L2 comprising the amino acid sequence of SEQ ID NO: 69, and an HVR-L3 comprising the amino acid sequence of SEQ ID NO: 70; and wherein the activatable antibody binds to human CD137 via the VH and the VL when the CM is cleaved.

34. The activatable antibody of claim 33, wherein:

(a) the VH comprises the amino acid sequence of SEQ ID NO: 49; and (b) the VL comprises the amino acid sequence of SEQ ID NO: 50.

35. The activatable antibody of claim 33, wherein the MM comprises the amino acid sequence of SEQ ID NO: 79.

36. The activatable antibody of claim 33, wherein:

(a) the MM comprises the amino acid sequence of SEQ ID NO: 79;

(b) the CM comprises the amino acid sequence of SEQ ID NO: 12;

(c) the VH comprises the amino acid sequence of SEQ ID NO: 49; and (d) the VL comprises the amino acid sequence of SEQ ID NO: 50.

37. The activatable antibody of claim 33, wherein the first polypeptide comprises, from N-terminus to C-terminus, the amino acid sequence of SEQ ID NO: 40 and the VL, and wherein:

(a) the VH comprises the amino acid sequence of SEQ ID NO: 49; and (b) the VL comprises the amino acid sequence of SEQ ID NO: 50.

38. The activatable antibody of claim 33, wherein the MM comprises the amino acid sequence of SEQ ID NO: 82.

39. The activatable antibody of claim 33, wherein:

(a) the MM comprises the amino acid sequence of SEQ ID NO: 82;

(b) the CM comprises the amino acid sequence of SEQ ID NO: 12;

(c) the VH comprises the amino acid sequence of SEQ ID NO: 49; and (d) the VL comprises the amino acid sequence of SEQ ID NO: 50.

40. The activatable antibody of claim 33, wherein the first polypeptide comprises, from N-terminus to C-terminus, the amino acid sequence of SEQ ID NO: 43 and the VL, and wherein:

(a) the VH comprises the amino acid sequence of SEQ ID NO: 49; and (b) the VL comprises the amino acid sequence of SEQ ID NO: 50.

41. The activatable antibody of claim 33, wherein the MM comprises the amino acid sequence of SEQ ID NO: 85.

42. The activatable antibody of claim 33, wherein:

(a) the MM comprises the amino acid sequence of SEQ ID NO: 85;

(b) the CM comprises the amino acid sequence of SEQ ID NO: 12;

(c) the VH comprises the amino acid sequence of SEQ ID NO: 49; and (d) the VL comprises the amino acid sequence of SEQ ID NO: 50.

43. The activatable antibody of claim 33, wherein the first polypeptide comprises, from N-terminus to C-terminus, the amino acid sequence of SEQ ID NO: 46 and the VL, and wherein:

(a) the VH comprises the amino acid sequence of SEQ ID NO: 49; and (b) the VL comprises the amino acid sequence of SEQ ID NO: 50.

* * * * *